(12) United States Patent
Sin et al.

(10) Patent No.: US 7,772,180 B2
(45) Date of Patent: *Aug. 10, 2010

(54) HEPATITIS C VIRUS INHIBITORS

(75) Inventors: Ny Sin, East Hampton, CT (US); Brian Lee Venables, Durham, CT (US); Li-Qiang Sun, Glastonbury, CT (US); Sing-Yuen Sit, Meriden, CT (US); Yan Chen, Guilford, CT (US); Paul Michael Scola, Glastonbury, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 221 days.

This patent is subject to a terminal disclaimer.

(21) Appl. No.: 11/934,840

(22) Filed: Nov. 5, 2007

(65) Prior Publication Data

US 2008/0119461 A1    May 22, 2008

Related U.S. Application Data

(60) Provisional application No. 60/865,034, filed on Nov. 9, 2006.

(51) Int. Cl.
*A01N 37/18* (2006.01)
(52) U.S. Cl. ........................................................ 514/2
(58) Field of Classification Search ........................ None
See application file for complete search history.

(56) References Cited

U.S. PATENT DOCUMENTS

| | | | |
|---|---|---|---|
| 5,223,432 | A | 6/1993 | Wirz et al. |
| 2005/0153877 | A1 | 7/2005 | Miao et al. |
| 2006/0172950 | A1 | 8/2006 | Wang et al. |
| 2006/0199773 | A1 | 9/2006 | Sausker et al. |
| 2006/0257980 | A1 | 11/2006 | Li |
| 2007/0078081 | A1 | 4/2007 | Casarez et al. |
| 2008/0032936 | A1 | 2/2008 | Gai et al. |
| 2008/0039375 | A1 | 2/2008 | Moore et al. |
| 2008/0039470 | A1 | 2/2008 | Niu et al. |

FOREIGN PATENT DOCUMENTS

| | | |
|---|---|---|
| WO | WO 98/17679 | 4/1998 |
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/008244 | 1/2002 |
| WO | WO 02/060926 | 8/2002 |
| WO | WO 03/053349 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 2003/099274 | 12/2003 |
| WO | WO 2003/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |
| WO | WO 2006/026352 | 3/2006 |

(Continued)

OTHER PUBLICATIONS

U.S. Appl. No. 11/923,918, filed Oct. 25, 2007, D'Andrea et al.

(Continued)

*Primary Examiner*—Cecilia Tsang
*Assistant Examiner*—Thomas S Heard
(74) *Attorney, Agent, or Firm*—Pamela A. Mingo

(57) ABSTRACT

Hepatitis C virus inhibitors having the general formula

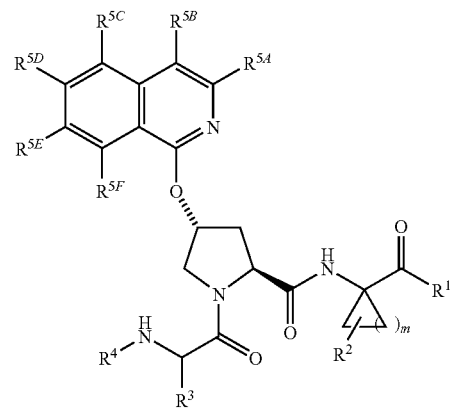

are disclosed. Compositions comprising the compounds and methods for using the compounds to inhibit HCV are also disclosed.

20 Claims, No Drawings

FOREIGN PATENT DOCUMENTS

| | | |
|---|---|---|
| WO | WO 2006/033878 | 3/2006 |
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |
| WO | WO 2006/130552 | 12/2006 |
| WO | WO 2006/130553 | 12/2006 |
| WO | WO 2006/130554 | 12/2006 |
| WO | WO 2006/130607 | 12/2006 |
| WO | WO 2006/130626 | 12/2006 |
| WO | WO 2006/130627 | 12/2006 |
| WO | WO 2006/130628 | 12/2006 |
| WO | WO 2006/130666 | 12/2006 |
| WO | WO 2006/130686 | 12/2006 |
| WO | WO 2006/130687 | 12/2006 |
| WO | WO 2006/130688 | 12/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015824 | 2/2007 |
| WO | WO 2007/015855 | 2/2007 |
| WO | WO 2007/016441 | 2/2007 |
| WO | WO 2007/016476 | 2/2007 |
| WO | WO 2007/017144 | 2/2007 |
| WO | WO 2007/025307 | 3/2007 |
| WO | WO 2007/044893 | 4/2007 |
| WO | WO 2007/044933 | 4/2007 |
| WO | WO 2007/056120 | 5/2007 |
| WO | WO 2007/082131 | 7/2007 |
| WO | WO 2007/106317 | 9/2007 |
| WO | WO 2007/131966 | 11/2007 |
| WO | WO 2007/143694 | 12/2007 |
| WO | WO 2007/148135 | 12/2007 |
| WO | WO 2008/002924 | 1/2008 |
| WO | WO 2008/005511 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |

OTHER PUBLICATIONS

U.S. Appl. No. 11/923,948, filed Oct. 25, 2007, D'Andrea et al.
U.S. Appl. No. 11/923,977, filed Oct. 25, 2007, D'Andrea et al.
U.S. Appl. No. 11/939,753, filed Nov. 14, 2007, Wang et al.
U.S. Appl. No. 11/939,768, filed Nov. 14, 2007, Wang et al.
U.S. Appl. No. 11/937,780, filed Nov. 14, 2007, Wang et al.
Lauer G. M. et al., "Hepatitis C Virus Infection," New England Journal of Medicine, vol. 345 No. 1, pp. 41-52, (2001).
Poupart, M.-A. et al., "Solid-Phase Synthesis of Peptidomimetic Inhibitors for the Hepatitis C Virus NS3 Protease," The Journal of Organic Chemistry, vol. 66 No. 14, pp. 4743-4751, (2001).
Llinas-Brunet et al. (2004) Journal of Medicinal Chemistry, vol. 47 pp. 6584-6594.

HEPATITIS C VIRUS INHIBITORS

CROSS-REFERENCE TO RELATED APPLICATIONS

This application claims the benefit of U.S. Provisional Application Ser. No. 60/865,034 filed Nov. 9, 2006.

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with one or two additional compounds having anti-HCV activity.

In a first aspect the present disclosure provides a compound of formula (I)

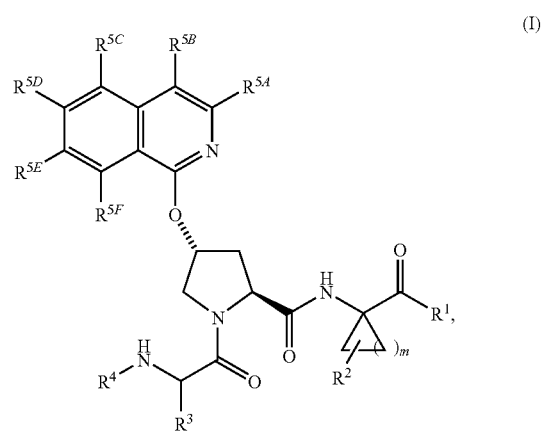

or a pharmaceutically acceptable salt thereof, wherein m is 1, 2, or 3;

$R^1$ is selected from hydroxy and —$NHSO_2R^6$; wherein $R^6$ is selected from alkyl, aryl, cycloalkyl, (cycloalkyl)alkyl, heterocyclyl, and —$NR^aR^b$, wherein the alkyl, the cycloalkyl and the cycloalkyl part of the (cycloalkyl)alkyl are optionally substituted with one, two, or three substituents selected from alkenyl, alkoxy, alkoxyalkyl, alkyl, arylalkyl, arylcarbonyl, cyano, cycloalkenyl, (cycloalkyl)alkyl, halo, haloalkoxy, haloalkyl, and ($NR^eR^f$)carbonyl;

$R^2$ is selected from hydrogen, alkenyl, alkyl, and cycloalkyl, wherein the alkenyl, alkyl, and cycloalkyl are optionally substituted with halo;

$R^3$ is selected from alkenyl, alkoxyalkyl, alkoxycarbonylalkyl, alkyl, arylalkyl, carboxyalkyl, cyanoalkyl, cycloalkyl, (cycloalkyl)alkyl, haloalkoxy, haloalkyl, (heterocyclyl)alkyl, hydroxyalkyl, ($NR^cR^d$)alkyl, and ($NR^eR^f$)carbonylalkyl;

$R^4$ is selected from phenyl and a five- or six-membered partially or fully unsaturated ring optionally containing one, two, three, or four heteroatoms selected from nitrogen, oxygen, and sulfur; wherein each of the rings is optionally substituted with one, two, three, or four substitutents independently selected from alkoxy, alkoxycarbonyl, alkyl, alkylcarbonyl, alkylsulfanyl, carboxy, cyano, cycloalkyl, cycloalkyloxy, halo, haloalkyl, haloalkoxy, —$NR^cR^d$, ($NR^eR^f$)carbonyl, ($NR^eR^f$)sulfonyl, and oxo; provided that when $R^4$ is a six-membered substituted ring all substituents on the ring other than fluoro must be in the meta and/or para positions relative to the ring's point of attachment to the parent molecular moiety;

$R^{5A}$, $R^{5B}$, $R^{5C}$, $R^{5D}$, $R^{5E}$ and $R^{5F}$ are each independently selected from hydrogen, alkoxy, alkoxycarbonyl, alkyl, alkylcarbonyl, aryl, carboxy, cyano, cyanoalkyl, cycloalkyl, halo, haloalkyl, haloalkoxy, heterocyclyl, hydroxy, hydroxyalkyl, nitro, —NR$^c$R$^d$, R$^c$R$^d$)alkyl, (NR$^c$R$^d$)alkoxy, (NR$^e$R$^f$)carbonyl, and (NR$^e$R$^f$)sulfonyl; or two adjacent R$^5$ groups, together with the carbon atoms to which they are attached, form a four- to seven-membered partially—or fully-unsaturated ring optionally containing one or two heteroatoms independently selected from nitrogen, oxygen, and sulfur, wherein the ring is optionally substituted with one, two, or three groups independently selected from alkoxy, alkyl, cyano, halo, haloalkoxy, and haloalkyl;

R$^a$ and R$^b$ are independently selected from hydrogen, alkoxy, alkyl, aryl, arylalkyl, cycloalkyl, (cycloalkyl)alkyl, heterocyclyl, and heterocyclylalkyl; or R$^a$ and R$^b$ together with the nitrogen atom to which they are attached form a four to seven-membered monocyclic heterocyclic ring;

R$^c$ and R$^d$ are independently selected from hydrogen, alkoxyalkyl, alkoxycarbonyl, alkyl, alkylcarbonyl, arylalkyl, and haloalkyl; and R$^e$ and R$^f$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

In a first embodiment of the first aspect the present disclosure provides a compound of formula (I), or a pharmaceutically acceptable salt thereof, wherein R$^1$ is —NHSO$_2$R$^6$.

In a second embodiment of the first aspect the present disclosure provides a compound of formula (I), or a pharmaceutically acceptable salt thereof, wherein m is 1 or 2;

R$^1$ is —NHSO$_2$R$^6$; wherein R$^6$ is selected from alkyl, aryl, cycloalkyl, (cycloalkyl)alkyl, heterocyclyl, and —NR$^a$R$^b$, wherein the alkyl, the cycloalkyl and the cycloalkyl part of the (cycloalkyl)alkyl are optionally substituted with one, two, or three substituents selected from alkenyl, alkoxy, alkoxyalkyl, alkyl, arylalkyl, arylcarbonyl, cyano, cycloalkenyl, (cycloalkyl)alkyl, halo, haloalkoxy, haloalkyl, and (NR$^e$R$^f$)carbonyl;

R$^2$ is selected from alkenyl, alkyl, and cycloalkyl, wherein the alkenyl, alkyl, and cycloalkyl are optionally substituted with halo;

R$^3$ is selected from alkenyl and alkyl;

R$^4$ is selected from phenyl and a five- or six-membered partially or fully unsaturated ring optionally containing one, two, three, or four heteroatoms selected from nitrogen, oxygen, and sulfur; wherein each of the rings is optionally substituted with one, two, three, or four substitutents independently selected from alkoxy, alkoxycarbonyl, alkyl, alkylcarbonyl, alkylsulfanyl, carboxy, cyano, cycloalkyl, cycloalkyloxy, halo, haloalkyl, haloalkoxy, —NR$^c$R$^d$, (NR$^e$R$^f$)carbonyl, (NR$^e$R$^f$)sulfonyl, and oxo; provided that when R$^4$ is a six-membered substituted ring all substituents on the ring other than fluoro must be in the meta and/or para positions relative to the ring's point of attachment to the parent molecular moiety;

R$^{5A}$, R$^{5B}$, R$^{5C}$, R$^{5D}$, R$^{5E}$ and R$^{5F}$ are each independently selected from hydrogen, alkoxy, alkoxycarbonyl, alkyl, alkylcarbonyl, aryl, carboxy, cyano, cyanoalkyl, cycloalkyl, halo, haloalkyl, haloalkoxy, heterocyclyl, hydroxy, hydroxyalkyl, nitro, —NR$^c$R$^d$, R$^c$R$^d$)alkyl, (NR$^c$R$^d$)alkoxy, (NR$^e$R$^f$)carbonyl, and (NR$^e$R$^f$)sulfonyl; or two adjacent R$^5$ groups, together with the carbon atoms to which they are attached, form a four- to seven-membered partially—or fully-unsaturated ring optionally containing one or two heteroatoms independently selected from nitrogen, oxygen, and sulfur, wherein the ring is optionally substituted with one, two, or three groups independently selected from alkoxy, alkyl, cyano, halo, haloalkoxy, and haloalkyl;

R$^a$ and R$^b$ are independently selected from hydrogen, alkoxy, alkyl, aryl, arylalkyl, cycloalkyl, (cycloalkyl)alkyl, heterocyclyl, and heterocyclylalkyl; or R$^a$ and R$^b$ together with the nitrogen atom to which they are attached form a four- to seven-membered monocyclic heterocyclic ring;

R$^c$ and R$^d$ are independently selected from hydrogen, alkoxyalkyl, alkoxycarbonyl, alkyl, alkylcarbonyl, arylalkyl, and haloalkyl; and R$^e$ and R$^f$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

In a third embodiment of the first aspect the present disclosure provides a compound of formula (I), or a pharmaceutically acceptable salt thereof, wherein R$^6$ is selected from unsubstituted cycloalkyl and —NR$^a$R$^b$.

In a fourth embodiment of the first aspect the present disclosure provides a compound formula (I), or a pharmaceutically acceptable salt thereof, wherein m is 1;

R$^1$ is —NHSO$_2$R$^6$; wherein R$^6$ is unsubstituted cycloalkyl;

R$^2$ is alkenyl;

R$^3$ is selected from alkenyl and alkyl;

R$^4$ is selected from phenyl and a five- or six-membered partially or fully unsaturated ring optionally containing one, two, three, or four heteroatoms selected from nitrogen, oxygen, and sulfur; wherein each of the rings is optionally substituted with one, two, or three substitutents independently selected from alkoxy, alkoxycarbonyl, alkyl, alkylcarbonyl, carboxy, cyano, cycloalkyl, cycloalkyloxy, halo, haloalkyl, haloalkoxy, —NR$^c$R$^d$, (NR$^e$R$^f$)carbonyl, (NR$^e$R$^f$)sulfonyl, and oxo; provided that when R$^4$ is a six-membered substituted ring all substituents on the ring other than fluoro must be in the meta and/or para positions relative to the ring's point of attachment to the parent molecular moiety;

R$^{5A}$, R$^{5B}$, R$^{5C}$, R$^{5D}$, R$^{5E}$ and R$^{5F}$ are each independently selected from hydrogen, alkoxy, aryl, and —NR$^c$R$^d$; or two adjacent R$^5$ groups, together with the carbon atoms to which they are attached, form a six-membered partially- or fully-unsaturated ring optionally containing one or two heteroatoms independently selected from nitrogen, oxygen, and sulfur, wherein the ring is optionally substituted with one, two, or three groups independently selected from alkoxy, alkyl, cyano, halo, haloalkoxy, and haloalkyl;

R$^c$ and R$^d$ are independently selected from hydrogen, alkoxycarbonyl, alkyl, alkylcarbonyl, and arylalkyl; and R$^e$ and R$^f$ are independently selected from hydrogen, alkyl, aryl, and arylalkyl.

In a fifth embodiment of the first aspect the present disclosure provides a compound formula (I), or a pharmaceutically acceptable salt thereof, wherein m is 1;

R$^1$ is —NHSO$_2$R$^6$; wherein R$^6$ is unsubstituted cycloalkyl;

R$^2$ is alkenyl;

R$^3$ is selected from alkenyl and alkyl;

R$^4$ is phenyl optionally substituted with one, two, or three substitutents independently selected from alkoxy, alkoxycarbonyl, alkyl, alkylcarbonyl, carboxy, cyano, cycloalkyl, cycloalkyloxy, halo, haloalkyl, haloalkoxy, —NR$^c$R$^d$, (NR$^e$R$^f$)carbonyl, (NR$^e$R$^f$)sulfonyl, and oxo; provided that all substituents on the ring other than fluoro must be in the meta and/or para positions relative to the ring's point of attachment to the parent molecular moiety;

$R^{5A}$, $R^{5B}$, $R^{5C}$, $R^{5D}$, $R^{5E}$ and $R^{5F}$ are each independently selected from hydrogen, alkoxy, aryl, and —$NR^cR^d$; or two adjacent $R^5$ groups, together with the carbon atoms to which they are attached, form a six-membered partially- or fully-unsaturated ring optionally containing one or two heteroatoms independently selected from nitrogen, oxygen, and sulfur, wherein the ring is optionally substituted with one, two, or three groups independently selected from alkoxy, alkyl, cyano, halo, haloalkoxy, and haloalkyl;

$R^c$ and $R^d$ are independently selected from hydrogen, alkoxycarbonyl, alkyl, alkylcarbonyl, and arylalkyl; and $R^e$ and $R^f$ are independently selected from hydrogen, alkyl, aryl, and arylalkyl.

In a sixth embodiment of the first aspect the present disclosure provides a compound formula (I), or a pharmaceutically acceptable salt thereof, wherein
m is 1;
$R^1$ is —$NHSO_2R^6$; wherein $R^6$ is unsubstituted cycloalkyl;
$R^2$ is alkenyl;
$R^3$ is selected from alkenyl and alkyl;
$R^4$ is a six-membered fully unsaturated ring containing one nitrogen atom; wherein the ring is optionally substituted with one, two, or three substituents independently selected from alkoxy, alkoxycarbonyl, alkyl, alkylcarbonyl, carboxy, cyano, cycloalkyl, cycloalkyloxy, halo, haloalkyl, haloalkoxy, —$NR^cR^d$, ($NR^eR^f$)carbonyl, ($NR^eR^f$)sulfonyl, and oxo; provided that all substituents on the ring other than fluoro must be in the meta and/or para positions relative to the ring's point of attachment to the parent molecular moiety;

$R^{5A}$, $R^{5B}$, $R^{5C}$, $R^{5D}$, $R^{5E}$ and $R^{5F}$ are each independently selected from hydrogen, alkoxy, aryl, and —$NR^cR^d$; or two adjacent $R^5$ groups, together with the carbon atoms to which they are attached, form a six-membered partially- or fully-unsaturated ring optionally containing one or two heteroatoms independently selected from nitrogen, oxygen, and sulfur, wherein the ring is optionally substituted with one, two, or three groups independently selected from alkoxy, alkyl, cyano, halo, haloalkoxy, and haloalkyl;

$R^c$ and $R^d$ are independently selected from hydrogen, alkoxycarbonyl, alkyl, alkylcarbonyl, and arylalkyl; and $R^e$ and $R^f$ are independently selected from hydrogen, alkyl, aryl, and arylalkyl.

In a second aspect the present disclosure provides a composition comprising a compound of formula (I), or a pharmaceutically acceptable salt thereof, and a pharmaceutically acceptable carrier. In a first embodiment of the second aspect the composition further comprises at least one additional compound having anti-HCV activity. In a second embodiment of the second aspect at least one of the additional compounds is an interferon or a ribavirin. In a third embodiment of the second aspect the interferon is selected from interferon alpha 2B, pegylated interferon alpha, consensus interferon, interferon alpha 2A, and lymphoblastiod interferon tau.

In a fourth embodiment of the second aspect the present disclosure provides a composition comprising a compound of formula (I), or a pharmaceutically acceptable salt thereof, a pharmaceutically acceptable carrier, and at least one additional compound having anti-HCV activity; wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the second aspect the present disclosure provides a composition comprising a compound of formula (I), or a pharmaceutically acceptable salt thereof, a pharmaceutically acceptable carrier, and at least one additional compound having anti-HCV activity; wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a third aspect the present disclosure provides a method of treating an HCV infection in a patient, comprising administering to the patient a therapeutically effective amount of a compound of formula (I), or a pharmaceutically acceptable salt thereof. In a first embodiment of the third aspect the method further comprises administering at least one additional compound having anti-HCV activity prior to, after, or simultaneously with the compound of formula (I), or a pharmaceutically acceptable salt thereof. In a second embodiment of the third aspect at least one of the additional compounds is an interferon or a ribavirin. In a fourth embodiment of the third aspect the interferon is selected from interferon alpha 2B, pegylated interferon alpha, consensus interferon, interferon alpha 2A, and lymphoblastiod interferon tau.

In a fifth embodiment of the third aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a sixth embodiment of the third aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fourth aspect the present disclosure provides a composition comprising a compound of formula (I), or a pharmaceutically acceptable salt thereof, one, two, three, four, or five additional compounds having anti-HCV activity, and a pharmaceutically acceptable carrier. In a first embodiment of the fourth aspect the composition comprises three or four additional compounds having anti-HCV activity. In a second embodiment of the fourth aspect the composition comprises one or two additional compounds having anti-HCV activity.

In a fifth aspect the present disclosure provides a method of treating an HCV infection in a patient, comprising administering to the patient a therapeutically effective amount of a compound of formula (I), or a pharmaceutically acceptable salt thereof and one, two, three, four, or five additional compounds having anti-HCV activity prior to, after, or simultaneously with the compound of formula (I), or a pharmaceutically acceptable salt thereof. In a first embodiment of the first aspect the method comprises administering three or four additional compounds having anti-HCV activity. In a second embodiment of the first aspect the method comprises administering one or two additional compounds having anti-HCV activity.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^5$ groups may be the same or different.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term 'aryl'.

In some instances, the number of carbon atoms in any particular group is denoted before the recitation of the group. For example, the term "$C_{1-2}$ alkyl" denotes an alkyl group containing one or two carbon atoms. Where these designations exist they supercede all other definitions contained herein.

As used herein, the singular forms "a", "an", and "the" include plural reference unless the context clearly dictates otherwise.

The term "alkenyl," as used herein, refers to a straight or branched chain group of two to six carbon atoms containing at least one carbon-carbon double bond.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkyl," as used herein, refers to a group derived from a straight or branched chain saturated hydrocarbon containing from one to ten carbon atoms.

The term "alkylcarbonyl," as used herein, refers to an alkyl group attached to the parent molecular moiety through a carbonyl group.

The term "alkylsulfanyl," as used herein, refers to an alkyl group attached to the parent molecular moiety through a sulfur atom.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure can be optionally substituted with one, two, three, four, or five substituents independently selected from alkoxy, alkoxycarbonyl, alkyl, alkylcarbonyl, carboxy, cycloalkyl, cycloalkyloxy, cyano, halo, haloalkoxy, haloalkyl, nitro, —$NR^cR^d$, ($R^cR^d$)carbonyl, and oxo.

The term "arylalkyl," as used herein, refers to an alkyl group substituted with one, two, or three aryl groups.

The term "arylcarbonyl," as used herein, refers to an aryl group attached to the parent molecular moiety through a carbonyl group.

The term "carbonyl," as used herein, refers to —C(O)—.

The term "carboxy," as used herein, refers to —$CO_2H$.

The term "carboxyalkyl," as used herein, refers to an alkyl group substituted with one, two, or three carboxy groups.

The term "cyano," as used herein, refers to —CN.

The term "cyanoalkyl," as used herein, refers to an alkyl group substituted with one, two, or three cyano groups.

The term "cycloalkenyl," as used herein, refers to a non-aromatic, partially unsaturated monocyclic, bicyclic, or tricyclic ring system having three to fourteen carbon atoms and zero heteroatoms. Representative examples of cycloalkenyl groups include, but are not limited to, cyclohexenyl, octahydronaphthalenyl, and norbornylenyl.

The term "cycloalkyl," as used herein, refers to a saturated monocyclic or bicyclic hydrocarbon ring system having three to ten carbon atoms and zero heteroatoms. Representative examples of cycloalkyl groups include, but are not limited to, cyclopropyl, cyclobutyl, and cyclopentyl.

The term "(cycloalkyl)alkyl," as used herein, refers to an alkyl group substituted with one, two, or three cycloalkyl groups.

The term "cycloalkyloxy," as used herein, refers to a cycloalkyl group attached to the parent molecular moiety through an oxygen atom.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkyl," as used herein, refers to an alkyl group substituted with one, two, three, or four halogen atoms.

The term "heterocyclyl," as used herein, refers to a five-, six-, or seven-membered ring containing one, two, or three heteroatoms independently selected from nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a four- to six-membered aromatic or non-aromatic carbocyclic ring or another monocyclic heterocyclyl group. The heterocyclyl groups of the present disclosure can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl. The heterocyclyl groups of the present disclosure can be optionally substituted with one, two, three, four, or five substituents independently selected from alkoxy, alkoxycarbonyl, alkyl, alkylcarbonyl, carboxy, cycloalkyl, cycloalkyloxy, cyano, halo, haloalkoxy, haloalkyl, nitro, —$NR^cR^d$, ($NR^cR^d$)carbonyl, and oxo.

The term "heterocyclylalkyl," as used herein, refers to an alkyl group substituted with one, two, or three heterocyclyl groups.

The term "hydroxy," as used herein, refers to —OH.

The term "hydroxyalkyl," as used herein, refers to an alkyl group substituted with one, two, or three hydroxy groups.

The term "nitro," as used herein, refers to —$NO_2$.

The term "—$NR^aR^b$," as used herein, refers to two groups, $R^a$ and $R^b$, which are attached to the parent molecular moiety through a nitrogen atom. $R^a$ and $R^b$ are independently selected from hydrogen, alkoxy, alkyl, aryl, arylalkyl, cycloalkyl, (cycloalkyl)alkyl, heterocyclyl, and heterocyclylalkyl; or $R^a$ and $R^b$ together with the nitrogen atom to which they are attached form a five or six-membered monocyclic heterocyclic ring.

The term "—$NR^cR^d$," as used herein, refers to two groups, $R^c$ and $R^d$ which are attached to the parent molecular moiety through a nitrogen atom. $R^c$ and $R^d$ are independently selected from hydrogen, alkoxycarbonyl, alkyl, and alkylcarbonyl.

The term "($NR^cR^d$)alkoxy," as used herein, refers to an ($NR^cR^d$)alkyl group attached to the parent molecular moiety through an oxygen atom.

The term "($NR^cR^d$)alkyl," as used herein, refers to an alkyl group substituted with one, two, or three —$NR^cR^d$ groups.

The term "($NR^cR^d$)carbonyl," as used herein, refers to an —$NR^cR^d$ group attached to the parent molecular moiety through a carbonyl group.

The term "—$NR^eR^f$," as used herein, refers to two groups, $R^e$ and $R^f$ which are attached to the parent molecular moiety through a nitrogen atom. $R^e$ and $R^f$ are independently selected from hydrogen, alkyl, aryl, and arylalkyl.

The term "($NR^eR^f$)carbonyl," as used herein, refers to an —$NR^eR^f$ group attached to the parent molecular moiety through a carbonyl group.

The term "($NR^eR^f$)carbonylalkyl," as used herein, refers to an ($NR^eR^f$)carbonyl group attached to the parent molecular moiety through an alkyl group.

The term "($NR^eR^f$)sulfonyl," as used herein, refers to an —$NR^eR^f$ group attached to the parent molecular moiety through a sulfonyl group.

The term "oxo," as used herein, refers to =O.

The term "sulfonyl," as used herein, refers to —$SO_2$—.

The term "prodrug," as used herein, represents compounds which are rapidly transformed in vivo to the parent compounds by hydrolysis in blood. Prodrugs of the present disclosure include esters of hydroxy groups on the parent molecule, esters of carboxy groups on the parent molecule, and amides of the amines on the parent molecule.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to treat the HCV virus.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

The following figure shows the designations for the compounds of the present disclosure.

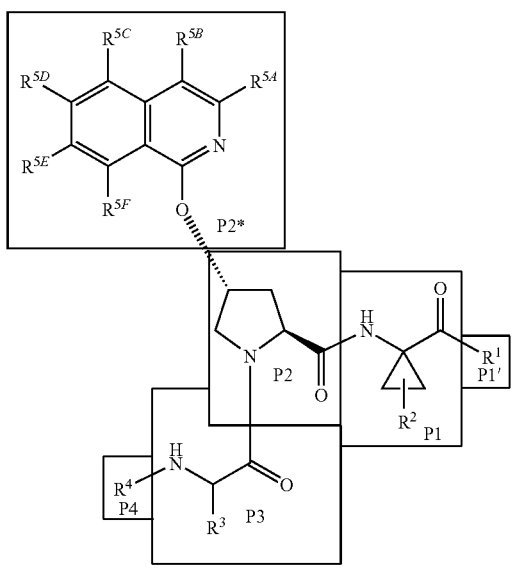

Asymmetric centers exist in the compounds of the present disclosure. For example, the compounds may include P1 cyclopropyl element of formula

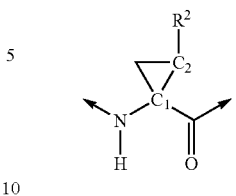

wherein $C_1$ and $C_2$ each represent an asymmetric carbon atom at positions 1 and 2 of the cyclopropyl ring.

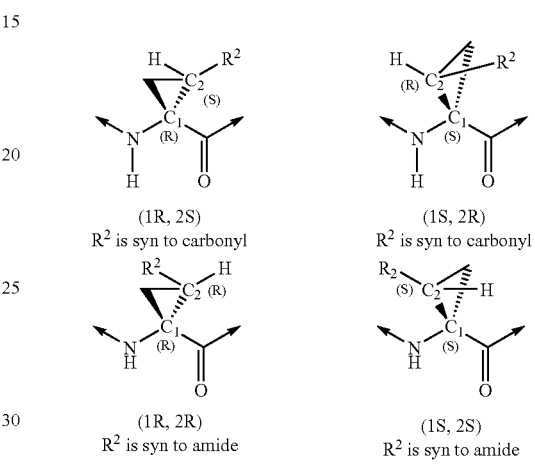

It should be understood that the disclosure encompasses all stereochemical forms, or mixtures thereof, which possess the ability to inhibit HCV protease.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts | Antiviral | HCV Inhibitors | Arrow Therapeutics |

TABLE 1-continued

| Brand Name | Physiological Class | Type of Inhibitor or Target | Source Company |
|---|---|---|---|
| From WO-2005047288 26 May 2005 | | | Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |

TABLE 1-continued

| Brand Name | Physiological Class | Type of Inhibitor or Target | Source Company |
|---|---|---|---|
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharmiceuticals Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |

TABLE 1-continued

| Brand Name | Physiological Class | Type of Inhibitor or Target | Source Company |
|---|---|---|---|
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| TMC-465350 | Antiviral | serine protease inhibitor | Medivir/Tibotec |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: 4-DMAP or DMAP for 4-N,N-dimethylaminopyridine; Boc or BOC for tert-butoxycarbonyl; Fmoc for 9-fluorenylmethyloxycarbonyl; CDI for 1,1'-carbonyldiimidazole; EDAC or EDC for 1-(3-dimethylaminopropyl)-3-ethylcarbodiimide hydrochloride; THF for tetrahydrofuran; DBU for 1,8-diazabicyclo[5.4.0]undec-7-ene; TFA for trifluoroacetic acid; HATU for O-(7-azabenzotriazol-1-yl)-N,N,N',N'-tetramethyluronium phosphate; PyBOP for benzotriazol-1-yl-oxy-tris-pyrrolidino-phosphoniumhexafluorophosphate; Me for methyl; MeI for methyl iodide; MOtBu for potassium, sodium, or lithium tert-butoxide; TBME or MTBE for tert-butyl methyl ether; DMF for N,N-dimethylformamide; DMSO for dimethylsulfoxide; Ph for phenyl; DEAD for diethylazodicarboxylate; POPd for [(t-Bu)$_2$POH]$_2$PdCl$_2$; NaOBu for sodium tert-butoxide; OAc for acetate; TBMDSCl for tert-butyldimethylsilyl chloride; 1,2-DME for 1,2-dimethoxyethane; DMA for N,N-dimethylacetamide; n-BuLi for n-butyllithium; t-BuLi or tBuLi for tert-butyllithium; DPPA for diphenylphosphoryl azide; TBAF for tetrabutylammonium fluoride; LiOt-Bu for lithium tert-butoxide; MeOH for methanol; DCM for dichloromethane; t-BuOK for potassium tert-butoxide; DIEA or DIPEA for diisopropylethylamine; MeCN for acetonitrile; NMM for N-methylmorpholine; DCE for 1,2-dichloroethane; LDA for lithium diisopropylamide; DMPU for 1,3-dimethyl-3,4,5,6-tetrahydro-2(1H)-pyrimidinone; EtOAc for ethyl acetate; and TEA for triethylamine.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

Scheme I shows the general process wherein compounds of Formula (I) are constructed by the coupling of tripeptide carboxylic acid intermediate (1) with a P1' sulfonamide. Said coupling reaction requires treatment of carboxylic acid (1) with a coupling reagent such as carbonyl diimidazole in a solvent such as THF, which can be heated to reflux, followed by the addition of the formed derivative of (1), to the P1' sulfonamide, in a solvent such as THF or methylene chloride in the presence of a base such as DBU.

Scheme I

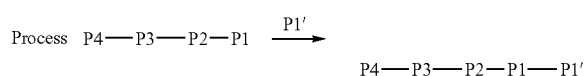

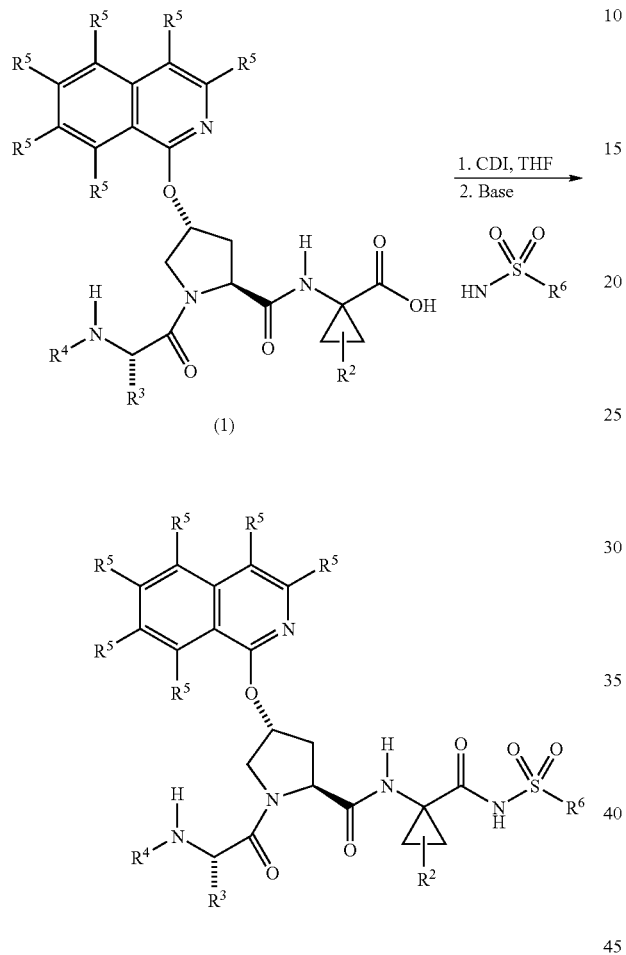

An alternative process for the construction of compounds of Formula (I) is shown in Scheme II. Therein the P1' sulfonamide element is coupled to the P1 element using the process employed in Scheme 1. The resulting P1-P1' moiety can then be deprotected at its amino terminus. In this general example a Boc protecting group is employed but one skilled in the art would recognize that a number of suitable amino protecting groups could be employed in this process. The Boc protecting group can be removed using acid such as trifluoroacetic acid in a solvent such as dichloroethane to provide the deprotected amine as the TFA salt. Said TFA amine salt can be directly employed in the subsequent coupling reaction or as an alternative the TFA amine salt can be first converted to the HCl amine salt, and this HCl amine salt is used in said coupling reaction as shown in Scheme II. The coupling of said HCl amine salt (3) with the carboxyl terminus of a P4-P3-P2 intermediate can be achieved using coupling reagents, such as HATU, in solvents such as dichloromethane to provide compounds of Formula (I) (4).

Scheme II

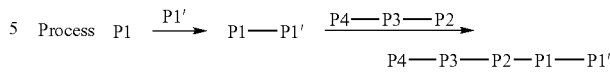

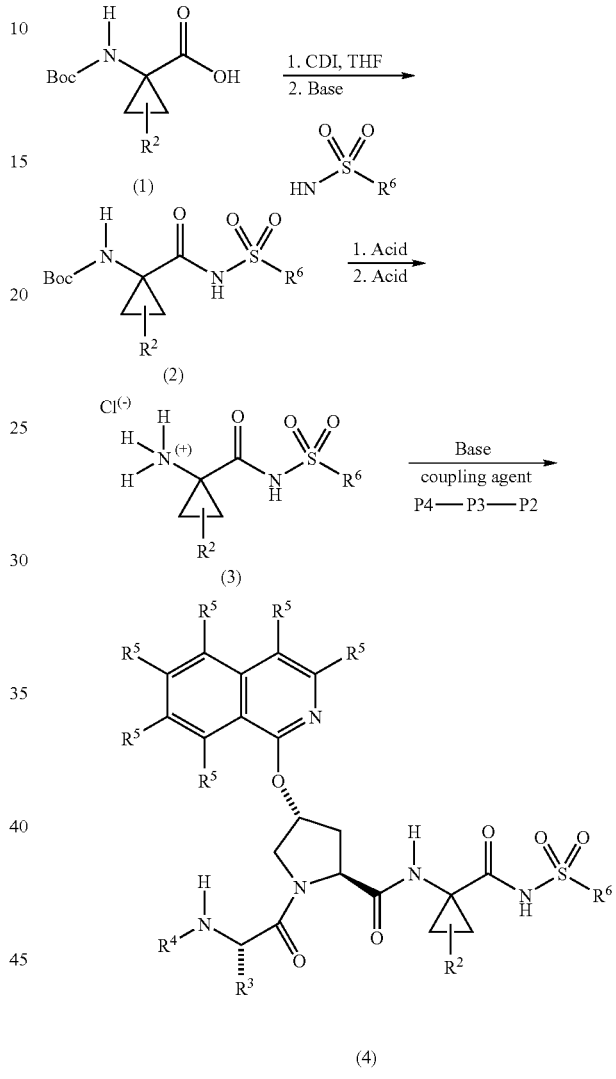

An alternative process for the construction of compounds of Formula (I) is shown in Scheme III. Here the hydrochloride salt of the P1-P1' terminal amine (1) is coupled to the free carboxyl group of the P2 element using coupling agents such as PyBOP, in the presence of a base such as diisopropylamine, and in a solvent such as methylene chloride. The resulting P2-P1-P1' intermediate can be converted to compounds of Formula (I) in a two step process wherein the first step is deprotection of the P2 amine terminus using an acid such as TFA in a solvent such as methylene chloride. The resulting trifluoroacetic acid salt can be coupled with the carboxyl terminus of the P4-P3 element using standard coupling agents such as PyBop in the presence of base such as diisopropyl amine, and using solvents such methylene chloride to provide compounds of Formula (I) (4).

Scheme III

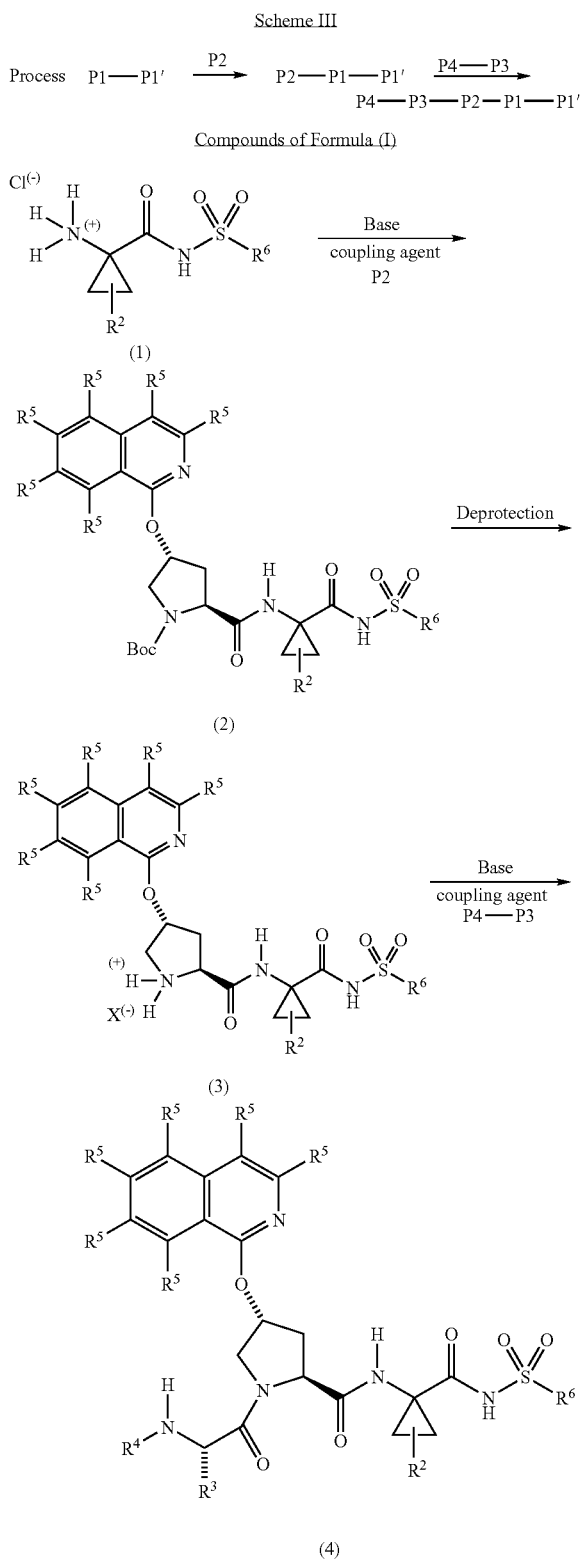

Scheme IV

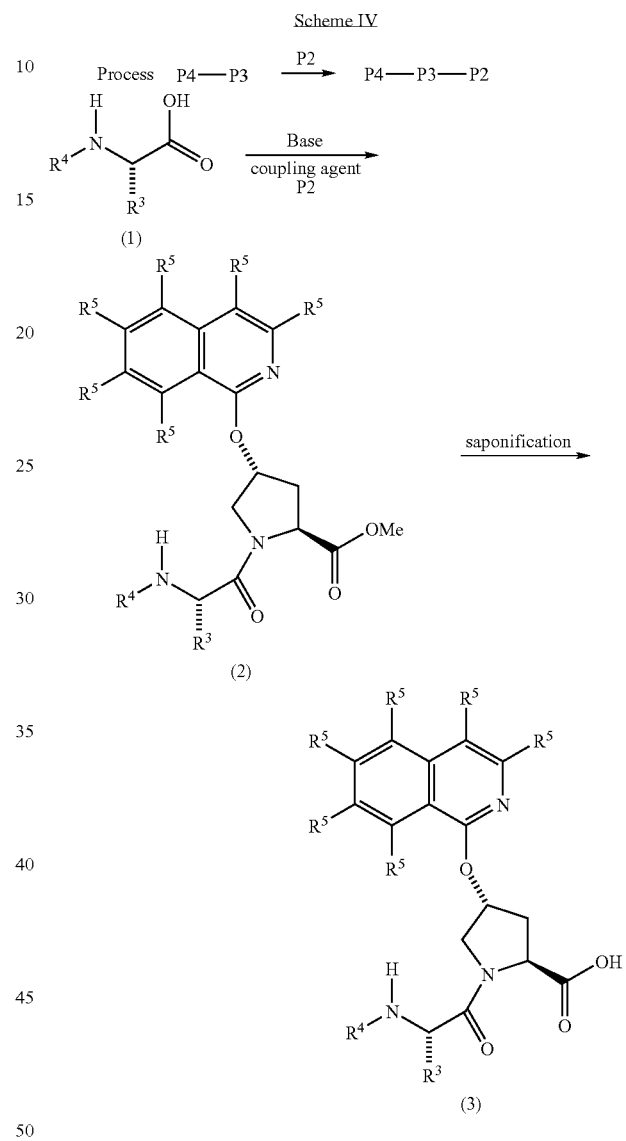

the P4-P3-P2 dipeptide (2). The carboxyl terminus of the P4-P3-P2 intermediate can be deprotected by saponification of the ester group to provide P4-P3-P2 as the free carboxylic acid (3). Intermediates like (3) can be converted to compounds of Formula (I) using the methods described herein.

The P4-P3-P2 intermediate utilized in the above schemes can be constructed as previously described with a further description of this process shown in general Scheme IV. The free carboxyl terminus of the P4-P3 intermediate (1), can be coupled to the amino terminus of the P2 element to provide In the construction of compounds of Formula (I), the P1' terminus is incorporated into the molecules using one of the general processes outlined above and described in more detail below. In some examples the P1' elements, that is the cycloalkyl or alkyl sulfonamides, are commercially available or can be prepared from the corresponding alkyl- or cycloalkylsulfonyl chloride by treating the sulfonyl chloride with ammonia. Alternatively, these sulfonamides can be synthesized using the general process outline in Scheme V. Commercially available 3-chloropropylsulfonyl chloride (1) is converted to a suitably protected sulfonamide, for example, by treatment with tert-butyl amine. The sulfonamide obtained (2) is then converted to the corresponding cycloalkylsulfonamide by treatment with two equivalents of a base such as butyllithium in a solvent such as THF at low temperature. The resulting cycloalkylsulfonamide can be deprotected by treatment with an acid to provide the desired unprotected cycloalkylsulfoamide.

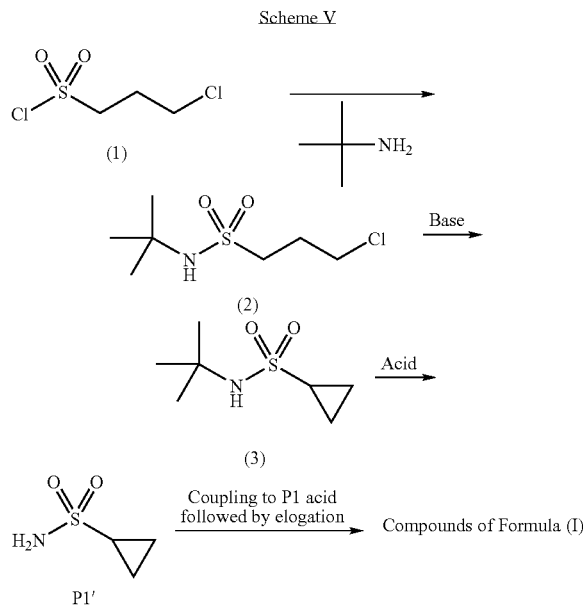

Scheme V

Substituted cycloalkylsulfonamides can also be incorporated into compounds of Formula (I) using a modification of the above said procedure. For example, intermediate 2 of Scheme VI can be treated with two equivalents of base such as butyllithium and the resulting reaction mixture can be treated with an electrophile such as methyl iodide to provide a substituted cycloalkylsulfonamide (3). This intermediate (3) can be deprotected at the N-terminus and the resulting compound (4) utilized as an intermediate in the preparation of compounds of Formula (I).

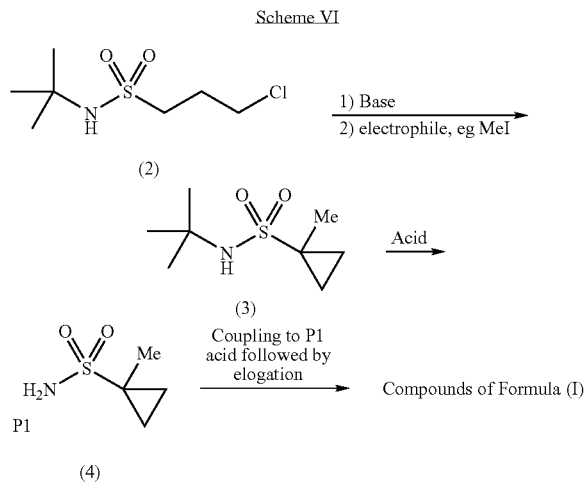

Scheme VI

The P1' intermediates employed in generating compounds of Formula (I) are in some cases derived from sulfamide derivatives. In such cases the sulfamide intermediates are available by several synthetic routes as, for example, by the pathway outlined in Scheme VII.

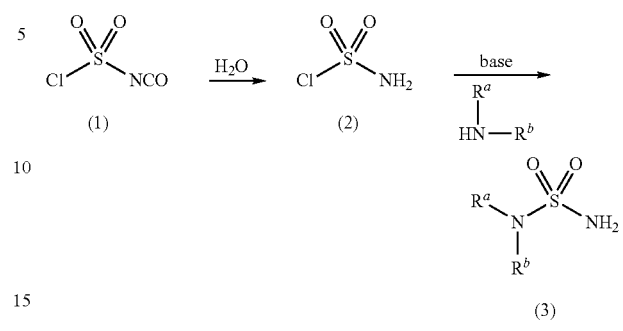

Scheme VII

Sulfamoyl chloride (2) can be prepared in situ by the addition of water (e.g., 1 equivalent) to chlorosulfonyl isocyanate 1 (e.g., 1 equivalent) in a solvent such as THF while maintained at a low temperature such as −20° C. The resulting solution is then allowed to warm to 0° C. To this solution a base, such as anhydrous triethylamine (e.g., 1 equivalent), is added followed by an amine (e.g., 1 equivalent). The reaction mixture is then warmed to room temperature, filtered, and the filtrate concentrated to provide the desired sulfamides (3).

The sulfamides can be incorporated into compounds of Formula (I) by several processes as, for example, by following the synthetic pathway defined in Scheme VIII. A carboxylic acid P1 element (1) is treated with an activating agent such as CDI. In a separate flask, a strong base is added to a solution of the above described sulfamide and the resulting reaction mixture is stirred for several hours after which this reaction mixture is added to the flask containing the activated carboxylic acid, to provide acylsulfamide derivatives (2). Intermediates like 2 can be converted to compounds of Formula (I) as described herein.

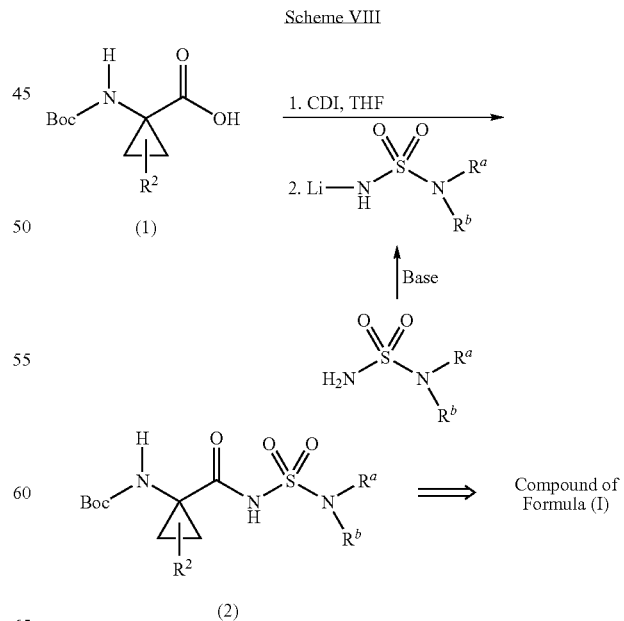

Scheme VIII

The P1 elements utilized in generating compounds of Formula (I) are in some cases commercially available, but are otherwise synthesized using the methods described herein and are subsequently incorporated into compounds of Formula (I) using the methods described herein. The substituted P1 cyclopropylamino acids can be synthesized following the general process outline in Scheme IX.

Treatment of commercially available or easily synthesized imine (1) with 1,4-dihalobutene (2) in presence of a base provides the resulting imine (3). Acid hydrolysis of 3 then provides 4, which has an allyl substituent syn to the carboxyl group, as a major product. The amine moiety of 4 can protected using a Boc group to provide the fully protected amino acid 5. This intermediate is a racemate which can be resolved by an enzymatic process wherein the ester moiety of 5 is cleaved by a protease to provide the corresponding carboxylic acid. Without being bound to any particular theory, it is believed that this reaction is selective in that one of the enantiomers undergoes the reaction at a much greater rate than its mirror image providing for a kinetic resolution of the intermediate racemate. In the examples cited herein, the more preferred stereoisomer for integration into compounds of Formula (I) is 5a which houses the (1R,2S) stereochemistry. In the presence of the enzyme, this enantiomer does not undergo ester cleavage and thereby this enantiomer, 5a, is recovered from the reaction mixture. However, the less preferred enantiomer, 5b, which houses the (1S,2R) stereochemistry, undergoes ester cleavage, i.e., hydrolysis, to provide the free acid 6. Upon completion of this reaction, the ester 5a can be separated from the acid product 6 by routine methods such as, for example, aqueous extraction methods or chromatography.

Procedures for making P2 intermediates and compounds of Formula (I) are shown in the schemes below. It should be noted that in many cases reactions are depicted for only one position of an intermediate. However, it is to be understood that such reactions could be used to impart modifications to other positions within this intermediate. Moreover, said intermediates, reaction conditions, and methods given in the specific examples are broadly applicable to compounds with other substitution patterns. Both general and specific examples are non-limiting.

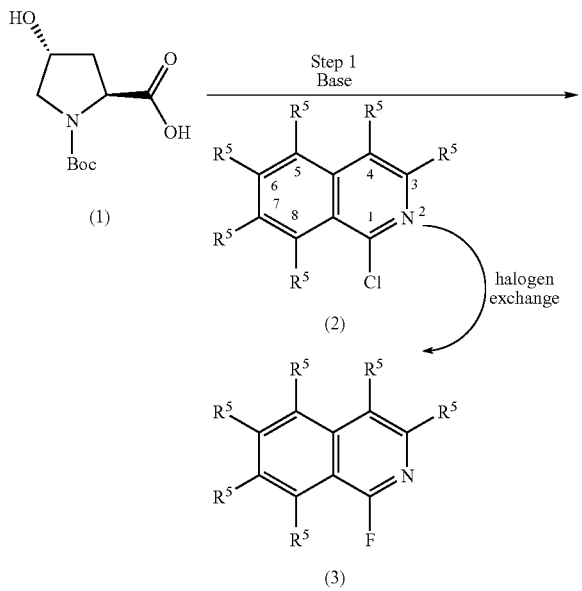

Scheme X

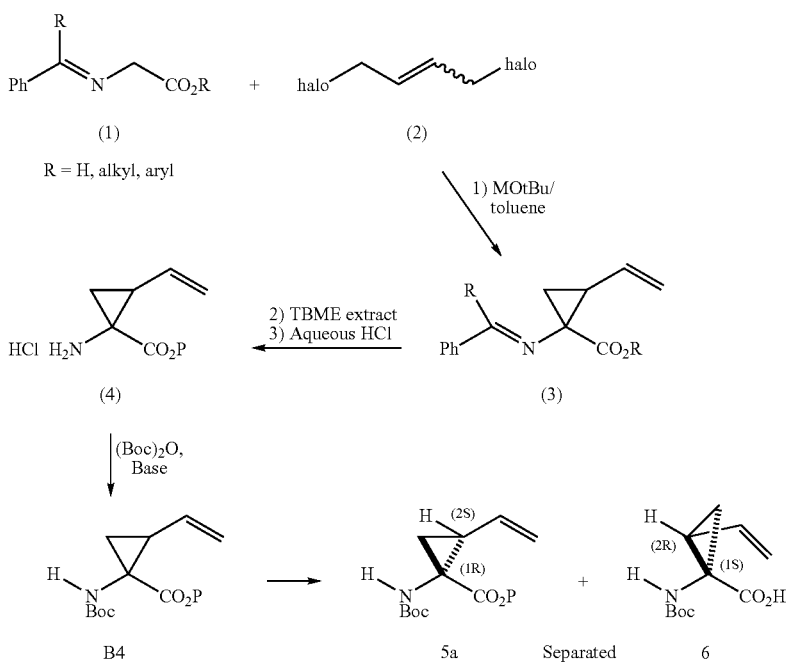

Scheme IX

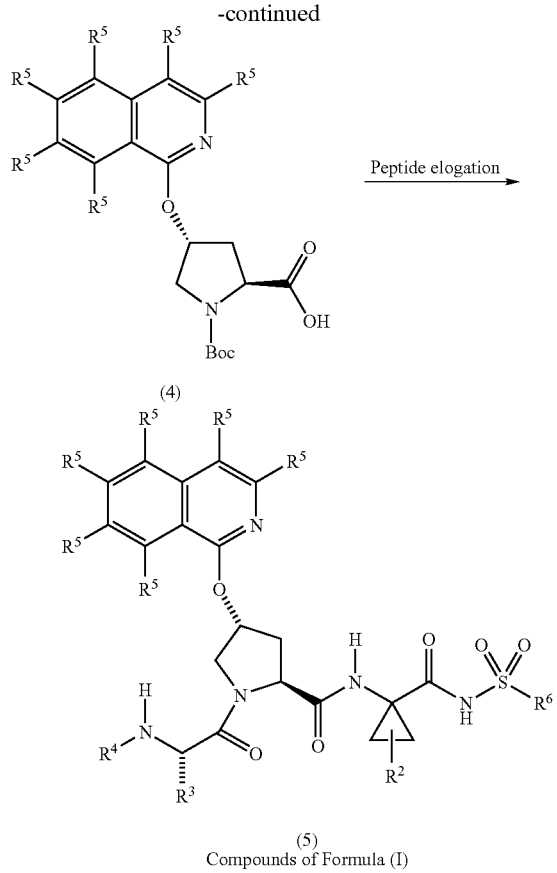

(4)

(5)
Compounds of Formula (I)

Scheme X shows the coupling of an N-protected C4-hydroxyproline moiety with a heterocycle to form intermediate (4) and the subsequent modification of said intermediate (4) to a compound of Formula (I) by the process of peptide elongation as described herein. It should be noted that in the first step, that is the coupling of the C4-hydroxy proline group with the heteroaryl element, a base is employed. One skilled in the art would recognized that this coupling can be done using bases such as potassium tert-butoxide, or sodium hydride, in a solvent such as DMF or DMSO or THF. This coupling to the isoquinoline ring system occurs at the C1 position (numbering for isoquinoline ring system shown in intermediate 2 of Scheme XI) and is directed by the chloro group which is displaced in this process. It should be noted that alternative leaving groups can be utilized at this position (e.g., fluoro) as shown in the scheme. Said fluoro intermediates (3) are available from the corresponding chloro compound using literature procedures described herein.

An alternative to the method described above for the coupling of the C4-hydroxyproline to the isoquinoline nucleus is provided in the Mitsunobu reaction as depicted in step 1 of Scheme XI. In this general reaction scheme a C4-hydroxy proline derivative is coupled to an isoquinoline ring system. This reaction makes use of reagents such as triphenylphosphine and DEAD (diethylazodicarboxylate) in aprotic solvents such as THF or dioxane and can be used for the formation of heteroaryl ethers. Note that in the course of this coupling reaction the stereochemistry of the C4 chiral center in the C4-hydroxyproline derivative is inverted and thereby it is necessary to use the C4-hydroxyproline derivative housing the (S) stereochemistry at the C4 position as starting material (as shown in Scheme XI). It should be noted that numerous modifications and improvements of the Mitsunobu reaction have been described in the literature, the teachings of which are incorporated herein.

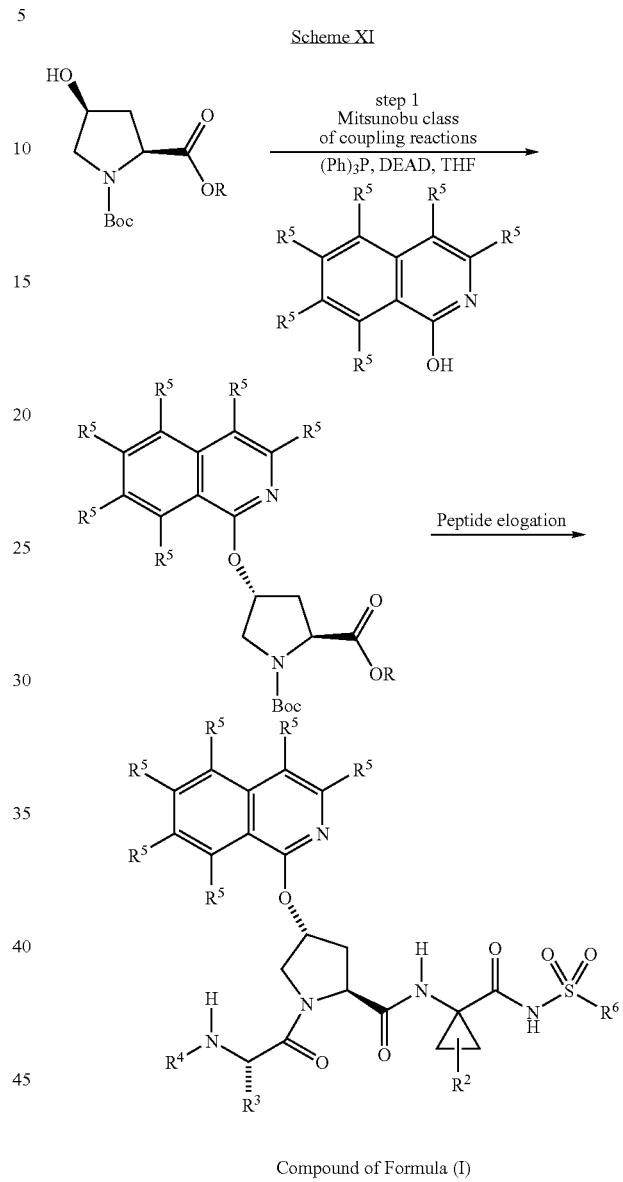

Compound of Formula (I)

In examples herein, isoquinolines are incorporated into the final compounds and specifically into the P2 region of said compounds. One skilled in the art would recognize that a number of general methods are available for the synthesis of isoquinolines. Moreover, the isoquinolines generated by these methods can be readily incorporated into final compounds of Formula (I) using the processes described herein. One general methodology for the synthesis of isoquinolines is shown in Scheme XII, wherein cinnamic acid derivatives, shown in general form as structure (2), are converted to 1-chloroisoquinolines in a four step process. The chloroisoquinolines can be subsequently used in coupling reactions to C4-hydroxyproline derivatives as described herein. The conversion of cinnamic acids to chloroquinolines begins with the treatment of cinnamic acid with an alkylcholorformate in the presence of a base. The resulting anhydride is then treated with sodium azide which results in the formation of an acylazide (3) as shown in the scheme. Alternate methods are available for the formation of acylazides from carboxylic acids as for example said carboxylic acid can be treated with diphenylphosphorylazide (DPPA) in an aprotic solvent such as methylene chloride in the presence of a base. In the next step of the reaction sequence the acylazide (3) is converted to the corresponding isoquinolone (4) while heating to a temperature of approximately 190° C. in a high boiling solvent such a diphenylmethane. This reaction is general and provides moderate to good yields of substituted isoquinolone from the corresponding cinnamic acid derivatives. It should noted that said cinnamic acid derivatives are available commercially or can be obtained from the corresponding benzaldehyde (1) derivative by direct condensation with malonic acid or derivatives thereof and also by employing a Wittig reaction. The intermediate isoquinolones (4) of Scheme XII can be converted to the corresponding 1-chloroisoquinoline by treatment with phosphorous oxychloride. This reaction is general and can be applied to the isoquinolones shown herein.

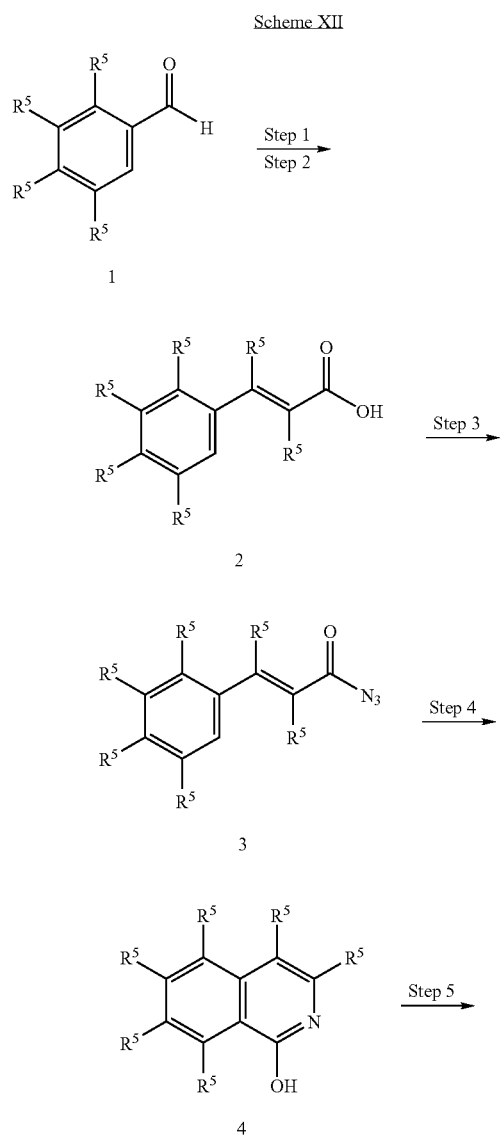

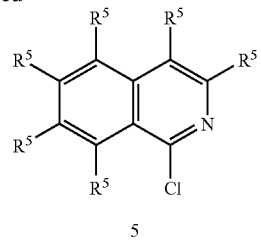

Reference: N. Briet at al, Tetrahedron, 2002, 5761

An alternative method for the synthesis of the isoquinoline ring system is the Pomeranz-Fritsh procedure. This general method is outlined in Scheme XIII. The process begins with the conversion of a benzaldehyde derivative (1) to a functionalized imine (2). The imine is then converted to the isoquinoline ring system by treatment with acid at elevated temperature. This isoquinoline synthesis of Scheme XIII is general, and it should be noted that this process is particularly useful in procuring isoquinoline intermediates that are substituted at the C8 position. The intermediate isoquinolines (3) can be converted to the corresponding 1-chloroquinolines (5) in a two step process as shown. The first step in this sequence is the formation of the isoquinoline N-oxide (4) by treatment of isoquinoline (3) with meta-chloroperbenzoic acid in an aprotic solvent such as dichloromethane. Intermediate (4) can be converted to the corresponding 1-chloroquinoline by treatment with phosphorous oxychloride in refluxing chloroform. Note that this two step process is general for the formation of chloroisoquinolines from isoquinolones.

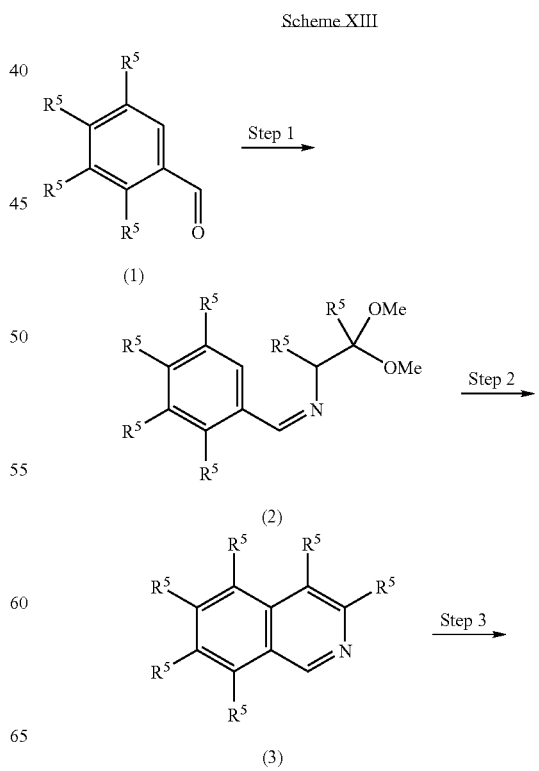

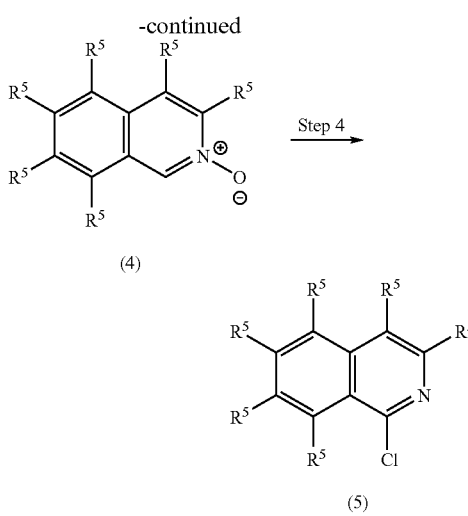

(4)

(5)

Pomeranz-Fritsch synthesis
K. Hirao, R. Tsuchiya, Y. Yano, H. Tsue, Heterocycles 42(1) 1996, 415-422

Another method for the synthesis of the isoquinoline ring system is shown in Scheme XIV. In this process an ortho-alkylbenzamide derivative (1) is treated with a strong base such as tert-butyllithium in a solvent such as THF at low temperature. To this reaction mixture is then added a nitrile derivative, which undergoes an addition reaction with the anion derived from deprotonation of (1), resulting in the formation of (2). This reaction is general and can be used for the formation of substituted isoquinolines. Intermediate (2) of Scheme XIV can be converted to the corresponding 1-chloroquinoline by the methods described herein.

Scheme XIV

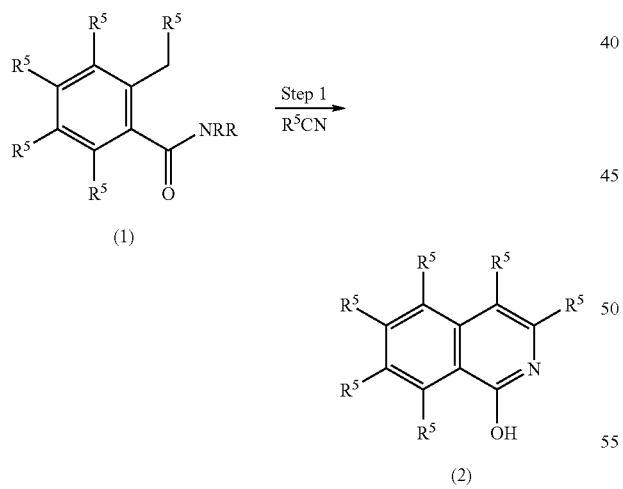

An additional method for the synthesis of isoquinolines is shown in Scheme XV. The deprotonation of intermediate (1) using tert-butyllithium is described above. In the present method however, the intermediate anion is trapped by an ester, resulting in the formation of intermediate (2) as shown below. In a subsequent reaction, ketone (2) is condensed with ammonium acetate at elevated temperature providing for the formation of quinolone (3). This reaction is general and can be applied to the construction of substituted isoquinolones which can then be converted to the corresponding 1-chloroisoquinolines as described herein.

Scheme XV

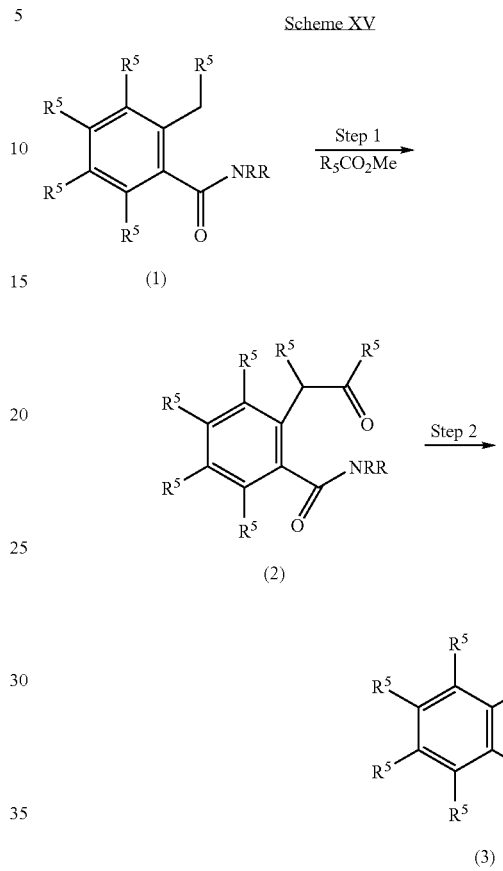

Another method for the construction of isoquinolines is found in Scheme XVI. In the first step of this process an ortho-alkylarylimine derivatives such as (1) are subjected to deprotonation conditions (sec-butyl lithium, THF) and the resulting anion is quenched by the addition of an activated carboxylic acid derivative such as a Weinreb amide. The resulting ketoimine (2) can be converted to the corresponding isoquinoline by condensation with ammonium acetate at elevated temperatures. This method is general and can be used for the synthesis of substituted isoquinolines. The isoquinolines can be converted to the corresponding 1-chloroquinoline by the methods described herein.

Scheme XVI

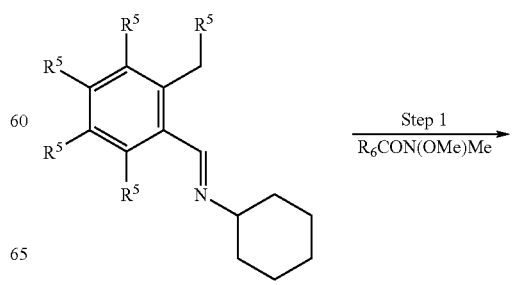

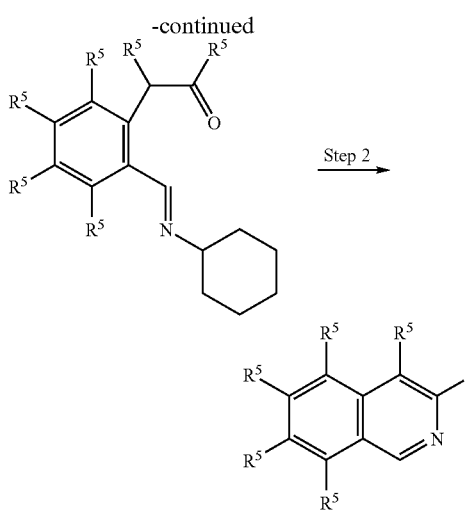

L. Flippin, J. Muchowski, JOC, 1993, 2631-2632

The isoquinolines described herein, and which are incorporated into the compounds of Formula (I), can be further functionalized. It is obvious to one skilled in the art that additional functionalization of said heterocycles can be done either before or after incorporation of these functionalities into compounds of Formula (I). The following schemes illustrate this point. For example Scheme XVII shows the conversion of a 1-chloro-6-fluoro-isoquinoline to the corresponding 1-chloro-6-alkoxy-isoquinoline species, by treatment of (1) with a sodium or potassium alkoxide species in the alcohol solvent from which the alkoxide is derived at room temperature. In some cases it may be necessary to heat the reaction to drive it to completion. The chloroquinoline can be incorporated into a compound of Formula (I) using the art described herein.

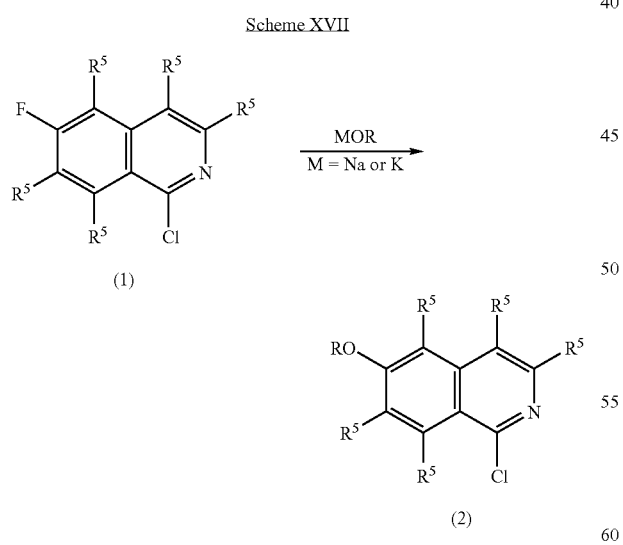

Scheme XVIII provides a general example for the modification of isoquinolines as defined herein by employing palladium mediated coupling reactions. The couplings can be employed to functionalize a heterocycle at each position of the ring system provided the ring is suitably activated or functionalized, as for example with a chloride as shown in the scheme. This sequence begins with 1-chloroisoquinoline (1) which upon treatment with metachloroperbenzoic acid can be converted to the corresponding N-oxide (2). Intermediate (2) can be converted to the corresponding 1,3-dichloroisoquinoline (3) by treatment with phosphorous oxychloride in refluxing chloroform. Intermediate (3) can be coupled with N-Boc-4-hydroxyproline by the methods described herein to provide intermediate (5) as shown in the scheme. Intermediate (5) can undergo a Suzuki coupling with an aryl boronic acid, in the presence of a palladium reagent and base, and in a solvent such as THF or toluene or DMF to provide the C3-arylisoquinoline intermediate (6). Heteroarylboronic acids can also be employed in this palladium-mediated coupling process to provide C3-heteroarylisoquinolines. Intermediate (6) can be converted into final compounds of Formula (I) by the methods described herein.

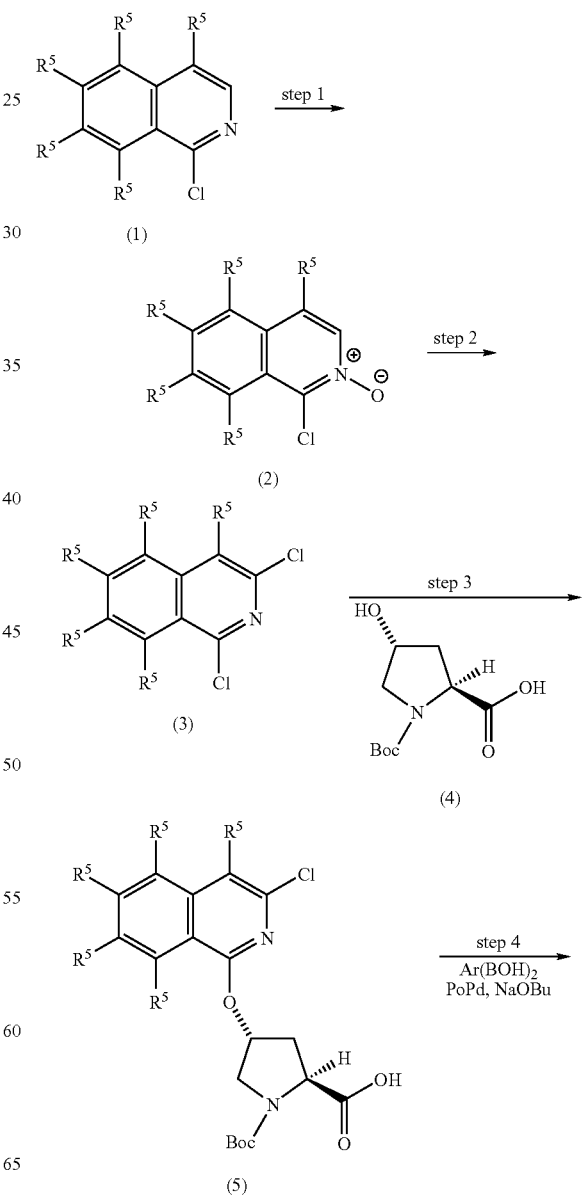

-continued

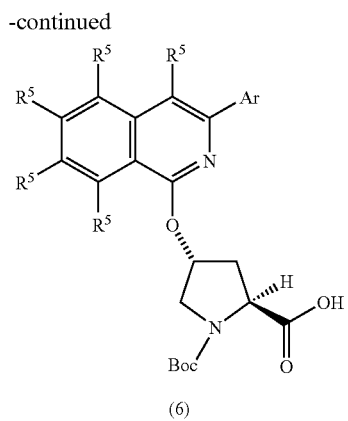

(6)

Palladium mediated couplings of isoquinoline systems with aryl or heteroaryl elements can also be employed at a later synthetic stage in the construction of compounds of Formula (I) as shown in Scheme XIX. Tripeptide acylsulfonamide intermediate (1) is coupled to a 1-chloro-3-bromoisoquinoline (2) using the previously described process to provide intermediate (3). The coupling of (1) and (2) is most efficient in the presence of a catalyst such as lanthanum chloride as described herein. The isoquinoline ring system of intermediate (3) can be further functionalized by employing either Suzuki couplings (Process 1: subjecting (3) to heteroaryl or aryl boronic acids in the presence of a palladium catalyst such as palladium tetrakistriphenylphosphine and a base such as cesium carbonate in solvents such as DMF) or Stille couplings (Process 2: subjecting (3) to heteraryl or aryl tin dervatives in the presence of a palladium catalyst such as palladium tetrakistriphenylphosphine in solvents such as toluene).

Scheme XIX

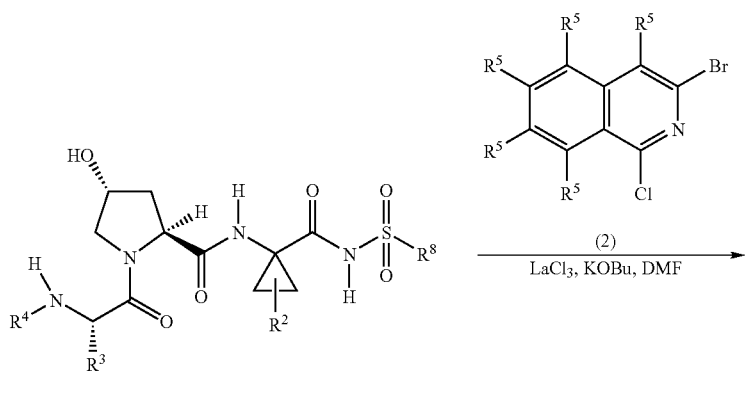

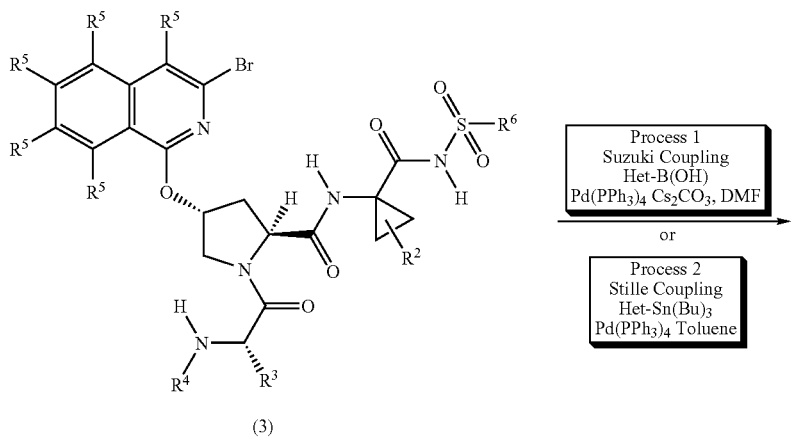

-continued

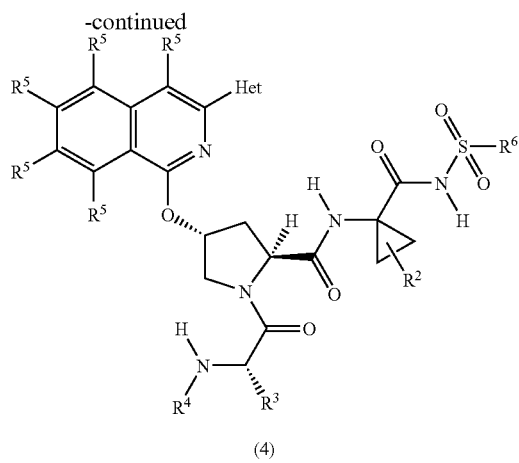

(4)

The P3 amino acids employed in the present invention are either commercially available or can be prepared using methods known to those of ordinary skill in the art. Non-limiting routes for the preparation of the P3 amino acid include:

Route 1: Nucleophilic aromatic substitution of a sufficiently electrophilic aromatic or heteroaromatic species (1) with an amino acid ester (2) as shown in Scheme XX. This reaction is then followed by a simple ester cleavage of 3 to provide the desired amino acid (4).

Scheme XX

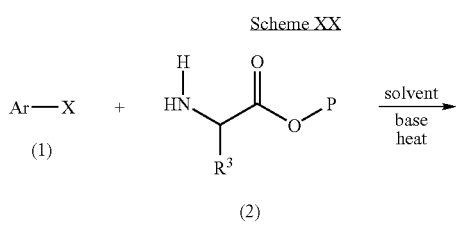

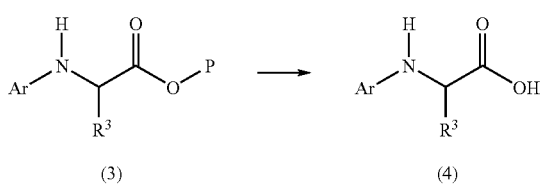

P = protecting group

Route 2: A Buchwald-Hartwig type reaction which involves palladium-catalyzed coupling an aryl or heteroaryl halide bond with a suitably protected amino acid (1) as shown in Scheme XXI. Simple saponification of intermediate 2 provides the desired amino acid (3). (Shen, Q.; Shekhar, S; Stambuli, J. P.; Hartwig, J. F. *Angew. Chem. Int. Ed.* 2005, 44, 1371-1375.):

Scheme XXI

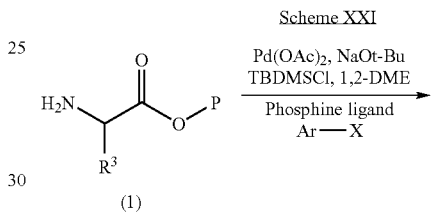

P = Protecting group

Route 3: A coupling process whereby an aryl or heteroaryl halide and a free amino acid are coupled via a CuI mediated process to give the arylamino acid directly as shown in Scheme XXII (Ma, D.; Zhang, Y.; Yao, J.; Wu, S.; Tao, F. *J. Am. Chem. Soc.* 1998, 120, 12459-12467.)

Scheme XXII

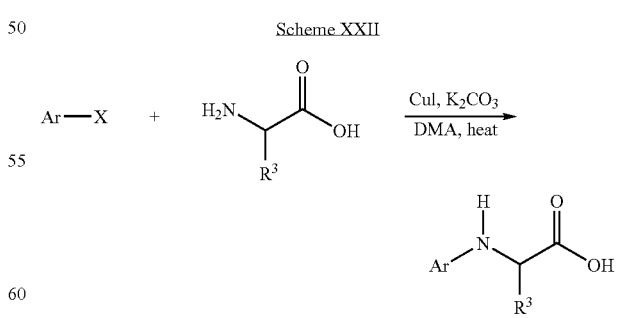

Route 4: A process which employs nucleophilic displacement of the dianion of a free amino acid and an aryl or heteroaryl halide, typically a fluoride (similar to Saitton, S.; Kihlberg, J.; Luthman, K. *Tetrahedron* 2004, 60, 6113-6120.):

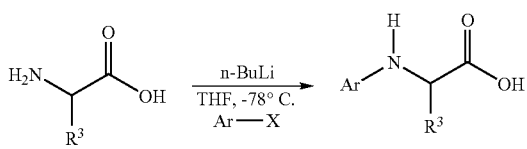

In some cases, as shown in Scheme XXIII, access to the aminoaryl final products can be achieved by direct nucleophilic aromatic substitution of the aryl ring with a fully assembled core tripeptide having a free amino group at the terminus of the P3 subregion.

Scheme XXIII

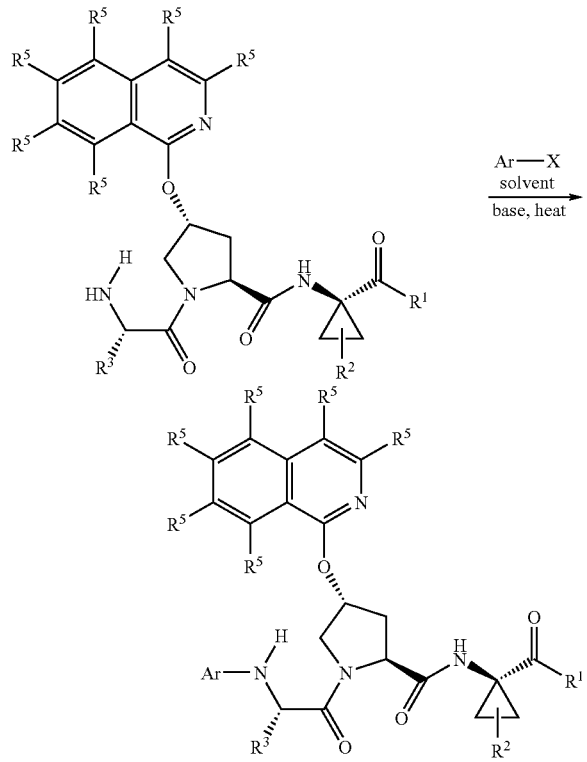

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts (δ) are reported in parts per million. Flash chromatography was carried out on silica gel ($SiO_2$) according to Still's flash chromatography technique (*J. Org. Chem.* 1978, 43, 2923).

I. Preparation of P1' Intermediates

1. Preparation of Cyclopropylsulfonamide

Method 1:

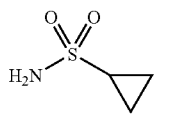

cyclopropylsulfonamide

Scheme 1

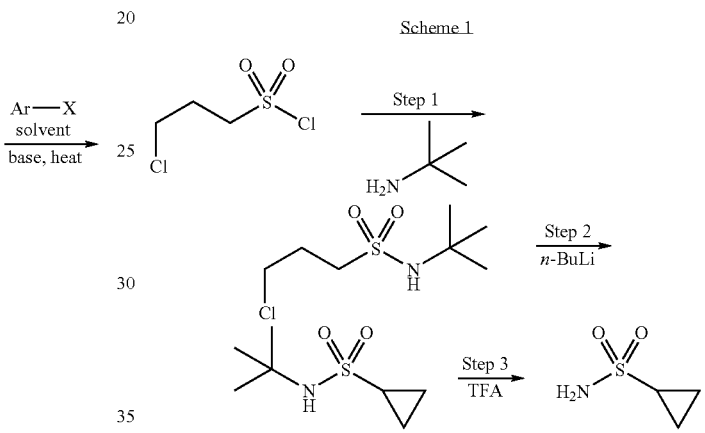

Step 1:

tert-Butylamine (3.0 mol, 315 mL) was dissolved in THF (2.5 L). The solution was cooled to −20° C. 3-Chloropropanesulfonyl chloride (1.5 mol, 182 mL) was added slowly. The reaction mixture was allowed to warm to room temperature and stirred for 24 hours. The mixture was filtered and the filtrate was concentrated in vacuo. The residue was dissolved in $CH_2Cl_2$ (2.0 L). The resulting solution was washed with 1.0M HCl (1.0 L), water (1.0 L), and brine (1.0 L), dried over $Na_2SO_4$, filtered, and concentrated in vacuo to give a slightly yellow solid, which was crystallized from hexane to provide the product as a white solid (316.0 g, 99%). $^1$H NMR ($CDCl_3$) δ 1.38 (s, 9H), 2.30-2.27 (m, 2H), 3.22 (t, J=7.35 Hz, 2H), 3.68 (t, J=6.2 Hz, 2H), 4.35 (b, 1H).

Step 2:

To a solution of the product of Step 1 (2.14 g, 10.0 mmol) in THF (100 mL) was added n-BuLi (2.5 M in hexane, 8.0 mL, 20.0 mmol) at −78° C. The reaction mixture was allowed to warm up to room temperature over period of 1 hour and concentrated in vacuo. The residue was partitioned between ethyl acetate and water (200 mL each). The separated organic phase was washed with brine, dried over $Na_2SO_4$, filtered, and concentrated in vacuo. The residue was recrystallized from hexane to provide the desired product as a white solid (1.0 g, 56%). $^1$H NMR ($CDCl_3$) δ 0.98-1.00 (m, 2H), 1.18-1.19 (m, 2H), 1.39 (s, 9H), 2.48-2.51 (m, 1H), 4.19 (b, 1H).

Step 3:

A solution of the product of Step 2 (110 g, 0.62 mmol) in TFA (500 mL) was stirred at room temperature for 16 hours.

The volatiles were removed in vacuo. The residue was recrystallized from ethyl acetate/hexane (60 mL/240 mL) to provide the desired product as a white solid (68.5 g, 91%). $^1$H NMR (DMSO-d$_6$) δ 0.84-0.88 (m, 2H), 0.95-0.98 (m, 2H), 2.41-2.58 (m, 1H), 6.56 (b, 2H).

Method 2:

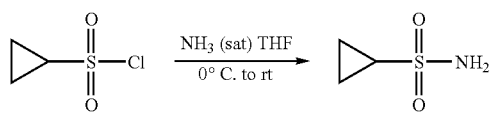

To a solution of 100 mL of THF cooled to 0° C. was bubbled in gaseous ammonia until saturation was reached. To this solution was added a solution of 5 g (28.45 mmol) of cyclopropylsulfonyl chloride (purchased from Array Biopharma) in 50 mL of THF. The solution was warmed to room temperature overnight and stirred one additional day. The mixture was concentrated until 1-2 mL of solvent remained and poured onto a 30 g plug of SiO$_2$ (eluted with 30% to 60% ethyl acetate/hexanes) to provide 3.45 g (100%) of cyclopropylsulfonamide as a white solid. $^1$H NMR (methanol-d$_4$) δ 0.94-1.07 (m, 4H), 2.52-2.60 (m, 1H); $^{13}$C NMR (methanol-d$_4$) δ 5.92, 33.01.

2. Preparation of C1-Substituted Cyclopropylsulfonamides

2a. Preparation of N-tert-butyl-(1-methyl)cyclopropyl-sulfonamide

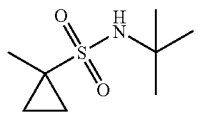

Step 1: Preparation of N-tert-butyl-(3-chloro)propylsulfonamide

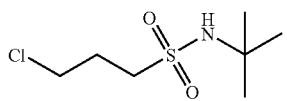

Prepared as described above.

Step 2: Preparation of N-tert-butyl-(1-methyl)cyclopropyl-sulfonamide

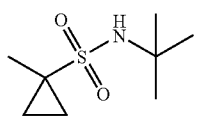

A solution of the product of Step 1 (4.3 g, 20 mmol) was dissolved in dry THF (100 mL) and cooled to −78° C. To this solution was added n-butyllithium (17.6 mL, 44 mmol, 2.5M in hexane) slowly. The dry ice bath was removed and the reaction mixture was warmed to room temperature over a period of 1.5 hours. This mixture was cooled to −78° C. and a solution of n-butyllithium (20 mmol, 8 mL, 2.5M in hexane) was added. The reaction mixture was warmed to room temperature, cooled to −78° C. over a period of 2 hours, and treated with a neat solution of methyl iodide (5.68 g, 40 mmol). The reaction mixture was warmed to room temperature overnight, then quenched with saturated NH$_4$Cl (100 mL) at room temperature and extracted with ethyl acetate (100 mL). The organic phase was washed with brine (100 mL), dried (MgSO$_4$), filtered, and concentrated in vacuo to provide a yellow oil which was crystallized from hexane to provide the desired product as a slightly yellow solid (3.1 g, 81%): $^1$H NMR (CDCl$_3$) δ 0.79 (m, 2H), 1.36 (s, 9H), 1.52 (m, 2H), 1.62 (s, 3H), 4.10 (br s, 1H).

Step 3: Preparation of 1-methylcyclopropylsulfonamide

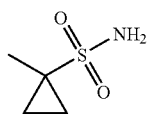

A solution of the product of Step 2 (1.91 g, 10 mmol) was dissolved in TFA (30 mL), and the reaction mixture stirred at room temperature for 16 hours. The solvent was removed in vacuo to provide a yellow oil which was crystallized from ethyl acetate/hexane (1:4, 40 mL) to provide the desired product as a white solid (1.25 g, 96%): $^1$H NMR (CDCl$_3$) δ 0.84 (m, 2H), 1.41 (m, 2H), 1.58 (s, 3H), 4.65 (br s, 2H). Anal. Calcd. For C$_4$H$_9$NO$_2$S: C, 35.54; H, 6.71; N, 10.36. Found: C, 35.67; H, 6.80; N, 10.40.

2b. Preparation of 1-propylcyclopropylsulfonamide

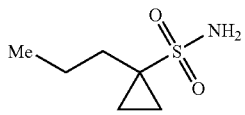

This compound was prepared using the procedure described for the preparation of 1-methylcyclopropylsulfonamide substituting propyl halide for methyl iodide in the second step of this process.

2c. Preparation of 1-allylcyclopropylsulfonamide

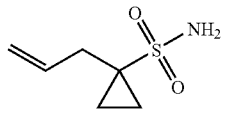

Step 1: Preparation of N-tert-butyl-(1-allyl)cyclopropylsulfonamide

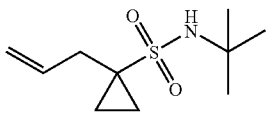

This compound was obtained in 97% yield according to the procedure described in the synthesis of N-tert-butyl-(1-methyl)cyclopropylsulfonamide using 1.25 equivalents of allyl bromide as the electrophile. The compound was used in the next reaction without further purification: $^1$H NMR (CDCl$_3$) δ 0.83 (m, 2H), 1.34 (s, 9H), 1.37 (m, 2H), 2.64 (d, J=7.3 Hz, 2H), 4.25 (br s, 1H), 5.07-5.10 (m, 2H), 6.70-6.85 (m, 1H).

Step 2: Preparation of 1-allylcyclopropylsulfonamide

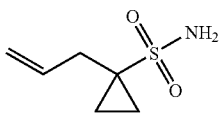

This compound was obtained in 40% yield from the product of Step 1 according to the procedure described in the synthesis of 1-methylcyclopropylsulfonamide. The compound was purified by column chromotography over SiO$_2$ using 2% methanol in dichloromethane as the eluent: $^1$H NMR (CDCl$_3$) δ 0.88 (m, 2H), 1.37 (m, 2H), 2.66 (d, J=7.0 Hz, 2H), 4.80 (s, 2H), 5.16 (m, 2H), 5.82 (m, 1H); $^{13}$C NMR (CDCl$_3$) δ 11.2, 35.6, 40.7, 119.0, 133.6.

2d. Preparation of 1-Benzylcyclopropylsulfonamide

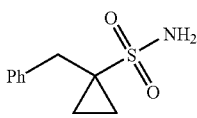

Step 1: Preparation of N-tert-butyl-(1-benzyl)cyclopropyl-sulfonamide

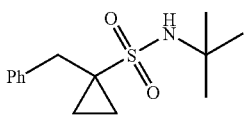

This compound was obtained in 60% yield using the procedure described for the synthesis of N-tert-butyl-(1-methyl)cyclopropylsulfonamide except 1.05 equivalents of benzyl bromide were used, followed by trituration with 10% ethyl acetate in hexane: $^1$H NMR (CDCl$_3$) δ 0.92 (m, 2H), 1.36 (m, 2H), 1.43 (s, 9H), 3.25 (s, 2H), 4.62 (br s, 1H), 7.29-7.36 (m, 5H).

Step 2: Preparation of 1-Benzylcyclopropylsulfonamide

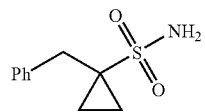

This compound was obtained in 66% yield from N-tert-butyl(1-benzyl)cyclopropylsulfonamide using the procedure described for the synthesis of 1-methylcyclopropylsulfonamide, followed by recrystallization from the minimum amount of 10% ethyl acetate in hexane: $^1$H NMR (CDCl$_3$) δ 0.90 (m, 2H), 1.42 (m, 2H), 3.25 (s, 2H), 4.05 (s, 2H), 7.29 (m, 3H), 7.34 (m, 2H); $^{13}$C NMR (CDCl$_3$) δ 11.1, 36.8, 41.9, 127.4, 128.8, 129.9, 136.5.

2e. Preparation of 1-(1-cyclohexenyl)cyclopropyl-sulfonamide

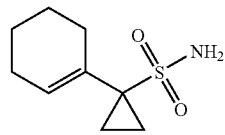

Step 1: Preparation of N-tert-butyl-[1-(1-hydroxy)cyclohexyl]-cyclopropylsulfonamide

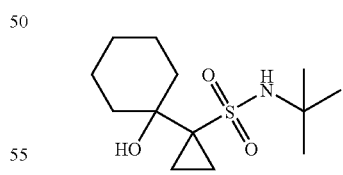

This compound was obtained in 84% yield using to the procedure described for the synthesis of N-tert-butyl-(1-methyl)cyclopropylsul-fonamide except 1.30 equivalents of cyclohexanone were used, followed by recrystallization from the minimum amount of 20% ethyl acetate in hexane: $^1$H NMR (CDCl$_3$) δ 1.05 (m, 4H), 1.26 (m, 2H), 1.37 (s, 9H), 1.57-1.59 (m, 6H), 1.97 (m, 2H), 2.87 (br s, 1H), 4.55 (br s, 1H).

Step 2: Preparation of 1-(1-cyclohexenyl)cyclopropyl-sulfonamide

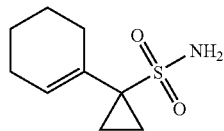

This compound, 1-(1-cyclohexenyl)-cyclopropylsulfonamide was obtained in 85% yield from N-tert-butyl-[1-(1-hydroxy)cyclohexyl]-cyclopropylsulfonamide using the procedure described for the synthesis of 1-methylcyclopropylsulfonamide, followed by recrystallization from the minimum amount of ethyl acetate and hexane: $^1$H NMR (DMSO-$d_6$) δ 0.82 (m, 2H), 1.28 (m, 2H), 1.51 (m, 2H), 1.55 (m, 2H), 2.01 (s, 2H), 2.16 (s, 2H), 5.89 (s, 1H), 6.46 (s, 2H); $^{13}$C NMR (DMSO-$d_6$) δ 11.6, 21.5, 22.3, 25.0, 27.2, 46.9, 131.6, 132.2; LR-MS (ESI): 200 (M$^+$−1).

2f. Preparation of 1-benzoylcyclo-propylsulfonamide

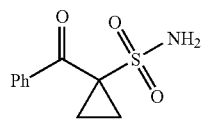

Step 1: Preparation of N-tert-butyl-(1-benzoyl)cyclopropyl-sulfonamide

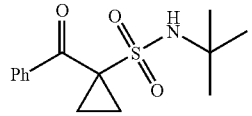

This compound was obtained in 66% yield using the procedure described for the synthesis of N-tert-butyl-(1-methyl)cyclopropylsulfonamide except 1.2 equivalents of methyl benzoate was used as the electrophile. The compound was purified by column chromatography over SiO$_2$ using 30% to 100% dichloromethane in hexane: $^1$H NMR (CDCl$_3$) δ 1.31 (s, 9H), 1.52 (m, 2H), 1.81 (m, 2H), 4.16 (br s, 1H), 7.46 (m, 2H), 7.57 (m, 1H), 8.05 (d, J=8.5 Hz, 2H).

Step 2: Preparation of 1-benzoylcyclo-propylsulfonamide

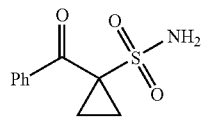

This compound was obtained in 87% yield from N-tert-butyl(1-benzoyl)cyclopropylsul-fonamide using the process described for the synthesis of 1-methylcyclopropylsulfonamide, followed by recrystallization from the minimum amount of ethyl acetate in hexane: $^1$H NMR (DMSO-$d_6$) δ 1.39 (m, 2H), 1.61 (m, 2H), 7.22 (s, 2H), 7.53 (t, J=7.6 Hz, 2H), 7.65 (t, J=7.6 Hz, 1H), 8.06 (d, J=8.2 Hz, 2H); $^{13}$C NMR (DMSO-$d_6$) δ 12.3, 48.4, 128.1, 130.0, 133.4, 135.3, 192.0.

2g. Preparation of N-tert-butyl-(1-phenylaminocarboxy)-cyclopropylsulfonamide

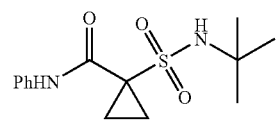

This compound was obtained in 42% yield using the procedure described for the synthesis of N-tert-butyl-(1-methyl)cyclopropylsulfonamide using 1 equivalent of phenylisocyanate, followed by recrystallization from the minimum amount of ethyl acetate in hexane $^1$H NMR (CDCl$_3$) δ 1.38 (s, 9H), 1.67-1.71 (m, 4H), 4.30 (br s, 1H), 7.10 (t, J=7.5 Hz, 1H), 7.34 (t, J=7.5 Hz, 2H), 7.53 (t, J=7.5 Hz, 2H).

3. Preparation of C1-Substituted Cyclopropanesulfonamides: The Use of an N-Boc Protecting Group

3a. Preparation of Cyclopropylsulfonylamine tert-butyl Carbamate, a Key Intermediate in the Preparation of C1-Substituted Cyclopropylsulfonamides

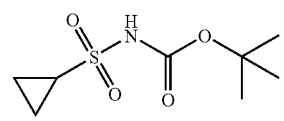

Step 1: Preparation of 3-chloropropylsulfonamide

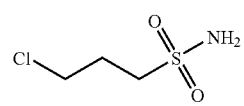

A solution of 3-chloropropanesulfonyl chloride (55 g, 310.7 mmol) was dissolved in THF (200 mL) and added dropwise over 30 minutes to a solution of NH$_4$OH (200 mL) at 0° C. The reaction mixture was warmed to room temperature, stirred 1 hour, and the aqueous layer extracted with dichloromethane (4×500 mL). The combined extracts were washed with 1N HCl (150 mL), water (150 mL), dried over MgSO$_4$, filtered, and concentrated in vacuo. The crude solid was recrystallized from the minimum amount of dichloromethane in hexanes to provide the desired product as a white solid (45.3 g, 93%). $^1$H NMR (CDCl$_3$) δ 2.34 (m, 2H), 3.32 (t, J=7.3 Hz, 2H), 3.70 (t, J=6.2 Hz, 2H), 4.83 (s, 2H); $^{13}$C NMR (CDCl$_3$) δ 27.10, 42.63, 52.57.

Step 2: Preparation of 3-chloropropylsulfonylamine tert-butylcarbamate

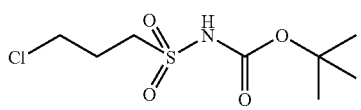

A solution of the product of Step 1 (30.2 g, 191.5 mmol), triethylamine (30.2 mL, 217.0 mmol), and 4-DMAP (2.40 g, 19.6 mmol) in dichloromethane (350 mL) at 0° C. was treated dropwise with a solution of di-tert-butyldicarbonate (47.2 g, 216.9 mmol) in dichloromethane (250 mL) over 30 minutes. The reaction mixture was warmed to room temperature, stirred an additional 3 hours, and was washed with 1N HCl (300 mL), water (300 mL), and brine (300 mL), dried over $MgSO_4$, filtered, and concentrated in vacuo to provide the crude product. This material was triturated with 70 mL of 5% dichloromethane in hexanes to provide the desired product as an off-white solid (47.2 g, 96%): $^1$H NMR ($CDCl_3$) δ 1.51 (s, 9H), 2.33 (m, 2H), 3.60 (t, J=7.3 Hz, 2H), 3.68 (t, J=6.21 Hz, 2H); $^{13}$C NMR ($CDCl_3$) δ 26.50, 27.95, 42.37, 50.40, 84.76, 149.53.

Step 3: Preparation of Cyclopropylsulfonylamine tert-butyl Carbamate

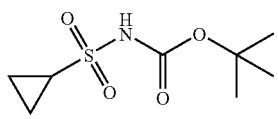

A solution of n-butyllithium (74.7 mL, 119.5 mmol, 1.6M in hexane) was dissolved in dry THF (105 mL) and cooled to −78° C. under an argon atmosphere. To this solution was added a solution of the product of Step 2 (14 g, 54.3 mmol) in dry THF (105 mL) dropwise over 20-30 minutes. The dry ice bath was removed and the reaction mixture was allowed to warm to room temperature over a period of 2 hours. The reaction mixture was quenched with glacial acetic acid (3.4 mL), concentrated in vacuo, and partitioned between dichloromethane (100 mL) and water (100 mL). The organic phase was washed with brine (100 mL), dried ($MgSO_4$), filtered, and concentrated in vacuo to provide the desired product as a waxy off-white solid (12.08 g, 100%): $^1$H NMR ($CDCl_3$) δ 1.10 (m, 2H), 1.34 (m, 2H), 1.50 (s, 9H), 2.88 (m, 1H), 7.43 (s, 1H). $^{13}$C NMR ($CDCl_3$) δ 6.21, 28.00, 31.13, 84.07, 149.82.

3b. Preparation of 1-methoxy-methylcyclopropy-sulfonamide

Step 1: Preparation of 1-methoxymethylcyclopropylsulfonylamine tert-butylcarbamate

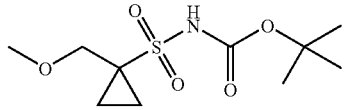

To a solution of cyclopropylsulfonylamine tert-butyl carbamate (1.0 g, 4.5 mmol) dissolved in THF (30 mL) cooled to −78° C., was added n-butyllithium (6.4 mL, 10.2 mmol, 1.6M in hexane) and the reaction mixture was stirred for 1 hour. To this solution was added a neat solution of chloromethyl methyl ether (0.40 mL, 5.24 mmol), and the mixture was slowly allowed to warm to room temperature overnight. The solution pH was adjusted to 3 using 1N aqueous HCl and was then extracted with ethyl acetate (4×50 mL portions). The combined extracts were dried ($MgSO_4$), filtered, and concentrated to afford 1-methoxymethylcyclopropylsulfonylamine tert-butylcarbamate, as a waxy solid (1.20 g, 100%) which was taken directly into the next reaction without further purification: $^1$H NMR ($CDCl_3$) δ 1.03 (m, 2H), 1.52 (s, 9H), 1.66 (m, 2H), 3.38 (s, 3H), 3.68 (s, 2H), 7.54 (s, 1H); $^{13}$C NMR ($CDCl_3$) δ 11.37, 28.29, 40.38, 58.94, 73.43, 83.61, 149.57.

Step 2: Preparation of 1-methoxymethylcyclopropysulfonamide

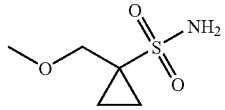

A solution of 1-methoxymethylcyclopropylsulfonylamine tert-butylcarbamate (1.14 g, 4.30 mmol) was dissolved in a solution of 50% TFA/dichloromethane (30 mL) and was stirred at room temperature for 16 hours. The solvent was removed in vacuo and the residue chromatographed over 80 g of $SiO_2$ (eluting with 0% to 60% ethyl acetate/hexanes to 1-methoxymethylcyclopropylsulfonamide as a white solid (0.55 g, 77% overall over two steps): $^1$H NMR ($CDCl_3$) δ 0.95 (m, 2H), 1.44 (m, 2H), 3.36 (s, 3H), 3.65 (s, 2H), 4.85 (s, 2H); $^{13}$C NMR ($CDCl_3$) δ 11.17, 40.87, 59.23, 74.80; LRMS m/z 183 ($M^+$+$NH_4$).

3c. Preparation of 1-cyclopropylmethylcyclopropylsulfonamide

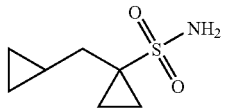

Step 1: Preparation of 1-cyclopropylmethylcyclopropylsulfonylamine tert-butylcarbamate

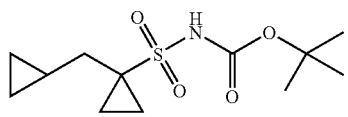

1-Cyclopropylmethylcyclopropylsulfonylamine tert-butylcarbamate was obtained in 92% yield according to the procedure described in the synthesis of 1-methoxymethylcyclopropylsulfonylamine tert-butylcarbamate, except 1.10 equivalents of cyclopropylmethyl bromide were used as electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

Step 2: Preparation of 1-cyclopropylmethyl-cyclopropylsulfonamide

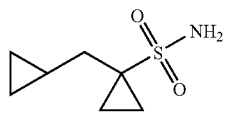

This compound was obtained in 65% yield from 1-cyclopropylmethylcyclopropylsulfonylamine tert-butylcarbamate according to the procedure described for the synthesis of 1-methoxymethylcyclopropylsulfonamide. The compound was purified by column chromatography over SiO$_2$ using 0% to 60% ethyl acetate in hexanes as the eluent: $^1$H NMR (CDCl$_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$).

3d. Preparation of 1-propylcarbamoylcyclopropane-sulfonamide

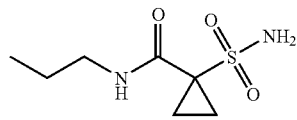

Step 1: Preparation of 1-propylcarbamoylcyclopropanesulfonamide tert-butylcarbamate

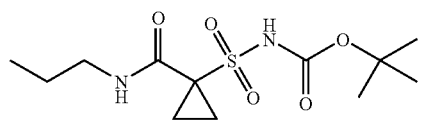

This compound was obtained in a crude 100% yield according to the procedure described for the synthesis of 1-methoxymethylcyclopropylsulfonylamine tert-butyl-carbamate except that 1.10 equivalents of n-propyl isocyanate was used as the electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

Step 2: Preparation of 1-propylcarbamoylcyclopropane-sulfonamide

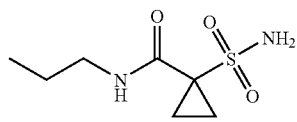

This compound was obtained in 50% yield from 1-propylcarbamoylcyclopropanesulfonamide tert-butylcarbamate according to the procedure described for the synthesis of 1-methoxymethylcyclopropylsulfonamide, except that no chromatography was used as the material was recrystallized from the minimum amount of dichloromethane/hexanes: $^1$H NMR (CDCl$_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$).

3e. Preparation of 1-(3,5-dimethylisoxazol-4-yl)carbamoylcyclopropanesulfonamide

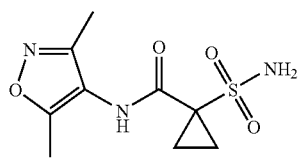

Step 1: Preparation of 1-(3,5-dimethylisoxazol-4-yl)carbamoylcyclopropanesulfonamide tert-butylcarbamate

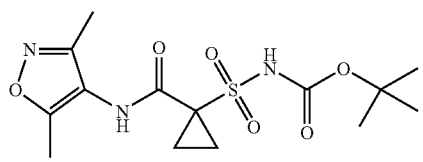

This compound was obtained in a crude 100% yield according to the procedure described for the synthesis of 1-methoxymethylcyclopropylsulfonylamine tert-butylcarbamate except that 1.20 equivalents of 3,5-dimethylisoxazole-4-isocyanate was used as the electrophile. The compound was taken directly into the next reaction without purification.

Step 2: Preparation of 1-(3,5-dimethylisoxazol-4-yl)carbamoylcyclopropanesulfonamide

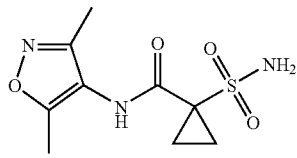

This compound was obtained in 50% yield (580 mg) from 1.62 g (4.52 mmol) of 1-(3,5-dimethylisoxazol-4-yl)carbamoylcyclo-propanesulfonamide tert-butylcarbamate using 30 mL (120 mmol) of 4N HCl/dioxanes, stirring overnight, concentration and chromatography over a Biotage 40M column (eluting with 0% to 5% methanol/dichloromethane: $^1$H NMR (methanol-$d_4$) δ 1.57 (m, 2H), 1.61 (m 2H), 2.15 (s, 3H), 2.30 (s, 3H), 4.84 (s, 3H); $^{13}$C NMR (methanol-$d_4$) δ 9.65, 10.94, 15.01, 46.11, 114.82, 159.45, 165.55, 168.15; LRMS m/z 260 (M$^+$+H).

4. Preparation of Cycloalkylsulfonamides from Cyloalkylbromides

4a. Preparation of Cyclobutylsulfonamide from Cyclobutyl Bromide

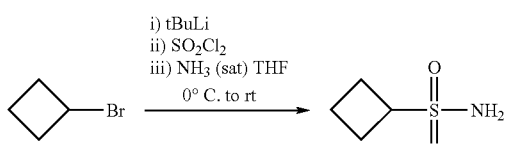

To a solution of 5.0 g (37.0 mmol) of cyclobutyl bromide in 30 mL of anhydrous diethyl ether (diethyl ether) cooled to −78° C. was added 44 mL (74.8 mmol) of 1.7M tert-butyllithium in pentanes. The solution was slowly warmed to −35° C. over 1.5 hours. This mixture was cannulated slowly into a solution of 5.0 g (37.0 mmol) of freshly distilled sulfuryl chloride in 100 mL of hexanes cooled to −40° C., warmed to 0° C. over 1 hour and carefully concentrated in vacuo. This mixture was redissolved in diethyl ether, washed once with some ice-cold water, dried (MgSO$_4$), filtered, and concentrated carefully. This mixture was redissolved in 20 mL of THF, added dropwise to 500 mL of saturated NH$_3$ in THF, and was allowed to stir overnight. The mixture was concentrated in vacuo to a crude yellow solid and was recrystallized from the minimum amount of dichloromethane in hexanes with 1-2 drops of methanol to provide 1.90 g (38%) of the desired product as a white solid. $^1$H NMR (CDCl$_3$) δ 1.95-2.06 (m, 2H), 2.30-2.54 (m, 4H), 3.86 (p, J=8 Hz, 1H), 4.75 (brs, 2H); $^{13}$C NMR (CDCl$_3$) δ 16.43, 23.93, 56.29. HRMS m/z (M−H)$^−$ calcd for C$_4$H$_8$NSO$_2$: 134.0276, found 134.0282.

4b. Preparation of Cyclopentyl Sulfonamide

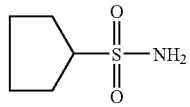

A solution of 18.5 mL (37.0 mmol) of 2M cyclopentylmagnesium chloride in ether was added dropwise to a solution of 3.0 mL (37.0 mmol) freshly distilled sulfuryl chloride (obtained from Aldrich) in 100 mL of hexanes cooled to −78° C. The mixture was warmed to 0° C. over 1 hour and was then carefully concentrated in vacuo. This mixture was redissolved in diethyl ether (200 mL), washed once with some ice-cold water (200 mL), dried (MgSO$_4$), filtered, and concentrated carefully. This mixture was redissolved in 35 mL of THF, added dropwise to 500 mL of saturated NH$_3$ in THF and was allowed to stir overnight. The mixture was concentrated in vacuo to a crude yellow solid, the residue filtered through 50 g of silica gel using 70% ethyl acetate-hexanes as the eluent and the solution was then concentrated. The residue was recrystallized from the minimum amount of dichloromethane in hexanes with 1-2 drops of methanol to provide 2.49 g (41%) of the desired product as a white solid. $^1$H NMR (CDCl$_3$) δ 1.58-1.72 (m, 2H), 1.74-1.88 (m, 2H), 1.94-2.14 (m, 4H), 3.48-3.59 (m, 1H), 4.80 (br s, 2H); $^{13}$C NMR (CDCl$_3$) δ 25.90, 28.33, 63.54; MS m/e 148 (M−H)$^−$.

4c. Preparation of Cyclohexyl Sulfonamide

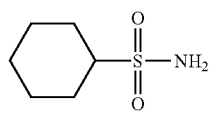

A solution of 18.5 mL (37.0 mmol) of 2M cyclohexylmagnesium chloride (TCI Americas) in diethyl ether was added dropwise to a solution of 3.0 mL (37.0 mmol) freshly distilled sulfuryl chloride in 100 mL of hexanes cooled to −78° C. The mixture was warmed to 0° C. over 1 hour and was then carefully concentrated in vacuo. This mixture was redissolved in diethyl ether (200 mL), washed once with some ice-cold water (200 mL), dried (MgSO$_4$), filtered, and concentrated carefully. This mixture was redissolved in 35 mL of THF, added dropwise to 500 mL of saturated NH$_3$ in THF and was allowed to stir overnight. The mixture was concentrated in vacuo to a crude yellow solid, the residue filtered through 50 g of silica gel using 70% ethyl acetate-hexanes as the eluent and was concentrated. The concentrate was recrystallized from the minimum amount of dichloromethane in hexanes with 1-2 drops of methanol to provide 1.66 g (30%) of the desired product as a white solid: $^1$H NMR (CDCl$_3$) δ 1.11-1.37 (m, 3H), 1.43-1.56 (m, 2H), 1.67-1.76 (m, 1H), 1.86-1.96 (m, 2H), 2.18-2.28 (m, 2H), 2.91 (tt, J=12, 3.5 Hz, 1H), 4.70 (br s, 2H); $^{13}$C NMR (CDCl$_3$) δ 25.04, 25.04, 26.56, 62.74; MS m/e 162 (M–1)$^-$.

4d. Preparation of Neopentylsulfonamide

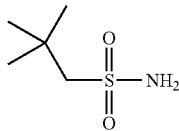

Following the procedure for the preparation of cyclohexylsulfonamide, 49 mL (37 mmol) of 0.75M neopentylmagnesium chloride (Alfa) in diethyl ether was converted to 1.52 g (27%) of the desired product as a white solid. $^1$H NMR (CDCl$_3$) δ 1.17 (s, 9H), 3.12 (s, 2H), 4.74 (brs, 2H); $^{13}$C NMR (CDCl$_3$) δ 29.46, 31.51, 67.38; MS m/e 150 (M–1)$^-$.

4e. Preparation of Cyclobutylcarbinylsulfonamide

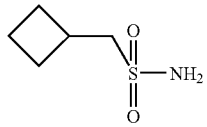

A solution of 12.3 g (83 mmol) of cyclobutylcarbinyl bromide (Aldrich) and 13.7 g (91 mmol) of sodium iodide in 150 mL of acetone was heated to reflux overnight and then cooled to room temperature. The inorganic solids were removed by filtration and the acetone and cyclopropylcarbinyl iodide (8.41 g, 46%) were removed by distillation (ambient temperature and 150 torr at 80° C., respectively).

A solution of 4.0 g (21.98 mmol) of cyclobutyl carbinyl iodide in 30 mL of anhydrous diethyl ether cooled to –78° C. was cannulated into a solution of 17 mL (21.98 mmol) of 1.3M sec-butyllithium in cyclohexanes and the solution was stirred for 5 minutes. To this mixture was cannulated a solution of 3.0 g (21.98 mmol) of freshly distilled sulfuryl chloride in 110 mL of hexanes cooled to –78° C., the mixture warmed to room temperature over 1 hour and was then carefully concentrated in vacuo. This mixture was redissolved in diethyl ether, washed once with some ice-cold water, dried (MgSO$_4$), filtered, and concentrated carefully. This mixture was redissolved in 30 mL of THF, added dropwise to 500 mL of saturated NH$_3$ in THF and was allowed to stir overnight. The mixture was concentrated in vacuo to a crude yellow solid and was recrystallized from the minimum amount of dichloromethane in hexanes with 1-2 drops of methanol to provide 1.39 g (42%) of the desired product as a white solid. $^1$H NMR (CDCl$_3$) δ 1.81-2.03 (m, 4H), 2.14-2.28 (m, 2H), 2.81-2.92 (m, 1H), 3.22 (d, J=7 Hz, 2H), 4.74 (brs, 2H); $^{13}$C NMR (CDCl$_3$) δ 19.10, 28.21, 30.64, 60.93. MS m/e 148 (M–H)$^-$.

4f. Preparation of Cyclopropylcarbinylsulfonamide

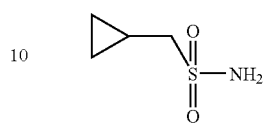

Using the procedure employed for the preparation of cyclobutylcarbinylsulfonamide, cyclopropylcarbinylsulfonamide was prepared from cyclopropylcarbinyl bromide (Aldrich) (see also *JACS* 1981, p. 442-445). $^1$H NMR (CDCl$_3$) δ 0.39-0.44 (m, 2H), 0.67-0.76 (m, 2H), 1.13-1.27 (m, 1H), 3.03 (d, J=7.3 Hz, 2H), 4.74 (brs, 2H); $^{13}$C NMR (CDCl$_3$) δ 4.33, 5.61, 59.93; MS m/e 134 (M–1).

4g. Preparation of 2-thiophenesulfonamide

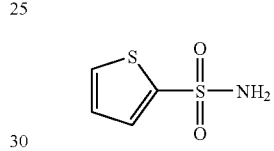

The desired product was prepared from 2-thiophenesulfonyl chloride (purchased from Aldrich) using the method described in *Justus Liebigs Ann. Chem.* 1933, 501, p. 174-182.

4h. Preparation of 4-bromobenzenesulfonamide

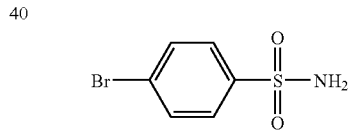

4-Bromophenylsulfonamide was prepared by treatment of commercially available 4-bromosulfonyl chloride with saturated ammonia in THF.

5. General Procedure for the Preparation of Sulfamides

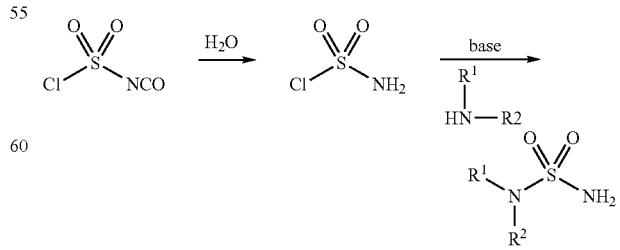

The intermediate sulfamoyl chloride was prepared by addition of water (1 equiv) in THF to a cold (–20° C.) stirred solution of chlorosulfonyl isocyanate (1 equiv) in THF and the resulting solution allowed to warm to 0° C. To this solution was added anhydrous triethylamine (1 equiv) followed by requisite secondary amine (1 equiv). The reaction mixture was warmed to room temperature, then filtered and the filtrate was concentrated to afford the desired sulfamides.

II Preparation of P1 Intermediates 5. 1-tert-Butoxycarbonylaminocyclopropane Carboxylic Acid is Commercially Available

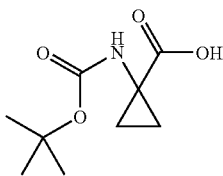

6. Preparation of 1-aminocyclobutanecarboxylic Acid Methyl ester-hydrochloride

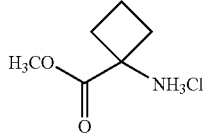

1-Aminocyclobutanecarboxylic acid (100 mg, 0.869 mmol)(Tocris) was dissolved in 10 mL of methanol. HCl gas was bubbled in for 2 hours. The reaction mixture was stirred for 18 hours, and then concentrated in vacuo to give 144 mg of a yellow oil. Trituration with 10 mL of diethyl ether provided 100 mg of the desired product as a white solid. $^1$H NMR (CDCl$_3$) δ 2.10-2.25 (m, 1H), 2.28-2.42 (m, 1H), 2.64-2.82 (m, 4H), 3.87 (s, 3H), 9.21 (br s, 3H).

7a. Preparation of (1R,2R)/(1S2S) 1-amino-2-ethylcyclopropanecarboxylic Acid tert-butyl Ester (Racemic Mixture)

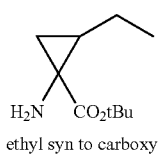
ethyl syn to carboxy

Step 1: Preparation of 2-ethylcyclopropane-1,1-dicarboxylic acid di-tert-butyl ester, Shown Below

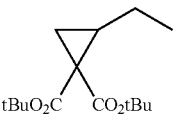

To a suspension of benzyltriethylammonium chloride (21.0 g, 92.2 mmol) in a 50% aqueous NaOH solution (92.4 g in 185 mL H$_2$O) was added 1,2-dibromobutane (30.0 g, 138.9 mmol) and di-tert-butylmalonate (20.0 g, 92.5 mmol). The reaction mixture was vigorously stirred for 18 hours at room temperature and treated with a mixture of ice and water. The crude product was extracted with dichloromethane (3×) and sequentially washed with water (3×), and brine. The organic extracts were combined, dried (MgSO$_4$), filtered, and concentrated in vacuo. The resulting residue was purified by flash column chromatography (100 g SiO$_2$, 3% diethyl ether in hexane) to provide the desired product (18.3 g, 67.8 mmol, 73% yield) which was used directly in the next reaction.

Step 2: Preparation of racemic 2-Ethylcyclopropane-1,1-dicarboxylic acid tert-butyl ester, Shown Below

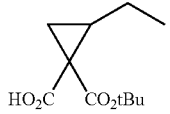

The product of Step 1 (18.3 g, 67.8 mmol) was added to a suspension of potassium tert-butoxide (33.55 g, 299.0 mmol) in dry diethyl ether (500 mL) at 0° C., treated with H$_2$O (1.35 mL, 75.0 mmol), and was vigorously stirred overnight at room temperature. The reaction mixture was poured in a mixture of ice and water and washed with diethyl ether (3×). The aqueous layer was adjusted to acidic pH with a 10% aqueous citric acid solution at 0° C. and extracted with ethyl acetate (3×). The combined organic layers were washed with water (2×), brine, dried (MgSO$_4$), filtered, and concentrated in vacuo to provide the desired product as a pale yellow oil (10 g, 46.8 mmol, 69% yield).

Step 3: Preparation of (1R,2R)/(1S,2S) 2-ethyl-1-(2-trimethylsilanylethoxycarbonylamino)cyclopropane-carboxylic Acid tert-butyl Ester, Shown Below

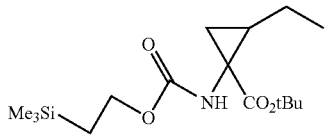

To a suspension of the product of Step 2 (10 g, 46.8 mmol) and 3 g of freshly activated 4 Å molecular sieves in dry benzene (160 mL) was added triethylamine (7.50 mL, 53.8 mmol) and DPPA (11 mL, 10.21 mmol). The reaction mixture was heated to reflux for 3.5 hours, treated with 2-trimethylsilylethanol (13.5 mL, 94.2 mmol), and heated to reflux overnight. The reaction mixture was filtered, diluted with diethyl ether, washed sequentially with 10% aqueous citric acid solution, water, saturated aqueous NaHCO$_3$, water (2×), and brine (2×), dried (MgSO$_4$), filtered, and concentrated in vacuo. The residue was suspended with 10 g of Aldrich polyisocyanate scavenger resin in 120 mL of dichloromethane, stirred at room temperature overnight, and filtered to provide the desired product (8 g, 24.3 mmol; 52%) as a pale yellow oil: $^1$H NMR (CDCl$_3$) δ 0.03 (s, 9H), 0.97 (m, 5H), 1.20 (br m, 1H), 1.45 (s, 9H), 1.40-1.70 (m, 4H), 4.16 (m, 2H), 5.30 (br s, 1H).

Step 4: Preparation of (1R,2R)/(1S,2S) 1-amino-2-ethylcyclopropanecarboxylic Acid tert-butyl Ester (Racemic Mixture) Shown Below

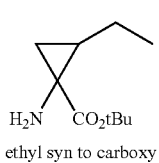

ethyl syn to carboxy

To the product of Step 3 (3 g, 9 mmol) was added a 1.0M TBAF solution in THF (9.3 mL, 9.3 mmol). The mixture was heated to reflux for 1.5 hours, cooled to room temperature, and diluted with 500 mL of ethyl acetate. The solution was successively washed with water (2×100 mL) and brine (2×100 mL), dried (MgSO$_4$), filtered, and concentrated in vacuo to provide the desired product.

7b. A General Method for the Conversion of Compounds of Formula I Bearing a P1 Vinyl P1 Substituent to the Corresponding Saturated P1 Analogue as Shown

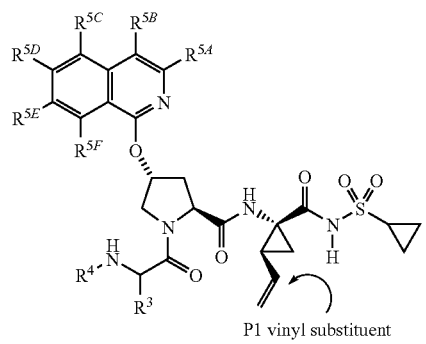

Compound A

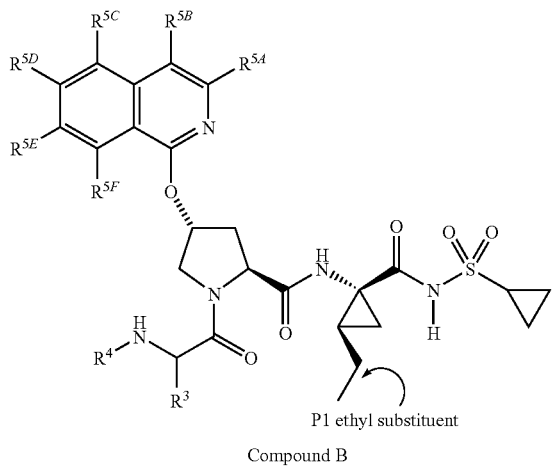

Compound B

A suspension of Compound A (approximately 100 mg) and Pt(S)/C (5%, 10 mg) in approximately 15 mL of EtOAc was hydrogenated, H$_2$ (30 PSI) for 0.5 h. After filtration through a Ceilite plug, the filtrate was concentrated and purified to give the desired product, Compound B.

8. Preparation of Racemic (1R,2S)/(1S,2R)-1-amino-2-vinylcyclopropane Carboxylic Acid Ethyl Ester Scheme 1

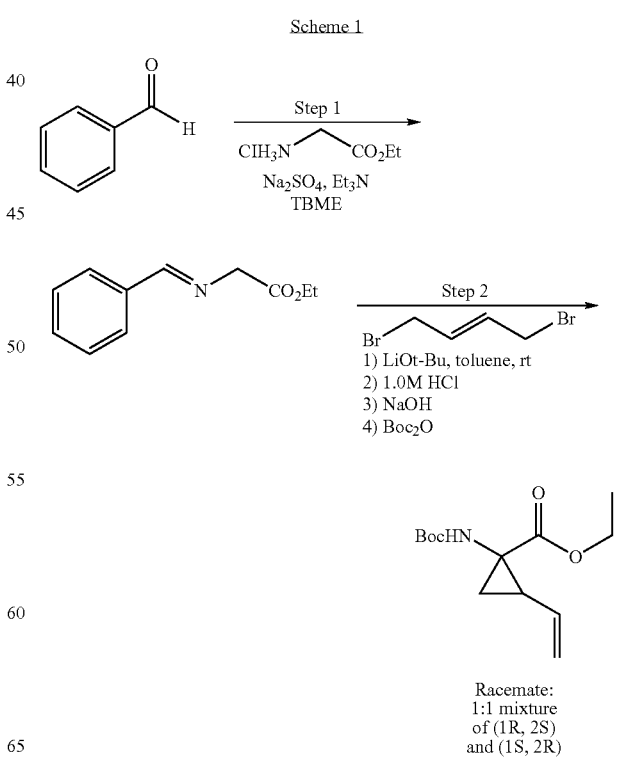

Racemate: 1:1 mixture of (1R, 2S) and (1S, 2R)

Step 1:

Glycine ethyl ester hydrochloride (304 g, 2.16 mole) was suspended in tert-butylmethyl ether (1.6 L). Benzaldehyde (231 g, 2.16 mole) and anhydrous sodium sulfate (155 g, 1.09 mole) were added, and the mixture was cooled to 0° C. using an ice-water bath. Triethylamine (455 mL, 3.26 mole) was added dropwise over 30 minutes and the mixture was stirred for 48 hours at room temperature. The reaction was then quenched by addition of ice-cold water (1 L) and the organic layer was separated. The aqueous phase was extracted with tert-butylmethyl ether (0.5 L) and the organic phases were combined and washed with a mixture of saturated aqueous $NaHCO_3$ (1 L) and brine (1 L). The organic layer was dried over $MgSO_4$, filtered, and concentrated in vacuo to provide 392.4 g of the N-benzyl imine product as a thick yellow oil that was used directly in the next step. $^1$H NMR ($CDCl_3$, 300 MHz) δ 1.32 (t, J=7.1 Hz, 3H), 4.24 (q, J=7.1 Hz, 2H), 4.41 (d, J=1.1 Hz, 2H), 7.39-7.47 (m, 3H), 7.78-7.81 (m, 2H), 8.31 (s, 1H).

Step 2:

To a suspension of lithium tert-butoxide (84.1 g, 1.05 mol) in dry toluene (1.2 L), was added dropwise a mixture of the N-benzyl imine of glycine ethyl ester (100 g, 0.526 mol) and trans-1,4-dibromo-2-butene (107 g, 0.500 mol) in dry toluene (0.6 L) over 60 minutes. Upon completion of the addition, the deep red mixture was quenched by addition of water (1 L) and tert-butylmethyl ether (TBME, 1 L). The aqueous phase was separated and extracted a second time with TBME (1 L). The organic phases were combined, 1.0M HCl (1 L) was added and the mixture stirred at room temperature for 2 hours. The organic phase was separated and extracted with water (0.8 L). The aqueous phases were then combined, saturated with salt (700 g), and TBME (1 L) was added and the mixture was cooled to 0° C. The stirred mixture was then made basic to pH=14 by the dropwise addition of 1010M NaOH, the organic layer was separated, and the aqueous phase was extracted with TBME (2×500 mL). The organic extracts were combined, dried over $MgSO_4$, filtered and concentrated to a volume of 1 L. To this solution of free amine was added $Boc_2O$ or di-tert-butyldicarbonate (131 g, 0.600 mol) and the mixture stirred for 4 days at room temperature. Additional di-tert-butyldicarbonate (50 g, 0.23 mol) was added to the reaction and the mixture was refluxed for 3 hours and was then allowed cool to room temperature overnight. The reaction mixture was dried over $MgSO_4$, filtered, and concentrated in vacuo to provide 80 g of crude material. This residue was purified by flash chromatography (2.5 kg of $SiO_2$, eluted with 1% to 2% $CH_3OH/CH_2Cl_2$) to provide 57 g (53%) of racemic N-Boc-(1R,2S)/(1S,2R)-1-amino-2-vinylcyclopropane carboxylic acid ethyl ester as a yellow oil which solidified while sitting in the refrigerator: $^1$H NMR ($CDCl_3$, 300 MHz) δ 1.26 (t, J=7.1 Hz, 3H), 1.46 (s, 9H), 1.43-1.49 (m, 1H), 1.76-1.82 (br m, 1H), 2.14 (q, J=8.6 Hz, 1H), 4.18 (q, J=7.2 Hz, 2H), 5.12 (dd J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M−1).

9. Resolution of N-Boc-(1R,2S)/(1S,2R)-1-amino-2-vinylcyclopropane Carboxylic Acid Ethyl Ester

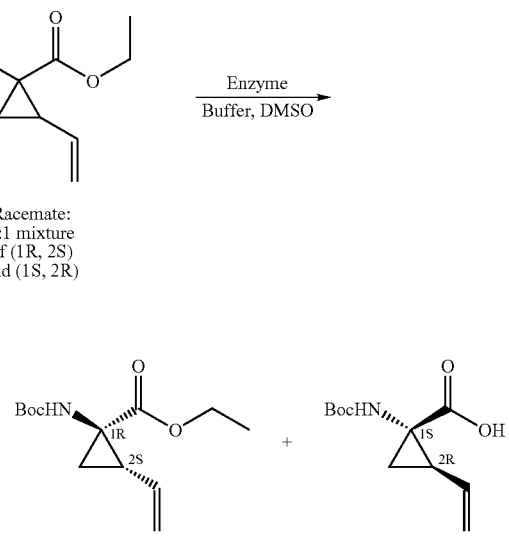

Scheme 2

Racemate:
1:1 mixture
of (1R, 2S)
and (1S, 2R)

Resolution A

To an aqueous solution of sodium phosphate buffer (0.1 M, 4.25 liter ("L"), pH 8) housed in a 12 Liter jacked reactor, maintained at 39° C., and stirred at 300 rpm was added 511 grams of Alcalase 2.4 L (about 425 mL) (Novozymes North America Inc.). When the temperature of the mixture reached 39° C., the pH was adjusted to 8.0 by the addition of a 50% NaOH in water. A solution of the racemic N-Boc-(1R,2S)/(1S,2R)-1-amino-2-vinylcyclopropane carboxylic acid ethyl ester (85 g) in 850 mL of DMSO was then added over a period of 40 minutes. The reaction temperature was then maintained at 40° C. for 24.5 hours during which time the pH of the mixture was adjusted to 8.0 at the 1.5 hour and 19.5 hour time points using 50% NaOH in water. After 24.5 hours, the enantio-excess of the ester was determined to be 97.2%, and the reaction was cooled to room temperature (26° C.) and stirred overnight (16 hours) after which the enantio-excess of the ester was determined to be 100%. The pH of the reaction mixture was then adjusted to 8.5 with 50% NaOH and the resulting mixture was extracted with MTBE (2×2 L). The combined MTBE extract was then washed with 5% $NaHCO_3$ (3×100 mL), water (3×100 mL), and concentrated in vacuo to give the enantiomerically pure N-Boc-(1R,2S)/-1-amino-2-vinylcyclopropane carboxylic acid ethyl ester as light yellow solid (42.55 g; purity: 97% @ 210 nm, containing no acid; 100% enantiomeric excess ("ee").

The aqueous layer from the extraction process was then acidified to pH 2 with 50% $H_2SO_4$ and extracted with MTBE (2×2 L). The MTBE extract was washed with water (3×100 mL) and concentrated to give the acid as light yellow solid (42.74 g; purity: 99% @ 210 nm, containing no ester).

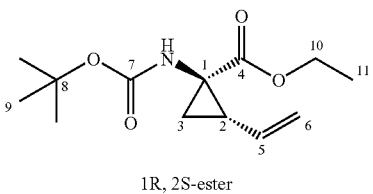

1R, 2S-ester

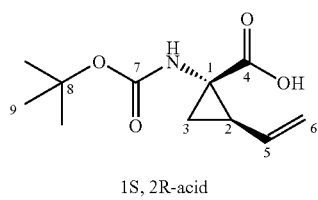

1S, 2R-acid

|  | ester | acid |
|---|---|---|
| High Resolution Mass Spec | (+) ESI, $C_{13}H_{22}NO_4$, $[M + H]^+$, calcd. 256.1549, found 256.1542 | (−) ESI, $C_{11}H_{16}NO_4$, $[M − H]^−$, calcd. 226.1079, found 226.1089 |

NMR observed chemical shift
Solvent: $CDCl_3$ (proton δ 7.24 ppm, C-13 δ 77.0 ppm)
Bruker DRX-500C: proton 500.032 MHz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10(q, J=9.0Hz) | 34.1 | 2.17(q, J=9.0Hz) | 35.0 |
| 3a | 1.76(br) | 23.2 | 1.79(br) | 23.4 |
| 3b | 1.46(br) |  | 1.51, (br) |  |
| 4 | — | 170.8 | — | 175.8 |
| 5 | 5.74 (ddd, J= 9.0, 10.0, 17.0Hz) | 133.7 | 5.75(m) | 133.4 |
| 6a | 5.25 (d, J= 17.0Hz) | 117.6 | 5.28(d, J= 17.0Hz) | 118.1 |
| 6b | 5.08 (dd, J= 10.0, 1.5Hz) |  | 5.12(d, J= 10.5Hz) |  |
| 7 | — | 155.8 | — | 156.2 |
| 8 | — | 80.0 | — | 80.6 |
| 9 | 1.43(s) | 28.3 | 1.43(s) | 28.3 |
| 10 | 4.16(m) | 61.3 | — | — |
| 11 | 1.23(t, J=7.5Hz) | 14.2 | — | — |

Resolution B

To 0.5 mL 100 mM Heps.Na buffer (pH 8.5) in a well of a 24 well plate (capacity: 10 mL/well), 0.1 mL of Savinase 16.0 L (protease from *Bacillus clausii*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hours, enantio-excess of the ester was determined to be 44.3% as following: 0.1 mL of the reaction mixture was removed and mixed well with 1 mL ethanol; after centrifugation, 10 microliter ("μL") of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 μL of the supernatant was analyzed with the chiral HPLC and enantio-excess of the ester was determined to be 100%.

Resolution C

To 0.5 mL 100 mM Heps.Na buffer (pH 8.5) in a well of a 24 well plate (capacity: 10 mL/well), 0.1 mL of Esperase 8.0 L, (protease from *Bacillus halodurans*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hour, enantio-excess of the ester was determined to be 39.6% as following: 0.1 mL of the reaction mixture was removed and mixed well with 1 mL ethanol; after centrifugation, 10 μL of the supernatant was analyzed with the chiral HPLC. To the remaining reaction mixture, 0.1 mL of DMSO was added, and the plate was incubated for additional 3 days at 250 rpm at 40° C., after which 4 mL of ethanol was added to the well. After centrifugation, 10 μL of the supernatant was analyzed with the chiral HPLC and enantio-excess of the ester was determined to be 100%.

Samples analysis was carried out in the following manner:
1) Sample preparation: About 0.5 mL of the reaction mixture was mixed well with 10 volume of ethanol. After centrifugation, 10 μL of the supernatant was injected onto HPLC column.
2) Conversion determination:
Column: YMC ODS A, 4.6×50 mm, S-5 μm
Solvent: A, 1 mM HCl in water; B, $CH_3CN$
Gradient: 30% B for 1 min; 30% to 45% B over 0.5 min; 45% B for 1.5 min; 45% to 30% B over 0.5 minutes.
Flow rate: 2 mL/min
UV Detection: 210 nm
Retention time: acid, 1.2 min; ester, 2.8 minutes.
3) Enantio-excess determination for the ester:
Column: CHIRACEL OD-RH, 4.6×150 mm, S-5 μm
Mobile phase: $CH_3CN$/50 mM $HClO_4$ in water (67/33)
Flow rate: 0.75 mL/min.
UV Detection: 210 nm.
Retention time:
(1S,2R)-1-amino-2-vinylcyclopropane carboxylic acid 5.2 min;
Racemate (1R,2S)/(1S,2R)-1-amino-2-vinylcyclopropane carboxylic acid ethyl ester 18.5 minutes and 20.0 min;
(1R,2S)-1-amino-2-vinylcyclopropane carboxylic acid ethyl ester 18.5 minutes.

Resolution D

5 L of 0.3 M sodium phosphate buffer (pH 8) was maintained at 38° C. in a 20 Liter jacked reactor, stirred at 130 rpm. Four liters of Alcalase 2.4 L (Novozymes North America Inc.) and 1 liter of DI water were added to the reactor. When temperature of the mixture closed to 38° C., pH was adjusted to 7.8 with 10 N NaOH. A solution of the racemic N-Boc-(1R,2S)/(1S,2R)-1-amino-2-vinylcyclopropane carboxylic acid ethyl ester (500 grams) in 5 liters DMSO was added to the reactor over a period of 1 hour via an addition funnel. The reaction temperature was then adjusted to 48° C. After 21 hours, enantio-excess of the ester reached 99.3%. Heating was stopped at 24 hours and the reaction was slowly cooled down to room temperature (about 25° C.) and stirred overnight. The pH of the reaction mixture was adjusted to 8.5 with 10 N NaOH and the mixture was extracted with MTBE (2×4 L). The combined MTBE extract was washed with 5% $NaHCO_3$ (3×400 mL) and water (3×400 mL), and concentrated to give enantiomerically pure N-Boc-(1R,2S)/-1-amino-2-vinylcyclopropane carboxylic acid ethyl ester as light yellow crystal (259 g; purity: 96.9% (210 nm, containing no acid; 100% ee).

Resolution E

10 L of 0.1 M sodium phosphate buffer (pH 8) was maintained at 40° C. in a 20 Liter jacked reactor, stirred at 360 rpm. 1.5 liters of Alcalase 2.4 L (Novozymes North America Inc.)

was added to the reactor. When the temperature of the mixture closed to 38° C., the pH was adjusted to 8.0 with 10 N NaOH. A solution of the racemic N-Boc-(1R,2S)/(1S,2R)-1-amino-2-vinylcyclopropane carboxylic acid ethyl ester (200 grams) in 2 liters DMSO was added to the reactor over a period of 1 hour via an addition funnel. The reaction temperature was then adjusted to 40° C. After 3 hours, the pH was adjusted to 8.0 with 10 N NaOH. After 21 hours, the reaction was cooled down to 25° C., the pH of the reaction mixture was adjusted to 8.5 with 10 N NaOH and the mixture was extracted with MTBE (2×5 L). The combined MTBE extract was washed with 5% NaHCO$_3$ (3×500 mL) and water (3×200 mL), and concentrated to give 110 gram of yellow oil. The oil was set at room temperature under house vacuum and gave enantiomerically pure N-Boc-(1R,2S)/-1-amino-2-vinylcyclopropane carboxylic acid ethyl ester as colorless long rod crystal (101 g; purity: 97.9% @ 210 nm, containing no acid; 100% ee).

The crystal structure enantiomerically pure N-Boc-(1R, 2S)/-1-amino-2-vinylcyclopropane carboxylic acid ethyl ester has been characterized by single crystal analysis (X-ray NB#: 52795-093, refcode: 634592N1). The absolute configuration is not established for lack of a known chiral center or heavier atom(s). A chain structure along the crystallographic a-axis is formed via intermolecular hydrogen bonding between the amide group and the carbonyl oxygen atom (N . . . O 3.159 Å).

Structure of N-Boc-(1R,2S)-1-amino-2-vinylcyclopropane carboxylic acid ethyl ester:

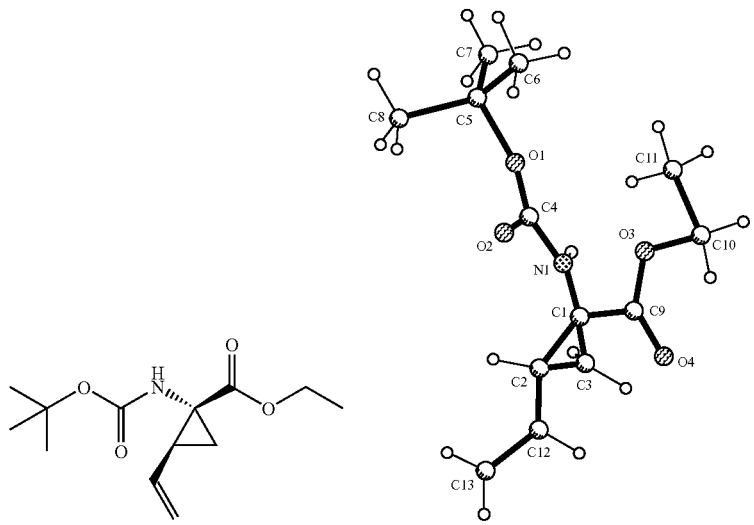

| Crystal Data: | Experimental: |
|---|---|
| Chemical formula: C13H21N1O4 | Crystallization |
| Crystal system: Orthorhombic | Crystal source: MTBE |
| Space Group: P2$_1$2$_1$2$_1$ | Crystal description: Colorless rod |
| a = 5.2902(1) Å α = 90° | Crystal size (mm): 0.12 × 0.26 × 0.30 |
| b = 13.8946(2) Å β = 90° | Data Collection |
| c = 19.9768(3) Å γ = 90° | Temperature (K.): 293 |
| V = 1468.40(4) Å$^3$ | θ$_{max}$ (°): 65.2 (Cu Kα) |
| Z = 4 d$_x$ = 1.155 g cm$^{-3}$ | No. of reflections measured: 7518 |
| No. of reflections for lattice parameters: 6817 | No. of independent reflections: 2390 (R$_{int}$ = 0.0776) |
| θrange for lattice parameters (°): 2.2-65.2 | No. of observed reflections (I ≧ 2σ: 2284 |
| Absorption coefficient (mm$^{-1}$): 0.700 | Absorption correction (T$_{min}$-T$_{max}$): 0.688-1.000 |

Resolution F

5 L of 0.2 M sodium borate buffer (pH 9) was maintained at 45° C. in a 20 liter jacked reactor, and stirred at 400 rpm. Three liter of DI water and four liters of Savinase 16 L, type EX (Novozymes North America Inc.) were added to the reactor. When temperature of the mixture closed to 45° C., pH was adjusted to 8.5 with 10 N NaOH. A solution of the racemic N-Boc-(1R,2S)/(1S,2R)-1-amino-2-vinylcyclopropane carboxylic acid ethyl ester (200 grams) in 2 liters DMSO was added to the reactor over a period of 40 minutes, via an addition funnel. The reaction temperature was then adjusted to 48° C. After 2 hours, pH was adjusted to pH 9.0 with 10 N NaOH. At 18 hour, enantio-excess of the ester reached 72%, pH was adjusted to 9.0 with 10 N NaOH. At 24 hours, temperature was lowered to 35° C. At 42 hours, the temperature was raised to 48° C. and the pH was adjusted to 9.0 with 10 N NaOH. Heating was stopped at 48 hours and the reaction was slowly cooled down to room temperature (about 25° C.) and stirred overnight. At 66 hour, pH of the reaction mixture was 8.6. The mixture was extracted with MTBE (2×4 L). The combined MTBE extract was washed with 5% NaHCO$_3$ (6×300 mL) and water (3×300 mL), and concentrated to give enantiomerically pure N-Boc-(1R,2S)/-1-amino-2-vinylcyclopropane carboxylic acid ethyl ester as light yellow crystal (101A g; purity: 95.9% @ 210 nm, containing no acid; 98.6% ee).

10. Preparation of Chiral (1R,2S)-1-amino-2-vinylcyclopropane Carboxylic Acid Ethyl Ester Hydrochloride

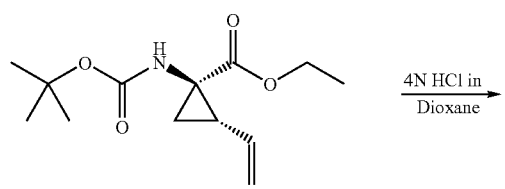

(1R,2S) N-Boc-1-amino-2-vinylcyclopropanecarboxylic acid ethyl ester (8.5 g, 33.3 mmol) was stirred under a nitrogen atmosphere with 200 mL of 4N HCl/dioxane (Aldrich) at room temperature for 3 hours. The solvent was removed under reduced pressure keeping the temperature below 40° C. This gave 6.57 g (~100%) of (1R,2S)-1-amino-2-vinylcyclopropanecarboxylic acid ethyl ester hydrochloride as a light tan solid. $^1$H NMR (300 MHz, CD$_3$OD) δ 1.31 (t, J=7.0 Hz, 3H), 1.69-1.82 (m, 2H), 2.38 (q, J=8.8 Hz, 1H), 4.29 (q, J=7.0 Hz, 2H), 5.22 (d, J=10.3 Hz, 1H), 5.40 (d, J=17.2 Hz, 1H), 5.69-5.81 (m, 1H). MS m/z 156 (M$^+$+1).

11. Preparation of N-Boc-(1R,2S)-1-amino-2-cyclopropylcyclopropane Carboxylic Acid Ethyl Ester

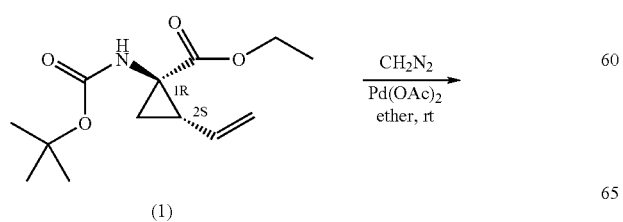

(1)

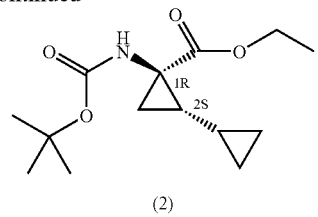

(2)

A solution of N-Boc-(1R,2S)-1-amino-2-vinylcyclopropane carboxylic acid (255 mg, 1.0 mmol) in diethyl ether (10 mL) was treated with palladium acetate (5 mg, 0.022 mmol). The orange/red solution was placed under a nitrogen atmosphere. An excess of diazomethane in diethyl ether was added dropwise over the course of 1 hour. The resulting solution was stirred at room temperature for 18 hours. The excess diazomethane was removed using a stream of nitrogen and the resulting solution was concentrated by rotary evaporation to give the crude product. Flash chromatography (10% ethyl acetate/hexane) provided 210 mg (78%) of (1R,2S)—N-Boc-1-amino-2-cyclopropylcyclopropane carboxylic acid ethyl ester as a colorless oil. MS m/z 270 (M$^+$+H).

III. Preparation of P1'-P1 Intermediates

12. Preparation of P1-P1'

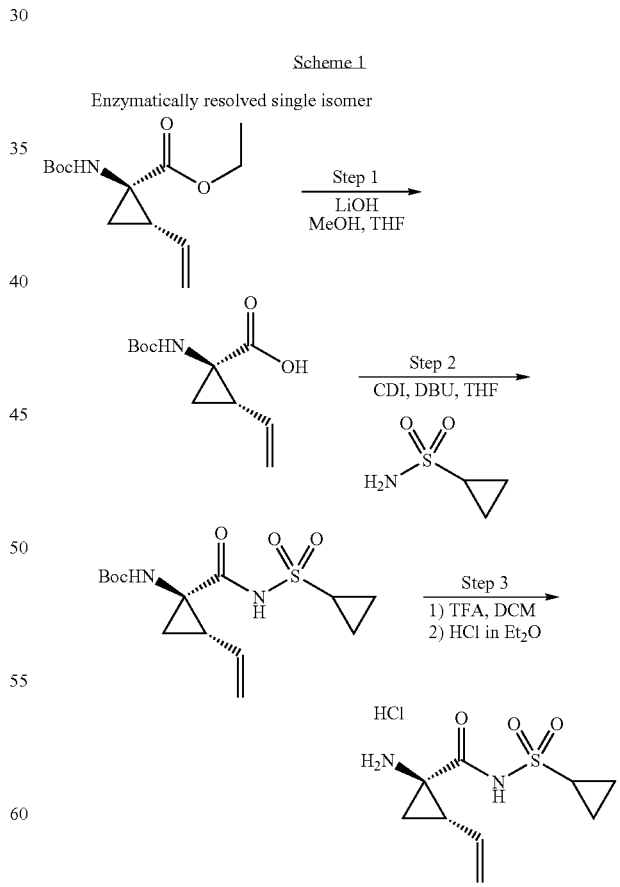

Step 1:

To a solution of 1(R)-tert-butoxycarbonylamino-2(S)-vinyl-cyclopropanecarboxylic acid ethyl ester (3.28 g, 13.2 mmol) in THF (7 mL) and methanol (7 mL) was added a suspension of LiOH (1.27 g, 53.0 mmol) in water (14 mL). The mixture was stirred overnight at room temperature. To the mixture was added 10M NaOH (15 mL), water (20 mL) and ethyl acetate (20 mL). The mixture was shaken, the phases were separated, and the organic phase was again extracted with 20 mL 0.5M NaOH. The combined aqueous phases were acidified with 1.0M HCl until pH=4 and extracted with ethyl acetate (3×40 mL). The combined organic extracts were washed with brine, dried (MgSO$_4$), and filtered to provide the desired product as a white solid (2.62 g, 87%). $^1$H NMR: (DMSO-d$_6$) δ1.22-1.26 (m, 1H), 1.37 (s, 9H), 1.50-1.52 (m, 1H), 2.05 (q, J=9 Hz, 1H), 5.04 (d, J=10 Hz, 1H), 5.22 (d, J=17 Hz, 1H), 5.64-5.71 (m, 1H), 7.18, 7.53 (s, NH (rotamers), 12.4 (br s, 1H)); LC-MS MS m/z 228 (M$^+$+H).

Step 2:

A solution of the product of Step 1 (2.62 g, 11.5 mmol) and CDI (2.43 g, 15.0 mmol) in THF (40 mL) was heated at reflux for 50 minutes under nitrogen. The solution was cooled to room temperature and transferred by cannula to a solution of cyclopropylsulfonamide (1.82 g, 15.0 mmol) in THF (10 mL). To the resulting solution was added DBU (2.40 mL, 16.1 mmol) and stirring was continued for 20 hours. The mixture was quenched with 1.0M HCl to pH=1, and THF was evaporated in vacuo. The suspension was extracted with ethyl acetate (2×50 mL) and the organic extracts were combined and dried (Na$_2$SO$_4$). Filtration, concentration, and purification by recrystallization from hexanes-ethyl acetate (1:1) provideed the desired product (2.4 g) as a white solid. The mother liquor was purified by a Biotage 40S column (eluted 9% acetone in dichloromethane) to give a second batch of the desired product (1.1 g). Both batches were combined (total yield 92%). $^1$H NMR: (DMSO-d$_6$) δ 0.96-1.10 (m, 4H), 1.22 (dd, J=5.5, 9.5 Hz, 1H), 1.39 (s, 9H), 1.70 (t, J=5.5 Hz, 1H), 2.19-2.24 (m, 1H), 2.90 (m, 1H), 5.08 (d, J=10 Hz, 1H), 5.23 (d, J=17 Hz, 1H), 5.45 (m, 1H), 6.85, 7.22 (s, NH (rotamers)); LC-MS, MS m/z 331 (M$^+$+H).

Step 3:

A solution of the product of Step 2 (3.5 g, 10.6 mmol) in dichloromethane (35 mL) and TFA (32 mL) was stirred at room temperature for 1.5 hours. The volatiles were removed in vacuo and the residue suspended in 1.0M HCl in diethyl ether (20 mL) and concentrated in vacuo. This procedure was repeated once. The resulting mixture was triturated with pentane and filtered to give the title compound as a hygroscopic, off-white solid (2.60 g, 92%). $^1$H NMR (DMSO-d$_6$) δ 1.01-1.15 (m, 4H), 1.69-1.73 (m, 1H), 1.99-2.02 (m, 1H), 2.38 (q, J=9 Hz, 1H), 2.92-2.97 (m, 1H), 5.20 (d, J=11 Hz, 1H), 5.33 (d, J=17 Hz, 1H), 5.52-5.59 (m, 1H), 9.17 (br s, 3H); LC-MS, MS m/z 231 (M$^+$+H).

13. Preparation of P1-P1' Sulfamide Derivative

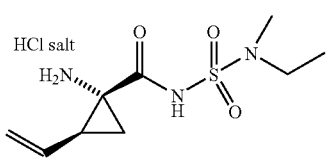

To a solution of (1R,2S) 1-tert-butoxycarbonylamino-2-vinyl-cyclopropanecarboxylic acid (217 mg, 1.194 mmol) in THF (5 mL), was added CDI (290 mg, 1.791 mmol) and the reaction mixture was heated to reflux for 45 minutes. In another round-bottomed flask, LiHMDS (1.0M solution in hexanes, 2.4 mL, 2.4 mmol) was added to a solution of N-ethylmethylsulfamide (330 mg, 2.388 mmol) in THF (5 mL) and the reaction mixture was stirred at room temperature for 1 hour. The two reaction mixtures were combined and stirred at room temperature for 2 hours. Water was added to quench the reaction and the reaction solution was extracted with ethyl acetate. The organic layer was separated and dried over MgSO$_4$. Filtration and concentration gave crude product which was purified by preparative HPLC to provide the desired N-Boc protected N-acylsulfamide. The Boc protecting group was then removed as the compound was dissolved in 4N HCl solution in dioxane (2 mL) and stirred at room temperature for 4 hours. Concentration provided a brownish oil as the HCl salt. (112 mg, 33% yield). $^1$H NMR (400Mz, CD$_3$OD) δ 1.16 (t, J=7.21 Hz, 3H), 1.68 (dd, J=10.03, 7.83 Hz, 1H), 2.15 (m, 1H), 2.37 (m, 1H), 2.89 (s, 3H), 3.30 (m, 2H), 5.31 (d, J=10.27 Hz, 1H), 5.42 (d, J=17.12 Hz, 3H), 5.68 (m, 1H). LC-MS (retention time: 0.883 minutes.), MS m/z 270 (M+Na$^+$).

Compound 1 Isomers

N-(4,6-dimethyl-2-pyridinyl)-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide and N-(4,6-dimethyl-2-pyridinyl)-D-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide Example 1

Preparation of Compounds 1A ad 1B

Compounds 1A and 1B

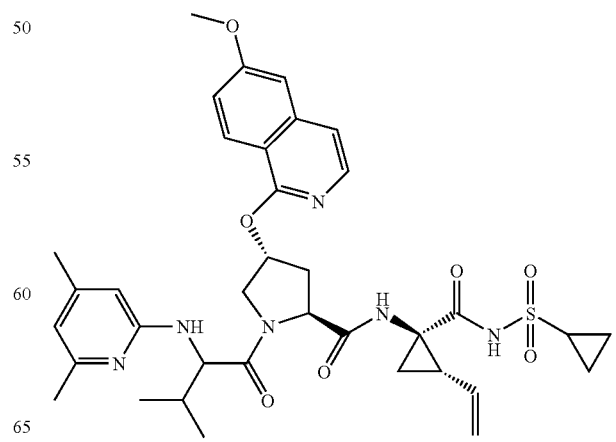

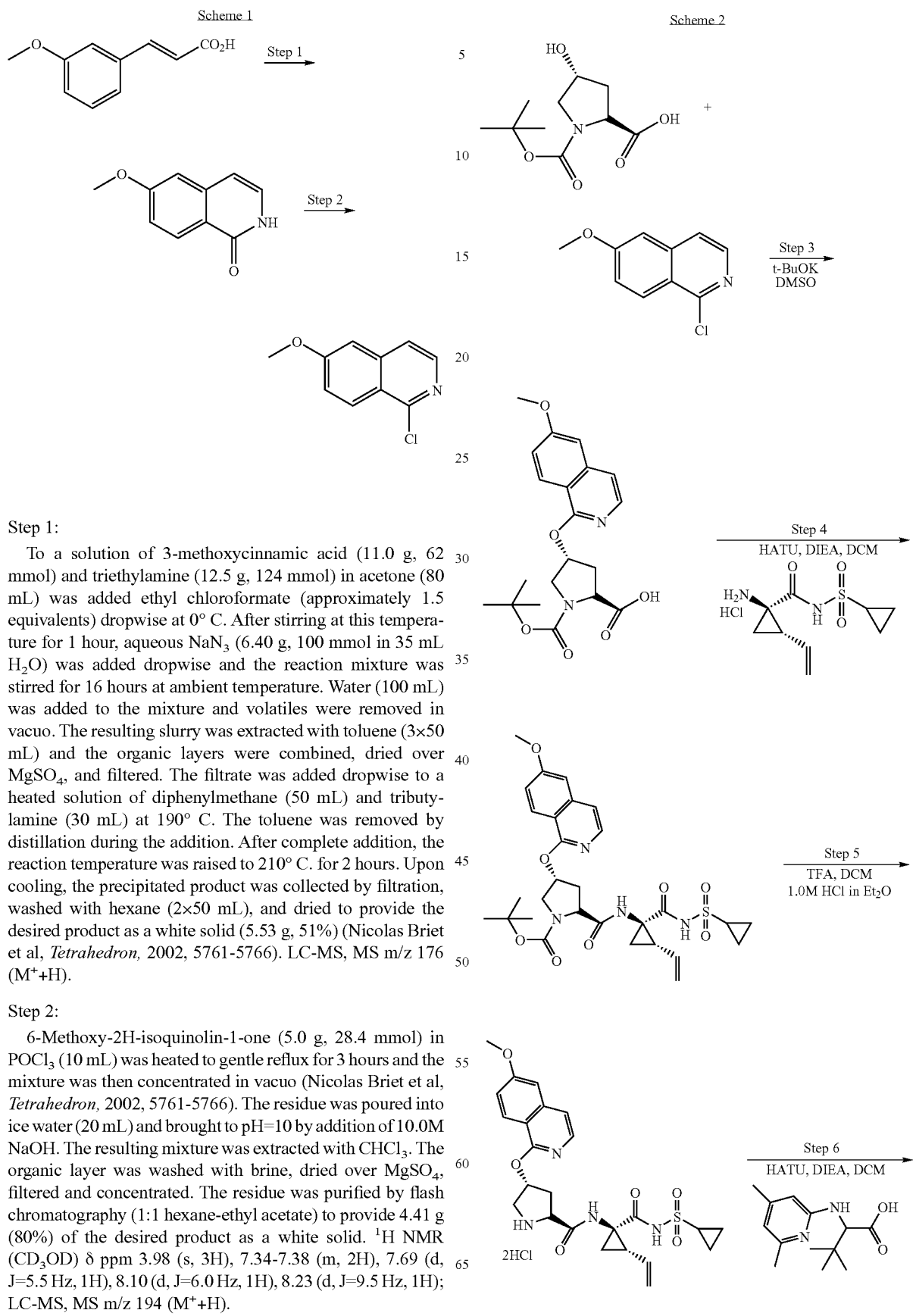

Scheme 1

Scheme 2

Step 1:

To a solution of 3-methoxycinnamic acid (11.0 g, 62 mmol) and triethylamine (12.5 g, 124 mmol) in acetone (80 mL) was added ethyl chloroformate (approximately 1.5 equivalents) dropwise at 0° C. After stirring at this temperature for 1 hour, aqueous $NaN_3$ (6.40 g, 100 mmol in 35 mL $H_2O$) was added dropwise and the reaction mixture was stirred for 16 hours at ambient temperature. Water (100 mL) was added to the mixture and volatiles were removed in vacuo. The resulting slurry was extracted with toluene (3×50 mL) and the organic layers were combined, dried over $MgSO_4$, and filtered. The filtrate was added dropwise to a heated solution of diphenylmethane (50 mL) and tributylamine (30 mL) at 190° C. The toluene was removed by distillation during the addition. After complete addition, the reaction temperature was raised to 210° C. for 2 hours. Upon cooling, the precipitated product was collected by filtration, washed with hexane (2×50 mL), and dried to provide the desired product as a white solid (5.53 g, 51%) (Nicolas Briet et al, *Tetrahedron*, 2002, 5761-5766). LC-MS, MS m/z 176 ($M^+$+H).

Step 2:

6-Methoxy-2H-isoquinolin-1-one (5.0 g, 28.4 mmol) in $POCl_3$ (10 mL) was heated to gentle reflux for 3 hours and the mixture was then concentrated in vacuo (Nicolas Briet et al, *Tetrahedron*, 2002, 5761-5766). The residue was poured into ice water (20 mL) and brought to pH=10 by addition of 10.0 M NaOH. The resulting mixture was extracted with $CHCl_3$. The organic layer was washed with brine, dried over $MgSO_4$, filtered and concentrated. The residue was purified by flash chromatography (1:1 hexane-ethyl acetate) to provide 4.41 g (80%) of the desired product as a white solid. $^1$H NMR ($CD_3OD$) δ ppm 3.98 (s, 3H), 7.34-7.38 (m, 2H), 7.69 (d, J=5.5 Hz, 1H), 8.10 (d, J=6.0 Hz, 1H), 8.23 (d, J=9.5 Hz, 1H); LC-MS, MS m/z 194 ($M^+$+H).

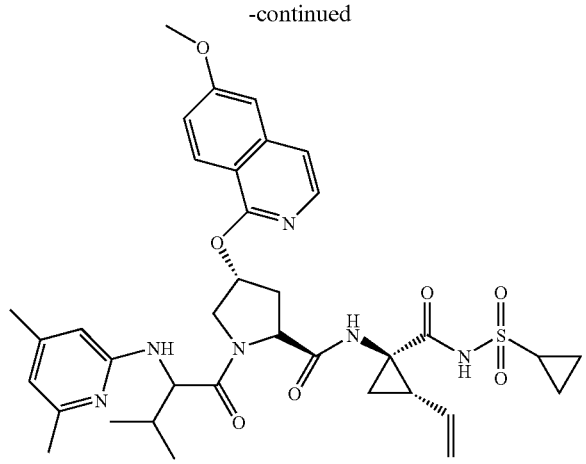

Compounds 1A and 1B
mixture of two isomers

Step 3:

To a solution of N-Boc-4-(R)-hydroxy-L-proline (0.892 g, 3.89 mmol) in DMSO (40 mL) at ambient temperature was added solid potassium tert-butoxide (1.34 g, 12.0 mmol) in one portion. The suspension was stirred at room temperature for 30 minutes before being cooled to 10° C. 1-Chloro-6-methoxy-isoquinoline (the product of Step 2, Example 1) (785 mg, 4.05 mmol) was added as a solid in one portion and the resulting mixture was stirred at ambient temperature for 12 hours. The mixture was quenched with ice cold 5% citric acid (aq) and was then extracted with ethyl acetate (100 mL). The aqueous phase was extracted with ethyl acetate once more. The combined organic layers were washed with 5% citric acid (aq) and brine respectively, dried over $MgSO_4$ and filtered. The filtrate was concentrated in vacuo to dryness to provide the desired product as an off-white foam (1.49 g, 99% yield). This crude material was used in the next reaction step without further purification. $^1$H NMR ($CD_3OD$) δ 1.42, 1.44 (rotamers, 9H), 2.38-2.43 (m, 1H), 2.66-2.72 (m, 1H), 3.80-3.87 (m, 2H), 3.92 (s, 3H), 4.44-4.52 (m, 1H), 5.73 (bs, 1H), 7.16-7.18 (m, 2H), 7.24-7.25 (m, 1H), 7.87-7.88 (m, 1H), 8.07 (d, J=8.5 Hz, 1H); LC-MS, MS m/z 389 ($M^+$+H).

Step 4:

To a mixture of the product of Step 3, Example 1 (1.49 g, 3.84 mmol), HATU (2.19 g, 5.76 mmol) and cyclopropanesulfonic acid (1-(R)-amino-2-(S)-vinyl-cyclopropanecarbonyl)-amide HCl salt (1.12 g, 4.22 mmol) in $CH_2Cl_2$ (50 mL) was added DIPEA (1.29 g, 11.5 mmol) at 0° C. After stirring at ambient temperature for 12 hours, the resulting solution was diluted with $CH_2Cl_2$ (50 mL) and washed with ice cold 5% citric acid (aq). The organic layer was washed with 5% citric acid (aq) and brine respectively, dried over $MgSO_4$ and filtered. The filtrate was concentrated in vacuo to dryness. The residue was recrystallized from methanol to provide 1.60 g (70%) of the desired product as a white solid. $^1$H NMR ($CD_3OD$) δ 1.05-1.08 (m, 2H), 1.16-1.20 (m, 1H), 1.24-1.27 (m, 1H), 1.42-1.45 (m, 10H), 1.88 (dd, J=8.09, 5.34 Hz, 1H), 2.24-2.30 (m, 2H), 2.53-2.57 (m, 1H), 2.94-2.98 (m, 1H), 3.80 (d, J=12.5 Hz, 1H), 3.86-3.89 (m, 1H), 3.93 (s, 3H), 4.40-4.42 (m, 1H), 5.13 (d, J=10.5 Hz, 1H), 5.32 (d, J=18.0 Hz, 1H), 5.72-5.81 (m, 2H), 7.17-7.20 (m, 2H), 7.26 (d, J=6.0 Hz, 1H), 7.88 (d, J=6.0 Hz, 1H), 8.07 (d, J=9.0 Hz, 1H); LC-MS, MS m/z 601 ($M^+$+H).

Step 5:

To an ice cold solution of the product of Step 4, Example 1 (1.50 g, 2.50 mmol) in $CH_2Cl_2$ (10 mL) was added TFA (10 mL). The resulting solution was allowed to warm to ambient temperature and was stirred for 2 hours. The solvent was removed in vacuo. The residue was triturated with 1M HCl in diethyl ether, collected by filtration, and the solid was washed with diethyl ether to provide the desired product as a hygroscopic white solid (1.43 g, 99.8%). $^1$H NMR ($CD_3OD$) δ ppm 1.03-1.21 (m, 4H), 1.26-1.31 (m, 1H), 1.37-1.40 (m, 1H), 1.95-1.97 (m, 1H), 2.32-2.37 (m, 1H), 2.42-2.48 (m, 1H), 2.95-2.99 (m, 1H), 3.88 (d, J=12.5 Hz, 2H), 3.98 (s, 3H), 4.40-4.42 (m. 1H), 5.16 (d, J=10.5 Hz, 1H), 5.33 (d, J=18.0 Hz, 1H), 5.62-5.69 (m, 1H), 5.97 (bs, 1H), 7.30-7.34 (m, 2H), 7.47 (d, J=6.0 Hz, 1H), 7.90 (d, J=6.5 Hz, 1H), 8.34 (d, J=9.0 Hz, 1H), 9.14 (bs, 1H); LC-MS, MS m/z 501 ($M^+$+H).

Step 6:

To a mixture of the product of Step 5, Example 1 (0.350 g, 0.610 mmol), HATU (0.302 g, 0.793 mmol), DIEA (0.277 g, 2.14 mmol) and dichloromethane (6 mL) was added (+/−)-2-(4,6-dimethylpyridin-2-ylamino)-3-methylbutanoic acid (0.135 g, 0.610 mmol, purchased from Specs, catalog #AP-836/41220382). The reaction was stirred at room temperature for 14 hours. Additional HATU (0.302 g, 0.793 mmol), DIEA (0.079 g, 0.61 mmol) and (+/−)-2-(4,6-dimethylpyridin-2-ylamino)-3-methylbutanoic acid (0.135 g, 0.610 mmol) were added and the resulting mixture was stirred for an additional 6 hours in an attempt to push the reaction further toward completion. The mixture was concentrated in vacuo, dissolved in ethyl acetate (75 mL), and washed with 1.0M aqueous HCl (3×10 mL). The combined HCl washes were extracted with ethyl acetate (50 mL). The organic phases were combined and washed with 10% aqueous $NaHCO_3$ (2×10 mL) and with brine, and were then dried over $MgSO_4$, filtered and concentrated in vacuo to a dark brown residue. Purification by reverse phase preparative HPLC gave two products with identical m/z by LCMS. The first isomer to elute by reverse phase preparative HPLC was labeled Compound 1A (47.7 mg, 11.1%) and the second isomer to elute was labeled Compound 1B (16.9 mg, 3.9%).

Compound 1A: $^1$H NMR (500 MHz, $CD_3OD$) δ ppm 1.01 (d, J=6.71 Hz, 3H), 1.10 (d. J=6.71 Hz, 3H), 1.12-1.17 (m, 2H), 1.26-1.30 (m, 2H), 1.47 (dd, J=9.46, 5.49 Hz, 1H), 1.85 (dd, J=8.09, 5.34 Hz, 1H), 2.17 (s, 3H), 2.31 (q, J=8.85 Hz, 2H), 2.36-2.40 (m, 2H), 2.41 (s, 3H), 2.65 (dd, J=13.73, 7.02 Hz, 1H), 2.97-3.03 (m, 1H), 3.95 (s, 3H), 4.16 (dd, J=12.05, 3.51 Hz, 1H), 4.30 (d, J=11.60 Hz, 1H), 4.49 (d, J=7.02 Hz, 1H), 4.68 (dd, J=10.22, 7.17 Hz, 1H), 5.17 (dd, J=10.38, 1.53 Hz, 1H), 5.35 (dd, J=17.24, 1.07 Hz, 1H), 5.77-5.86 (m, 1H), 5.99 (s, 1H), 6.59 (s, 1H), 6.65 (s, 1H), 7.11 (dd, J=9.16, 2.44 Hz, 1H), 7.23 (d, J=2.44 Hz, 1H), 7.30 (d, J=5.80 Hz, 1H), 7.94 (d, J=5.80 Hz, 1H), 7.98 (d, J=9.16 Hz, 1H); LC-MS, MS m/z 705 ($M^+$+H).

Compound 1B: $^1$H NMR (500 MHz, MeOD) δ ppm 1.02 (d, J=6.7 Hz, 3H), 1.03-1.06 (m, J=2.1 Hz, 2H), 1.07 (d, J=6.7 Hz, 3H), 1.14-1.19 (m, 1H), 1.20-1.25 (m, 1H), 1.32 (dd, J=9.5, 5.2 Hz, 1H), 1.81 (dd, J=8.1, 5.3 Hz, 1H), 2.14 (q, J=8.9 Hz, 1H), 2.25-2.39 (m, 2H), 2.55 (dd, J=13.9, 6.9 Hz, 1H), 2.88-2.94 (m, 1H), 3.82 (s, 3H), 4.12 (dd, J=11.7, 4.1 Hz, 1H), 4.43 (dd, J=10.4, 7.0 Hz, 1H), 4.55 (d, J=11.9 Hz, 1H), 4.62 (d, J=9.2 Hz, 1H), 5.03 (d, J=10.4 Hz, 1H), 5.20 (d, J=17.1 Hz, 1H), 5.65-5.74 (m, 1H), 5.79 (t, J=3.5 Hz, 1H), 6.99 (dd, J=9.2, 2.4 Hz, 1H), 7.04 (d, J=2.1 Hz, 1H), 7.11 (d, J=6.1 Hz, 1H), 7.68 (t, J=7.6 Hz, 1H), 7.73 (t, J=7.3 Hz, 1H), 7.77 (d, J=6.1 Hz, 1H), 7.79 (d, J=7.6 Hz, 1H), 8.01 (d, J=7.6 Hz, 1H), 8.07 (d, J=9.2 Hz, 1H); LC-MS, MS m/z 705 (M$^+$+H).

Example 2

Preparation of Compound 2: N-(5-(trifluoromethyl)-2-pyridinyl)valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide Compound 2

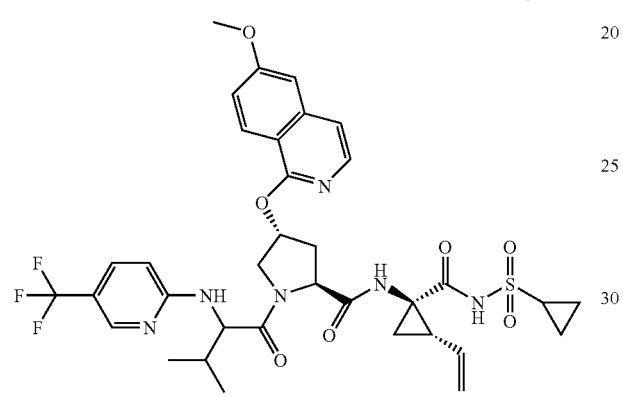

To a mixture of the product of Step 5, Example 1 (0.350 g, 0.610 mmol), HATU (0.464 g, 1.22 mmol), DIEA (0.316 g, 2.44 mmol) and dichloromethane (6 mL) was added N-[5-(trifluoromethyl)-pyridin-2-yl]valine (0.320 g, 1.22 mmol). The reaction was stirred at room temperature for 72 hours. The mixture was concentrated in vacuo, dissolved in ethyl acetate (50 mL), and washed with 1.0M aqueous HCl (3×5 mL). The HCl washes were combined and extracted with ethyl acetate (25 mL). The organic phases were combined and washed with 10% aqueous NaHCO$_3$ (2×5 mL) and with brine, and were then dried over MgSO$_4$, filtered and concentrated in vacuo to a residue. The crude material was passed through a plug of silica gel using 95:5 dichloromethane:methanol. Further purification by reverse phase preparative HPLC gave Compound 2 (0.174 g, 38.3%) as a white solid. Compound 2 was the major of two isomers that had formed in the reaction. $^1$H NMR (500 MHz, MeOD) δ ppm 0.68 (d, J=5.5 Hz, 1H), 0.77-0.85 (m, 2H), 0.93 (d, J=6.7 Hz, 3H), 0.99 (d, J=6.4 Hz, 3H), 1.14 (t, J=7.2 Hz, 3H), 1.31 (dd, J=9.3, 5.0 Hz, 1H), 1.74-1.81 (m, 1H), 2.02-2.12 (m, 1H), 2.28-2.41 (m, 1H), 2.48-2.61 (m, 1H), 3.83 (s, 2H), 3.84 (s, 1H), 3.99-4.03 (m, 1H), 4.29-4.40 (m, 1H), 4.50 (q, J=8.4 Hz, 1H), 4.98 (d, J=9.2 Hz, 1H), 5.17 (d, J=17.4 Hz, 1H), 5.60-5.72 (m, 1H), 5.76 (s, 1H), 6.35 (d, J=8.9 Hz, 1H), 6.95 (dd, J=9.2, 2.4 Hz, 1H), 7.04-7.12 (m, 2H), 7.15-7.23 (m, 2H), 7.79-7.84 (m, 2H); LC-MS, MS m/z 745 (M$^+$+H).

Example 3

Preparation of Compound 3: N-(4,6-dimethoxy-1,3,5-triazin-2-yl)-3-methyl-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide Compound 3

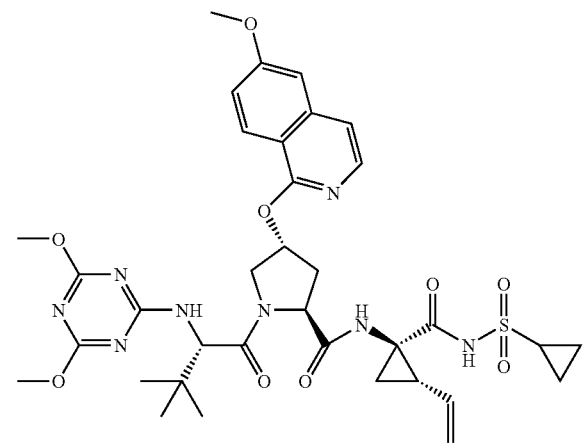

Scheme 1

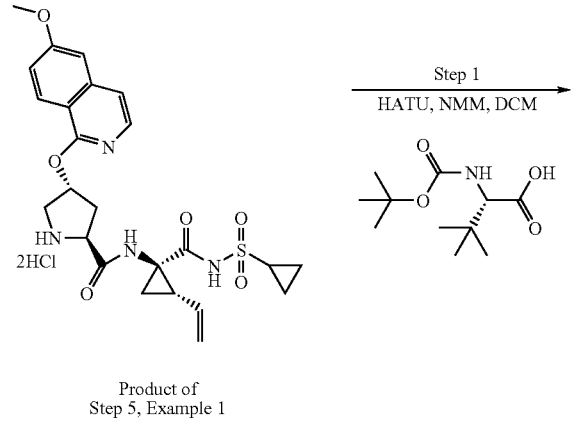

Product of Step 5, Example 1

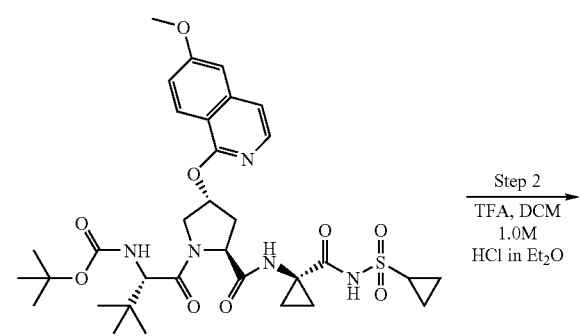

-continued

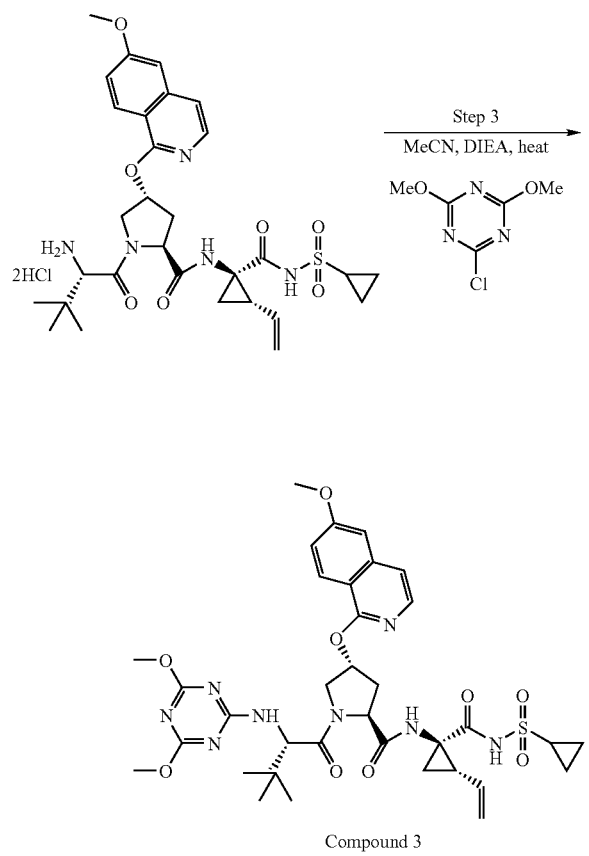

Compound 3

Step 1:

A mixture of the product of Step 5, Example 1 (70.2 g, 122 mmol), Boc-tert-leucine (31.2 g, 135 mmol), NMM (63.1 g, 624 mmol) and HATU (60.5 g, 159 mmol) in dichloromethane (750 mL) was stirred at room temperature overnight. The mixture was concentrated in vacuo and to the residue was added ethyl acetate (3 L) and pH=4 buffer (1 L). The mixture was shaken and the phases were separated. The organic phase was again washed with pH=4 buffer (2×1 L) and with brine (300 mL). The organic phase was dried over MgSO$_4$, filtered, and concentrated to an orange foam. The crude solid was purified by silica gel chromatography (step elution with dichloromethane, followed by 10:1 dichloromethane:acetone, then with 7:1 dichloromethane:acetone). Iterative crystallizations from isopropanol of the concentrated material gave pure product as large colorless flakes (58.3 g, 67% yield). LC-MS, MS m/z 714 (M$^+$+H).

Step 2:

To a stirred solution of the product of Step 1, Example 3 (15.0 g, 21.0 mmol) in dry dichloromethane (200 mL) was added TFA (100 mL). The mixture was stirred for 80 minutes and was then concentrated in vacuo to a residue. 1,2-Dichloroethane (200 mL) was added, and the mixture was again concentrated in vacuo to give a white foam. The material was dissolved in dry dichloromethane (50 mL) and diethyl ether (50 mL) was added. The rapidly stirred solution was then treated slowly with a mixture of 2.0M HCl in ether (150 mL) and dry diethyl ether (250 mL). The resulting suspension was stirred under nitrogen for 30 minutes, and was then filtered. The filtrant solid was rinsed with diethyl ether and allowed to air dry. The solid was dried in a vacuum oven at 40° C. overnight to yield a white free flowing powder product as the bis-HCl salt (13.9 g, 96.3% yield). LC-MS, MS m/z 614 (M$^+$+H).

Step 3:

To a solution of the product of Step 2, Example 3 (0.253 g, 0.369 mmol) and DIEA (0.215 g, 1.66 mmol) in acetonitrile (4 mL) was added 2-chloro-4,6-dimethoxy-1,3,5-triazene (0.100 g, 0.553 mmol). The mixture was heated to 135° C. in a Chemglass pressure vessel for 2 hours. The mixture was concentrated in vacuo, and the residue was dissolved in ethyl acetate (50 mL) and washed with 1.0M HCl aqueous (2×5 mL) followed by 10% aqueous sodium carbonate and brine. The organic was dried over MgSO$_4$, filtered, and concentrated. Purification by silica gel flash chromatography (97:3 dichloromethane:methanol) gave pure Compound 3 (0.252 g, 91% yield) as a white solid. $^1$H NMR (500 MHz, MeOD) δ ppm 1.07 (s, 9H), 1.09-1.14 (m, 2H), 1.25-1.33 (m, 2H), 1.48 (dd, J=9.5, 5.5 Hz, 1H), 1.93 (dd, J=8.1, 5.3 Hz, 1H), 2.24-2.39 (m, 2H), 2.94-3.03 (m, 1H), 3.55 (s, 3H), 3.83 (s, 3H), 3.95 (s, 3H), 4.04 (dd, J=4.9, 3.1 Hz, 1H), 4.08 (s, 2H), 4.45 (d, J=11.9 Hz, 1H), 4.67 (dd, J=10.4, 7.3 Hz, 1H), 4.91 (s, 1H), 5.16 (d, J=10.4 Hz, 1H), 5.34 (d, J=17.1 Hz, 1H), 5.75-5.84 (m, 1H), 5.90-5.94 (m, 1H), 7.03 (dd, J=9.2, 2.4 Hz, 1H), 7.16 (d, J=2.1 Hz, 1H), 7.26 (d, J=5.8 Hz, 1H), 7.80 (d, J=8.9 Hz, 1H), 7.89 (d, J=5.8 Hz, 1H); LC-MS, MS m/z 753 (M$^+$+H).

Example 4

Preparation of Compound 4: N-(4,6-dimethoxy-1,3,5-triazin-2-yl)valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide

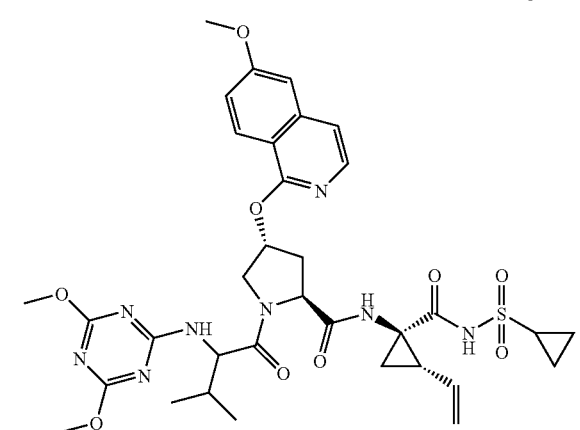

Compound 4

Scheme 1
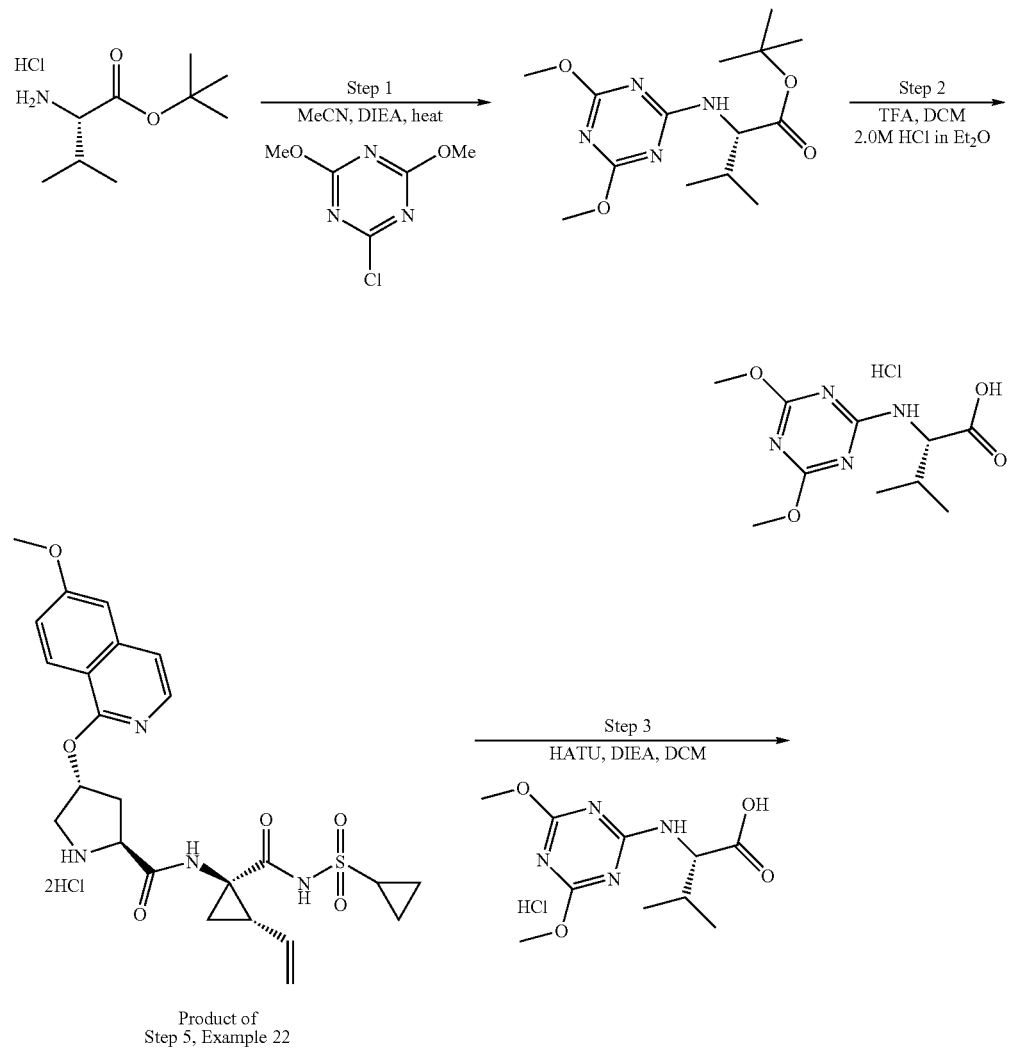
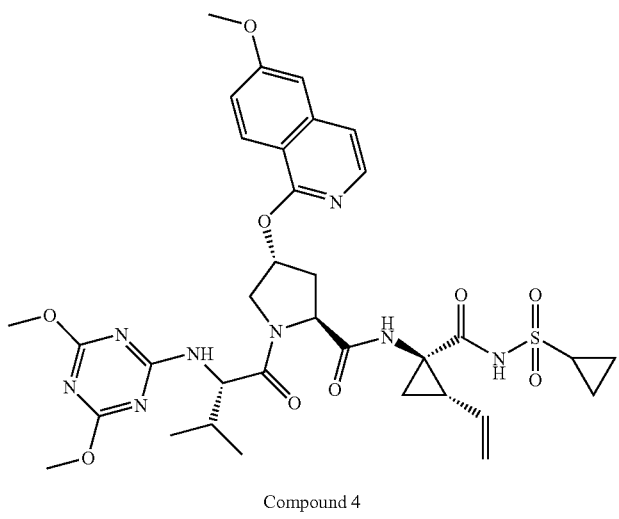
Compound 4

Step 1:

To a mixture of valine tert-butyl ester hydrochloride (0.367 g, 1.75 mmol) and DIEA (0.567 g, 4.38 mmol) in acetonitrile (5 mL) was added 2-chloro-4,6-dimethoxy-1,3,5-triazene (0.476 g, 2.63 mmol). The mixture was heated to 130° C. in a microwave reactor for 1 hours. Solvent was removed and the viscous brown residue was dissolved in ethyl acetate (75 mL) and the solution was washed with 1.0M aqueous HCl (2×10 mL). The aqueous extracts were combined and back-extracted with ethyl acetate (50 mL), and the organic phases were combined and washed with 10% aqueous sodium carbonate (15 mL) and then with brine. The organic phase was dried over anhydrous MgSO$_4$, filtered and concentrated to a brown oil which was purified by flash silica gel chromatography (97:3 dichloromethane:methanol) to give the product as a light brown viscous oil (0.521 g, 95% yield).

Step 2:

The product of Step 1, Example 4 (0.500 g, 1.60 mmol) was dissolved in dichloromethane (5 mL) and treated with TFA (5 mL). The mixture was stirred at room temperature for 3 hours and was then concentrated in vacuo. The residue was then dissolved in 1,2-dichloroethane (20 mL) and again concentrated in vacuo. The residue was then dissolved in dichloromethane (3 mL) and was added dropwise to a rapidly stirred solution of 2.0M HCl in ether (10 mL). No precipitation occurred. The solution was concentrated in vacuo to give a slightly yellow solid which was dried in vacuo. Thus was obtained a yellow solid (0.45 g, 96% yield) which was subsequently used without further purification.

Step 3:

To a mixture of the product of Step 5, Example 1 (0.421 g, 0.734 mmol) and DIEA (0.428 g, 3.30 mmol) in dichloromethane (7 mL) was added the product of Step 2, Example 4 (0.215 g, 0.734 mmol) and HATU (0.335 g, 0.881 mmol). The mixture was stirred at room temperature for 80 minutes. Solvent was removed and the viscous brown residue was dissolved in ethyl acetate (50 mL) and the solution was washed with 1.0M aqueous HCl (2×10 mL). The aqueous extracts were combined and back-extracted with ethyl acetate (50 mL), and the organic phases were combined and washed with 10% aqueous sodium carbonate (15 mL) and then with brine. The organic phase was dried over anhydrous MgSO$_4$, filtered and concentrated to a brown solid which was purified by flash silica gel chromatography (97:3 dichloromethane:methanol) to give Compound 4 as a white solid (0.243 g, 45% yield). $^1$H NMR (500 MHz, MeOD) δ ppm 0.71 (d, J=6.4 Hz, 3H), 0.73-0.78 (m, 1H), 0.79-0.88 (m, 1H), 0.90-0.98 (m, 1H), 1.01-1.07 (m, 1H), 1.08 (d, J=6.7 Hz, 3H), 1.23 (dd, J=9.0, 5.3 Hz, 1H), 1.90 (q, J=8.5 Hz, 1H), 1.99-2.06 (m, 1H), 2.09-2.20 (m, 1H), 2.22-2.33 (m, 1H), 2.33-2.41 (m, 1H), 2.47 (dd, J=13.4, 6.1 Hz, 1H), 3.25 (s, 3H), 3.45 (s, 2H), 3.75 (s, 3H), 4.11 (dd, J=11.7, 3.5 Hz, 1H), 4.41 (d, J=12.2 Hz, 1H), 4.52 (dd, J=11.9, 6.4 Hz, 1H), 4.63-4.70 (m, 1H), 4.85 (d, J=10.7 Hz, 1H), 4.95 (d, J=17.4 Hz, 1H), 5.81 (t, J=3.2 Hz, 1H), 5.85-5.97 (m, 1H), 6.48 (d, J=9.2 Hz, 1H), 7.04 (s, 1H), 7.18 (d, J=5.8 Hz, 1H), 7.35 (d, J=8.9 Hz, 1H), 7.80 (d, J=6.1 Hz, 1H); LC-MS, MS m/z 739 (M$^+$+H).

Example 5

Preparation of Compound 5: N-(4,6-dimethoxy-2-pyrimidinyl)valyl-(4R)—N-((1R,2S)-1-((cyclopropylsulfonyl)carbamoyl)-2-vinylcyclopropyl)-4-((6-methoxy-1-isoquinolinyl)oxy)-L-prolinmide

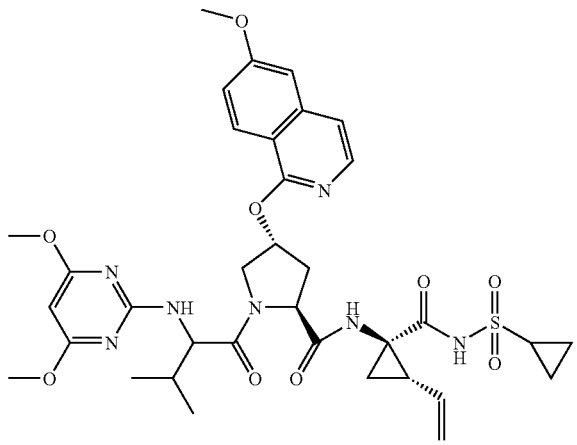

Compound 5

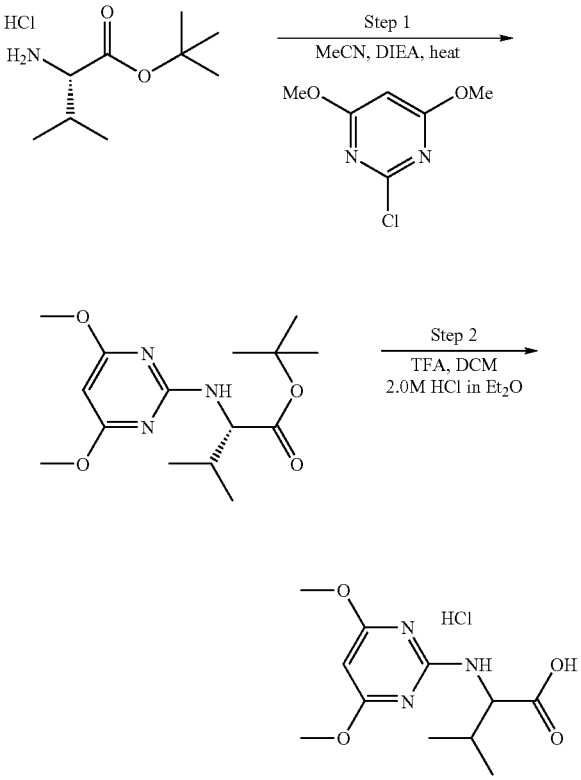

Scheme 1

85

-continued

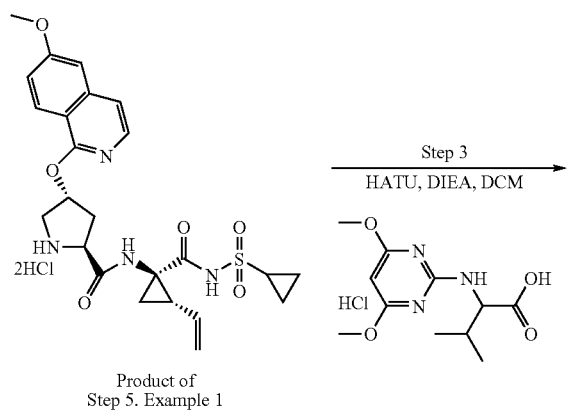

Product of
Step 5. Example 1

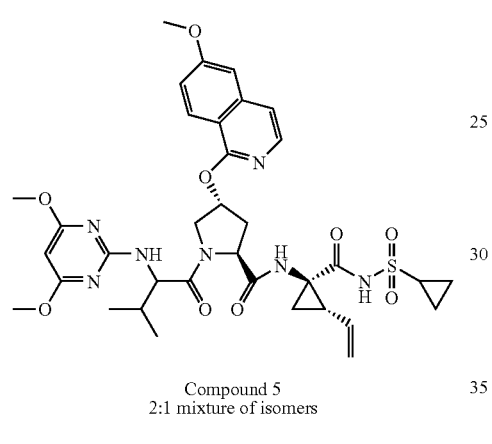

Compound 5
2:1 mixture of isomers

Step 1:

To a mixture of valine tert-butyl ester hydrochloride (1.55 g, 7.39 mmol) and DIEA (2.01 g, 15.5 mmol) in acetonitrile (37 mL) was added 2-chloro-4,6-dimethoxypyrimidine (1.55 g, 8.87 mmol). The mixture was heated to 130° C. in a Chemglass pressure vessel for 48 hours. Solvent was removed and the viscous brown residue was dissolved in ethyl acetate (100 mL) and the solution was washed with 1.0M aqueous HCl (2×25 mL). The aqueous extracts were combined and back-extracted with ethyl acetate (50 mL), and the organic phases were combined and washed with 10% aqueous sodium carbonate and then with brine. The organic phase was dried over anhydrous MgSO₄, filtered and concentrated to a brown oil which was purified by flash silica gel chromatography (step gradient 9:1 hexanes:ethyl acetate then 1:1 hexanes:ethyl acetate) to give the product as a brown viscous oil (1.02 g, 44% yield).

Step 2:

The product of Step 1, Example 5 (0.944 g, 3.03 mmol) was dissolved in dichloromethane (10 mL) and treated with TFA (10 mL). The mixture was stirred at room temperature for 4 hours and was then concentrated in vacuo. The residue was then dissolved in 1,2-dichloroethane (50 mL) and again concentrated in vacuo. The residue was then dissolved in dichloromethane (3 mL) and was added dropwise to a rapidly stirred solution of 1.0M HCl in ether and hexanes (100 mL). No

86 precipitate occurred. The solution was concentrated in vacuo to give a brown foamy solid which was subsequently used without further purification.

Step 3:

To a mixture of the product of Step 5, Example 1 (0.425 g, 0.741 mmol) and DIEA (0.432 g, 3.34 mmol) in dichloromethane (7 mL) was added the product of Step 2, Example 5 (0.259 g, 0.889 mmol) and HATU (0.366 g, 0.963 mmol). The mixture was stirred at room temperature for 16 hours. The solvent was removed and the viscous brown residue was dissolved in ethyl acetate (50 mL) and the solution was washed with 1.0M aqueous HCl (2×10 mL). The aqueous extracts were combined and extracted with ethyl acetate (30 mL), and the organic phases were combined and washed with 10% aqueous sodium carbonate (15 mL) and then with brine. The organic phase was dried over anhydrous MgSO₄, filtered and concentrated to a viscous brown oil which was passed through a plug of silica gel (95:5 dichloromethane:methanol). The product was further purified by reverse phase preparative HPLC to give white solid Compound 5 (0.243 g, 45% yield) as an apparent mixture of two isomers in a 2 to 1 ratio. The isomers were not separated. LC-MS, MS m/z 738 (M⁺+H).

Compound 6 Isomers

N-(4,6-dimethyl-2-pyrimidinyl)-D-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide N-(4,6-dimethyl-2-pyrimidinyl)-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide Example 6

Preparation of Compounds 6A and 6B

Compounds 6A and 6B

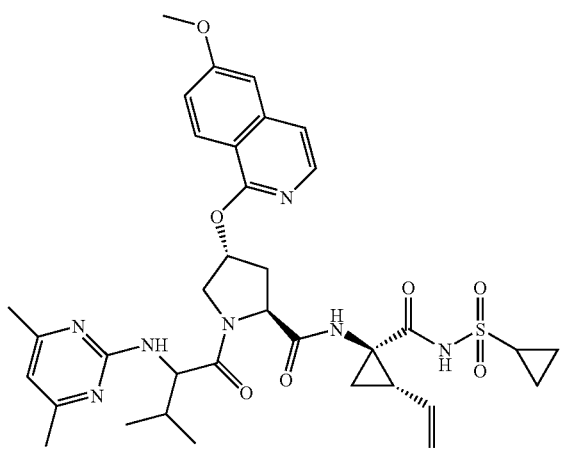

Scheme 1

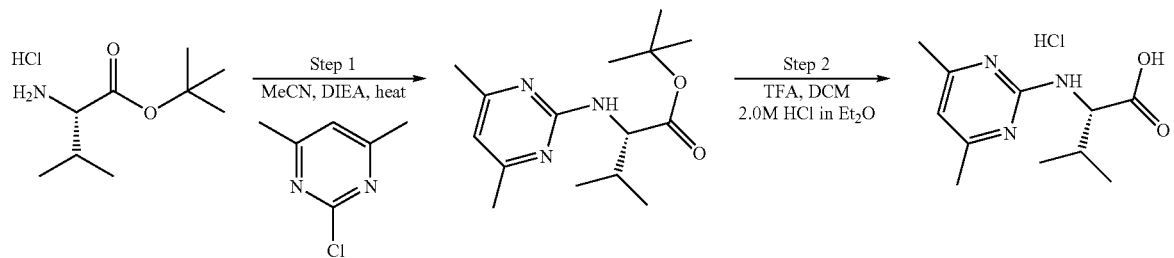

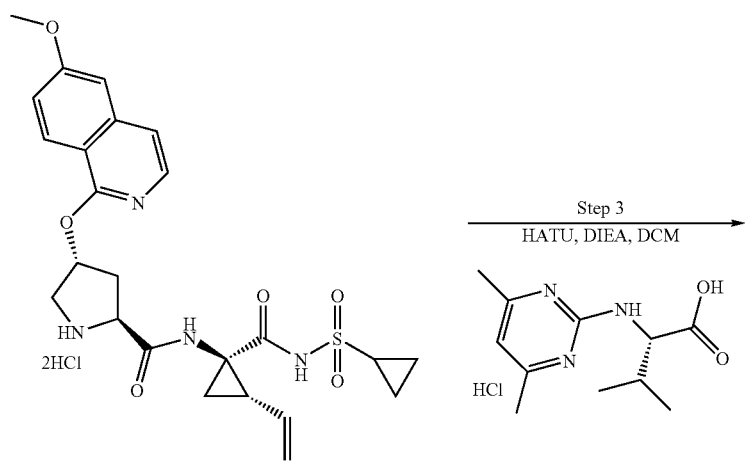

Product of
Step 5, Example 1

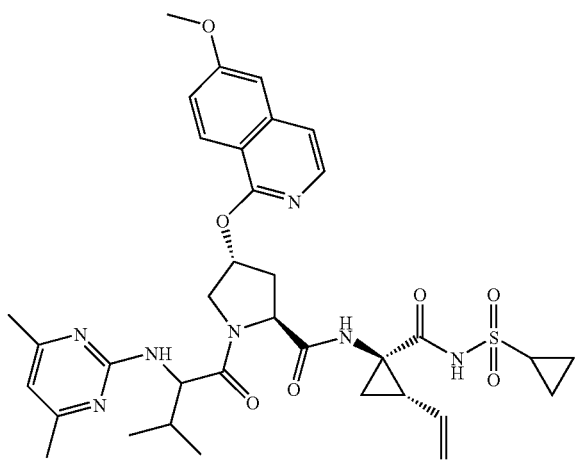

Compounds 6A and 6B
Mixture of isomers

Step 1:

To a mixture of valine tert-butyl ester hydrochloride (3.09 g, 14.7 mmol) and DIEA (4.01 g, 31.0 mmol) in acetonitrile (50 mL) was added 2-chloro-4,6-dimethylpyrimidine (2.31 g, 16.2 mmol). The mixture was heated to 135° C. in a Chemglass pressure vessel for 72 hours. The solvent was removed and the viscous brown residue was dissolved in ethyl acetate (150 mL) and the solution was washed with 1.0M aqueous HCl (2×50 mL). The aqueous extracts were combined and back-extracted with ethyl acetate (2×50 mL), and the organic phases were combined and washed with 10% aqueous sodium carbonate and then with brine. The organic phase was dried over anhydrous MgSO$_4$, filtered and concentrated to a brown oil which was purified by flash silica gel chromatography (4:1 hexanes:ethyl acetate) to give the product which was used directly in the next step.

Step 2:

The product of Step 1, Example 6 (1.80 g, 6.44 mmol) was dissolved in dichloromethane (25 mL) and treated with TFA (25 mL). The mixture was stirred at room temperature for 3 hours and was then concentrated in vacuo. The residue was then dissolved in 1,2-dichloroethane (50 mL) and again concentrated in vacuo. The residue was then dissolved in ethyl acetate (50 mL) and extracted with aqueous 1N HCl (2×50). The combined acid extracts were concentrated in vacuo to give a yellow solid (1.23 g). LC-MS, MS m/z 224 (M$^+$+H).

Step 3:

To a mixture of the product of Step 5, Example 1 (0.438 g, 0.764 mmol) and DIEA (0.495 g, 3.82 mmol) in dichloromethane (10 mL) was added the product of Step 2, Example 6 (0.218 g, 0.840 mmol) and HATU (0.378 g, 0.993 mmol). The mixture was stirred at room temperature for 15 hours. The solvent was removed and the viscous brown residue was dissolved in ethyl acetate (75 mL) and the solution was washed with 1.0M aqueous HCl (2×10 mL). The aqueous extracts were combined and extracted with ethyl acetate (50 mL), and the organic phases were combined and washed with 10% aqueous sodium carbonate (15 mL) and then with brine. The organic phase was dried over anhydrous MgSO$_4$, filtered and concentrated to a viscous brown oil which was purified by flash silica gel chromatography (gradient 97:3 dichloromethane:methanol then 95:5 dichloromethane:methanol). Two distinct compounds with identical m/z by LCMS were separated. The first product to elute was the minor compound and was labeled Compound 6A (light yellow solid, 0.0408 g, 7.6% yield). The major product eluted second from the column (yellow solid, 0.280 g) and was further purified by reverse phase preparative HPLC to give Compound 6B (0.040 g, 7.4% yield) as a yellow solid bis-HCl salt.

Compound 6A: $^1$H NMR (500 MHz, MeOD) δ ppm 0.85 (d, J=7.0 Hz, 3H), 0.96 (d, J=6.7 Hz, 3H), 1.00 (dd, J=12.8, 7.0 Hz, 1H), 1.05-1.14 (m, 2H), 1.23-1.29 (m, 1H), 1.37 (dd, J=9.6, 5.3 Hz, 1H), 1.87 (dd, J=8.1, 5.3 Hz, 1H), 1.99-2.05 (m, 1H), 2.25 (q, J=8.7 Hz, 1H), 2.30 (d, J=6.4 Hz, 1H), 2.36-2.47 (m, 5H), 2.60-2.66 (m, 1H), 2.83-2.85 (m, 1H), 2.87-2.93 (m, 1H), 3.96 (s, 3H), 4.28-4.32 (m, 1H), 4.37-4.42 (m, 1H), 4.57-4.62 (m, 1H), 4.72 (d, J=8.2 Hz, 1H), 5.14 (dd, J=10.4, 1.5 Hz, 1H), 5.33 (dd, J=17.1, 1.5 Hz, 1H), 5.71-5.80 (m, 1H), 5.95 (s, 1 H), 7.19 (dd, J=9.2, 2.4 Hz, 1H), 7.24 (d, J=2.4 Hz, 1H), 7.31 (d, J=6.1 Hz, 1H), 7.94 (d, J=6.1 Hz, 1H), 8.05 (d, J=9.2 Hz, 1H); LC-MS, MS m/z 706 (M$^+$+H).

Compound 6B: $^1$H NMR (500 MHz, MeOD) δ ppm 1.17 (d, J=6.7 Hz, 1H), 1.28 (d, J=6.7 Hz, 1H), 1.31 (d, J=6.7 Hz, 3H), 1.39 (d, J=6.7 Hz, 3H), 1.43-1.56 (m, 2H), 1.69 (dd, J=9.5, 5.2 Hz, 1H), 2.15-2.26 (m, 3H), 2.50-2.56 (m, 1H), 2.57-2.62 (m, 1H), 2.63-2.72 (m, 3H), 2.89 (dd, J=13.9, 6.6 Hz, 1H), 3.20-3.27 (m, 1H), 4.22 (s, 3H), 4.48 (dd, J=12.2, 3.7 Hz, 1H), 4.79 (d, J=11.9 Hz, 1H), 4.85-4.92 (m, 1H), 5.02 (d, J=7.9 Hz, 1H), 5.40 (d, J=11.6 Hz, 1H), 5.59 (d, J=16.8 Hz, 1H), 6.00-6.09 (m, 1H), 6.25 (t, J=3.2 Hz, 1H), 6.94 (s, 1H), 7.42 (dd, J=9.0, 2.3 Hz, 1H), 7.54 (d, J=2.1 Hz, 1H), 7.64 (d, J=6.1 Hz, 1H), 8.19 (d, J=6.1 Hz, 1 H), 8.23 (d, J=9.2 Hz, 1H); LC-MS, MS m/z 706 (M$^+$+H).

Example 7

Preparation of Compound 7: N-2-pyridinylvalyl-(4R)—N-((1R,2S)-1-((cyclopropylsulfonyl)carbamoyl)-2-vinylcyclopropyl)-4-((6-methoxy-1-isoquinolinyl)oxy)-L-prolinamide

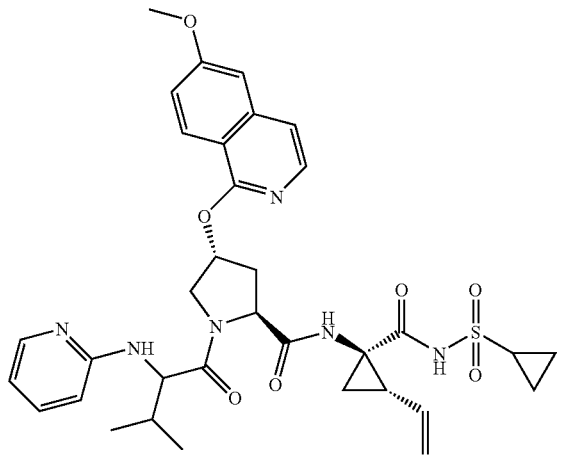

Compound 7

Scheme 1

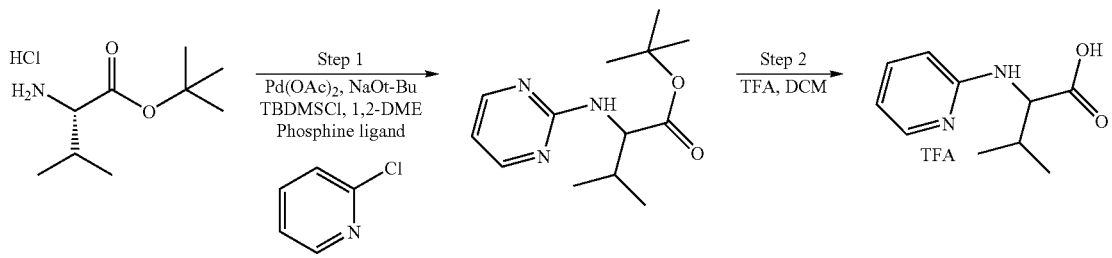

-continued

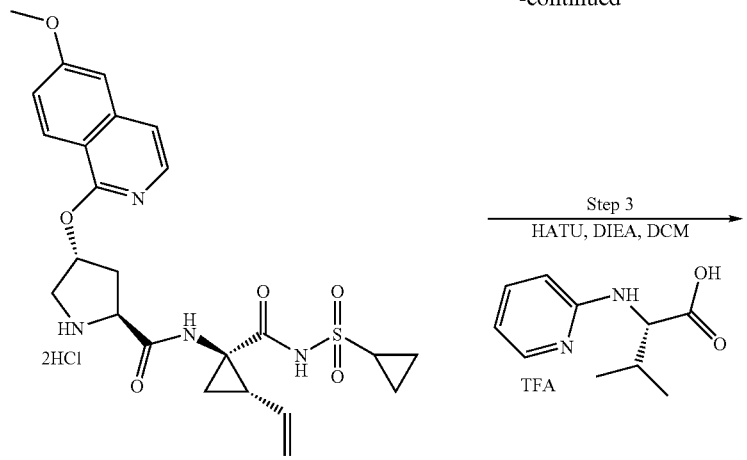

Product of
Step 5, Example 1

Step 3
HATU, DIEA, DCM

TFA

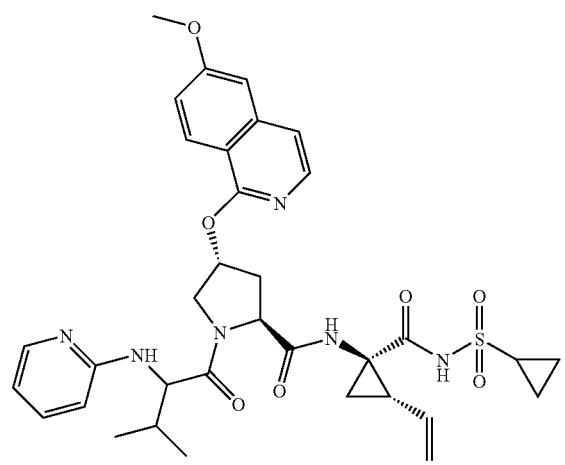

Compound 7
(Major isomer)

Step 1:

To a mixture of 2-chloropyridine (0.205 g, 1.80 mmol) and sodium tert-butoxide (0.590 g, 6.13 mmol) in dry 1,2-dichloroethane (1 mL) was added a pre-mixed solution of Pd(OAc)$_2$ (0.0405 g, 0.180 mmol) and (R)-(−)-1-[(S)-(dicyclohexylphosphino)ferrocenyl]ethyl di-tert-butyl phosphine (0.100 g, 0.180 mmol, Strem Chemicals catalog #26-0975, CAS # [158923-11-6]) in dry 1,2-dimethoxyethane (1 mL). The mixture was shaken, and was quickly treated with TBDMSCl (0.598 g, 3.97 mmol). The mixture was shaken briefly, and quickly added valine tert-butyl ester hydrochloride (0.454 g, 2.16 mmol) and shook again. A moderate exotherm resulted immediately. After 10 minutes stirring, the mixture was added to rapidly stirred pH=7 buffer solution (50 mL). Added ethyl acetate (50 mL) and shook and separated the phases. The aqueous was saturated by addition of NaCl and was extracted again with ethyl acetate (2×50 mL). The organic extracts were combined and washed with brine (20 mL), dried over MgSO$_4$, filtered and concentrated in vacuo to a dark residue. The crude product was purified by flash silica gel chromatography (8:1 hexanes:ethyl acetate) to give a colorless liquid (0.365 g) which was determined to contain the desired product plus 0.6 equivalents of TBDMS byproduct. The material was carried on to the next step without further purification. Approximate yield was 61%. LC-MS, MS m/z 251 (M$^+$+H).

Step 2:

The product of Step 1, Example 7 (0.944 g, 3.03 mmol) was dissolved in dichloromethane (10 mL) and treated with TFA (10 mL). The mixture was stirred at room temperature for 1.5 hours and was then concentrated in vacuo. The residue was then purified by reverse phase preparative HPLC, and then purified further by flash silica gel chromatography (gradient, 10:1 dichloromethane:methanol to 5:1 dichloromethane:methanol) to give a colorless waxy solid (0.126 g, 59.0% yield). LC-MS, MS m/z 195 (M$^+$+H).

Step 3:

To a mixture of the product of Step 5, Example 1 (0.250 g, 0.436 mmol) and NMM (0.176 g, 1.74 mmol) in dichloromethane (2 mL) was added the product of Step 2, Example 7 (0.085 g, 0.44 mmol) and HATU (0.199 g, 0.523 mmol). The mixture was stirred at room temperature for 96 hours. The solvent was removed, the viscous brown residue was dissolved in ethyl acetate (50 mL), and the solution was washed with 1.0M aqueous HCl. The aqueous extracts were combined and extracted with ethyl acetate, and the organic phases were combined and washed with 10% aqueous sodium carbonate and then with brine. The organic phase was dried over anhydrous MgSO$_4$, filtered and concentrated to a residue which was purified by reverse phase preparative HPLC to give Compound 7 (0.243 g, 45% yield) as a white solid. Compound 7 was the major of two isomers formed in the reaction with identical MS m/z by LCMS. The minor isomer (more retained on the reverse phase preparative HPLC column than the major isomer) was not isolated. $^1$H NMR (500 MHz, MeOD) δ ppm 0.99 (d, J=6.71 Hz, 3H) 1.12 (d, J=6.41 Hz, 3H) 1.14-1.19 (m, 2H) 1.24-1.31 (m, 1H) 1.31-1.37 (m, 1H) 1.48 (dd, J=9.46, 5.49 Hz, 1H) 1.95 (dd, J=8.09, 5.34 Hz, 1H) 2.32 (q, J=8.85 Hz, 1H) 2.42 (ddd, J=13.96, 10.15, 4.27 Hz, 1H) 2.47-2.55 (m, 1H) 2.68 (dd, J=13.73, 7.02 Hz, 1H) 3.02 (ddd, J=12.59, 8.16, 4.88 Hz, 1H) 3.37 (s, 1H) 3.95 (s, 3H) 4.22 (dd, 1H) 4.31 (d, J=11.90 Hz, 1H) 4.34 (d, J=8.54 Hz, 1H) 4.70 (dd, J=10.22, 7.17 Hz, 1H) 5.17 (d, J=10.38 Hz, 1H) 5.36 (d, J=17.09 Hz, 1H) 5.82 (ddd, J=17.24, 9.61, 9.46 Hz, 1H) 5.97 (t, J=3.20 Hz, 1H) 6.93 (t, J=6.71 Hz, 1H) 7.02 (d, J=9.16 Hz, 1H) 7.14 (dd, J=9.00, 2.29 Hz, 1H) 7.23 (d, J=2.14 Hz, 1H) 7.31 (d, J=6.10 Hz, 1H) 7.83 (t, J=7.93 Hz, 1H) 7.88 (d, J=6.41 Hz, 1H) 7.93 (d, J=6.10 Hz, 1H) 8.03 (d, J=9.16 Hz, 1H); LC-MS, MS m/z 677 (M$^+$+H).

Example 8

Preparation of Compound 8: N-(4-methoxy-2-pyridinyl)valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide

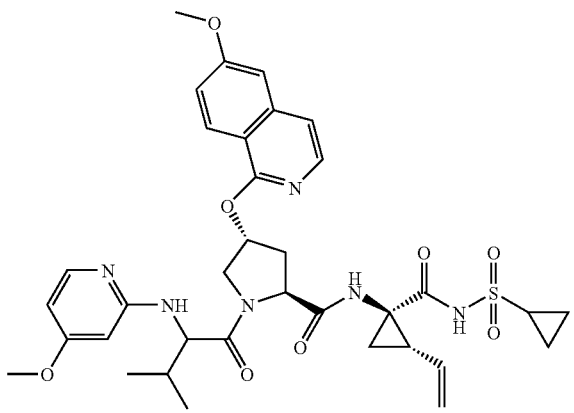

Compound 8

Compound 8 was prepared by the same procedure as that described for the preparation of Compound 7, except 2-chloro-4-methoxypyridine (259 mg, 1.80 mmol) was used in Step 1 in place of the 2-chloropyridine, and 2.0M HCl in ether was added to the concentrated Step 1 product in dichloromethane to give the hydrochloride salt in Step 2. The scale of Steps 2 and 3 were also adjusted based on the yields of the previous steps. Compound 8 (0.0290 g, 11.6% yield) was obtained as an off-white powder bis-TFA salt from reverse phase preparative HPLC. This compound was a single isomer. $^1$H NMR (500 MHz, MeOD) δ ppm 1.00 (d, J=6.71 Hz, 3H) 1.11 (d, J=6.71 Hz, 3H) 1.16 (d, J=7.63, 2.75 Hz, 2H) 1.22-1.42 (m, 4H) 1.48 (dd, J=9.61, 5.34 Hz, 1H) 1.93-1.97 (m, 1H) 2.32 (q, J=8.85 Hz, 1H) 2.36-2.50 (m, 2H) 2.67 (dd, J=13.43, 7.02 Hz, 1H) 2.89 (s, 1H) 3.01 (ddd, J=12.82, 8.09, 4.73 Hz, 1H) 3.17-3.27 (m, 1H) 3.84 (s, 3H) 3.95 (s, 3H) 3.98-4.08 (m, 1H) 4.20 (dd, 1H) 4.26-4.33 (m, 2H) 4.70 (dd, J=10.38, 7.02 Hz, 1H) 5.17 (dd, J=10.53, 1.37 Hz, 1H) 5.36 (dd, J=17.09, 1.22 Hz, 1H) 5.77-5.87 (m, J=17.17, 9.58, 9.58 Hz, 1H) 5.97 (t, J=3.36 Hz, 1H) 6.32 (d, J=2.44 Hz, 1H) 6.55 (dd, J=7.32, 2.14 Hz, 1H) 7.14 (dd, J=9.16, 2.44 Hz, 1H) 7.22 (d, J=2.44 Hz, 1H) 7.30 (d, J=5.80 Hz, 1H) 7.72 (d, J=7.32 Hz, 1H) 7.93 (d, J=5.80 Hz, 1H) 8.01 (d, J=9.16 Hz, 1H); LC-MS, MS m/z 707 (M$^+$+H).

Example 9

Preparation of Compound 9: N-(4-(trifluoromethyl)-2-pyridinyl)valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide

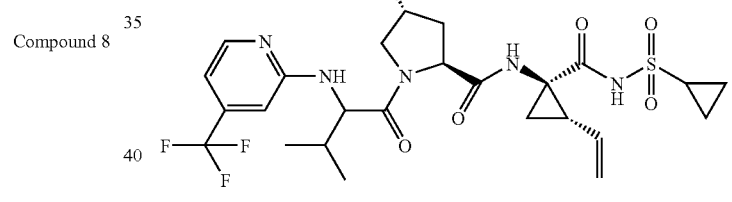

Compound 9

Compound 9 was prepared by the same procedure as that described for the preparation of Compound 7, except 2-chloro-4-trifluoromethyl pyridine (0.328 g, 1.80 mmol) was used in Step 1 in place of the 2-chloropyridine, and 2.0M HCl in ether was added to the concentrated Step 1 product in dichloromethane to give the hydrochloride salt in Step 2. The scale of Steps 2 and 3 were also adjusted based on the yields of the previous steps. Compound 9 (0.0630 g, 12.6% yield) was obtained as a deep blue turquoise solid bis-TFA salt from reverse phase preparative HPLC. This compound was a single isomer. $^1$H NMR (500 MHz, MeOD) δ ppm 1.04 (d, J=6.41 Hz, 3H) 1.08 (d, J=6.41 Hz, 3H) 1.10-1.16 (m, 2H) 1.18-1.38 (m, 3H) 1.45 (dd, J=9.46, 5.19 Hz, 1H) 1.93 (dd, J=7.93, 5.49 Hz, 1H) 2.18-2.24 (m, 1H) 2.29 (q, J=8.95 Hz, 1H) 2.33-2.42 (m, 1H) 2.58 (dd, J=12.97, 6.56 Hz, 1H) 2.89 (s, 1H) 2.96-3.05 (m, 1H) 3.85-3.93 (m, 1H) 3.96 (s, 3H) 4.10 (dd, J=11.60, 2.75 Hz, 1H) 4.49 (d, J=9.77 Hz, 1H) 4.57 (dd, J=10.68, 6.71 Hz, 1H) 4.92 (d, J=11.90 Hz, 1H) 5.16 (d, J=10.38 Hz, 1H) 5.34 (d, J=17.40 Hz, 1H) 5.75-5.86 (m, 1H) 5.94 (s, 1H) 6.20 (d, J=4.58 Hz, 1H) 6.69 (s, 1H) 7.05 (dd, J=9.00, 2.29 Hz, 2 H) 7.25 (d, J=2.14 Hz, 1H) 7.86 (d, J=9.16 Hz, 1H) 7.96 (d, J=5.80 Hz, 1H); LC-MS, MS m/z 745 (M$^+$+H).

Example 10

Preparation of Compound 10: N-(4-methyl-2-pyridinyl)valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide Compound 10

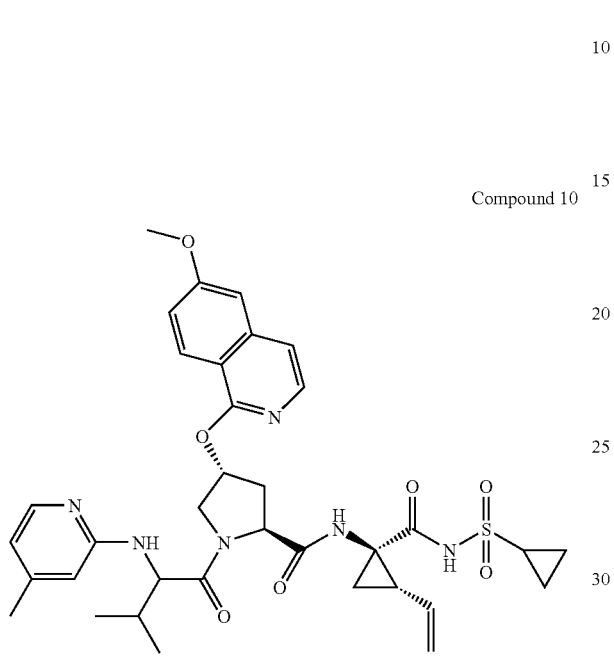

Compound 10 was prepared by the same procedure as that described for the preparation of Compound 7, except 2-bromo-4-methylpyridine (0.310 g, 1.80 mmol) was used in Step 1 in place of the 2-chloropyridine, and 2.0M HCl in ether was added to the concentrated Step 1 product in dichloromethane to give the hydrochloride salt in Step 2. The scale of Steps 2 and 3 were also adjusted based on the yields of the previous steps. Compound 10 (0.0110 g, 8.9% yield) was obtained as an off-white powder bis-TFA salt from reverse phase preparative HPLC. This compound was a single isomer. $^1$H NMR (500 MHz, MeOD) δ ppm 0.98 (d, J=6.41 Hz, 3H) 1.11 (d, J=6.71 Hz, 3H) 1.14-1.19 (m, 2H) 1.23-1.38 (m, 4H) 1.48 (dd, J=9.46, 5.49 Hz, 1H) 1.95 (dd, J=7.93, 5.49 Hz, 1H) 2.30 (s, 3H) 2.31-2.36 (m, 1H) 2.37-2.52 (m, 2H) 2.67 (dd, J=14.04, 7.02 Hz, 1H) 2.89 (s, 1H) 2.98-3.05 (m, 1H) 3.95 (s, 3H) 3.96 (d, J=1.83 Hz, 1H) 4.21 (dd, 1H) 4.26-4.33 (m, 2H) 4.69 (dd, J=10.22, 7.17 Hz, 1H) 5.18 (d, J=10.38 Hz, 1H) 5.36 (d, J=17.09 Hz, 1H) 5.77-5.87 (m, J=17.17, 9.58, 9.58 Hz, 1H) 5.97 (s, 1H) 6.78 (d, J=6.41 Hz, 1H) 6.81 (s, 1H) 7.13 (dd, J=9.00, 2.29 Hz, 1H) 7.22 (d, J=2.14 Hz, 1H) 7.30 (d, J=6.10 Hz, 1H) 7.72 (d, J=6.41 Hz, 1H) 7.93 (d, J=6.10 Hz, 1H) 8.01 (d, J=9.16 Hz, 1H); LC-MS, MS m/z 691 (M$^+$+H).

Example 11

Preparation of Compound 11: N-(4-cyano-2-pyridinyl)valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide Compound 11

Compound 11 was prepared by the same procedure as that described for the preparation of Compound 7, except 2-chloro-4-cyano pyridine (0.328 mg, 1.80 mmol) was used in Step 1 in place of the 2-chloropyridine, and 2.0M HCl in ether was added to the concentrated Step 1 product in dichloromethane to give the hydrochloride salt in Step 2. The scale of Steps 2 and 3 were also adjusted based on the yields of the previous steps. Compound 11 (0.0210 g, 6.0% yield) was obtained as a purple solid bis-TFA salt from reverse phase preparative HPLC. This material was an inseparable mixture of two isomers in a ratio of approximately 2 to 1. LC-MS, MS m/z 702 (M$^+$+H).

Compound 12 Isomers 3-methyl-N-2-pyridinyl-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide 3-methyl-N-2-pyridinyl-D-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide

Example 12

Preparation of Compounds 12A and 12B

Compound 12A and 12B

Compounds 12A and 12B were prepared by the same procedure as that described for the preparation of Compound 7, except tert-leucine tert-butyl ester hydrochloride (0.486 g, 2.16 mmol) was used in Step 1 in place of the valine tert-butyl ester hydrochloride, and 2.0M HCl in ether was added to the concentrated Step 1 product in dichloromethane to give the hydrochloride salt in Step 2. The scale of Steps 2 and 3 were also adjusted based on the yields of the previous steps. Purification of the crude product of Step 3 by reverse phase preparative HPLC gave two compounds in good purity with identical MS m/z. Compound 12A (0.0772 g, 20.9% yield) was the first of two isomers formed in the reaction to elute from reverse phase preparative HPLC and was obtained as a beige glassy solid bis-TFA salt. Compound 12B (0.0204 g, 5.5% yield) was the second of two isomers formed in the reaction to elute from reverse phase preparative HPLC and was obtained as a beige solid bis-TFA salt.

Compound 12A: $^1$H NMR (500 MHz, MeOD) δ ppm 1.09-1.14 (m, 2H) 1.15 (s, 9H) 1.28 (d, J=3.05 Hz, 2H) 1.47 (dd, J=9.00, 5.04 Hz, 1H) 1.91-1.97 (m, 1H) 2.25-2.38 (m, 2H) 2.66 (dd, J=13.28, 6.56 Hz, 1H) 2.95-3.03 (m, 1H) 3.95 (s, 3H) 4.14 (d, J=11.60 Hz, 1H) 4.39 (d, J=12.51 Hz, 1H) 4.54 (s, 1H) 4.65-4.71 (m, 1H) 5.17 (d, J=10.68 Hz, 1H) 5.34 (d, J=17.09 Hz, 1H) 5.74-5.84 (m, 1H) 5.94 (s, 1H) 6.78 (t, J=6.71 Hz, 1H) 6.96 (d, J=9.16 Hz, 1H) 7.07 (d, J=9.16 Hz, 1H) 7.22 (s, 1H) 7.30 (d, J=6.10 Hz, 1H) 7.57 (t, J=8.09 Hz, 1H) 7.75 (d, J=6.10 Hz, 1H) 7.92 (d, J=9.46 Hz, 1H) 7.94 (d, J=6.10 Hz, 1H); LC-MS, MS m/z 691 (M$^+$+H).

Compound 12B: $^1$H NMR (500 MHz, MeOD) δ ppm 0.91 (s, 9H) 1.02-1.17 (m, 3H) 1.20-1.31 (m, 2H) 1.32-1.38 (m, 1H) 1.40-1.46 (m, 1H) 1.90-1.96 (m, 1H) 2.30-2.37 (m, 1H) 2.39-2.47 (m, 1H) 2.69 (dd, J=15.11, 8.09 Hz, 1H) 2.89 (s, 1H) 2.91-2.99 (m, 1H) 3.97 (s, 3H) 4.21 (dd, J=12.05, 2.90 Hz, 1H) 4.44 (d, J=12.21 Hz, 1H) 4.66 (s, 1H) 4.68-4.73 (m, 1H) 5.18 (d, J=10.38 Hz, 1H) 5.38 (d, J=17.09 Hz, 1H) 5.77-5.86 (m, 1H) 5.95 (s, 1H) 6.99 (t, J=6.56 Hz, 1H) 7.21 (d, J=9.16 Hz, 1H) 7.24-7.29 (m, 2H) 7.32 (d, J=6.41 Hz, 1H) 7.95 (d, J=6.10 Hz, 1H) 7.97-8.02 (m, 1H) 8.05 (d, J=8.85 Hz, 1H); LC-MS, MS m/z 691 (M$^+$+H).

Compound 13 Isomers 3-methyl-N-3-pyridinyl-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide and 3-methyl-N-3-pyridinyl-D-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide Example 13

Preparation of Compounds 13A and 13B

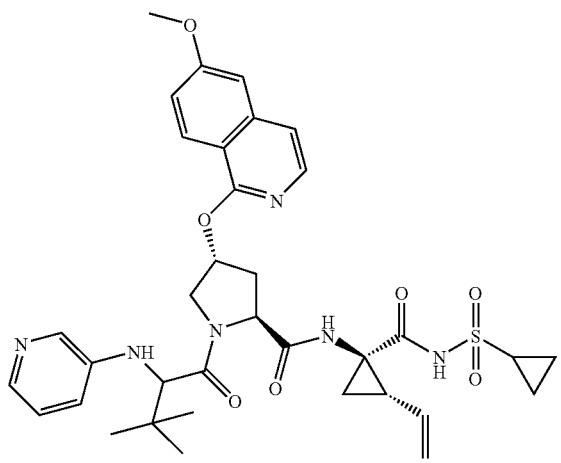

Compound 13A and 13B

Scheme 1

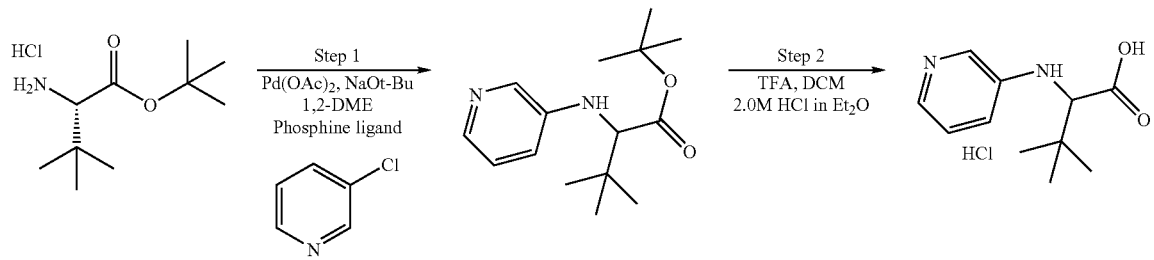

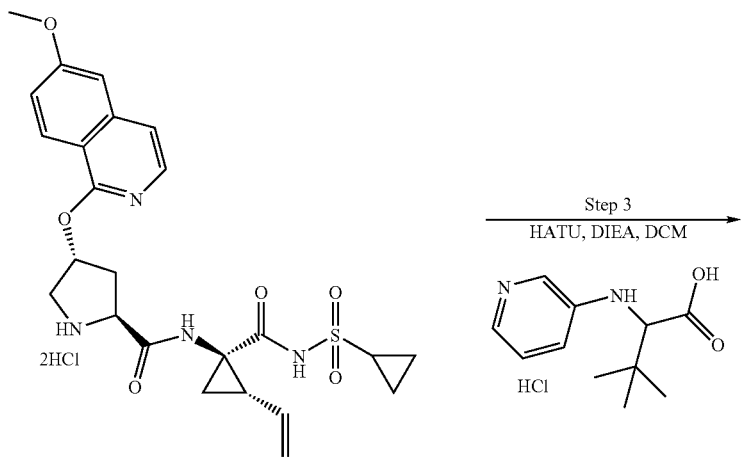

Product of
Step 5, Example 1

Step 3
HATU, DIEA, DCM

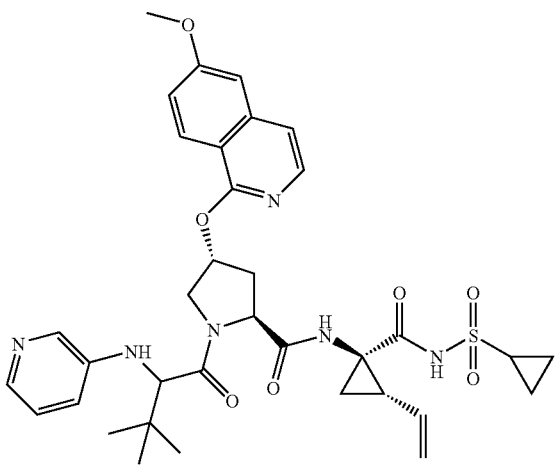

Compounds 13A and 13B
Mixture of isomers

Step 1:

To a mixture of 3-chloropyridine (0.410 g, 3.61 mmol) and sodium tert-butoxide (1.18 g, 12.3 mmol) in dry 1,2-dichloroethane (5 mL) was added a pre-mixed solution of Pd(OAc)$_2$ (0.0405 g, 0.180 mmol) and (R)-(−)-1-[(S)-(dicyclohexylphosphino) ferrocenyl]ethyl di-tert-butyl phosphine (0.100 g, 0.180 mmol, Strem Chemicals catalog #26-0975, CAS # [158923-11-6]) in dry 1,2-dimethoxyethane (2 mL). The mixture was shaken briefly, treated quickly with tert-leucine tert-butyl ester hydrochloride (0.970 g, 4.33 mmol) and shaken again. The mixture was heated to 100° C. for 20 hours, added to a rapidly stirred mixture of pH=7 buffer solution (100 mL) and 1.0M aqueous HCl (12 mL), treated with ethyl acetate, and shaken. The phases were allowed to separate and the organic extract was washed with brine, dried over MgSO$_4$, filtered and concentrated in vacuo to a deep orange residue. The crude product was purified by flash silica gel chromatography (linear gradient 100% hexanes to 1:1 hexanes:ethyl acetate) to give a flesh colored solid (0.583 g, 61.1% yield). LC-MS, MS m/z 265 (M$^+$+H).

Step 2:

The product of Step 1, Example 13 (0.200 g, 0.756 mmol) was dissolved in dichloromethane (5 mL) and treated with TFA (5 mL). The mixture was stirred at room temperature for 5 hours and was then concentrated in vacuo. The residue was then dissolved in 1,2-dichloroethane (15 mL) and again concentrated in vacuo. The residue was then dissolved in dichloromethane (3 mL) and was added dropwise to rapidly stirred 2.0M HCl in ether (40 mL). The resulting beige precipitate was isolated by filtration and allowed to air dry. Beige powder (0.160 g, 86.4% yield). LC-MS, MS m/z 209 (M$^+$+H).

Step 3:

To a mixture of the product of Step 5, Example 1 (0.242 g, 0.422 mmol) and NMM (0.203 g, 2.01 mmol) in dichloromethane (2 mL) was added the product of Step 2, Example 13 (0.098 g, 0.40 mmol) and HATU (0.242 g, 0.422 mmol). The mixture was stirred at room temperature for 18 hours. The solvent was removed in vacuo and the viscous brown residue was directly purified by reverse phase preparative HPLC to give two compounds in good purity with identical MS m/z. Compound 13A (0.154 g, 41.6% yield) was the first of the two isomers to elute from the reverse phase preparative HPLC column and was obtained as an off-white solid bis-TFA salt. Compound 13B (0.118 g, 31.9% yield) was the second of the two isomers to elute from the reverse phase preparative HPLC column and was obtained as a beige powder bis-TFA salt.

Compound 13A: $^1$H NMR (500 MHz, MeOD) δ ppm 1.06-1.18 (m, 12H) 1.24-1.36 (m, 2H) 1.42-1.48 (m, 1H) 1.93 (t, J=6.71 Hz, 1H) 2.23-2.33 (m, 2H) 2.61 (dd, J=13.73, 7.02 Hz, 1H) 2.96-3.05 (m, 1H) 3.96 (s, 3H) 3.98-4.04 (m, 1H) 4.23 (s, 1H) 4.38 (d, J=12.21 Hz, 1H) 4.66 (t, J=8.70 Hz, 1H) 5.17 (dd, J=10.53, 0.76 Hz, 1H) 5.34 (d, J=17.09 Hz, 1H) 5.74-5.83 (m, 1H) 5.89 (s, 1H) 7.08 (dd, J=9.16, 0.92 Hz, 1H) 7.22 (s, 1H) 7.23-7.28 (m, 1H) 7.30 (d, J=6.10 Hz, 1H) 7.57 (d, J=8.85 Hz, 1H) 7.80 (d, J=5.49 Hz, 1H) 7.86 (d, J=9.16 Hz, 1H) 7.94 (d, J=6.10 Hz, 1H) 8.09 (s, 1H) 9.26 (s, 1H); LC-MS, MS m/z 691 (M$^+$+H).

Compound 13B: $^1$H NMR (500 MHz, MeOD) δ ppm 0.94 (s, 9H) 1.10 (d, J=7.32 Hz, 2H) 1.17-1.35 (m, 2H) 1.41 (dd, J=9.46, 5.19 Hz, 1H) 1.87-1.94 (m, 1H) 2.31 (q, J=8.65 Hz, 1H) 2.35-2.43 (m, 1H) 2.59-2.69 (m, 1H) 2.92-3.01 (m, 1H) 3.97 (s, 3H) 4.12 (d, J=11.90 Hz, 1H) 4.38 (s, 1H) 4.49 (d, J=11.90 Hz, 1H) 4.67 (t, J=8.85 Hz, 1H) 5.17 (d, J=10.38 Hz, 1H) 5.36 (d, J=17.09 Hz, 1H) 5.75-5.87 (m, 1H) 5.94 (s, 1H) 7.20 (d, J=8.85 Hz, 1H) 7.25 (s, 1H) 7.31 (d, J=5.80 Hz, 1H) 7.71-7.78 (m, 1H) 7.89-7.99 (m, 3H) 8.04 (d, J=8.85 Hz, 1H) 8.22 (s, 1H) 9.57 (s, 1H); LC-MS, MS m/z 691 (M$^+$+H).

Compound 14 Isomers

N-(4,6-dimethyl-2-pyridinyl)-3-methyl-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide and N-(4,6-dimethyl-2-pyridinyl)-3-methyl-D-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide Example 14

Preparation of Compounds 14A and 14B

Compounds 14A and 14B

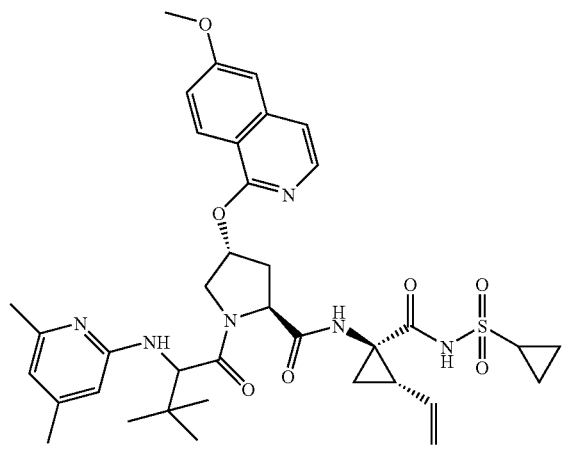

Scheme 1

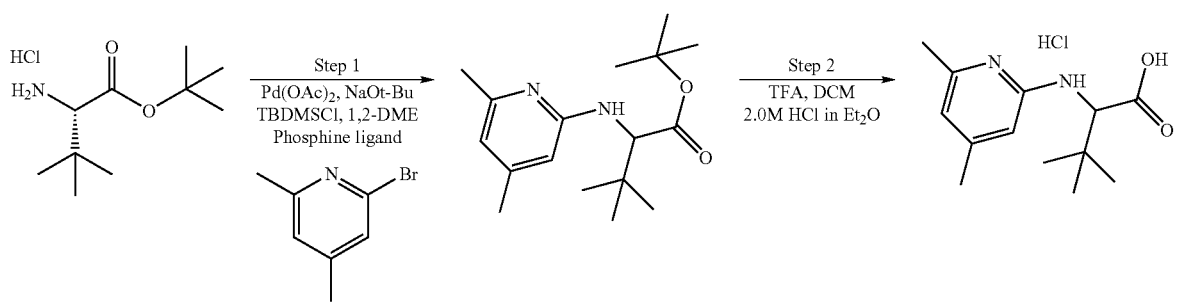

-continued

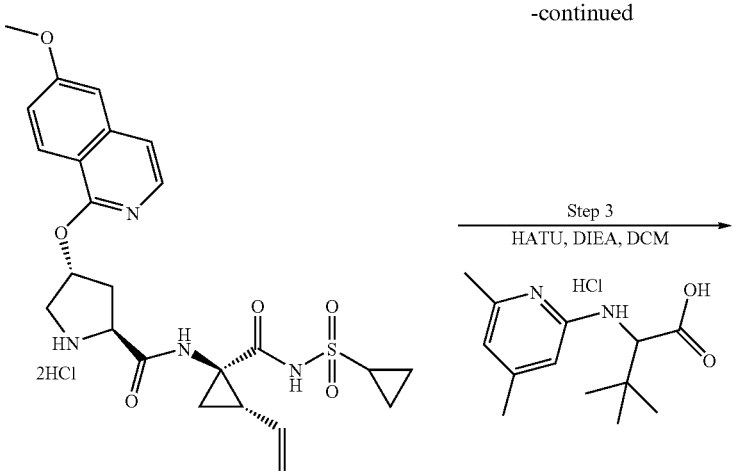

Product of
Step 5, Example 1

Step 3
HATU, DIEA, DCM

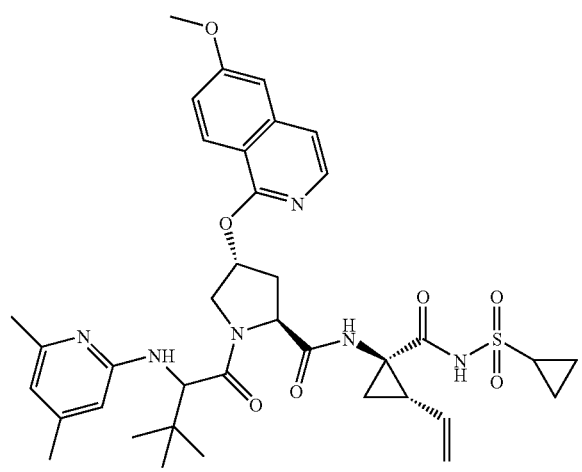

Compounds 14A and 14B
Mixture of isomers

Step 1:

2-Bromo-4,6-dimethylpyridine (0.839 g, 4.51 mmol), sodium tert-butoxide (1.47 g, 15.3 mmol), tert-leucine tert-butyl ester hydrochloride (1.21 g, 5.41 mmol) and TBDMSCl (1.5 g, 9.9 mmol) were combined and treated with 1,2-dimethoxyethane (6 mL). The mixture was shaken and a pre-mixed solution of Pd(OAc)$_2$ (0.202 g, 0.902 mmol) and (R)-(−)-1-[(S)-(dicyclohexylphosphino) ferrocenyl]ethyl di-tert-butyl phosphine (0.500 g, 0.902 mmol, Strem Chemicals catalog #26-0975, CAS # [158923-11-6]) in dry 1,2-dimethoxyethane (2 mL) was immediately added. A moderate exotherm resulted and the mixture became deep brown in color. After 10 minutes, the mixture was orange in color. The mixture was stirred at room temperature for 72 hours. The mixture was then added to a rapidly stirred mixture of pH=7 buffer solution (75 mL) and 1.0M aqueous HCl (15 mL). Ethyl acetate (40 mL) was added and the mixture was shaken and separated the phases. The aqueous phase was extracted with ethyl acetate (2×50 mL). The organic extracts were combined and washed with brine (40 mL), dried over MgSO$_4$, filtered and concentrated in vacuo to a brown residue. The crude product was purified by flash silica gel chromatography (linear gradient 100% hexanes to 10:1 hexanes:ethyl acetate) to give a yellow oil (0.786 g) which was determined to contain the desired product plus 1.9 equivalents of TBDMS byproduct. The material was carried on to the next step without further purification. LC-MS, MS m/z 293 (M$^+$+H).

Step 2:

The product of Step 1, Example 14 (0.750 g) was dissolved in dichloromethane (10 mL) and treated with TFA (10 mL). The mixture was stirred at room temperature for 7 hours and was then concentrated in vacuo. The residue was then dissolved in 1,2-dichloroethane (15 mL) and again concentrated in vacuo. The residue was then dissolved in dichloromethane (3 mL) and was added dropwise to rapidly stirred 2M HCl in diethyl ether (40 mL). No precipitation occurred. Iterative precipitations of the crude material from dichloromethane using hexanes and ethyl acetate as the countersolvents eventually yielded a yellow powder (0.286 g, 23% yield over 2 steps). LC-MS, MS m/z 237 (M$^+$+H).

Step 3:

To a mixture of the product of Step 5, Example 1 (0.189 g, 0.330 mmol) and NMM (0.167 g, 1.65 mmol) in dichloromethane (2 mL) was added the product of Step 2, Example 14 (0.090 g, 0.33 mmol) and HATU (0.151 g, 0.396 mmol).

The mixture was stirred at room temperature for 18 hours. Additional product of Step 2, Example 14 (0.049 g, 0.18 mmol), HATU (0.082 g, 0.216 mmol) and NMM (0.0381 g, 0.377 mmol) were added to the mixture, and the solution was stirred at 40° C. overnight. The solvent was removed in vacuo and the residue was directly purified by reverse phase preparative HPLC to give two separate compounds with identical MS m/z. Compound 14A (0.118 g, 37.8% yield) was the first of the two isomers to elute from the reverse phase preparative HPLC column and was obtained as an off-white powder bis-TFA salt. Compound 14B (0.044 g, 14.1% yield) was the second of the two isomers to elute from the reverse phase preparative HPLC column and was obtained as a beige powder bis-TFA salt.

Compound 14A: $^1$H NMR (500 MHz, MeOD) δ ppm 1.07-1.11 (m, 2H) 1.13 (s, 9H) 1.25-1.30 (m, 2H) 1.46 (dd, J=9.46, 5.49 Hz, 1H) 2.25-2.37 (m, 2H) 2.38 (s, 3H) 2.65 (dd, J=13.58, 7.78 Hz, 1H) 2.94-3.03 (m, 1H) 3.95 (s, 3H) 4.09 (dd, J=12.21, 2.75 Hz, 1H) 4.36 (d, J=12.21 Hz, 1H) 4.48 (s, 1H) 4.69-4.75 (m, 1H) 5.17 (d, J=10.38 Hz, 1H) 5.35 (d, J=17.40 Hz, 1H) 5.72-5.83 (m, 1H) 5.96 (s, 1H) 6.53 (s, 1H) 6.60 (s, 1H) 7.02-7.07 (m, 1H) 7.19-7.22 (m, 1H) 7.30 (d, J=6.10 Hz, 1H) 7.87 (d, J=9.16 Hz, 1H) 7.94-7.97 (m, 1H); LC-MS, MS m/z 719 (M$^+$+H).

Compound 14B: $^1$H NMR (500 MHz, MeOD) δ ppm 0.92 (s, 9H) 1.05-1.10 (m, 2H) 1.13-1.19 (m, 1H) 1.21-1.26 (m, 1H) 1.41 (dd, J=9.46, 5.19 Hz, 1H) 1.89-1.94 (m, 1H) 2.32 (q, J=8.75 Hz, 1H) 2.40-2.44 (m, 1H) 2.45 (s, 3H) 2.48 (s, 3H) 2.65-2.71 (m, 1H) 2.90-2.96 (m, 1H) 3.96 (d, J=1.83 Hz, 1H) 3.97 (d, J=1.53 Hz, 3H) 4.20 (dd, J=12.36, 2.90 Hz, 1H) 4.51 (d, J=12.51 Hz, 1H) 4.62 (s, 1H) 4.69 (t, J=8.39 Hz, 1H) 5.17 (d, J=10.07 Hz, 1H) 5.36 (d, J=17.40 Hz, 1H) 5.75-5.83 (m, 1H) 5.97 (s, 1H) 6.71 (s, 1H) 6.88 (s, 1H) 7.19-7.23 (m, 1H) 7.25 (d, J=2.14 Hz, 1H) 7.32 (d, J=5.80 Hz, 1H) 7.95 (dd, J=5.95, 1.68 Hz, 1H) 8.05 (d, J=9.16 Hz, 1H); LC-MS, MS m/z 719 (M$^+$+H).

Compound 15 Isomers 3-methyl-N-phenyl-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide and 3-methyl-N-phenyl-D-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide Example 15

Preparation of Compounds 15A and 15B

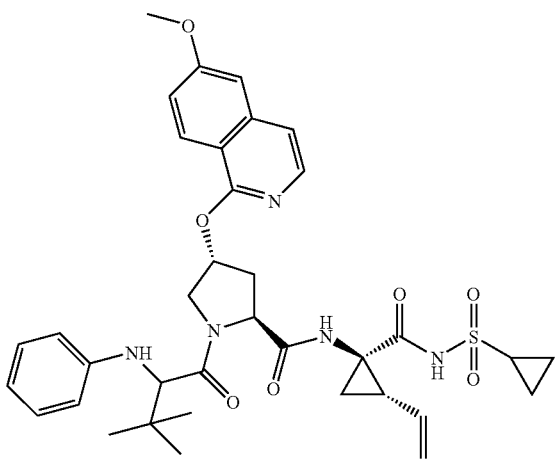

Compounds 15A and 15B

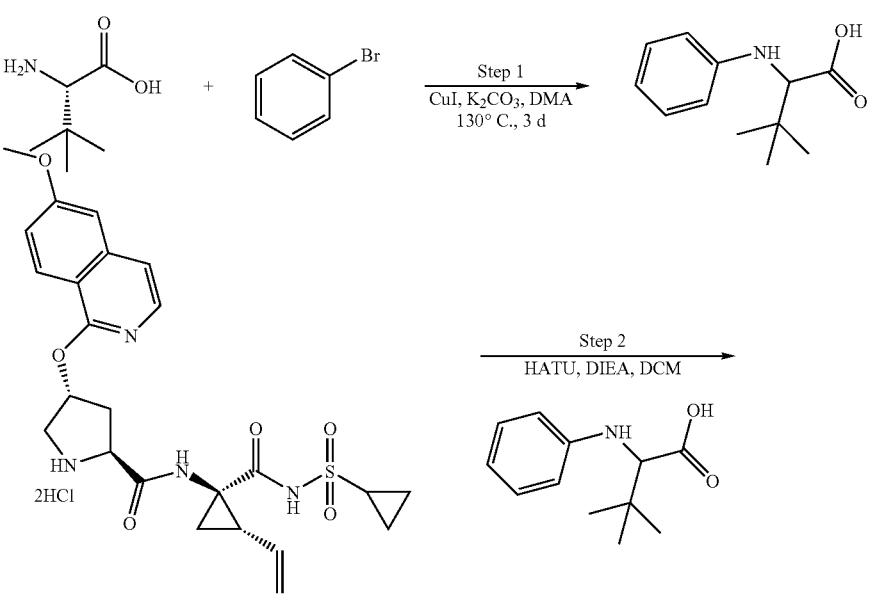

Scheme 1

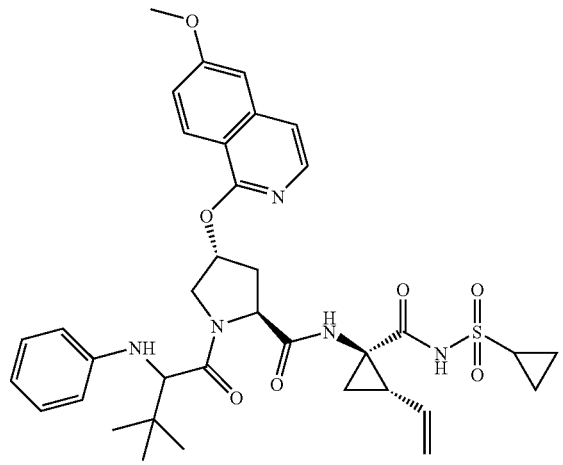

Compounds 15A and 15B
Mixture of isomers

Step 1:

L-tert-Leucine (0.840 g, 6.40 mmol), $K_2CO_3$ (1.33 g, 9.60 mmol) and CuI (0.122 g, 0.64 mmol) were combined in a 35 mL Chemglass pressure vessel. Bromobenzene (1.01 g, 6.4 mmol) and DMA (8 mL) were added, the vessel headspace was with nitrogen, the vessel was sealed, and the mixture was heated to 90° C. overnight. Additional DMA (8 mL) was added to facilitate stirring and the mix was heated to 130° C. overnight. With only a small amount of product formation as determined by LCMS, the mixture was charged with an excess of CuI (approximately 1 g), the reaction was resealed and heated to 130° C. for 2 days. The mixture was cooled to room temperature and treated with 1.0M aqueous HCl until pH=5 was achieved, then pH=7 buffer (50 mL) and ethyl acetate (50 mL) were added and the mixture was shaken and phases were separated. The aqueous phase was extracted with ethyl acetate (2×50 mL), and the organics were combined and washed with brine, dried over $MgSO_4$, filtered and concentrated in vacuo to a solid residue. Purification by silica gel flash chromatography (20:1 dichloromethane:methanol) gave a waxy flesh-colored solid (0.286 g) which contained approximately 1.2 equivalents of entrained DMA by $^1H$ NMR. LC-MS, MS m/z 208 ($M^+$+H).

Step 2:

To a mixture of the product of Step 5, Example 1 (0.200 g, 0.349 mmol) and NMM (0.141 g, 1.40 mmol) in dichloromethane (2 mL) was added the product of Step 1, Example 15 (0.108 g, 0.35 mmol, 67% pure) and HATU (0.160 g, 0.418 mmol). The mixture was stirred at room temperature for 18 hours. The solvent was removed in vacuo and to the residue was added ethyl acetate (30 mL) and water (30 mL). Not all solids dissolved. The mixture was transferred to a 250 mL round bottom flask with 1:1 dichloromethane:methanol solvent, and the mixture was concentrated in vacuo until the organic solvents were removed, leaving the aqueous phase and undissolved solids. It was determined by LCMS that a crude purification had occurred where the aqueous phase held mostly water soluble byproducts with little product, and the solid consisted mostly of product. The solid was filtered from the liquid to give a white powder (0.225 g). Further purification of the white powder by reverse phase preparative HPLC gave two separate compounds with identical MS m/z. Compound 15A (0.124 g, 38.8% yield) was the first of the two isomers to elute from the reverse phase preparative HPLC column and was obtained as a brown powder bis-TFA salt. Compound 15B (0.0633 g, 19.8% yield) was the second of the two isomers to elute from the reverse phase preparative HPLC column and was obtained as a brown powder bis-TFA salt.

Compound 15A: $^1H$ NMR (500 MHz, MeOD) δ ppm 1.09-1.15 (m, 2H) 1.19 (s, 9H) 1.27-1.33 (m, J=2.44 Hz, 2H) 1.43-1.48 (m, 1H) 1.89-1.94 (m, 1H) 2.21-2.30 (m, 1H) 2.57 (dd, J=13.58, 7.17 Hz, 1H) 2.96-3.03 (m, 1H) 3.99 (d, J=1.83 Hz, 3H) 4.02-4.08 (m, 1H) 4.14 (s, 1H) 4.28 (d, J=12.21 Hz, 1H) 4.44-4.51 (m, 1H) 5.16 (d, J=10.38 Hz, 1H) 5.32 (d, J=17.09 Hz, 1H) 5.73-5.83 (m, 2 H) 6.41 (t, J=7.17 Hz, 1H) 6.69-6.73 (m, 2H) 6.76 (t, J=7.02 Hz, 2H) 7.10 (d, J=9.16 Hz, 1H) 7.26 (s, 1H) 7.30-7.34 (m, 1H) 7.73 (dd, J=9.00, 1.37 Hz, 1H) 7.92 (dd, J=5.80, 1.83 Hz, 1H); LC-MS, MS m/z 690 ($M^+$+H).

Compound 15B: $^1H$ NMR (500 MHz, DMSO-D6) δ ppm 0.87 (s, 9H) 0.94-1.00 (m, 1H) 1.00-1.05 (m, J=6.41 Hz, 2H) 1.10-1.19 (m, 1H) 1.28 (dd, J=9.31, 5.04 Hz, 1H) 1.72 (dd, J=7.63, 5.19 Hz, 1H) 2.05-2.13 (m, 1H) 2.21-2.28 (m, 1H) 2.40-2.48 (m, 1H) 2.81-2.88 (m, 1H) 3.91 (d, J=1.83 Hz, 3H) 3.94-4.00 (m, 1H) 4.19 (s, 1H) 4.41 (d, J=11.90 Hz, 1H) 4.43-4.49 (m, 1H) 5.12 (d, J=10.07 Hz, 1H) 5.27 (d, J=17.09 Hz, 1H) 5.58-5.71 (m, 1H) 5.87 (s, 1H) 6.55 (t, J=7.17 Hz, 1H) 6.74 (d, J=7.63 Hz, 2H) 7.03-7.10 (m, 2H) 7.22-7.27 (m, 1H) 7.31-7.37 (m, 2H) 7.88 (d, J=9.16 Hz, 1H) 7.97 (dd, J=5.80, 2.14 Hz, 1H) 9.18 (s, 1H) 10.74 (s, 1H); LC-MS, MS m/z 690 ($M^+$+H).

Example 16

Preparation of Compound 16: N-(4,6-dimethyl-2-pyridinyl)valyl-(4R)—N-((1R,2S)-1-((dimethylsulfamoyl)carbamoyl)-2-vinylcyclopropyl)-4-((6-methoxy-1-isoquinolinyl)oxy)-L-prolinamide Compound 16

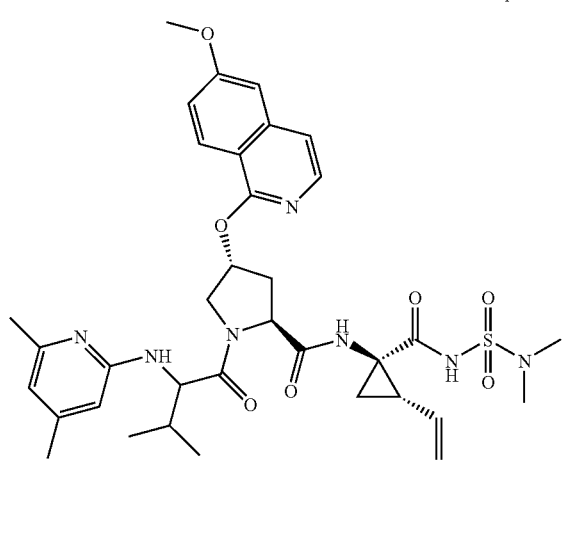

Scheme 1

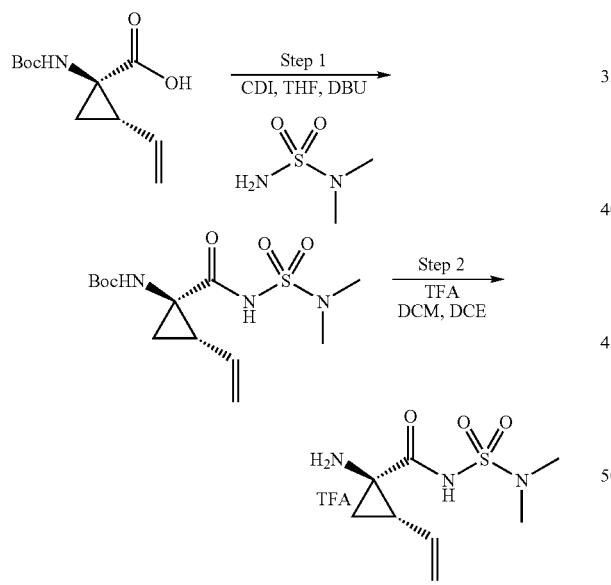

Step 1:

To a solution of N-Boc-vinylcyclopropane carboxylic acid (1.83 g, 8.05 mmol) and THF (32 mL) was added 1,1'-carbonyldiimidazole (1.44 g, 8.86 mmol). After stirring at room temperature for 3 hours, the reaction mixture was treated with N,N-dimethylsulfamide (1.0 g, 8.05 mmol) followed by DBU (2.45 g, 16.1 mmol) and was stirred at room temperature for an additional 15 hours. The reaction was then diluted with ethyl acetate (50 mL) and washed with 1.0M aqueous HCl (2×25 mL). The aqueous layer was extracted with ethyl acetate (2×50 mL). The combined organic portion was washed with $H_2O$ (25 mL) and brine, dried over $MgSO_4$, filtered, and concentrated to a light yellow solid (2.6 g, 97% yield) which was used without further purification. LC-MS, MS m/z 356 ($M^+$+Na).

Step 2:

To a solution of the product of Step 2, Example 16, (1.42 g, 4.26 mmol) in 1:1 dichloromethane: 1,2-dichloroethane (20 mL) was added TFA (10 mL). After stirring at room temperature for 0.5 hours, the solvent and excess TFA were removed and the residue was redissolved in 1,2-dichloroethane (20 mL) and concentrated again to give a yellow solid (1.46 g, 99% yield). LC-MS, MS m/z 234 ($M^+$+H).

Scheme 2

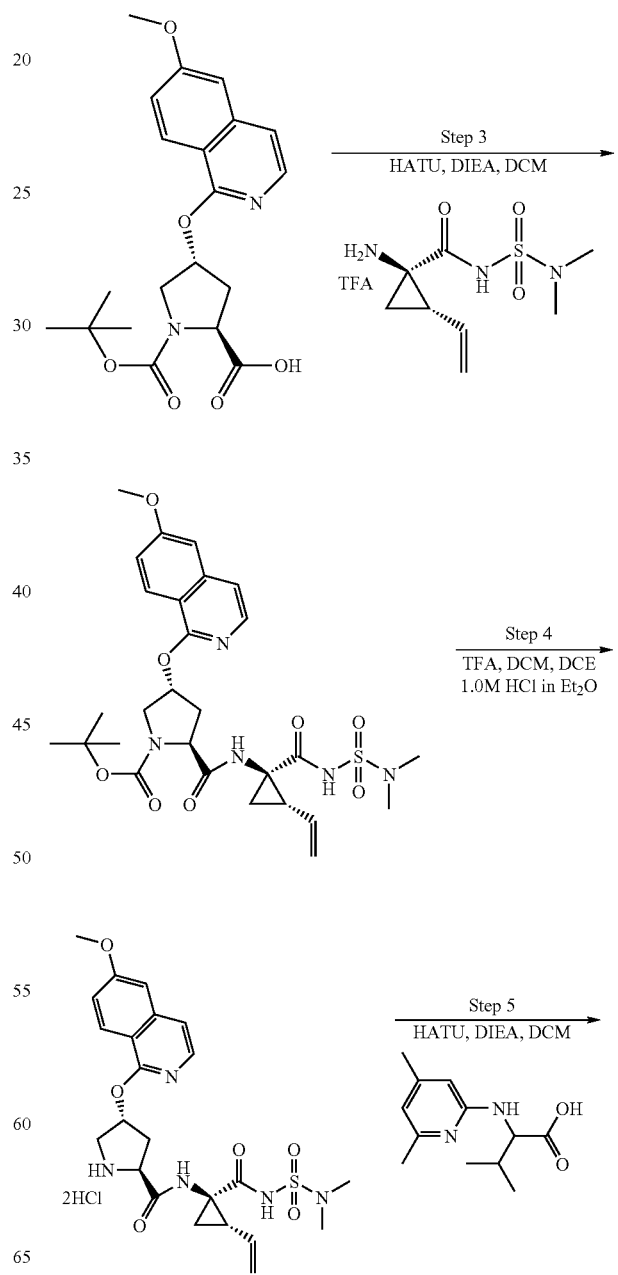

-continued

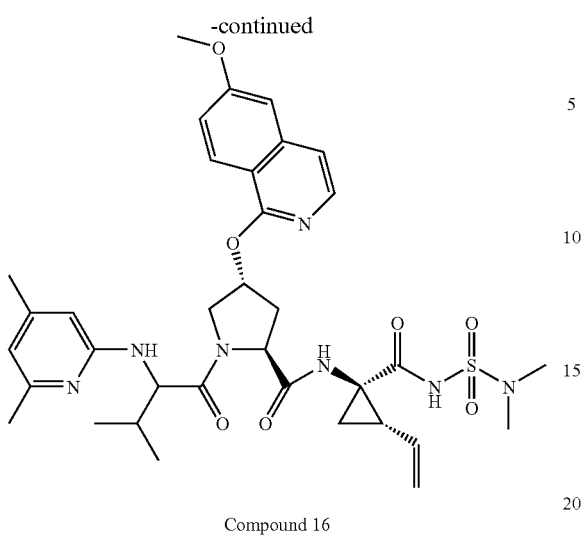

Compound 16

Step 3:
The product of Step 3, Example 16, was prepared in 91% yield from the product of Step 2, Example 16, by the same procedure as described for the preparation of the product of Step 4, Example 1.

Step 4:
The product of Step 4, Example 16, was prepared in 95% yield from the product of Step 3, Example 16, by the same procedure as described for the preparation of the product of Step 5, Example 1. LC-MS, MS m/z 504 (M$^+$+H).

Step 5:
To a mixture of the product of Step 4, Example 16 (0.200 g, 0.347 mmol) and DIEA (0.180 g, 1.39 mmol) in dichloromethane (4 mL) was added 2-(4,6-dimethylpyridine-2-ylamino)-3-methylbutanoic acid (0.092 g, 0.416 mmol) and HATU (0.198 g, 0.520 mmol). The mixture was stirred at room temperature for 8 hours. The reaction was incomplete by LCMS. Additional 2-(4,6-dimethylpyridine-2-ylamino)-3-methylbutanoic acid (0.039 g, 0.174 mmol) and HATU (0.066 g, 0.174 mmol) were added and the mixture was stirred at room temperature for another 16 hours. The reaction was still incomplete by LCMS. Again, additional 2-(4,6-dimethylpyridine-2-ylamino)-3-methylbutanoic acid (0.039 g, 0.174 mmol) and HATU (0.066 g, 0.174 mmol) were added and the mixture was stirred at room temperature for another 16 hours. The solvent was removed and the residue was dissolved in ethyl acetate (50 mL) and the solution was washed with 1.0M aqueous HCl (2×5 mL). The aqueous extracts were combined and back-extracted with ethyl acetate (50 mL), and the organic phases were combined and washed with 10% aqueous sodium carbonate and then with brine. The organic phase was dried over anhydrous MgSO$_4$, filtered, and concentrated to a residue which was purified by reverse phase preparative HPLC to give Compound 16 (the major of two isomers formed) as a yellow solid bis-HCl salt (0.060 g, 22.1% yield). $^1$H NMR (500 MHz, MeOD) δ ppm 1.01 (d, J=6.7 Hz, 3H), 1.10 (d, J=6.7 Hz, 3H), 1.43 (dd, J=9.5, 5.2 Hz, 1H), 1.88-1.95 (m, 1H), 2.20 (s, 3H), 2.23-2.32 (m, 1H), 2.39 (s, 1H), 2.43 (s, 3H), 2.69 (dd, J=13.7, 7.0 Hz, 1H), 2.77-2.80 (m, 1H), 2.87-2.90 (m, 1H), 2.93 (s, 6H), 3.97 (s, 3H), 4.18 (dd, J=12.2, 3.4 Hz, 1H), 4.38 (d, J=12.2 Hz, 1H), 4.57 (d, J=6.7 Hz, 1H), 4.70 (dd, J=10.1, 7.0 Hz, 1H), 5.18 (dd, J=10.4, 1.8 Hz, 1H), 5.35 (d, J=17.1 Hz, 1H), 5.72-5.83 (m, 1H), 5.98 (d, J=2.7 Hz, 1H), 6.60 (s, 1H), 6.69 (s, 1H), 7.17 (dd, J=9.2, 2.4 Hz, 1H), 7.28 (d, J=2.4 Hz, 1H), 7.39 (d, J=6.1 Hz, 1H), 7.94 (d, J=6.1 Hz, 1H), 8.05 (d, J=9.2 Hz, 1H); LC-MS, MS m/z 708 (M$^+$+H).

Example 17

Preparation of Compound 17: N-(4,6-dimethyl-2-pyridinyl)valyl-(4R)—N-((1R,2S)-1-((cyclopropylsulfonyl)carbamoyl)-2-vinylcyclopropyl)-4-((3-(dimethylamino)-6-methoxy-1-isoquinolinyl)oxy)-L-prolinamide

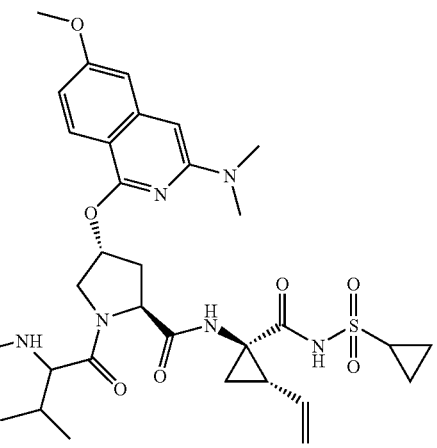

Compound 17

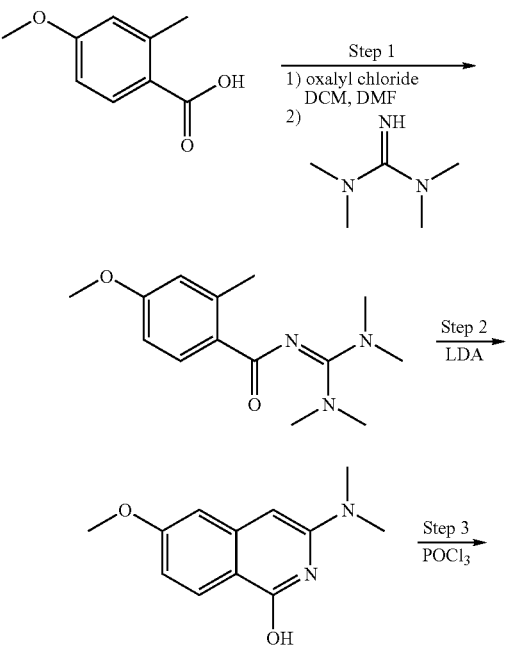

Scheme 1

-continued

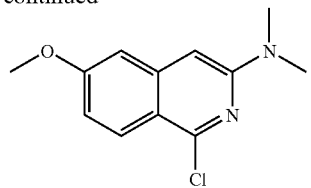

Step 1:
A solution of 4-methoxy-2-methylbenzoic acid (10.2 g, 61.4 mmol) in dichloromethane (200 mL) was treated slowly with oxalyl chloride. A drop of DMF was added and the reaction was stirred at room temperature for 12 hours. The mixture was then treated with 1,1,3,3-tetramethylguanidine (14.9 g, 128.9 mmol) and stirred at room temperature for 4 hours. The mixture was washed with 5% aqueous citric acid (2×100 mL). The aqueous phase was back-extracted with dichloromethane (2×100 mL), and the organic phases were combined, dried over anhydrous $MgSO_4$, filtered, and concentrated to provide a minimal amount of desired product. The aqueous phase was made basic by addition of 10.0M aqueous NaOH until pH=13 was achieved and was then extracted with dichloromethane (4×200 mL). The organic phases were combined, dried over anhydrous $MgSO_4$, filtered and concentrated. The resulting oil was combined with the earlier obtained product and the mixture was treated with diethyl ether to give a white precipitate which was removed by filtration. The filtrate was concentrated to give the desired product (11.3 g, 70% yield) as a viscous yellow oil. $^1$H NMR ($CD_3OD$) δ 2.54 (s, 3H), 3.97 (s, 6H), 3.79 (s, 3H), 6.60 (d, J=9.2 Hz, 1H), 6.75 (s, 1H), 7.65 (d, J=8.9 Hz, 1H). LC-MS, MS m/z 264 ($M^+$+H).

Step 2:
A solution of the product of Step 1, Example 17 (0.461 g, 1.78 mmol) in THF (5 mL) at 0° C. was treated with LDA solution (1.8M in THF/hexanes, 1.2 mL, 2.14 mmol). The reaction was stirred at room temperature for 5 hours and was then treated with additional LDA (1 mL) and stirred at room temperature for 14 hours. The mixture was quenched with saturated ammonium chloride (10 mL) and extracted with ethyl acetate (3×25 mL). The organic phases were combined, dried over anhydrous $MgSO_4$, filtered and concentrated. The concentrate was dissolved in minimal dichloromethane and diethyl ether was added. The resulting precipitate was collected by filtration to provide the desired product (0.312 g, 80% yield) as a brown solid. $^1$H NMR ($CD_3OD$) δ 2.94 (s, 6H), 3.86 (s, 3H), 5.71 (s, 1H), 6.75 (dd, J=8.9, 2.4 Hz, 1H), 6.83 (d, J=2.4 Hz, 1H). 7.97 (d, J=9.2 Hz, 1H). LC-MS, MS m/z 219 ($M^+$+H).

Step 3:
The product of Step 2, Example 17 (10.0 g, 45.8 mmol) was treated with $POCl_3$ (43 mL) and the mixture was heated to 110° C. for 5 hours in a Chemglass pressure vessel. Upon cooling to room temperature, the resulting cake was dissolved in dichloromethane (200 mL) and the solution was quenched by slow addition of saturated aqueous sodium bicarbonate. Vigorous gas evolution ensued. When gas evolution ceased, the mixture was shaken in a separatory funnel and the phases were separated. The aqueous phase was extracted with dichloromethane (3×200 mL). The combined organic phase was washed with brine, dried over anhydrous $MgSO_4$, filtered and concentrated. Diethyl ether was added to the residue to effect the precipitation of a black solid which was collected by filtration and washed with ether. Thus was obtained the desired product (5.72 g, 53.0% yield). LC-MS, MS m/z 237 ($M^+$+H).

Scheme 2

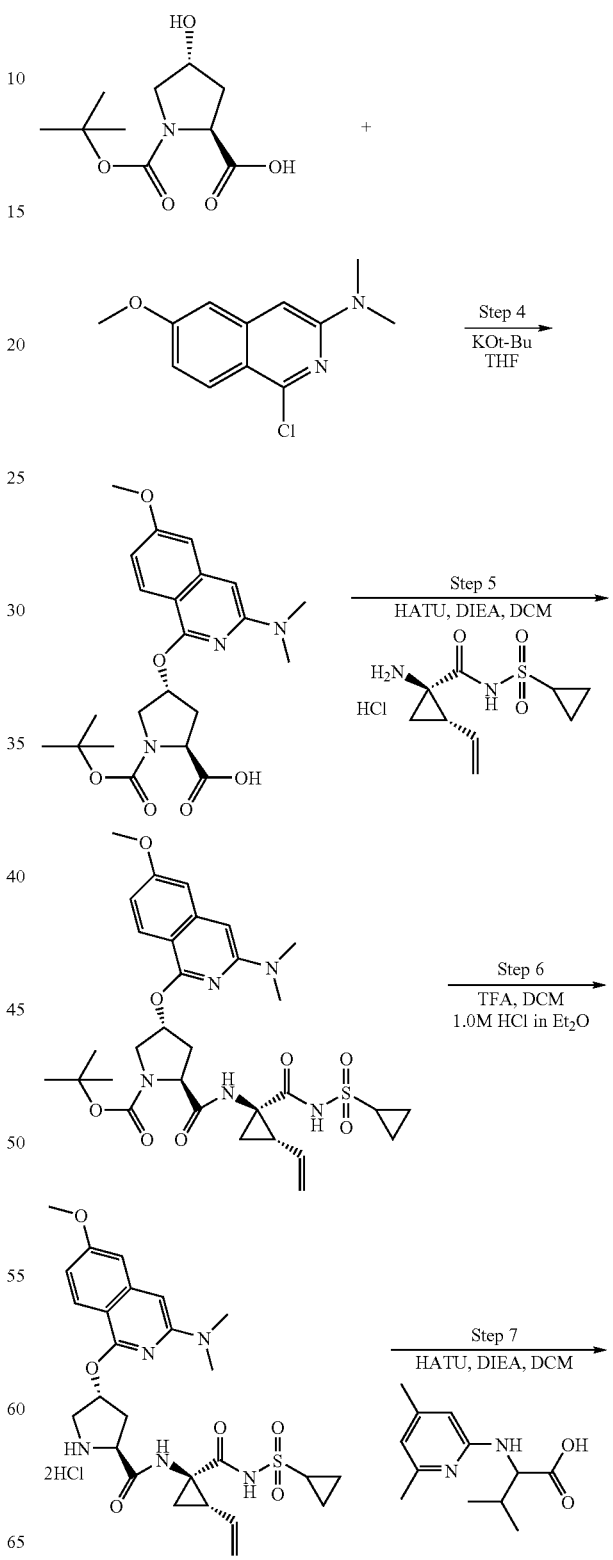

-continued

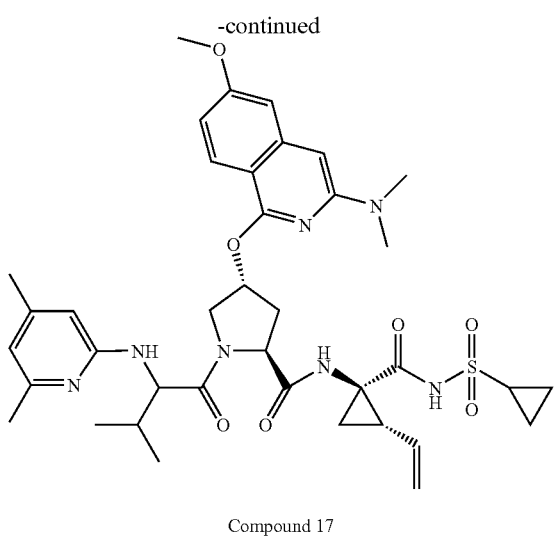

Compound 17

Step 4:

To a solution of Boc-Hyp-OH (5.60 g, 24.2 mmol) in THF (100 mL) was added potassium tert-butoxide (1.0M in THF, 53.2 mL, 53.2 mmol). The mixture turned brown and became a gel which broke with vigorous stirring. After 15 minutes, the product of Step 3, Example 17 (5.72 g, 24.2 mmol) was added in portions. The mixture was heated to 70° C. for 48 hours. The mixture was quenched by addition of 1.0M HCl and was then extracted with ethyl acetate. The aqueous phase was extracted with ethyl acetate once more. The organic phases were combined and washed with brine, dried over $MgSO_4$, and filtered. The filtrate was evaporated in vacuo to dryness to give the desired product. LC-MS, MS m/z 430 (M−H).

Step 5:

A mixture of the product of Step 4, Example 17 (8.90 g, 20.6 mmol), DIEA (8.01 g, 61.9 mmol), and cyclopropanesulfonic acid (1-(R)-amino-2-(S)-vinyl-cyclopropanecarbonyl)-amide HCl salt (6.60 g, 24.8 mmol) in dichloromethane (150 mL) was treated with HATU (10.2 g, 26.8 mmol), and the resulting brown solution was stirred at room temperature for 18 hours. The solvent was removed in vacuo, and the residue was taken up in ethyl acetate (200 mL) and washed with water (100 mL). The phases were separated and the aqueous phase was back-extracted with ethyl acetate (3×100 mL). The combined organic phase was washed with 0.10 M aqueous HCl (100 mL), then with 10% aqueous sodium carbonate (50 mL) and finally with brine. The organic phase was dried over $MgSO_4$, filtered, and concentrated to give a dark brown foamy solid. The product was purified by flash silica gel chromatography (95:5 dichloromethane:methanol) to give a brown solid (12.9 g, 97% yield). LC-MS, MS m/z 642 (M−H).

Step 6:

To a solution of the product of Step 5, Example 17 (12.7 g, 19.6 mmol) in 1:1 dichloromethane: 1,2-dichloroethane (100 mL) was added TFA (50 mL). The mixture was stirred at room temperature for 30 minutes and was then concentrated in vacuo. The residue was redissolved in 1,2-dichloroethane (100 mL) and again concentrated in vacuo. The residue was then dissolved in dichloromethane (50 mL) and was added dropwise to vigorously stirred 1.0M HCl in diethyl ether (500 mL). The resulting light brown solid precipitate was isolated by filtration and washed with 1.0M HCl in diethyl ether to give a brown powder (10.2 g, 85.0% yield). LC-MS, MS m/z 544 ($M^+$+H).

Step 7:

The product of Step 6, Example 17 (0.258 g, 0.419 mmol), 2-(4,6-dimethylpyridin-2-ylamino)-3-methyl butanoic acid (0.111 g, 0.503 mmol), DIEA (0.217 g, 1.68 mmol) and HATU (0.239 g, 0.629 mmol) were combined in dichloromethane (4 mL) and the mixture was stirred for 8 hours at room temperature. Additional 2-(4,6-dimethylpyridin-2-ylamino)-3-methylbutanoic acid (0.0465 g, 0.210 mmol) and HATU (0.080 g, 0.21 mmol) were added and the mixture was stirred at room temperature for an additional 14 hours. Solvent was removed and the residue was redissolved in ethyl acetate (50 mL) and washed with 1.0M aqueous HCl (2×5 mL). The aqueous extracts were combined and back-extracted with ethyl acetate (50 mL), and the organic phases were combined and washed with 10% aqueous sodium carbonate and then with brine. The organic phase was dried over anhydrous $MgSO_4$, filtered, and concentrated to a residue which was purified by reverse phase preparative HPLC to give Compound 17 (0.037 g, 10.8% yield) as a brown powder bis-HCl salt. $^1$H NMR (500 MHz, MeOD) δ ppm 1.02 (d, J=6.7 Hz, 3H), 1.10 (d, J=6.4 Hz, 3H), 1.12-1.18 (m, 3H), 1.22-1.30 (m, 2H), 1.35 (t, J=7.3 Hz, 1H), 1.46 (dd, J=9.6, 5.3 Hz, 1H), 1.95 (dd, J=7.9, 5.5 Hz, 1H), 2.22 (s, 3H), 2.28-2.36 (m, 2H), 2.41 (s, 3H), 2.52 (d, J=14.6 Hz, 1H), 2.66 (dd, J=13.7, 7.3 Hz, 1H), 2.96-3.03 (m, 2H), 3.21 (s, 6H), 3.91 (s, 3H), 4.01-4.06 (m, 1H), 4.18 (dd, J=11.9, 3.4 Hz, 1H), 4.31 (d, J=11.9 Hz, 1H), 4.56 (d, J=7.0 Hz, 1H), 4.68 (dd, J=9.9, 7.2 Hz, 1H), 5.14-5.19 (m, 1H), 5.35 (d, J=17.1 Hz, 1H), 5.75-5.85 (m, 1H), 6.01 (s, 1H), 6.60 (s, 1H), 6.69 (s, 1H), 6.83 (d, J=8.9 Hz, 1H), 7.05 (s, 1H), 7.81 (d, J=9.2 Hz, 1H); LC-MS, MS m/z 748 ($M^+$+H).

Example 18

Preparation of Compound 18: N-(4,6-dimethyl-2-pyridinyl)-3-methylvalyl-(4R)—N-((1R,2S)-1-((cyclopropylsulfonyl)carbamoyl)-2-vinylcyclopropyl)-4-((3-(dimethylamino)-6-methoxy-1-isoquinolinyl)oxy)-L-prolinamide

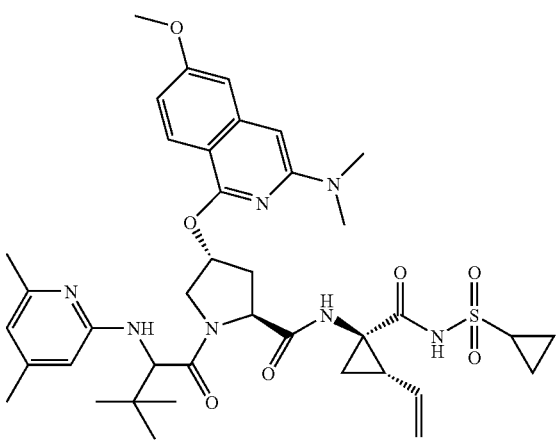

Compound 18

Compound 18 was prepared by the same method as described in Step 3, Example 14, except the product of Step 6, Example 17 (0.203 g, 0.330 mmol) was used in place of the product of Step 5, Example 1. Two products with identical LCMS m/z were formed in the reaction, but only the single isomer Compound 18 was isolated in reasonable purity. Compound 18 was the first of the two isomers to elute by reverse phase preparative HPLC and was obtained as a brown powder bis-TFA salt (0.102 g, 40.6% yield). $^1$H NMR (500 MHz, MeOD) δ ppm 1.08-1.11 (m, J=3.05 Hz, 2H) 1.13 (s, 9H) 1.15-1.19 (m, J=1.83 Hz, 2H) 1.25-1.30 (m, 2H) 1.43-1.48 (m, 1H) 1.92-1.97 (m, 1H) 2.06 (s, 3H) 2.26-2.35 (m, 2H) 2.37 (s, 3H) 2.61-2.67 (m, 1H) 2.96-3.03 (m, 2H) 3.13 (d, J=1.83 Hz, 6H) 3.88 (d, J=1.83 Hz, 3H) 4.06 (dd, J=12.21, 2.75 Hz, 1H) 4.28 (d, J=12.51 Hz, 1H) 4.47 (s, 1H) 4.71 (t, J=8.70 Hz, 1H) 5.17 (d, J=10.38 Hz, 1H) 5.35 (d, J=17.09 Hz, 1H) 5.73-5.82 (m, 1H) 5.99 (s, 1H) 6.52 (s, 1H) 6.54-6.58 (m, 1H) 6.61 (s, 1H) 6.87 (t, J=1.98 Hz, 1H) 7.56 (dd, J=9.00, 1.98 Hz, 1H); LC-MS, MS m/z 762 (M$^+$+H).

Compound 19 Isomers 3-methyl-N-phenyl-L-valyl-(4R)—N-((1R,2S)-1-((cyclopropylsulfonyl)carbamoyl)-2-vinylcyclopropyl)-4-((3-(dimethylamino)-6-methoxy-1-isoquinolinyl)oxy)-L-prolinamide and 3-methyl-N-phenyl-D-valyl-(4R)—N-((1R,2S)-1-((cyclopropylsulfonyl)carbamoyl)-2-vinylcyclopropyl)-4-((3-(dimethylamino)-6-methoxy-1-isoquinolinyl)oxy)-L-prolinamide Example 19

Preparation of Compounds 19A and 19B

Compound 19A and 19B

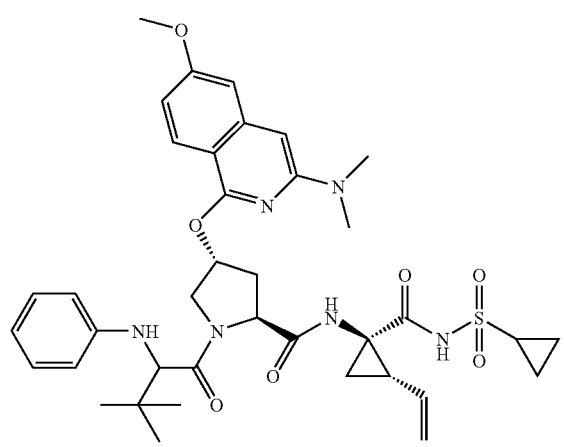

The product of Step 6, Example 17 (0.203 g, 0.330 mmol), NMM (0.134 g, 1.32 mmol), HATU (0.151 g, 0.396 mmol) and the product of Step 1, Example 15 (0.102 g, 0.330 mmol) were combined in dichloromethane (2 mL) and stirred for 72 hours. Two products with identical LCMS m/z were formed in the reaction. The mixture was concentrated and purified by reverse phase preparative HPLC. Compound 19A was the first of the two isomers to elute by reverse phase preparative HPLC and was obtained as a brown powder bis-TFA salt (0.0806 g, 33.3% yield). Compound 19B was the second of the two isomers to elute by reverse phase preparative HPLC and was obtained as a brown powder bis-TFA salt (0.0573 g, 23.7% yield).

Compound 19A

LC-MS, MS m/z 733 (M$^+$+H).

Compound 19B

LC-MS, MS m/z 733 (M$^+$+H).

Compound 20 Isomers 3-methyl-N-phenyl-L-valyl-(4R)—N-((1R,2S)-1-((cyclopropylsulfonyl)carbamoyl)-2-vinylcyclopropyl)-4-((3,6-dimethoxy-1-isoquinolinyl)oxy)-L-prolinamide and 3-methyl-N-phenyl-D-valyl-(4R)—N-((1R,2S)-1-((cyclopropylsulfonyl)carbamoyl)-2-vinylcyclopropyl)-4-((3,6-dimethoxy-1-isoquinolinyl)oxy)-L-prolinamide Example 20

Preparation of Compounds 20A and 20B

Compounds 20A and 20B

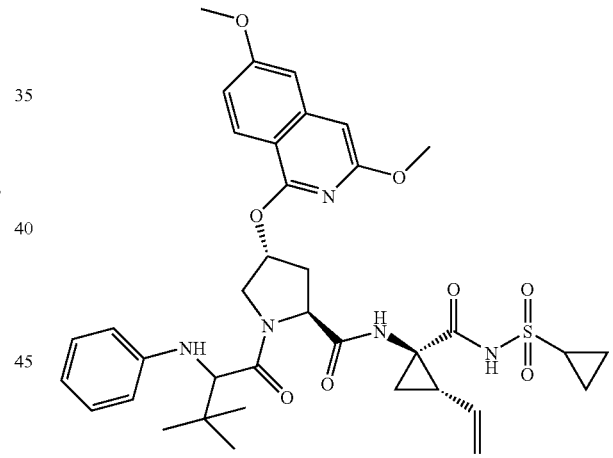

Scheme 1

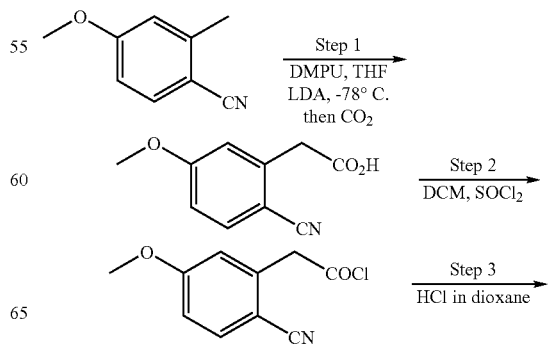

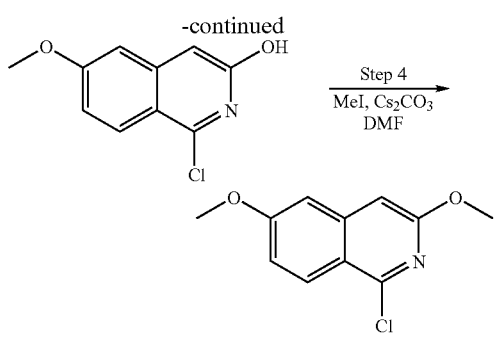

NaOH (aq), and brine sequentially, dried over MgSO$_4$, and filtered. The filtrate was concentrated and the residue was purified by flash column silica gel chromatography. Elution with dichloromethane furnished the desired product as an off-white solid (0.152 g, 68.0% yield). LC-MS MS m/z 224 (M$^+$+H).

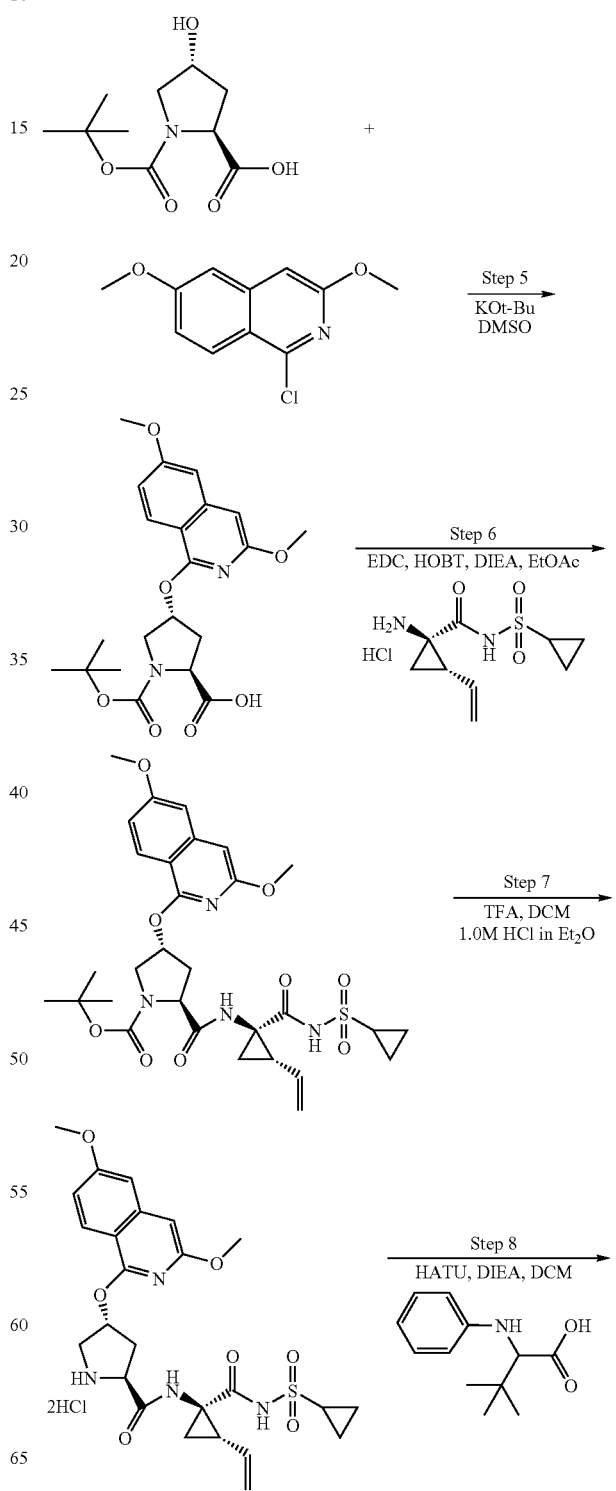

Step 1:

To a solution of 1,3-dimethyl-3,4,5,6-tetrahydro-2(1H)-pyrimidinone (DMPU, 7.02 g, 55 mmol) in THF (100 mL) was added LDA (2.0M in THF, 27.5 mL, 55 mmol) dropwise at −78° C. The resulting orange solution was kept at this temperature for 10 minutes with stirring and then 4-methoxy-2-methylbezonitrile (7.36 g, 50 mmol in 5 mL THF) was added dropwise. The resulting dark orange solution was kept at this temperature for 30 minutes with stirring. CO$_2$ gas was then bubbled into this solution at −78° C. until it became colorless. The final solution was kept at this temperature for an additional 30 minutes with stirring before being purged with N$_2$ for 5 minutes. The mixture was quenched with H$_2$O (80 mL) at −78° C., then allowed to warm up to room temperature. 10.0M NaOH (aq, 20 mL, 200 mmol) was added, resulting in a homogeneous solution which was extracted with diethyl ether (100 mL). The aqueous layer was acidified by concentrated HCl to pH=2, and the resulting precipitate was collected by filtration. The cake was washed with H$_2$O thoroughly and dried in vacuo overnight to furnish the desired product (7.90 g 83.0% yield) as a white fakes. $^1$H NMR (300 MHz, CD$_3$OD) δ ppm 3.83 (s, 2H), 3.86 (s, 3H), 6.99 (m, 2H), 7.64 (d, J=8.42 Hz, 1H).

Step 2:

A slurry of 2-(2-cyano-5-methoxyphenyl)acetic acid in dichloromethane (40 mL) and thionyl chloride (40 mL) was stirred at room temperature overnight. The volatiles were removed, and the residue was triturated with dichloromethane (50 mL) and filtered. The filtrate was concentrated in vacuo to yield the desired product as a brownish viscous oil (6.80 g, 97% yield). $^1$H NMR (300 MHz, CDCl$_3$) δ ppm 3.86 (m, 3H), 4.35 (s, 2H), 6.92 (m, 2H), 7.63 (d, J=8.78 Hz, 1H).

Step 3:

A solution of 2-(2-cyano-5-methoxyphenyl)acetyl chloride (6.40 g, 30.6 mmol) in 4.0M HCl in 1,4-dioxane (100 mL) was heated in a sealed vessel at 60° C. with stirring overnight. After cooling to room temperature, the mixture was filtered and the cake was washed with ethyl acetate thoroughly and dried in vacuo to provide the desired product as a fine pale yellow powder (6.14 g, 96% yield). $^1$H NMR (500 MHz, CD$_3$OD) δ ppm 3.98 (s, 3H), 6.94 (s, 1H), 7.14 (m, 2H), 8.10 (d, J=9.16 Hz, 1H); LC-MS MS m/z 210 (M$^+$+H).

Step 4:

A slurry of 1-chloro-6-methoxyisoquinolin-3-ol (0.209 g, 1.0 mmol), Cs$_2$CO$_3$ (0.715 g, 2.2 mmol), and CH$_3$I (0.284 g, 2.0 mmol) in DMF (2.5 mL) was heated to 85° C. in a sealed tube for 3 hours. Upon cooling to room temperature, the upper layer of brownish solution was decanted into iced 5% citric acid. The mixture was extracted with ethyl acetate (20 mL). The organic layer was washed with 5% citric acid, 1.0M

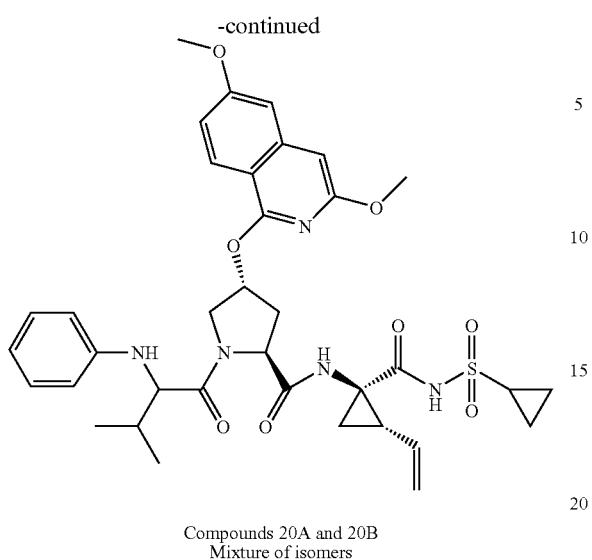

Compounds 20A and 20B
Mixture of isomers

Step 5:

The product of Step 5, Example 20 was obtained by the same procedure as described for the preparation of the product of Step 3, Example 1, except the product of Step 4, Example 20 (1.25 g, 5.60 mmol) was used as starting material instead of the product of Step 2 Example 1. The crude product was purified by silica gel flash chromatography (step gradient 3:1 hexanes:acetone, followed by 2:1 and then 1:1 of the same) to give an off-white foam (2.34 g, 91.6% yield). LC-MS MS m/z 419 (M$^+$+H).

Step 6:

To a 0° C. solution of the product of Step 5, Example 20 (1.94 g, 5.68 mmol) in ethyl acetate (150 mL) was added cyclopropanesulfonic acid (1-(R)-amino-2-(S)-vinyl-cyclopropanecarbonyl)-amide HCl salt (2.29 g, 5.68 mmol) in one portion. The mixture was stirred for 15 minutes, and then DIPEA (1.91 g, 17.0 mmol) was added dropwise and the suspension was stirred for 5 minutes. The mixture was then treated with EDC (1.41 g, 7.38 mmol) and HOBT (0.767 g, 5.68 mmol) and was stirred overnight. The mixture was poured into ice cold 5% aqueous citric acid and the resulting mixture was shaken and the phases were separated. The organic phase was washed with 5% aqueous citric acid, 5% aqueous sodium citrate, and finally with brine. The organic was dried over MgSO$_4$, filtered and concentrated. Purification by flash column silica gel chromatography (1:1 hexanes: acetone) gave the product as a white foam (2.50 g, 79% yield). LC-MS MS m/z 631 (M$^+$+H).

Step 7:

The product of Step 6, Example 20 (3.20 g, 5.08 mmol) was dissolved in dichloromethane (20 mL) and the solution was treated with TFA (20 mL) at room temperature for 1 hours. Solvent was removed in vacuo, and the residue was combined with 1.0M HCl in ether and stirred overnight. The resulting solid was isolated by filtration, rinsed with ether and dried in vacuo to give an off-white solid (2.97 g, 95.0% yield). LC-MS MS m/z 531 (M$^+$+H).

Step 8:

Compounds 20A and 20B were prepared by the same procedure as described for the preparation of Compounds 19A and 19B, except the product of Step 7, Example 20 (0.100 g, 0.166 mmol) was used in place of the product of Step 6, Example 17. Compound 20A was the first of the two isomers to elute by reverse phase preparative HPLC and was obtained as a beige powder bis-TFA salt (0.0564 g, 35.9% yield). Compound 20B was the second of the two isomers to elute by reverse phase preparative HPLC and was obtained as a beige powder bis-TFA salt (0.0367 g, 23.4% yield).

Compound 20A

LC-MS, MS m/z 720 (M$^+$+H).

Compound 20B $^1$H NMR (500 MHz, MeOD) δ ppm 0.98 (s, 9H) 1.00-1.09 (m, 2H) 1.14-1.21 (m, 1H) 1.28-1.41 (m, 3H) 1.88 (dd, J=8.09, 5.34 Hz, 1H) 2.25 (q, J=9.05 Hz, 1H) 2.31-2.39 (m, 1H) 2.60 (dd, J=13.73, 7.02 Hz, 1H) 2.79-2.87 (m, 1H) 3.92 (s, 3H) 3.98 (d, J=1.53 Hz, 3H) 4.08 (dd, J=12.21, 3.36 Hz, 1H) 4.20 (s, 1H) 4.45 (d, J=11.90 Hz, 1H) 4.54-4.60 (m, 1H) 5.15 (d, J=10.38 Hz, 1H) 5.34 (d, J=17.09 Hz, 1H) 5.76-5.86 (m, 1H) 5.91 (s, 1H) 6.57-6.63 (m, 2H) 6.77 (d, J=8.54 Hz, 2H) 6.93 (dd, J=9.16, 2.44 Hz, 1H) 7.05-7.13 (m, 3H) 7.87 (d, J=9.16 Hz, 1H) 9.33 (s, 1H); LC-MS, MS m/z 720 (M$^+$+H).

Example 21

Preparation of Compound 21: N-(4,6-dimethyl-2-pyridinyl)valyl-(4R)—N-((1R,2S)-1-((cyclopropyl-sulfonyl)carbamoyl)-2-vinylcyclopropyl)-4-((3, 6-dimethoxy-1-isoquinolinyl)oxy)-L-prolinamide Compound 21

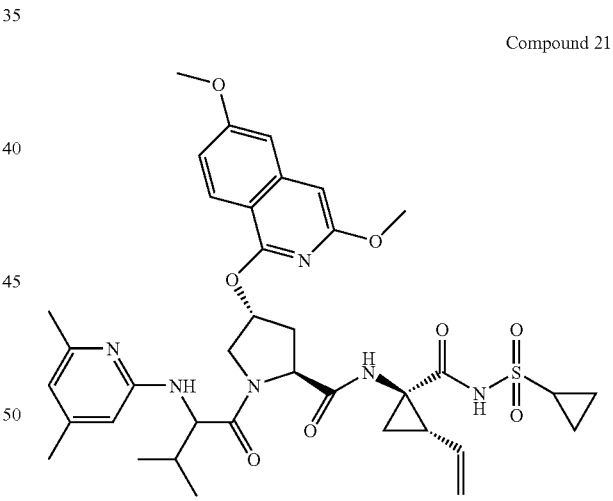

Compound 21 was prepared by the same procedure as described in Step 7, Example 17, except the product of Step 7, Example 20 (0.253 g, 0.419 mmol) was used in place of the product of Step 6, Example 17. Compound 21 (0.052 g, 15.3% yield) was obtained as a brown powder bis-HCl salt. $^1$H NMR (500 MHz, MeOD) δ ppm 1.01 (d, J=6.7 Hz, 1H), 1.10 (d, J=6.7 Hz, 3H), 1.12-1.16 (m, 2H), 1.23-1.29 (m, 2H), 1.30-1.37 (m, 1H), 1.43-1.49 (m, 1H), 1.91-1.97 (m, 1H), 2.19 (s, 3H), 2.26-2.34 (m, 1H), 2.40 (s, 3H), 2.62-2.70 (m, 1H), 2.89 (s, 1H), 2.95-3.03 (m, 1H), 3.16-3.22 (m, 1H), 3.92 (s, 3H), 3.99 (s, 3H), 4.17 (dd, J=12.1, 3.5 Hz, 1H), 4.23-4.29 (m, 1H), 4.50 (d, J=7.0 Hz, 1H), 4.64-4.70 (m, 1H), 5.17 (d, J=10.4 Hz, 1H), 5.35 (d, J=17.1 Hz, 1H), 5.75-5.86 (m, 1H), 5.98 (d, J=2.1 Hz, 1H), 6.60 (d, J=8.2 Hz, 1H), 6.66 (s, 1H), 6.87 (dd, J=9.2, 2.4 Hz, 1H), 7.06 (t, J=2.1 Hz, 1H), 7.83 (d, J=9.2 Hz, 1H); LC-MS, MS m/z 748 (M$^+$+H).

Compound 22 Isomers

N-(4,6-dimethyl-2-pyridinyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(4,6-dimethyl-2-pyridinyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 22

Preparation of Compounds 22A and 22B

Compounds 22A and 22B

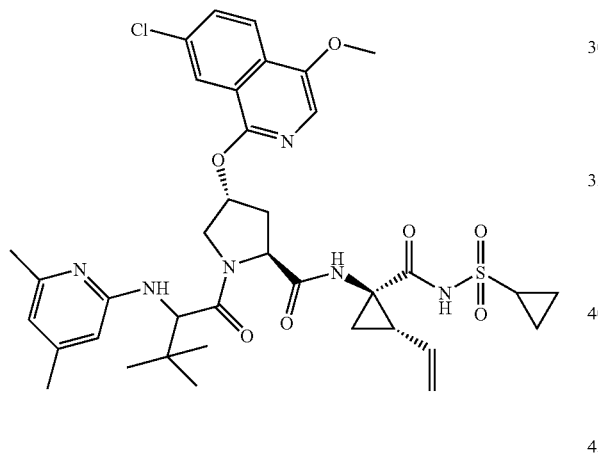

Scheme 1 of Example 22

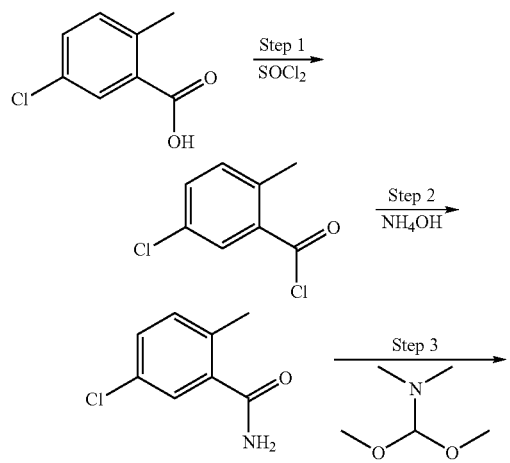

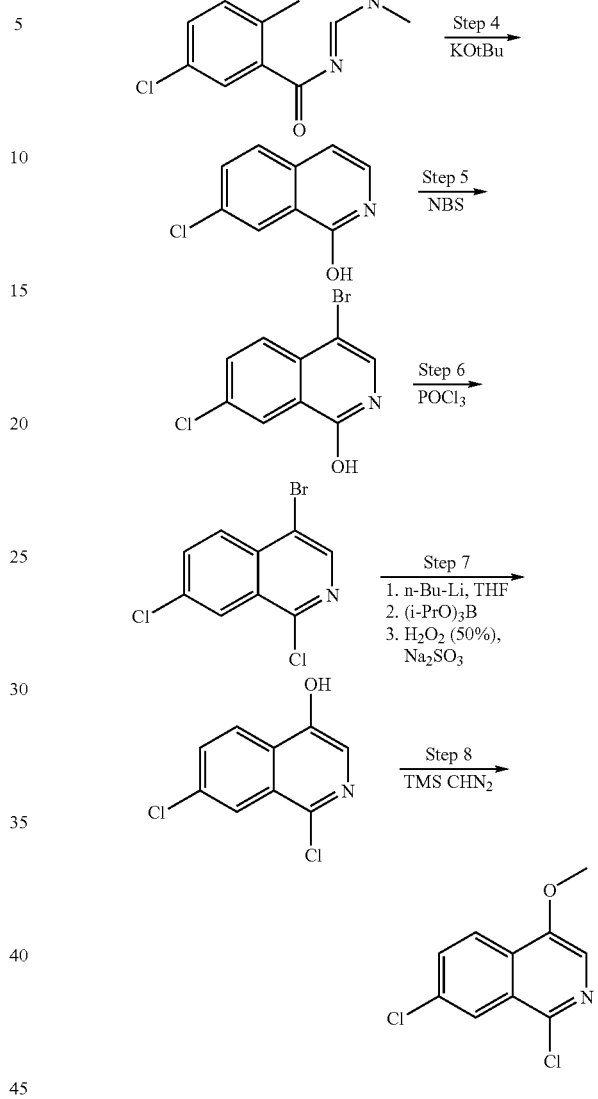

Step 1:

A slurry of 3-chloro-6-methylbenzoic acid (17.0 g, 0.10 mol) in thionyl chloride (23.5 ml, 0.30 mol) was heated slowly to a gentle reflux and maintained at this temperature for 2 h. The reaction mixture was then cooled to RT and the excess thionyl chloride removed in vacuo. The residue was taken up in DCM (50 ml), and the solvent then removed in vacuo. (It should be noted that this process was repeated several times to ensure removal of residual thionyl chloride and HCl). The resulting product was then dissolved in THF (80 ml) which was used directly in the next reaction as described below.

Step 2:

To a solution of 30% ammonia (58 ml) in water (240 ml), cooled by salt-ice bath (−10° C.), was added dropwise a THF solution of the product of Step 1 above. After the addition was complete, the resulting reaction mixture (slurry) was stirred at −10° C. for 1 hr. The reaction mixture was then warmed to room temperature and decanted. The remaining solid in the reaction vessel was then triturated with water (50 ml). This process of trituration and decanting was then repeated. The remaining solid was then filtered and the filter cake washed with water. The solid was then dried in vacuo overnight to yield 13.8 g (82%) of desired product as a white crystalline material. $^1$H NMR (DMSO-D$_6$) δ ppm 2.33 (s, 3H), 7.24-7.27 (m, 1H), 7.35-7.38 (m, 2H), 7.44 (b, 1H), 7.80 (b, 1H); $^{13}$C NMR (100 MHz, DMSO-D$_6$) δ ppm 18.87, 126.64, 128.86, 129.81, 132.31, 134.19, 138.65, 169.41; LC-MS, MS m/z 170.

Step 3:

A mixture of the product of Step 2 (11.5 g, 68 mmol), DMF-acetal (10.9 ml, 82 mmol), and THF (150 ml) was heated to reflux and maintained at this temperature for 2 hr. The reaction mixture was then cooled to room temperature and the volatiles were removed in vacuo. The resulting residue was recrystallized from hexane (150 ml) to yield 14.7 g (96%) of the desired product as white needles.

$^1$H NMR (DMSO-D$_6$) δ 2.49-2.51 (m, 3H), 3.09 (s, 3H), 3.20 (s, 3H), 7.24, 7.27 (d, J=13.5 Hz, 1H), 7.37-7.41 (dd, J1=14 Hz, J2=4.5 Hz, 1H), 7.91, 7.92 (d, J=4.0 Hz, 1H), 8.55 (s, 1H); $^{13}$C NMR (100 MHz, DMSO-D$_6$) δ ppm 20.69, 35.09, 40.91, 129.50, 129.72, 132.98, 136.86, 138.87, 160.60, 177.04; LC-MS, MS m/z 225.

Step 4:

A mixture of the product of Step 3 and KOtBu (14.7 g, 131 mmol) in THF (300 ml) was heated to reflux and maintained at this temperature for 2 hr (reaction mixture became a dark solution upon heating). The volume of the reaction mixture was then reduced by distilling off approximately 100 ml of solvent. The resulting solution was then carefully poured into water (1 L) and the resulting mixture was acidified with 1M HCl to a resulting pH of 4. The mixture was then filtered, and the collected solid was washed thoroughly with water, then dried in vacuo overnight to yield 7.0 g (60%) of the desired product as a off-white powder.

$^1$H NMR (400 Hz, CD$_3$OD) δ ppm 6.66 (d, J=7.05 Hz, 1H), 7.18 (d, J=7.05 Hz, 1H), 7.66 (s, 1H) 7.67 (d, J=2.01 Hz, 1H), 8.24 (d, J=2.27 Hz, 1H); $^{13}$C NMR (100 MHz, DMSO-D$_6$) δ ppm 104.05, 125.62, 127.21, 128.54, 129.52, 130.77, 132.43, 136.55, 160.72; LC-MS, MS m/z 180.

Step 5:

A slurry of the product of Step 4 and NBS (39.747 g, 223.3 mmol) in MeCN (500 mL, anhydrous) was slowly heated to a gentle reflux over a period of approximately 2 h and maintained at a gentle reflux for 1.5 h (This reaction can be monitored by LC/MS). The reaction mixture was then slowly cooled to room temperature over a period of 3 h and the observed solid was removed by simple filtration. The collected solid was washed with MeCN (100 mL×3) to provide 47 g of the desired product. This material was used in the next step without further purification.

$^1$H NMR (400 MHz, CD$_3$OD) δ ppm 7.46 (s, 1H), 7.81 (dd, J=8.40, 2.00 Hz, 1H), 7.88 (d, J=8.8 Hz, 1H), 8.27 (d, J=2.00 Hz, 1H); $^{13}$C NMR (100 MHz, DMSO-D$_6$) δ ppm 96.68, 126.34, 127.58, 127.71, 130.73, 132.20, 133.47, 134.46, 159.88; LC-MS, MS m/z 258.

Step 6:

A heterogeneous solution of the product of Step 5 (47 g, 182 mmol) in POCl$_3$ (200 mL, 2.15 mol) slowly heated to reflux over a period of 1 h. The reaction mixture was maintained at reflux for 4 h. The reaction mixture was then cooled to room temperature and concentrated in vacuo to remove excess POCl$_3$. The resulting residue was then taken-up into 600 mL of CH$_2$Cl$_2$, cooled to at −35° C., then neutralized carefully with 1 N NaOH (400 mL) until the mixture was slightly basic (pH=8). The resulting organic layer was separated, washed with water, dried over MgSO$_4$ and concentrated in vacuo. The resulting residue was crystallized from EtOAc (approximately 50 mL) to give 32 g of desired product. The collected solid was washed with 10% EtOAc/Hexanes (3×50 ml).

The mother liquid was concentrated and purified by Biotage (elution with 16% EtOAc in hexanes) to give 4 g of the desired product as a solid.

$^1$H NMR (400 MHz, CDCl$_3$) δ ppm 7.80 (dd, J=8.81, 2.01 Hz, 1H), 8.14 (d, J=9.06 Hz, 1H), 8.34 (d, J=1.76 Hz, 1H), 8.48 (s, 1H); $^{13}$C NMR (100 MHz, DMSO-D$_6$) δ ppm 118.39, 125.06, 127.59, 128.71, 133.89, 134.14, 134.93, 143.18, 148.98; LC-MS, MS m/z 275.

Step 7:

To a slurry of the product of Step 6 (22.16 g, 80 mmol) in THF (500 ml) at −78° C. was added 100 ml of 1.6 M n-BuLi (in hexanes, 160 mmol) dropwise via cannula over 15 min (maintaining the internal temperature <−65° C.). The resulting solution was stirred for 0.5 h, after such time, (i-PrO)$_3$B (37 ml, 160 mmol) was added dropwise via syringe over 10 min (maintaining the internal temperature <−65° C.). The resulting reaction mixture was stirred for 0.5 h. After checking the reaction by LC/MS for completion, 80 ml of 30% H$_2$O$_2$ (776 mmol) was added dropwise via addition funnel over 10 min (the internal temperature rose to −60° C. during addition), followed by addition of 80 ml of 1 N NaOH (80 mmol). The cooling bath was removed, and the reaction mixture was allowed to warm to room temperature and stirred at room temperature for additional 1 h. After conforming the completion of the reaction by LC/MS, the reaction mixture was then cooled to −40° C., and a solution of 100 g of Na$_2$SO$_3$ (0.793 moles) in 400 ml of water was added dropwise via addition funnel as a means to quench excess H$_2$O$_2$ over 30 min (maintaining the internal temperature 5-10° C.). The resulting slurry was then neutralized with 6 N HCl (approximately 50 ml) at 0°C till pH ~6, then diluted with 500 ml of EtOAc and decanted to a 2 L separatory funnel. To the remaining solid in the reaction vessel was added 500 mL of water and 300 ml of EtOAc, then neutralized with 6 N HCl (approximately 20 ml). The combined organic layers were washed with brine (300 ml×3), then water (200 ml×3), dried over MgSO$_4$ and concentrated to give a crude product which was triturated with 50 ml of EtOAc. The solid was collected by filtration, rinsed with EtOAc (3×25 ml) and dried to give desired product (2 runs: 12.0 g, 70% and 13.8 g, 81%). The filtrates were combined, concentrated and purified by Biotage eluted with 35% EtOAc in hexanes to give 2.1 g of product. Overall, 44.4 g of bromide gave 27.9 g (81%) of 4-OH product.

$^1$H NMR (400 MHz, CD$_3$OD) δ ppm 4.05 (s, 3H), 7.4 (s, 1H), 7.76 (dd, J=8.8, 2, Hz, 1H), 8.16 (d, J=2 Hz, 1H), 8.23 (d, J=8.8 Hz, 1H); $^{13}$C NMR (100 MHz, DMSO-D$_6$) δ ppm 123.78, 124.66, 125.62, 127.03, 127.71, 130.72, 133.80, 137.63; 148.88; LC-MS, MS m/z 213.

Step 8:

To a slurry of the product of Step 7 (16 g, 75.5 mmol) in MeOH-MeCN (30 mL/300 mL) at 0° C. was added dropwise 60 ml of 2 M solution of TMSCHN$_2$ in hexanes (120 mmol). The reaction mixture was allowed to warm to room temperature, then stirred for 14 h. The solution was then concentrated and the resulting solid was recrystallized from EtOAc (about 50 mL) to give 8.1 g of the desired product which was washed with 25% EtOAc in hexances; 20×3 times. The mother liquid was concentrated and purified by Biotage (elution with 16% EtOAc in hexanes) to provide 3.2 g of the desired product as a solid.
$^1$H NMR (400 MHz, CDCl$_3$) δ ppm 4.05 (s, 3H), 7.67 (dd, J=9.06, 2.01 Hz, 1H), 7.80 (s, 1H), 8.16 (d, J=8.81 Hz, 1H), 8.23 (d, J=2.01 Hz, 1H); $^{13}$C NMR (100 MHz, DMSO-D$_6$) δ ppm 56.68, 122.70, 123.99, 124.14, 126.67, 127.83, 131.43, 134.10, 139.75, 149.94; LC-MS, MS m/z 229.
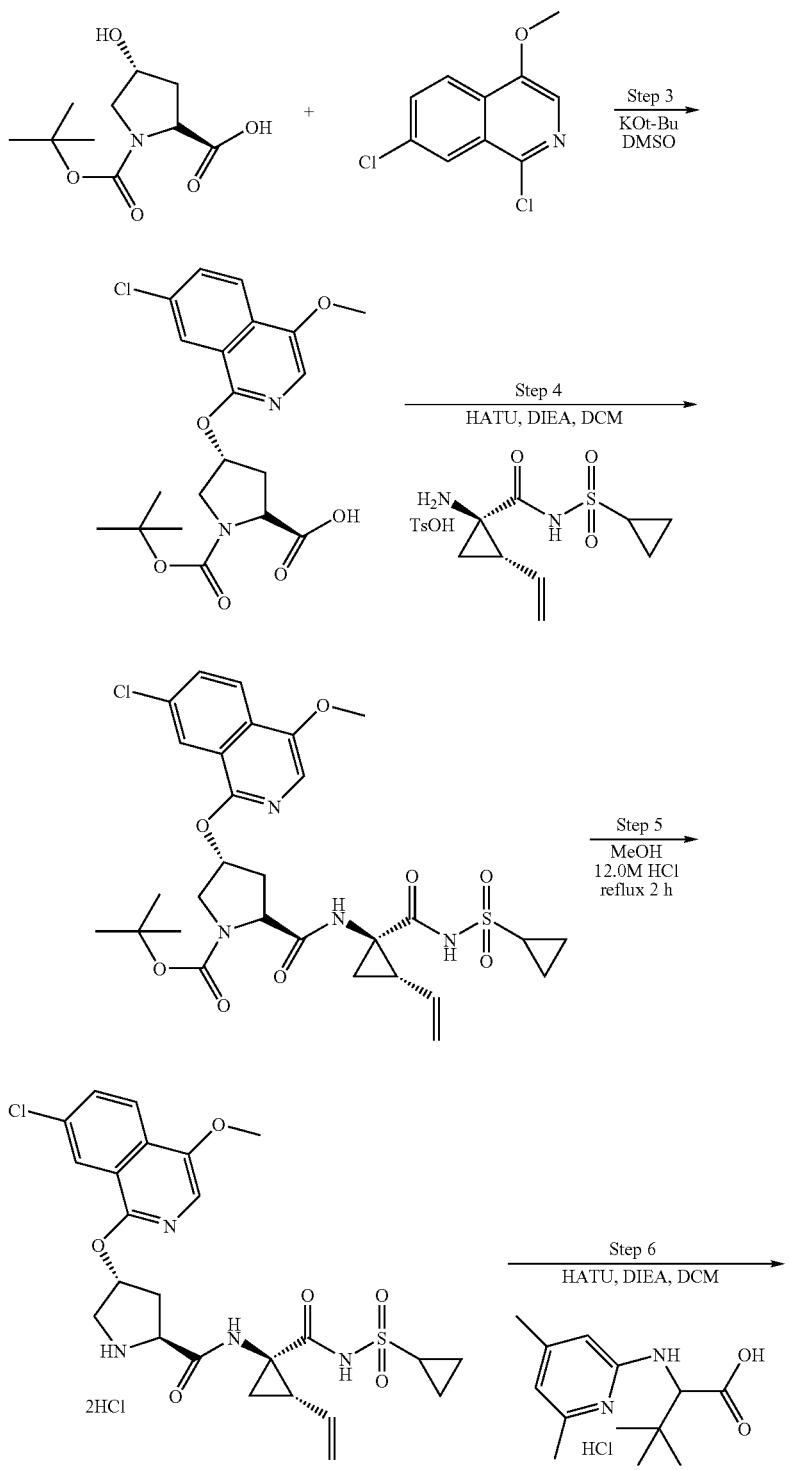

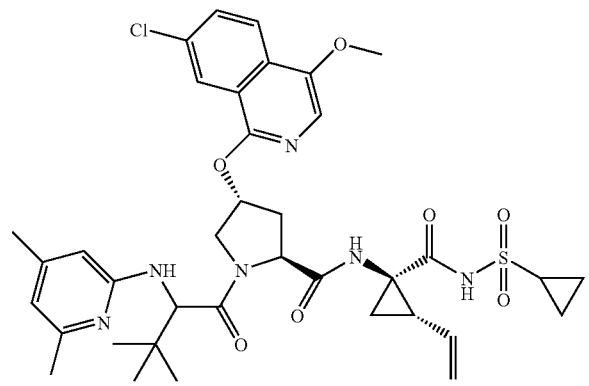

Compounds 22A and 22B
Mixture of isomers

Step 3:

The product of Step 2, Example 22 (0.452 g, 1.98 mmol), Boc-HYP—OH (0.508 g, 2.20 mmol), and potassium tert-butoxide (0.672 g, 6.0 mmol) in DMSO (20 mL) was stirred at room temperature for 4 hours. The mixture was quenched with water and neutralized with 1.0M aqueous HCl. The mixture was extracted with ethyl acetate and the organic was washed with brine, dried over anhydrous $MgSO_4$, filtered and concentrated to give a crude solid (0.844 g, quantitative) which was used in the next step without further purification.

Step 4:

The product of Step 3, Example 22 (0.422 g, 1.00 mmol) was dissolved in dichloromethane (10 mL) and DIEA (2 mL). To the solution were added cyclopropanesulfonic acid (1-(R)-amino-2-(S)-vinyl-cyclopropanecarbonyl)-amide p-toluenesulfonic acid salt (0.402 g, 1.00 mmol) and HATU (0.600 g, 1.58 mmol) and the mixture was stirred for 6 hours and concentrated. Purification by flash column silica gel chromatography (1:1 hexane:acetone) gave solid desired product (0.600 g, 94.5% yield). LC-MS, MS m/z 636 ($M^+$+H).

Step 5:

The product of Step 4, Example 22 (6.34 g, 9.98 mmol) dissolved in methanol (50 mL) was treated with 12M HCl (3 mL) and the mixture was heated to reflux for 2 hours and concentrated. The crude material was used directly in the next step.

Step 6:

A solution of the product of Step 5, Example 22 (0.480 g, 0.790 mmol), DIEA (1 mL) and the product of Step 2, Example 14 (0.240 g, 0.880 mmol) in DMF (5 mL) was sparged with nitrogen. The mixture was cooled to 0° C., treated with HATU (0.456 g, 1.12 mmol) and stirred at room temperature for 5 hours. The reaction was then heated to 46° C. for 25 hours. The mixture was concentrated, and the residue was purified by reverse phase preparative HPLC to give two separate products with identical MS m/z as observed by LCMS. Compound 22A (0.045 g, 7.6% yield) was the first of the two isomers to elute by reverse phase preparative HPLC. Compound 22B (0.050 g, 8.4% yield) was the second of the two isomers to elute by reverse phase preparative HPLC.

Compound 22A

LC-MS, MS m/z 754 ($M^+$+H).

Compound 22B

LC-MS, MS m/z 754 ($M^+$+H).

Example 23

Preparation of Compound 23: 3-methyl-N-(4-methyl-5-nitro-2-pyridinyl)valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Compound 23

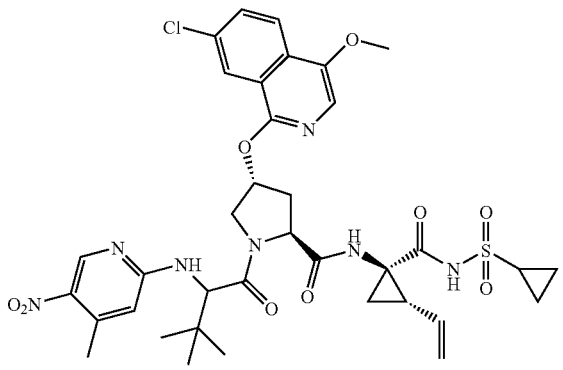

Scheme 1
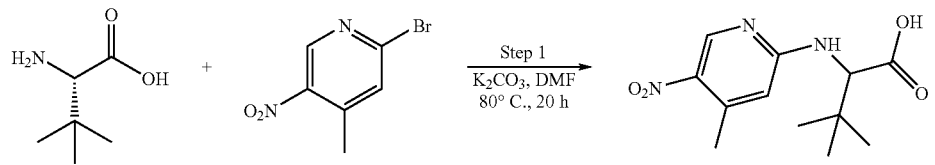
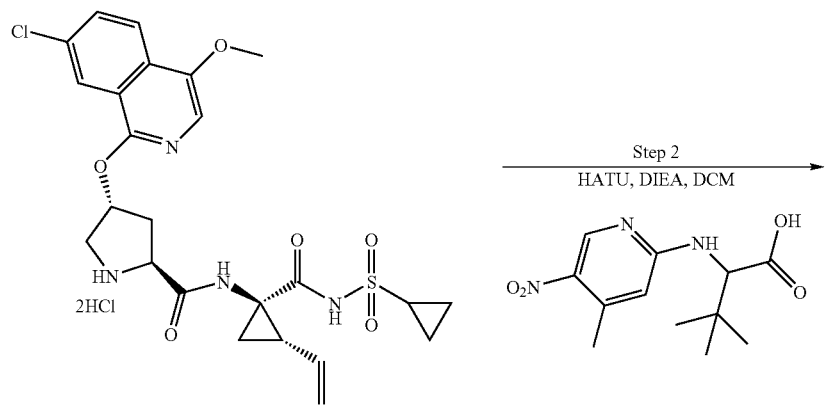
Product of
Step 5, Example 22
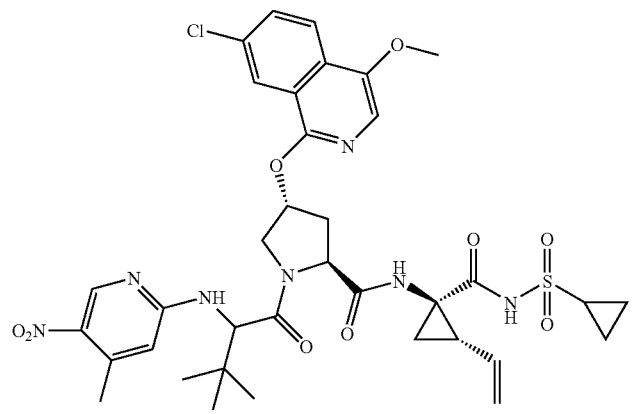
Compound 23

Step 1:

A mixture of 2-bromo-5-nitro-4-picoline (2.00 g, 9.22 mmol), L-tert-leucine (1.27 g, 9.68 mmol) and potassium carbonate (3.18 g, 23.0 mmol) in anhydrous DMF (50 mL) was heated to 80° C. for 20 h. The mixture was concentrated in vacuo to a residue (approx 25 mL), then DCM (200 mL) and water (100 mL) were added and the resulting mixture was shaken and the two phases were separated. The aqueous phase was extracted with DCM (3×100 mL), and the organic extracts were combined and dried over anhydrous magnesium sulfate, filtered and concentrated in vacuo to a deep red solid. Purification by reverse phase preparative HPLC afforded a yellow solid (0.66 g, 27% yield). LC-MS, MS m/z 268 ($M^++H$).

Step 2:

The product of Step 1, Example 23, (0.145 g, 0.543 mmol) was combined with the product of Step 5, Example 22, (0.300 g, 0.493 mmol) and HATU (0.281 g, 0.740 mmol) in DCM (4 mL). To the mixture was added N-methylmorpholine (0.250 g, 2.47 mmol), and the resulting mixture was agitated at room temperature overnight, then at 60° C. for 3 d. Additional product of Step 1, Example 23 (0.145 g, 0.543 mmol) and HATU (0.281 g, 0.740 mmol) were added, and the mixture was stirred at rt overnight. Purification by reverse phase preparative HPLC gave compound 23 as an orange/brown solid bis-TFA salt (0.097 g, 19.4% yield). $^1$H NMR (500 MHz, $CD_3OD$) δ ppm 1.10 (s, 9H) 1.11-1.15 (m, 2H) 1.23-1.32 (m, 2H) 1.43-1.50 (m, 1H) 1.93 (dd, J=8.24, 5.49 Hz, 1H) 2.24-2.32 (m, 2H) 2.33 (s, 3H) 2.60 (dd, J=13.58, 6.87 Hz, 1H) 2.96-3.03 (m, 1H) 3.99-4.03 (m, 1H) 4.05 (s, 3H) 4.65 (dd, J=10.68, 7.02 Hz, 1H) 4.78-4.83 (m, 1H) 4.90 (s, 1H) 5.16 (dd, J=10.38, 1.53 Hz, 1H) 5.31-5.37 (m, 1H) 5.78 (ddd, J=17.17, 10.15, 9.00 Hz, 1H) 5.87 (t, J=3.05 Hz, 1H) 6.29 (s, 1H) 7.57-7.64 (m, 2H) 7.71 (s, 1H) 7.76 (d, J=2.14 Hz, 1H) 8.03 (d, J=8.85 Hz, 1H) 9.22 (s, 1H); LC-MS, MS m/z 785 ($M^++H$).

Compound 24 Isomers

N-5-pyrimidinyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-5-pyrimidinyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide

Example 24

Preparation of Compounds 24A and 24B

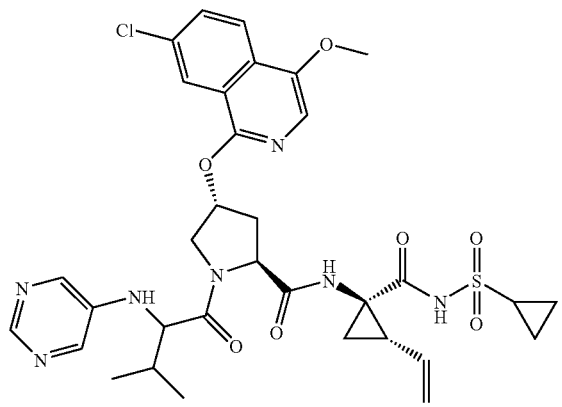

Compounds 24A and 24B

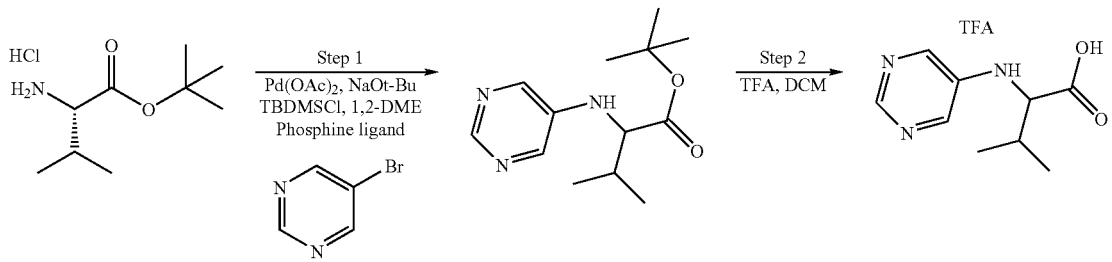

Scheme 1

-continued

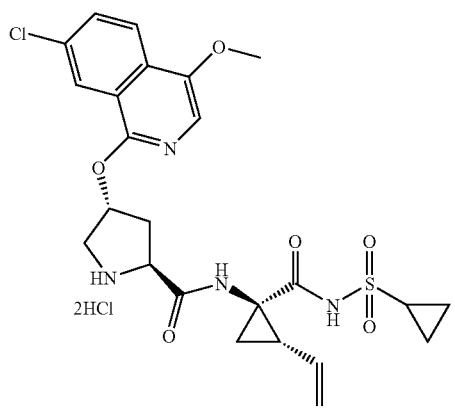

Product of
Step 5, Example 22

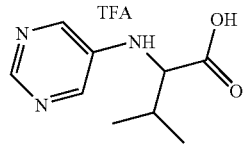

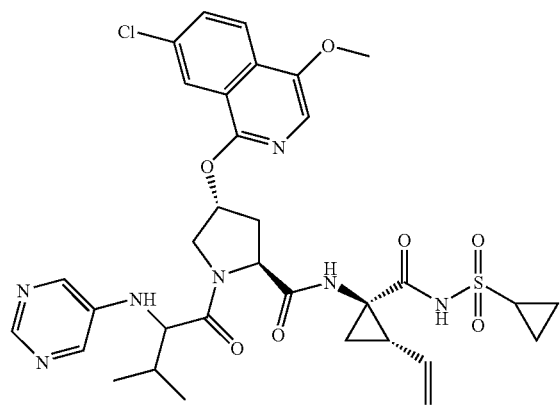

Compounds 24A and 24B
Mixture of isomers

Step 1:

5-Bromopyrimidine (1.15 g, 7.21 mmol) and sodium tert-butoxide (2.36 g, 24.5 mmol), were combined with anhydrous 1,2-dimethoxyethane (15 mL) in a 75 mL Chemglass pressure vessel. The mixture was shaken, and a pre-mixed solution of Pd(OAc)$_2$ (0.0405 g, 0.180 mmol) and (R)-(−)-1-[(S)-(dicyclohexylphosphino) ferrocenyl]ethyl di-tert-butyl phosphine (0.100 g, 0.180 mmol, Strem Chemicals catalog #26-0975, CAS # [158923-11-6]) in dry 1,2-dimethoxyethane (2 mL) was immediately added. L-valine tert-butyl ester hydrochloride (1.18 g, 5.62 mmol) was then quickly added to the resulting mixture. The pressure vessel was sealed and the mixture was stirred at 110° C. for 20 hours. The crude product was passed through a plug of silica gel (elution 100% DCM then 100% EtOAc) to remove baseline contaminants. Solvent was removed in vacuo, and the 300 mg of recovered crude material was purified by flash silica gel chromatography (gradient 4:1 hexanes:EtOAc to 1:1 hexanes:EtOAc) to give a yellow solid (0.200 g, 14.2% yield). $^1$H NMR (500 MHz, CHLOROFORM-D) δ ppm 1.03 (t, J=6.87 Hz, 6H) 1.45 (s, 9H) 2.11-2.19 (m, 1H) 3.75 (dd, J=9.16, 5.19 Hz, 1H) 4.24 (d, J=9.16 Hz, 1H) 8.13 (s, 2H) 8.60 (s, 1H); LC-MS, MS m/z 252 (M$^+$+H).

Step 2:

The product of Step 1, Example 24, (0.200 g) was dissolved in dichloromethane (10 mL) and treated with TFA (10 mL). The mixture was stirred at room temperature for 3 h and was then concentrated in vacuo. The residue was then dissolved in 1,2-dichloroethane (15 mL) and again concentrated in vacuo. The dark green residue was then purified by reverse phase preparative HPLC to yield a dark green glassy solid as the HCl salt (0.091 g, 49% yield). $^1$H NMR (500 MHz, DMSO-D$_6$) δ ppm 0.99 (dd, J=9.16, 7.02 Hz, 6H) 2.14 (td, J=13.28, 6.71 Hz, 1H) 3.90 (d, J=5.80 Hz, 1H) 6.32 (s, 1H) 8.22 (s, 2H) 8.44 (s, 1H); LC-MS, MS m/z 196 (M$^+$+H).

Step 3:

A mixture of the product of Step 2, Example 24, (0.084 g, 0.362 mmol), the product of Step 5, Example 22, (0.200 g, 0.329 mmol) and HATU (0.188 g, 0.493 mmol) suspended in DCM (4 mL) was treated with NMM (0.167 g, 1.65 mmol). The mixture was stirred at room temperature for 3 hours. The solvent was removed under a nitrogen stream and the crude mixture was purified by reverse phase preparative HPLC to give two separate compounds with identical MS m/z. Compound 24A (0.0902 g, 29.2% yield) was the first of the two isomers to elute from the reverse phase preparative HPLC column and was obtained as a beige powder bis-TFA salt. Compound 24B (0.0957 g, 30.9% yield) was the second of the two isomers to elute from the reverse phase preparative HPLC column and was obtained as a beige powder bis-TFA salt.

Compound 24A

¹H NMR (300 MHz, CD₃OD) δ ppm 0.91 (dd, J=6.95, 3.29 Hz, 2H) 1.04 (d, J=6.59 Hz, 3H) 1.09 (d, J=6.59 Hz, 3H) 1.19-1.38 (m, 8H) 1.43 (dd, J=9.51, 5.12 Hz, 1H) 1.91 (dd, J=8.23, 5.31 Hz, 1H) 2.03 (s, 1H) 2.19-2.38 (m, 3H) 2.57 (dd, J=13.54, 7.32 Hz, 1H) 2.94-3.06 (m, 1H) 4.03 (s, 3H) 4.06-4.21 (m, 2H) 4.34 (d, J=12.08 Hz, 1H) 4.57 (dd, J=10.25, 6.95 Hz, 1H) 5.14 (dd, J=10.61, 1.10 Hz, 1H) 5.32 (dd, J=17.20, 1.46 Hz, 1H) 5.72-5.87 (m, 1H) 5.89 (s, 1H) 7.56 (s, 1H) 7.70 (dd, J=8.78, 2.20 Hz, 1H) 7.99 (d, J=2.20 Hz, 1H) 8.07-8.16 (m, 3H) 8.29 (s, 1H); LC-MS, MS m/z 713 (M⁺+H).

Compound 24B

¹H NMR (300 MHz, CD₃OD) δ ppm 0.91 (d, J=6.95 Hz, 3H) 0.95 (d, J=6.59 Hz, 3H) 0.98-1.13 (m, 3H) 1.20-1.31 (m, 2H) 1.40 (dd, J=9.51, 5.12 Hz, 1H) 1.90 (dd, J=8.23, 5.31 Hz, 1H) 1.98-2.07 (m, 1H) 2.22-2.41 (m, 2H) 2.57-2.66 (m, 1H) 2.82-2.93 (m, J=7.82, 7.82, 5.12, 4.85 Hz, 1H) 4.04 (s, 3H) 4.05-4.16 (m, 1H) 4.23 (d, J=6.95 Hz, 1H) 4.41 (d, J=12.08 Hz, 1H) 4.62 (dd, J=9.70, 7.14 Hz, 1H) 5.15 (dd, J=10.43, 1.65 Hz, 1H) 5.34 (dd, J=17.20, 1.46 Hz, 1H) 5.78 (ddd, J=17.20, 10.25, 8.78 Hz, 1H) 5.87 (s, 1H) 7.61 (s, 1H) 7.73 (dd, J=8.97, 2.01 Hz, 1H) 7.96 (d, J=1.83 Hz, 1H) 8.13 (d, J=9.15 Hz, 1H) 8.21 (s, 2H) 8.33 (s, 1H); LC-MS, MS m/z 713 (M⁺+H).

Example 25

Preparation of Compound 25: 3-methyl-N-(5-methyl-3-pyridinyl)valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide

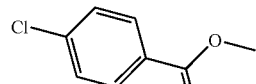

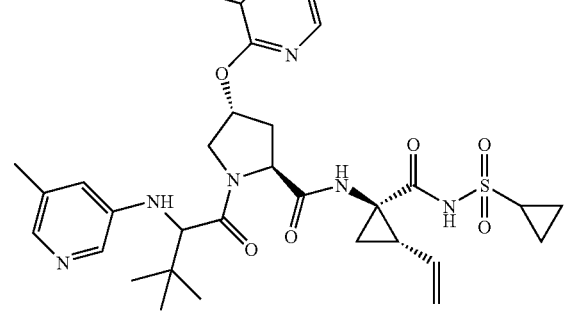

Scheme 1

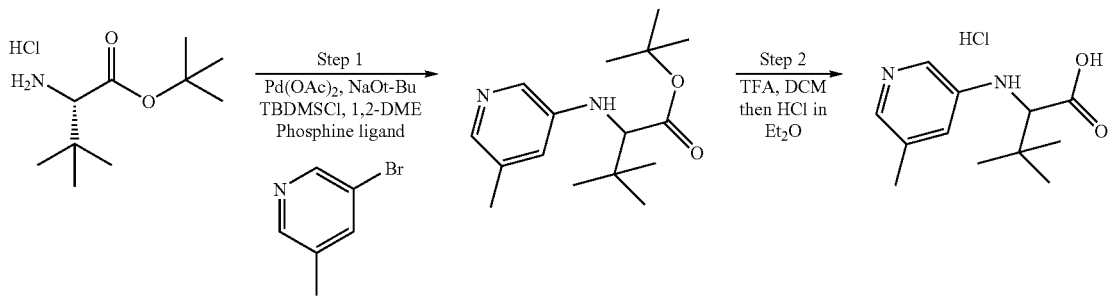

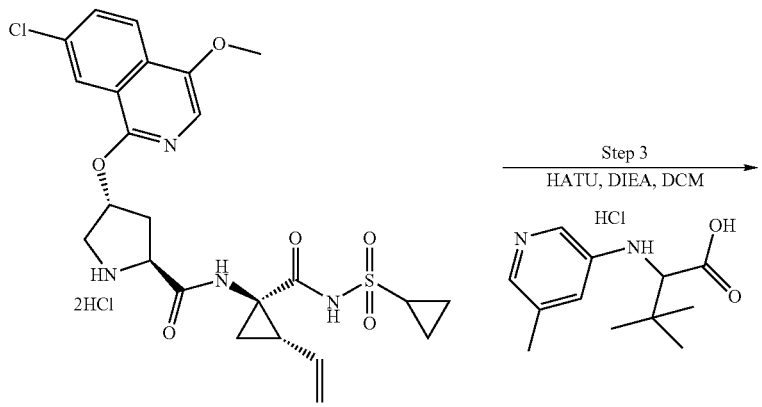

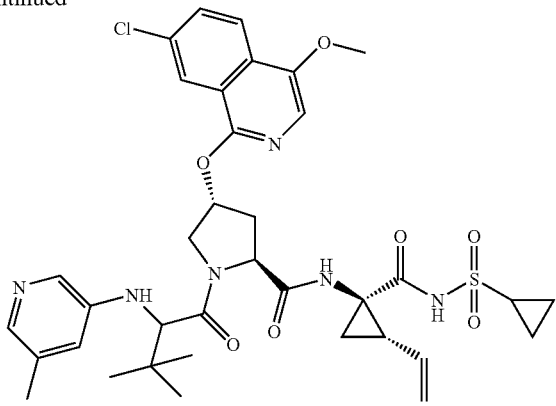

Compound 25

Step 1:

5-Bromo-3-picoline (1.00 g, 5.81 mmol), sodium tert-butoxide (1.90 g, 19.8 mmol) and tert-leucine tert-butyl ester hydrochloride (1.665 g, 6.98 mmol) were combined in anhydrous 1,2-dimethoxyethane (20 mL) in a 75 mL Chemglass pressure vessel. The mixture was stirred briefly, and a premixed solution of Pd(OAc)$_2$ (0.0652 g, 0.291 mmol) and (R)-(−)-1-[(S)-(dicyclohexylphosphino) ferrocenyl]ethyl di-tert-butyl phosphine (0.161 g, 0.291 mmol, Strem Chemicals catalog #26-0975, CAS # [158923-11-6]) in dry 1,2-dimethoxyethane (2 mL) was immediately added. The pressure vessel was sealed and the mixture was stirred at 100° C. for 20 hours. The mixture was poured into a rapidly stirred mixture of pH=7 buffer (200 mL), 10M aqueous HCl (25 mL) and ethyl acetate (100 mL). The phases were separated and the aqueous was extracted with ethyl acetate (2×50 mL). The organic phases were combined, dried over anhydrous magnesium sulfate, filtered and concentrated in vacuo to a residue. The crude material was purified by flash silica gel chromatography (gradient hexanes to 1:1 hexanes:EtOAc) to give a red oil (0.852 g, 52.6% yield). 1H NMR (500 MHz, CHLOROFORM-D) δ ppm 1.06 (s, 9H) 1.40 (s, 9H) 2.23 (s, 3H) 3.63 (d, J=10.38 Hz, 1H) 4.11 (dd, J=8.55, 1.22 Hz, 1H) 6.74 (s, 1H) 7.81 (s, 1H) 7.89 (d, J=2.75 Hz, 1H); LC-MS, MS m/z 279 (M$^+$+H).

Step 2:

The product of Step 1, Example 25, (0.809 g, 2.91 mmol) was dissolved in dichloromethane (20 mL) and treated with TFA (20 mL). The mixture was stirred at room temperature for 20 h and was then concentrated in vacuo. The residue was then dissolved in 1,2-dichloroethane (15 mL) and again concentrated in vacuo to give a brown oil. The residue was then dissolved in minimum DCM and added dropwise to a rapidly stirred mixture of 2.0M HCl in ether (30 mL), diethyl ether (30 mL) and 1,2-DCE (50 mL). The mixture was stirred for 10 min and was then concentrated in vacuo. The resulting brown foamy solid was then taken up in 1.0M aqueous HCl and the solution was concentrated in vacuo to give a glassy yellow solid (0.600 g, 80% yield). 1H NMR (500 MHz, DMSO-D$_6$) δ ppm 1.05 (s, 9H) 2.35 (s, 3H) 4.02 (d, J=9.77 Hz, 1H) 7.03 (d, J=9.77 Hz, 1H) 7.68 (s, 1H) 7.95 (s, 1H) 8.13 (s, 1H) LC-MS, MS m/z 223 (M$^+$+H).

Step 3:

A mixture of the product of Step 2, Example 25 (0.094 g, 0.362 mmol), the product of Step 5, Example 22, (0.200 g, 0.329 mmol) and HATU (0.188 g, 0.493 mmol) suspended in DCM (2 mL) was treated with NMM (0.167 g, 1.65 mmol). The mixture was stirred at room temperature for 20 hours. The solvent was removed in vacuo and the crude mixture was purified by reverse phase preparative HPLC to give compound 25 (0.1421 g, 44.7% yield) as a white powder bis-TFA salt. $^1$H NMR (500 MHz, CD$_3$OD) δ ppm 1.07-1.21 (m, 11H) 1.23-1.34 (m, 2H) 1.45 (dd, J=9.46, 5.19 Hz, 1H) 1.93 (dd, J=8.09, 5.65 Hz, 1H) 2.14 (s, 3H) 2.22-2.32 (m, 2H) 2.59 (dd, J=13.73, 7.32 Hz, 1H) 2.96-3.05 (m, 1H) 4.01 (dd, J=12.21, 3.05 Hz, 1H) 4.04 (s, 3H) 4.26 (s, 1H) 4.33 (d, J=12.21 Hz, 1H) 4.66 (dd, J=10.22, 7.48 Hz, 1H) 5.16 (d, J=10.38 Hz, 1H) 5.34 (d, J=17.40 Hz, 1H) 5.72-5.83 (m, 1H) 5.89 (s, 1H) 7.48 (s, 1H) 7.59 (s, 1H) 7.67-7.72 (m, 2H) 7.81 (d, J=2.14 Hz, 1H) 7.96 (d, J=1.83 Hz, 1H) 8.11 (d, J=8.85 Hz, 1H) 9.27 (s, 1H); LC-MS, MS m/z 740 (M$^+$+H).

Compound 26 Isomers 3-methyl-N-(6-methyl-3-pyridinyl)-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and 3-methyl-N-(6-methyl-3-pyridinyl)-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 26

Preparation of Compounds 26A and 26B

Compound 26A and 26B

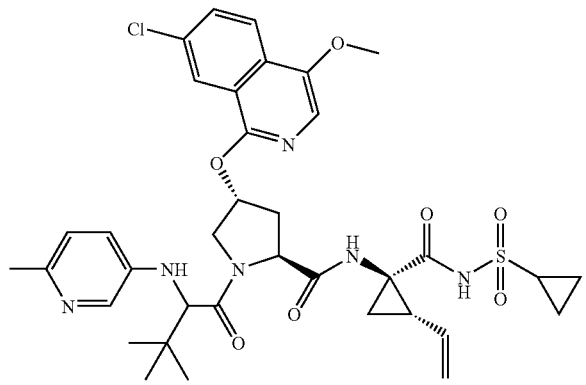

Compounds 26A and 26B were prepared by a similar procedure as that described for the preparation of compound 25, except 5-bromo-2-methylpyridine was used in place of 5-bromo-3-picoline in Step 1, and the reaction scales were altered for Steps 2 and 3. Two isomeric compounds were isolated from Step 3: the first isomer to elute from a preparative HPLC column was compound 26A (0.111 g) isolated as a slightly off-white solid bis-TFA salt, and the second isomer to elute from the preparative HPLC column was compound 26B (0.0944 g) isolated as a slightly yellow solid bis TFA salt. The combined yield for both compounds 26A and 26B was 12.2% over three steps.

Product of Step 1, Example 26: Flesh-colored waxy solid; ¹H NMR (500 MHz, CHLOROFORM-D) δ ppm 1.06 (s, 9H) 1.40 (s, 9H) 2.42 (s, 3H) 3.59 (d, J=10.38 Hz, 1H) 4.02 (d, J=10.38 Hz, 1H) 6.87 (dd, 1H) 6.93 (d, 1H) 7.99 (d, J=2.75 Hz, 1H); LC-MS, MS m/z 279 (M⁺+H).

Product of Step 2 Example 26: Yellow solid; ¹H NMR (500 MHz, DMSO-D₆) δ ppm 1.05 (s, 9H) 2.52 (s, 3H) 3.98 (d, J=9.16 Hz, 1H) 6.84 (d, J=9.77 Hz, 1 H) 7.59 (d, J=9.16 Hz, 1H) 7.81 (dd, J=9.00, 2.59 Hz, 1H) 8.05 (d, J=2.75 Hz, 1H); LC-MS, MS m/z 223 (M⁺+H).

Compound 26A

¹H NMR (500 MHz, CD₃OD) δ ppm 1.07-1.18 (m, 11H) 1.25-1.32 (m, 2H) 1.45 (dd, J=9.46, 5.49 Hz, 1H) 1.93 (dd, J=7.93, 5.49 Hz, 1H) 2.22-2.31 (m, 4H) 2.46 (s, 3H) 2.60 (dd, J=13.43, 6.71 Hz, 1H) 2.96-3.04 (m, 1H) 4.00 (dd, J=12.36, 2.90 Hz, 1H) 4.05 (s, 3H) 4.23 (s, 1H) 4.37 (d, J=12.21 Hz, 1H) 4.65 (dd, J=10.07, 7.32 Hz, 1H) 5.14-5.19 (m, 1H) 5.34 (d, J=17.09 Hz, 1H) 5.77 (ddd, J=17.17, 10.15, 9.00 Hz, 1H) 5.88 (s, 1H) 7.05 (d, J=8.85 Hz, 1H) 7.53 (dd, J=8.85, 2.75 Hz, 1H) 7.62 (s, 1H) 7.73 (dd, J=8.85, 2.14 Hz, 1H) 7.84 (d, J=1.83 Hz, 1H) 7.93 (d, J=2.75 Hz, 1H) 8.14 (d, J=8.85 Hz, 1H) 9.25 (s, 1H); LC-MS, MS m/z 740 (M⁺+H).

Compound 26B n

¹H NMR (500 MHz, CD₃OD) δ ppm 0.97 (s, 9H) 1.07-1.14 (m, 2H) 1.18-1.24 (m, 1H) 1.28-1.34 (m, 1H) 1.41 (dd, J=9.46, 5.49 Hz, 1H) 1.90 (dd, J=8.09, 5.34 Hz, 1H) 2.30 (q, J=8.75 Hz, 1H) 2.37 (ddd, J=13.89, 9.92, 4.27 Hz, 1H) 2.58 (s, 3H) 2.65 (dd, J=13.89, 7.48 Hz, 1H) 2.93-3.00 (m, 1H) 4.04 (s, 3H) 4.09 (dd, J=12.21, 3.36 Hz, 1H) 4.34 (s, 1H) 4.50 (d, J=11.90 Hz, 1H) 4.65 (dd, J=9.46, 7.32 Hz, 1H) 5.16 (d, J=10.07 Hz, 1H) 5.36 (d, J=17.40 Hz, 1H) 5.75-5.86 (m, 1H) 5.89 (s, 1H) 7.57 (d, J=9.16 Hz, 1H) 7.62 (s, 1H) 7.75 (dd, J=8.85, 2.14 Hz, 1H) 7.85 (dd, J=9.00, 2.90 Hz, 1H) 8.05 (dd, J=4.12, 2.59 Hz, 2H) 8.15 (d, J=9.16 Hz, 1H) 9.56 (s, 1H); LC-MS, MS m/z 740 (M⁺+H).

Compound 27 Isomers 3-methyl-N-(5-(trifluoromethyl)-3-pyridinyl)-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and 3-methyl-N-(5-(trifluoromethyl)-3-pyridinyl)-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 27

Preparation of Compounds 27A and 7B

Compound 27A and 27B

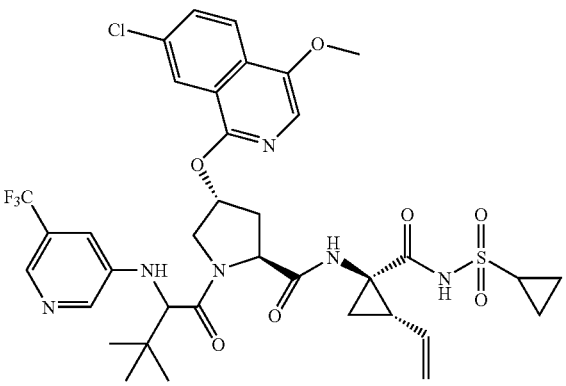

Compounds 27A and 27B were prepared by a similar procedure as that described for the preparation of compound 25, except 3-bromo-5-trifluoromethylpyridine was used in place of 5-bromo-3-picoline in Step 1, and the reaction scales were different. Also, the product from Step 2 was not isolated as the HCl salt but was instead carried on to Step 3 directly as a TFA salt. Two isomeric compounds were isolated from Step 3: the first isomer to elute from a preparative HPLC column was compound 27A (0.128 g) isolated as a slightly off-white solid bis-TFA salt, and the second isomer to elute from the preparative HPLC column was compound 27B (0.0564 g) isolated as a slightly off-white solid bis TFA salt. The combined yield for both compounds 27A and 27B was 17.9% over three steps.

Product of Step 1, Example 27: Orange waxy solid; ¹H NMR (500 MHz, CHLOROFORM-D) δ ppm 1.08 (s, 9H) 1.43 (s, 9H) 3.66 (d, J=10.07 Hz, 1H) 4.45 (d, J=10.07 Hz, 1H) 7.06 (s, 1H) 8.22 (s, 1H) 8.24 (d, J=2.75 Hz, 1H); LC-MS, MS m/z 333 (M⁺+H).

Product of Step 2, Example 27: Brown glassy solid; ¹H NMR (500 MHz, DMSO-D₆) δ ppm 1.06 (s, 9H) 3.90 (s, 1H) 3.92 (s, 1H) 6.56 (s, 1H) 7.42 (s, 1H) 8.16 (s, 1H) 8.40 (s, 1H); LC-MS, MS m/z 277 (M⁺+H).

Compound 27A

¹H NMR (500 MHz, CD₃OD) δ ppm 1.10-1.13 (m, 2H) 1.15 (s, 9H) 1.27-1.31 (m, 2H) 1.45 (dd, J=9.46, 5.49 Hz, 1H) 1.92 (dd, J=7.93, 5.49 Hz, 1H) 2.23-2.32 (m, 2H) 2.57 (dd, J=13.58, 7.17 Hz, 1H) 2.91 (d, J=14.04 Hz, 1H) 2.97-3.03 (m, 1H) 4.02 (s, 3H) 4.11 (dd, J=12.21, 3.36 Hz, 1H) 4.29-4.35 (m, 2H) 4.60 (dd, J=10.22, 7.17 Hz, 1H) 5.15 (dd, J=10.38, 1.53 Hz, 1H) 5.33 (d, J=17.09 Hz, 1H) 5.73-5.83 (m, 1H) 5.87 (s, 1H) 7.54 (s, 1H) 7.55 (s, 1H) 7.66 (dd, J=8.85, 2.14 Hz, 1H) 7.82 (d, J=1.83 Hz, 1H) 8.04 (s, 1H) 8.08 (d, J=8.85 Hz, 1H) 8.23 (s, 1H) 9.23 (s, 1H); LC-MS, MS m/z 794 (M⁺+H).

Compound 27B

¹H NMR (500 MHz, CD₃OD) δ ppm 0.97 (s, 9H) 1.04-1.12 (m, 2H) 1.21-1.28 (m, 2H) 1.40 (dd, J=9.46, 5.19 Hz, 1H) 1.91 (dd, J=8.09, 5.34 Hz, 1H) 2.30 (q, J=8.65 Hz, 1H) 2.38 (ddd, J=13.81, 9.84, 4.12 Hz, 1H) 2.65 (dd, J=13.89, 7.17 Hz, 1H) 2.87-2.98 (m, 1H) 4.04 (s, 3H) 4.09 (dd, J=12.21, 3.36 Hz, 1H) 4.46 (s, 1H) 4.55 (d, J=12.21 Hz, 1H) 4.65 (dd, J=9.46, 7.32 Hz, 1H) 5.16 (d, J=10.38 Hz, 1H) 5.36 (d, J=17.40 Hz, 1H) 5.76-5.85 (m, 1H) 5.89 (s, 1H) 7.63 (s, 1H) 7.75 (dd, J=8.85, 2.14 Hz, 1H) 7.78 (s, 1H) 8.05 (d, J=1.83 Hz, 1H) 8.15 (d, J=9.16 Hz, 1H) 8.19 (s, 1H) 8.37 (s, 1H) 9.56 (s, 1H); LC-MS, MS m/z 794 (M⁺+H).

Compound 28 Isomers 3-methyl-N-(6-methyl-2-pyridinyl)-L-valyl-(4R)-4-((7-chloro-4-methoxy-1-isoquinolinyl)oxy)-N-((1R, 2S)-1-((cyclopropylsulfonyl)carbamoyl)-2-vinylcyclopropyl)-L-prolinamide and 3-methyl-N-(6-methyl-2-pyridinyl)-D-valyl-(4R)-4-((7-chloro-4-methoxy-1-isoquinolinyl)oxy)-N-((1R, 2S)-1-((cyclopropylsulfonyl)carbamoyl)-2-vinylcyclopropyl)-L-prolinamide Example 28

Preparation of Compounds 28A and 28B

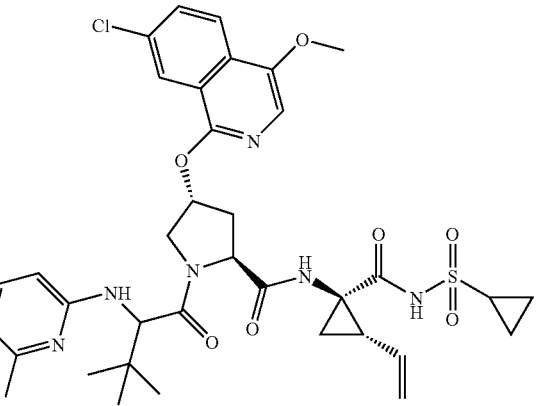

Compounds 28A and 28B

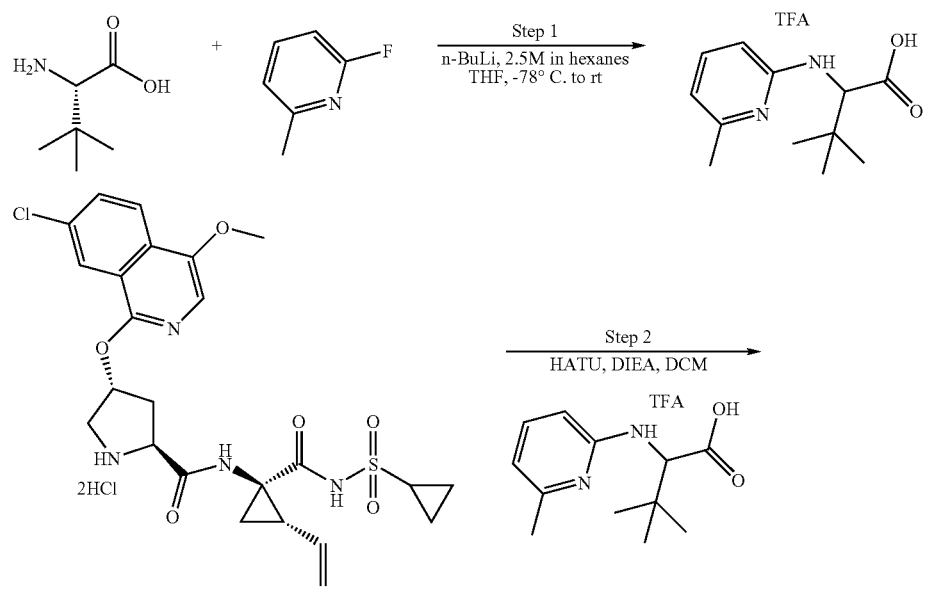

Scheme 1

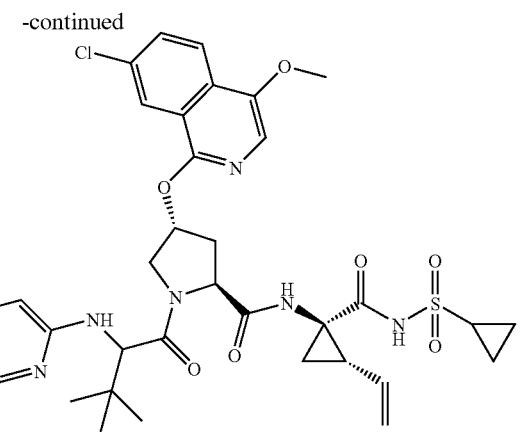

Compounds 28A and 28B

Step 1:

L-tert-leucine (0.734 g, 5.60 mmol) was suspended with stirring in dry THF (10 mL). The suspension was cooled to −78° C., and n-buLi, 2.5M in hexanes (4.48 mL, 11.2 mmol) was added dropwise. The yellow mixture was stirred at −78° C. for 30 min, then the cold bath was removed and the suspension was allowed to warm to rt for 25 min. The mixture was again cooled to −78° C., and 2-fluoro-6-methylpyridine (0.311 g, 2.80 mmol) was added dropwise. The color changed from yellow to deep orange and finally brown over time. The cold bath was removed and the mixture was stirred at rt overnight. The crude mixture was poured into rapidly stirred saturated aqueous ammonium chloride solution (100 mL) and EtOAc (50 mL) was added. The phases were separated, and the aqueous phase was extracted with EtOAc (2×50 mL). The aqueous phase had to be saturated with NaCl and extracted with DCM (4×100 mL) to remove the product. The organics were combined and concentrated in vacuo to a residue. Purification of the residue by reverse phase preparative HPLC gave the product as a sticky yellow oil (0.279 g, 44.8% yield) TFA salt. $^1$H NMR (300 MHz, CHLOROFORM-D) δ ppm 1.02 (s, 9H) 2.49 (s, 3H) 3.94 (s, 1H) 3.96-4.16 (m, 1H) 6.54 (d, J=7.32 Hz, 1H) 6.70 (d, J=8.78 Hz, 1H) 7.63-7.73 (m, 1H); LC-MS, MS m/z 223 (M$^+$+H).

Step 2:

A mixture of the product of Step 1, Example 28, (0.111 g, 0.329 mmol), the product of Step 5, Example 22, (0.200 g, 0.329 mmol) and HATU (0.163 g, 0.428 mmol) suspended in DCM (2 mL) was treated with NMM (0.167 g, 1.65 mmol). The mixture was stirred at room temperature for 20 hours. The solvent was removed by concentrating under a stream of nitrogen, and the crude mixture was purified by reverse phase preparative HPLC. Compound 28A (0.0916 g, 28.8% yield) was the first of two isomers to elute from the preparative HPLC column and was isolated as as an off-white powder bis-TFA salt. Compound 28B (0.0353 g, 11.1% yield) was the second of two isomers to elute from the preparative HPLC column and was also isolated as an off-white powder bis-TFA salt.

Compound 28A $^1$H NMR (500 MHz, CD$_3$OD) δ ppm 1.09-1.14 (m, 2H) 1.15 (s, 9H) 1.25-1.30 (m, 2H) 1.46 (dd, J=9.46, 5.49 Hz, 1H) 1.94 (dd, J=8.24, 5.49 Hz, 1H) 2.25-2.37 (m, 2H) 2.45 (s, 3H) 2.66 (dd, J=13.89, 7.17 Hz, 1H) 2.99 (ddd, J=12.82, 8.09, 4.73 Hz, 1H) 4.05 (s, 3H) 4.09 (dd, J=12.21, 3.36 Hz, 1H) 4.40 (d, J=11.90 Hz, 1H) 4.53 (s, 1H) 4.69 (dd, J=10.07, 7.32 Hz, 1H) 5.17 (dd, J=10.38, 1.53 Hz, 1H) 5.34 (dd, J=17.24, 1.37 Hz, 1H) 5.77 (ddd, J=17.17, 10.15, 9.00 Hz, 1H) 5.92 (s, 1H) 6.67 (d, J=7.32 Hz, 1H) 6.77 (d, J=8.85 Hz, 1H) 7.43 (dd, J=9.00, 7.48 Hz, 1H) 7.64 (s, 1H) 7.71 (dd, J=8.85, 2.14 Hz, 1H) 7.90 (d, J=1.83 Hz, 1H) 8.13 (d, J=8.85 Hz, 1H); LC-MS, MS m/z 740 (M$^+$+H).

Compound 28B $^1$H NMR (500 MHz, CD$_3$OD) δ ppm 0.97 (s, 9H) 1.03-1.12 (m, 2H) 1.13-1.20 (m, 1H) 1.22-1.29 (m, 1H) 1.41 (dd, J=9.46, 5.19 Hz, 1H) 1.91 (dd, J=8.24, 5.19 Hz, 1H) 2.31 (q, J=8.75 Hz, 1H) 2.43 (ddd, J=13.96, 9.54, 4.27 Hz, 1H) 2.54 (s, 3H) 2.69 (dd, J=14.04, 7.32 Hz, 1H) 2.86-2.96 (m, 2H) 4.04 (s, 3H) 4.20 (dd, J=12.21, 3.36 Hz, 1H) 4.50 (d, J=11.90 Hz, 1H) 4.65-4.71 (m, 2H) 5.13-5.19 (m, 1H) 5.36 (dd, J=17.24, 1.37 Hz, 1H) 5.79 (ddd, J=17.24, 10.22, 8.85 Hz, 1H) 5.92 (s, 1H) 6.84 (d, J=7.32 Hz, 1H) 7.06 (d, J=8.85 Hz, 1H) 7.63 (s, 1H) 7.76 (dd, J=9.16, 2.14 Hz, 1H) 7.96 (dd, J=8.85, 7.32 Hz, 1H) 8.06 (d, J=2.14 Hz, 1H) 8.16 (d, J=8.85 Hz, 1H) 9.56 (s, 1H); LC-MS, MS m/z 740 (M$^+$+H).

Compound 29 Isomers

N-(2,6-dimethyl-4-pyridinyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(2,6-dimethyl-4-pyridinyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide

Example 29

Preparation of Compounds 29A and 29B

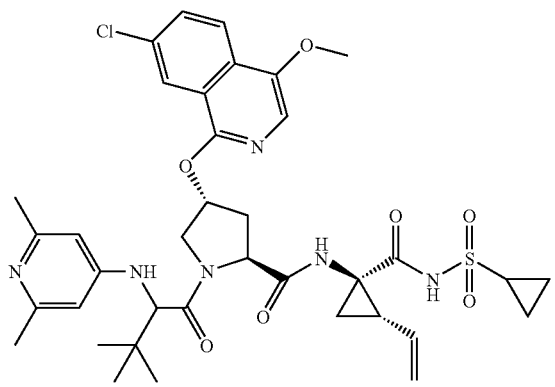

Compound 29A and 29B

Compounds 29A and 29B were prepared by a similar procedure as that described for the preparation of compound 25, except 4-bromo-2,6-dimethylpyridine 1.06 hydrobromide (0.980 g, 3.61 mmol) was used in place of 5-bromo-3-picoline in Step 1, and the reaction scales were different. Also, the product from Step 2 was not isolated as the HCl salt but was instead carried on to Step 3 directly as a TFA salt. Two isomeric compounds were isolated from Step 3: the first isomer to elute from a preparative HPLC column was compound 29A (0.127 g) isolated as a white solid bis-TFA salt, and the second isomer to elute from the preparative HPLC column was compound 29B (0.103 g) isolated as a white solid bis TFA salt. The combined yield for both compounds 29A and 29B was 47.8% over three steps.

Product of Step 1, Example 29: Light brown waxy solid; $^1$H NMR (500 MHz, CHLOROFORM-D) δ ppm 1.04 (s, 9H) 1.43 (s, 9H) 2.37 (s, 6H) 3.71 (d, J=9.77 Hz, 1H) 4.46 (d, J=9.77 Hz, 1H) 6.20 (s, 2H); LC-MS, MS m/z 293 (M$^+$+H).

Product of Step 2, Example 29: Brown glassy solid; $^1$H NMR (500 MHz, DMSO-D$_6$) δ ppm 1.03 (s, 9H) 2.38 (s, 3H) 2.42 (s, 3H) 4.17 (d, J=9.77 Hz, 1H) 6.79 (s, 1H) 6.88 (s, 1H) 8.23 (d, J=9.77 Hz, 1H) 13.11 (s, 1H); LC-MS, MS m/z 237 (M$^+$+H).

Compound 29A $^1$H NMR (500 MHz, CD$_3$OD) δ ppm 0.99 (s, 1H) 1.05 (s, 9H) 1.07-1.13 (m, 2H) 1.21-1.27 (m, 2H) 1.42 (dd, J=9.61, 5.34 Hz, 1H) 1.46 (s, 1H) 1.90 (dd, J=8.09, 5.34 Hz, 1H) 2.12 (s, 3H) 2.21-2.29 (m, 2H) 2.31 (s, 3H) 2.60 (dd, J=13.89, 7.48 Hz, 1H) 2.92-3.00 (m, 1H) 4.01 (s, 3H) 4.24 (d, J=11.60 Hz, 1H) 4.35 (d, J=9.77 Hz, 1H) 4.66 (dd, J=10.07, 7.32 Hz, 1H) 5.13 (dd, J=10.38, 1.53 Hz, 1H) 5.31 (dd, J=17.09, 1.22 Hz, 1H) 5.74 (ddd, J=17.17, 10.15, 9.00 Hz, 1H) 5.87 (s, 1H) 6.49 (d, J=13.12 Hz, 2H) 7.58 (s, 1H) 7.66 (dd, J=8.85, 2.14 Hz, 1H) 7.80 (d, J=1.83 Hz, 1H) 7.92 (d, J=9.77 Hz, 1H) 8.07 (d, J=8.85 Hz, 1H) 9.22 (s, 1H); LC-MS, MS m/z 754 (M$^+$+H).

Compound 29B $^1$H NMR (500 MHz, CD$_3$OD) δ ppm 0.92 (s, 9H) 1.03-1.11 (m, 2H) 1.19-1.26 (m, 2H) 1.39 (dd, J=9.46, 5.49 Hz, 1H) 1.88 (dd, J=8.24, 5.19 Hz, 1H) 2.28 (q, J=8.95 Hz, 1H) 2.36 (ddd, J=14.04, 9.77, 4.27 Hz, 1H) 2.44 (br s, 6H) 2.63 (dd, J=14.04, 7.32 Hz, 1H) 2.93 (ddd, J=12.74, 8.01, 4.58 Hz, 1H) 4.01 (s, 3H) 4.06 (dd, J=12.21, 3.36 Hz, 1H) 4.47 (d, J=12.21 Hz, 1H) 4.52 (d, J=9.16 Hz, 1H) 4.63 (dd, J=9.77, 7.32 Hz, 1H) 5.13 (dd, J=10.38, 1.53 Hz, 1H) 5.33 (dd, J=17.09, 1.53 Hz, 1H) 5.78 (ddd, J=17.09, 10.38, 8.85 Hz, 1H) 5.87 (s, 1H) 6.71 (br s, 1H) 6.87 (br s, 1H) 7.14 (d, J=9.16 Hz, 1H) 7.58 (s, 1H) 7.72 (dd, J=8.85, 2.14 Hz, 1H) 8.01 (d, J=2.14 Hz, 1H) 8.12 (d, J=9.16 Hz, 1H) 9.54 (s, 1H); LC-MS, MS m/z 754 (M$^+$+H).

Compound 32 Isomers

N-(4,6-dichloro-2-pyridinyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(4,6-dichloro-2-pyridinyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide

Example 32

Preparation of Compounds 32A and 32B

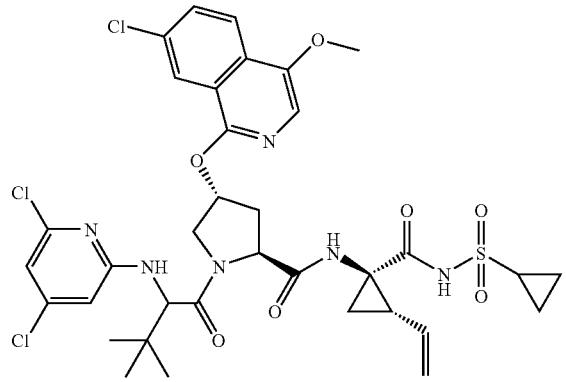

Compound 32A and 32B

Compounds 32A and 32B were prepared by a similar procedure as that described for the preparation of compound 7, except 2,4,6-trichloropyridine (0.658 g, 3.61 mmol) was used in place of 2-chloropyridine in Step 1, and the reaction scales were different. Also, in Step 3, the product from Step 5, Example 22, was used in place of the product of Step 5, Example 1. Two isomeric compounds were isolated from Step 3: the first isomer to elute from a preparative HPLC column was compound 32A (0.0783 g) isolated as an off-white solid bis-TFA salt, and the second isomer to elute from the preparative HPLC column was compound 32B (0.0207 g) isolated as an off-white solid bis TFA salt. The combined yield for both compounds 32A and 32B was 5.8% over three steps.

Product of Step 1, Example 32: Yellow oil; $^1$H NMR (500 MHz, CHLOROFORM-D) δ ppm 1.03 (s, 9H) 1.46 (s, 9H) 4.10 (d, J=8.85 Hz, 1H) 5.13 (d, J=9.16 Hz, 1H) 6.33 (d, J=1.22 Hz, 1H) 6.60 (d, J=1.22 Hz, 1H); LC-MS, MS m/z 334 (M$^+$+H).

Product of Step 2, Example 32: Sticky brown oil; LC-MS, MS m/z 278 (M$^+$+H).

Compound 32A $^1$H NMR (500 MHz, CD$_3$OD) δ ppm 1.04-1.08 (m, 2H) 1.09 (s, 9H) 1.21-1.29 (m, 2H) 1.41 (dd, J=9.61, 5.34 Hz, 1H) 1.87 (dd, J=8.09, 5.34 Hz, 1H) 2.19-2.31 (m, 2H) 2.54 (dd, J=13.58, 6.87 Hz, 1H) 2.92-2.98 (m, J=8.09, 8.09, 4.73, 4.73 Hz, 1H) 4.00 (s, 3H) 4.12 (dd, J=11.75, 3.81 Hz, 1H) 4.53 (dd, J=10.53, 6.87 Hz, 1H) 4.68 (d, J=11.60 Hz, 1H) 4.72 (s, 1H) 5.11 (dd, J=10.22, 1.68 Hz, 1H) 5.28 (dd, J=17.24, 1.37 Hz, 1H) 5.74 (ddd, J=17.09, 10.22, 9.00 Hz, 1H) 5.88 (t, J=3.36 Hz, 1H) 6.26 (d, J=1.22 Hz, 1H) 6.48 (d, J=1.22 Hz, 1 H) 7.54 (s, 1H) 7.64 (dd, J=8.85, 2.14 Hz, 1H) 7.82 (d, J=2.14 Hz, 1H) 8.05 (d, J=8.85 Hz, 1H) 9.14 (s, 1H); LC-MS, MS m/z 795 (M$^+$+H).

Compound 32B $^1$H NMR (500 MHz, CD$_3$OD) δ ppm 0.90 (s, 9H) 0.97-1.11 (m, 3H) 1.26-1.37 (m, 2H) 1.85 (dd, J=8.24, 5.19 Hz, 1H) 2.23 (q, J=8.95 Hz, 1H) 2.35 (ddd, J=13.96, 9.84, 4.27 Hz, 1H) 2.58 (dd, J=13.73, 7.32 Hz, 1H) 2.81-2.88 (m, 1H) 4.01 (s, 3H) 4.23 (dd, J=12.05, 3.51 Hz, 1H) 4.38 (d, J=12.21 Hz, 1H) 4.56 (dd, J=9.92, 7.17 Hz, 1H) 4.90 (s, 1H) 5.12 (dd, J=10.22, 1.68 Hz, 1H) 5.31 (dd, J=17.24, 1.37 Hz, 1H) 5.77 (ddd, J=17.09, 10.38, 8.85 Hz, 1H) 5.83 (s, 1H) 6.56 (d, J=1.53 Hz, 1H) 6.58 (d, J=1.53 Hz, 1H) 7.61 (s, 1H) 7.71 (dd, J=8.85, 2.14 Hz, 1H) 8.02 (d, J=2.14 Hz, 1H) 8.11 (d, J=8.85 Hz, 1H) 9.35 (s, 1H); LC-MS, MS m/z 795 (M$^+$+H).

Example 33

Preparation of Compound 33: N-(5-chloro-3-pyridinyl)-3-methylvalyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Compound 33

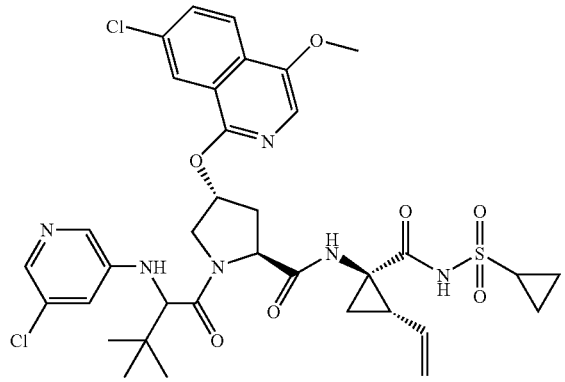

Compound 33 was prepared by a similar procedure as that described for the preparation of compound 7, except 3,5-dichloropyridine (0.534 g, 3.61 mmol) was used in place of 2-chloropyridine in Step 1, and the reaction scales were different. Also, in Step 3, the product from Step 5, Example 22, was used in place of the product of Step 5, Example 1. Compound 33 (0.187 g, 9.0% yield over 3 steps) was isolated as a beige solid bis TFA salt.

Product of Step 1, Example 33: Yellow oil; $^1$H NMR (500 MHz, CHLOROFORM-D) δ ppm 1.06 (s, 9H) 1.44 (s, 9H) 3.61 (d, J=10.07 Hz, 1H) 4.30 (d, J=10.07 Hz, 1H) 6.91 (t, J=2.29 Hz, 1H) 7.92 (d, J=1.83 Hz, 1H) 7.95 (d, J=2.44 Hz, 1H); LC-MS, MS m/z 299 (M$^+$+H).

Product of Step 2, Example 33: Sticky brown oil; LC-MS, MS m/z 243 (M$^+$+H).

Compound 33: $^1$H NMR (500 MHz, CD$_3$OD) δ ppm 1.03-1.08 (m, 2H) 1.09 (s, 9H) 1.22-1.27 (m, 2H) 1.42 (ddd, J=9.54, 5.42, 0.92 Hz, 1H) 1.89 (dd, J=8.24, 5.49 Hz, 1H) 2.19-2.29 (m, 2H) 2.56 (dd, J=13.73, 7.02 Hz, 1H) 2.92-2.99 (m, 1H) 3.96-4.05 (m, 4H) 4.21 (s, 1H) 4.29 (d, J=12.21 Hz, 1H) 4.60 (dd, J=10.22, 7.17 Hz, 1H) 5.12 (dd, J=10.38, 1.53 Hz, 1H) 5.30 (dd, J=17.09, 1.53 Hz, 1H) 5.74 (ddd, J=17.09, 10.38, 8.85 Hz, 1H) 5.84 (s, 1H) 7.33 (s, 1H) 7.54 (s, 1H) 7.65 (dd, J=8.85, 2.14 Hz, 1H) 7.72 (s, 1H) 7.81 (d, J=1.83 Hz, 1H) 7.94 (s, 1H) 8.07 (d, J=8.85 Hz, 1H) 9.20 (s, 1H); LC-MS, MS m/z 760 (M$^+$+H).

Example 35

Preparation of Compound 35: N-(4-ethyl-1,3-thiazol-2-yl)-3-methyl-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide Compounds 35

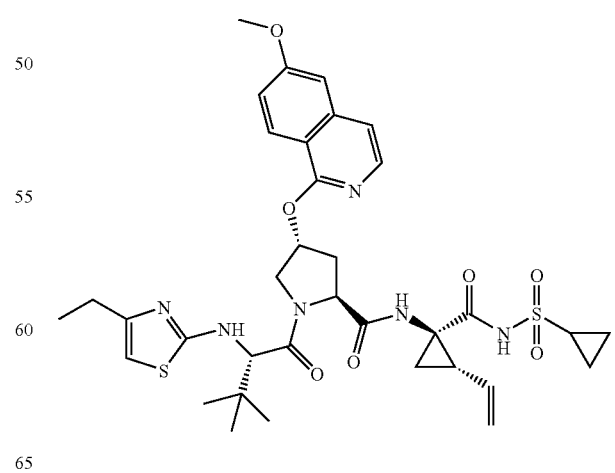

Scheme 1
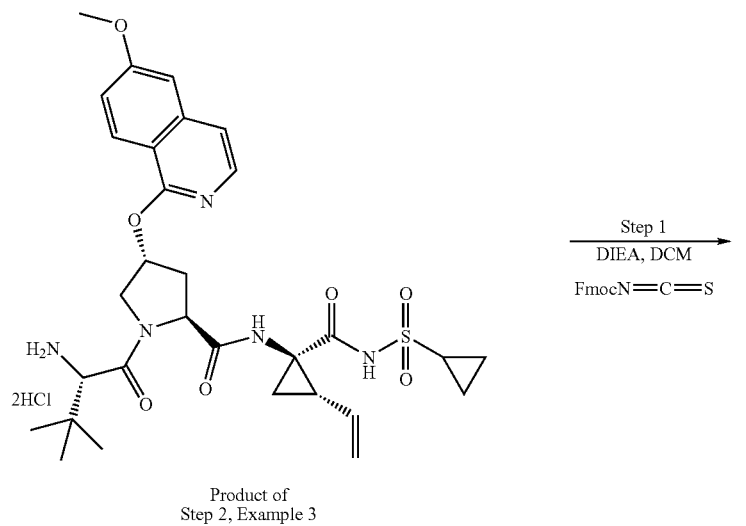
Product of
Step 2, Example 3
Step 1
DIEA, DCM
FmocN=C=S
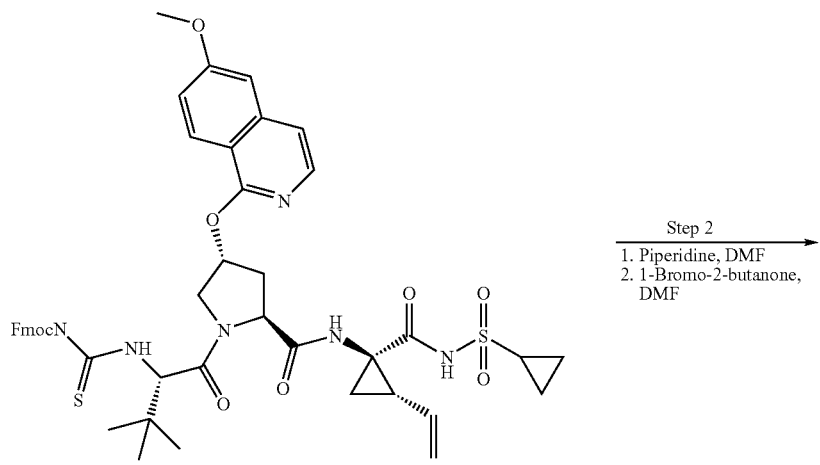
Step 2
1. Piperidine, DMF
2. 1-Bromo-2-butanone, DMF
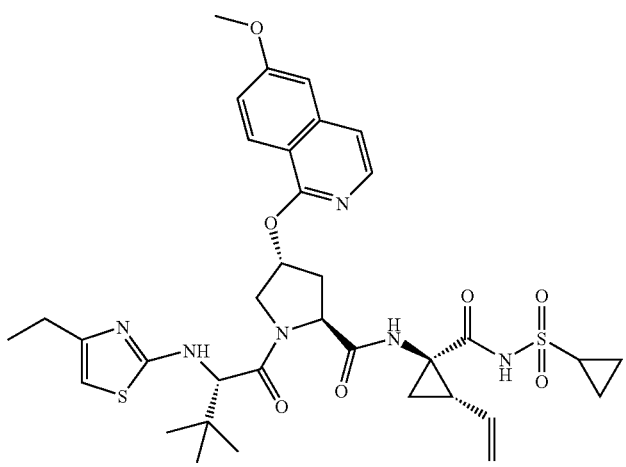
Compound 35

Step 1:

To a solution mixture of product of step 2, Example 3 (1.5 g, 2.18 mmol) and DIEA (0.707 g, 5.46 mmol) in DCM (20 mL) was added Fmoc-thioisocyanate (0.799, 2.84 mmol). Reaction mixture was stirred at for 48 h. Reaction was not completed as determined by LC/MS, then was added more Fmoc-thioisocyanate (0.307 g, 1.09 mmol). Reaction mixture was allowed to stir at rt for an additional 24 h. White solid precipitation by-product was removed by vacuum filtration and washed with EtOAc. The liquid filtrate was concentrated, the resulting residue redissolved in EtOAc (100 mL) and washed with 2×25 mL H$_2$O. The aqueous layers were combined and extracted with EtOAc (50 mL). The combined organic layer was washed with brine, dried over MgSO$_4$, filtered and concentrated to a yellow solid. More un-identified by-products were removed by trituration with EtOAc, chilled to 0° C.; solid precipitation was filtered and discarded. The liquid filtration was concentrated and residue was purified through a column of SiO$_2$ which was eluted with 3:1, 1:1 then 1:3 hexanes:EtOAc to give the product of step 1, Example 35 (0.798 g, 41% yield) as a light yellow foamy solid. LC-MS, MS m/z 895 (M$^+$+H).

Step 2:

To a yellow solution of the product form step 1, Example 35 (0.489 g, 0.546 mmol) in DMF (4 mL) was added piperidine (1 mL). Reaction was stirred at rt. After 5 h solvent was removed under vacuo and dried to give a solid glassy crude product which was taken up in DMF (5 mL) and treated with 1-bromo-2-butanone (0.275 g, 1.64 mmol). Reaction mixture was stirred at rt overnight. After 14 h, solvent was removed under vacuo to give viscous red oil which was redissolved in MeOH and filtered to remove brown gel like substance. The liquid filtrated was concentrated and remaining residue was purified br reversed phase HPLC to give Example 35 (139.7, 35% yield) as a light yellow solid. $^1$H NMR (500 MHz) δ ppm 0.81 (t, J=7.5 Hz, 3H), 1.06-1.12 (m, 3H), 1.14 (s, 9H), 1.25-1.30 (m, 2H), 1.46 (dd, J=9.6, 5.3 Hz, 1H), 1.91 (dd, J=8.1, 5.3 Hz, 1H), 1.93-1.97 (m, 1H), 1.99-2.07 (m, 1H), 2.23-2.29 (m, 1H), 2.30-2.36 (m, 1H), 2.59 (dd, J=13.4, 6.7 Hz, 1H), 3.96 (s, 3H), 4.15 (dd, J=11.7, 3.8 Hz, 1H), 4.46 (s, 1H), 4.57 (dd, J=10.5, 6.9 Hz, 1H), 4.68 (d, J=11.6 Hz, 1H), 5.15 (d, J=10.4 Hz, 1H), 5.32 (d, J=17.1 Hz, 1H), 5.75 (s, 1H), 5.76-5.82 (m, 1H), 5.90 (s, 1H), 7.09 (dd, J=8.9, 2.4 Hz, 1H), 7.23 (d, J=2.4 Hz, 1H), 7.29 (d, J=5.8 Hz, 1H), 7.89 (d, J=9.2 Hz, 1H), 7.93 (d, J=6.1 Hz, 1H). LC-MS, MS m/z 725 (M$^+$+H).

Example 36

Preparation of Compound 36: N-(5,6-dihydro-4H-1,3-thiazin-2-yl)-3-methyl-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide

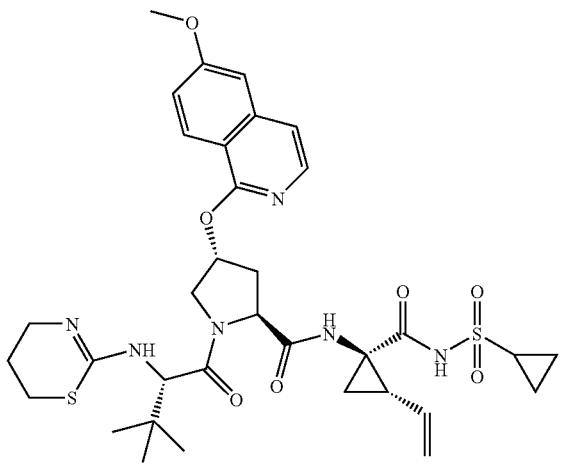

Compound 36

Scheme 1

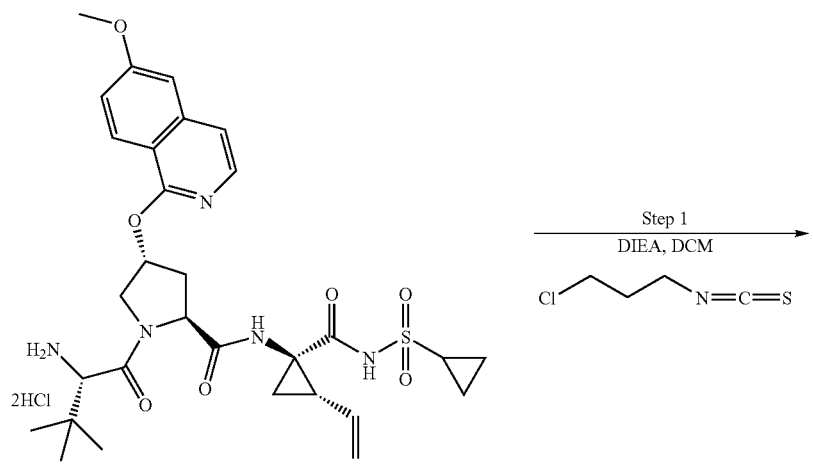

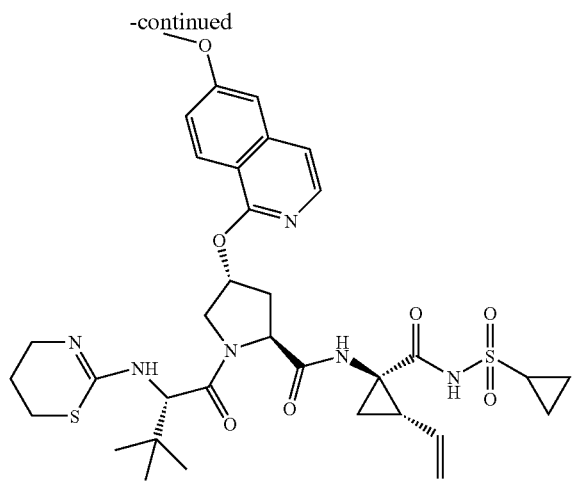

Compound 36

Step 1:
To a solution mixture of the product of step 2, example 3 (0.267 g, 0.389 mmol) and DIEA (0.101 g, 0.778 mmol) in DCM (4 mL) was added 3-chloropropyl isothiocyanate (0.053 g, 0.389 mmol) and heated to 45° C. After 3 h, solvent was removed and residue was redissolved in hot EtOAc with minimal DCM, Et$_2$O was added to effect light green precipitation which was obtained by filtration. Product was purified by reversed phase HPLC to give Example 36 (0.166 g, 54%) as light yellow bis-HCl salt solid. $^1$H NMR (500 MHz, CD$_3$OD) δ ppm 1.12 (s, 9H), 1.24-1.28 (m, 3H), 1.47 (dd, J=9.5, 5.5 Hz, 1H), 1.94 (dd, J=8.2, 5.5 Hz, 1H), 2.27-2.38 (m, 2H), 2.70 (dd, J=13.7, 7.0 Hz, 1H), 2.94-3.01 (m, 1H), 3.97 (s, 3H), 4.05-4.10 (m, 1H), 4.12 (q, J=7.3 Hz, 1H), 4.39 (d, J=11.9 Hz, 1H), 4.73 (dd, J=10.2, 7.5 Hz, 1H), 5.17 (dd, J=10.4, 1.5 Hz, 1H), 5.35 (d, J=17.1 Hz, 1H), 5.74-5.83 (m, 1H), 5.91 (s, 1H), 7.26 (dd, J=9.2, 2.4 Hz, 1H), 7.30 (d, J=2.1 Hz, 1H), 7.35 (d, J=6.1 Hz, 1H), 7.97 (d, J=5.8 Hz, 1H), 8.11 (d, J=9.2 Hz, 1H). LC-MS, MS m/z 713 (M$^+$+H).

Example 37

Preparation of Compound 37: N-(5,6-dihydro-4H-1,3-thiazin-2-yl)-3-methyl-L-valyl-(4R)—N-((1R,2S)-1-((cyclopropylsulfonyl)carbamoyl)-2-vinylcyclopropyl)-4-((6-methoxy-3-(4-(trifluoromethoxy)phenyl)-1-isoquinolinyl)oxy)-L-prolinamide Compound 37

Scheme 1

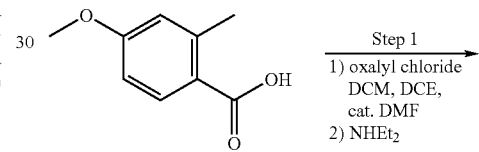

Step 1
1) oxalyl chloride DCM, DCE, cat. DMF
2) NHEt$_2$

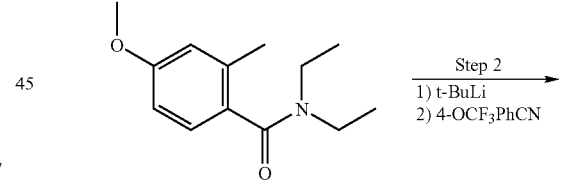

Step 2
1) t-BuLi
2) 4-OCF$_3$PhCN

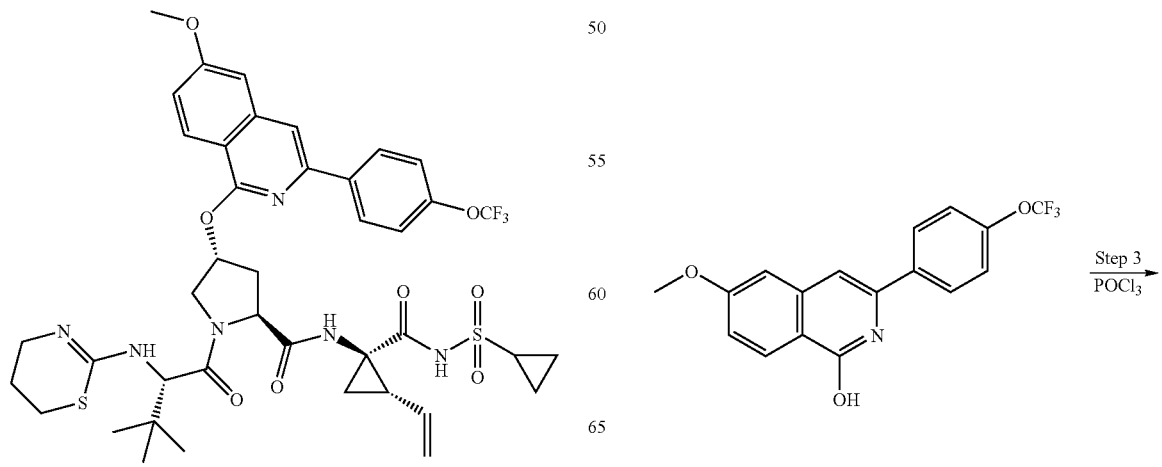

Step 3
POCl$_3$

-continued

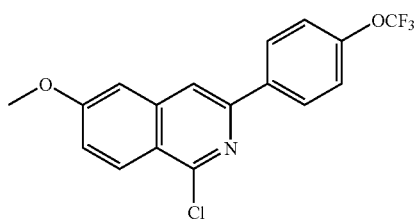

Step 1:

A mixture of 4-methoxy-2-methyl-benzoic acid (25.3 g, 152 mmol) in 1:1 DCM:DCE was treated with oxalyl chloride (38.6 g, 304 mmol), followed by addition of DMF (0.111 g, 1.50 mmol). Vigorous gas evolution ensued, and the reaction eventually became clear after 1 h. The volatiles were removed in vacuo and the white solid residue was placed under high vacuum for 2 h. The crude material was redissolved in DCM (200 mL) and the mixture was cooled to 0° C. Diethylamine (22.8 g, 312 mmol) was added dropwise with stirring. The mixture was allowed to warm to rt for 1 h with stirring. The mixture was concentrated in vacuo to approximately ⅓ volume, and Et$_2$O (300 mL) was added and the mixture was chilled. The solid precipitate which had formed was removed by filtration. The filtrate was concentrated to give a viscous brown oil which was redissolved in DCM (200 mL) and washed with 0.1M HCl (2×50 mL). The organic phase was dried over MgSO$_4$, filtered and concentrated in vacuo to give the desired product (33.1 g, 98% yield). LC-MS, MS m/z 222 (M$^+$+H).

Step 2:

To a stirred solution of N,N-diethyl-4-methoxy-2-methyl-benzamide (10.0 g, 45.2 mmol) in THF (150 mL) at −78° C. under nitrogen atmosphere was added t-BuLi (29.2 mL of 1.7M in pentane, 49.7 mmol) dropwise. The resulting red solution was kept at this temperature for additional 10 min before dropwise addition of 4-(trifluoromethoxy)-benzonitrile (9.49 g, 49.7 mmol). The brown solution was stirred at −78° C. for 2 h; tests by LCMS showed incomplete reaction. Thus to the mixture was added an additional amount of 4-(trifluoromethoxy)-benzonitrile (3.38 g, 18.1 mmol) and the resulting mixture was stirred for an additional 1 h. The mixture was then allowed to warm to rt and was quenched by pouring into aqueous 1.0M HCl (50 mL). EtOAc (100 mL) was added and the mixture was shaken and phases were separated. A precipitate occurred within the EtOAc phase which was isolated by filtration and allowed to dry (3.0 g). This 3.0 g of isolated solid was determined to be impure product and was set aside for later purification. The EtOAc filtrate was set aside. The aqueous acid washes were combined and extracted with DCM (3×100 mL). The DCM extracts were combined, washed with brine, dried over MgSO$_4$, filtered and concentrated in vacuo. This residue was combined with the original EtOAc filtrate and the combined organics were concentrated to a slurry. A solid was isolated by filtration to give the desired product (8.84 g, 58.0% yield). LC-MS, MS m/z 336 (M$^+$+H).

Step 3:

The solid product from Step 2, Example 37 (8.84 g, 26.4 mmol) was dissolved in POCl$_3$ (100 mL) and the mixture was heated to reflux for 3 h. The mixture was concentrated in vacuo, and to the resulting residue was added water (100 mL) and EtOAc (100 mL). The rapidly stirred mixture was treated slowly with solid sodium bicarbonate until pH=7 was reached. The phases were separated, and the aqueous phase was extracted with EtOAc (2×40 mL). The organic extracts were combined and washed with saturated aqueous sodium bicarbonate (40 mL) and then with brine (40 mL), dried over MgSO$_4$, filtered and concentrated in vacuo. The product (9.21 g, 98.7% yield) was isolated without chromatography as a slightly yellow viscous oil. $^1$H NMR (500 MHz, CHLOROFORM-D) δ ppm 3.97 (s, 3H) 7.11 (d, J=2.44 Hz, 1H) 7.26 (dd, J=9.46, 2.44 Hz, 1H) 7.31 (d, J=8.85 Hz, 2H) 7.84 (s, 1H) 8.10 (d, J=8.85 Hz, 2H) 8.20 (d, J=9.46 Hz, 1H); LC-MS, MS m/z 354 (M$^+$+H).

Scheme 2

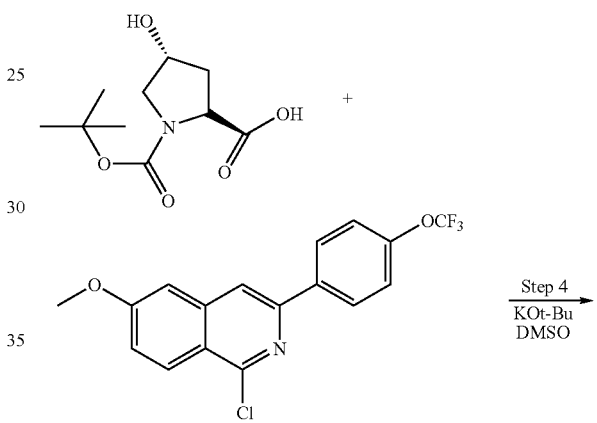

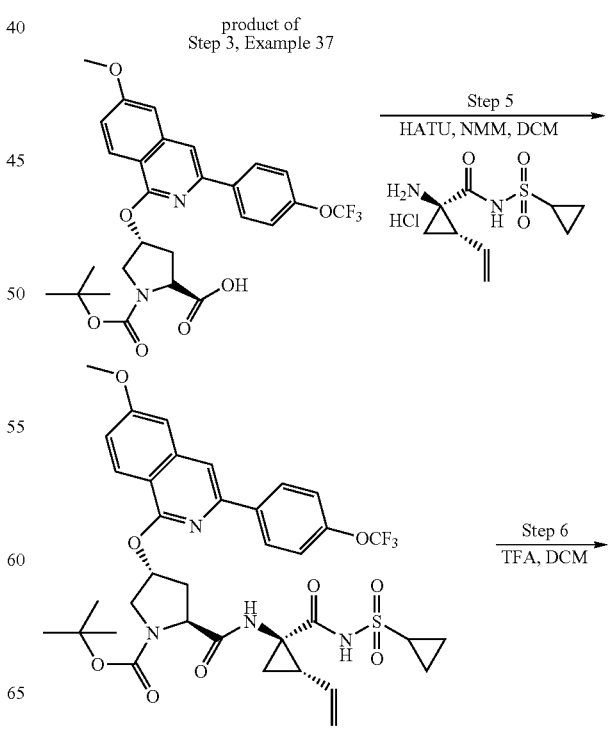

-continued

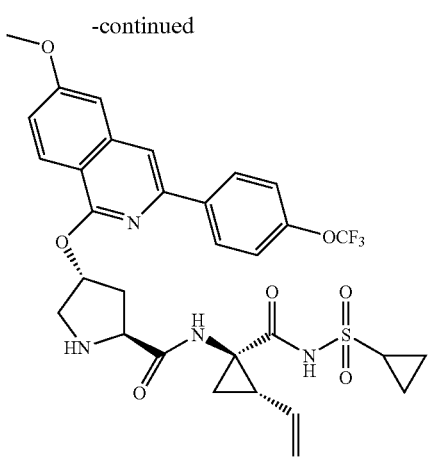

0.5% TEA). The pure product fractions were combined to give the desired product (9.13 g, 54% yield) which was determined to have 2.0 equivalents of TEA associated with it. Mixed fractions were combined and concentrated to give 5.27 g of material which was set aside for purification at a later date. $^1$H NMR (500 MHz, MeOD) δ ppm 0.81-0.91 (m, 2H) 1.02-1.13 (m, 2H) 1.33 (t, J=7.32 Hz, 18H) 1.88 (dd, J=7.63, 4.88 Hz, 1H) 2.11 (dd, 1H) 2.48 (ddd, J=14.19, 9.31, 5.19 Hz, 1H) 2.77 (dd, J=14.34, 7.63 Hz, 1H) 2.88 (tt, J=8.24, 4.88 Hz, 1H) 3.22 (q, J=7.32 Hz, 12H) 3.66 (d, J=13.12 Hz, 1H) 3.79 (dd, J=12.97, 4.43 Hz, 1H) 3.96 (s, 3H) 4.44 (dd, J=9.31, 7.78 Hz, 1H) 5.03 (dd, J=10.38, 1.83 Hz, 1H) 5.24 (dd, J=17.09, 1.83 Hz, 1H) 5.88 (ddd, J=17.17, 10.15, 9.31 Hz, 1H) 5.99 (t, J=4.73 Hz, 1H) 7.19 (dd, J=9.16, 2.44 Hz, 1H) 7.28 (d, J=2.44 Hz, 1H) 7.38 (d, J=8.24 Hz, 2H) 7.82 (s, 1H) 8.19 (d, J=9.16 Hz, 1H) 8.22-8.27 (m, 2H); LC-MS, MS m/z 661 (M$^+$+H).

Step 4:

To a mechanically stirred solution of Boc-Hyp-OH (6.31 g, 27.3 mmol) in DMSO (100 mL) was added solid potassium tert-butoxide (8.05 g, 68.2 mmol). The mixture was stirred for 1.5 h, and the product of Step 3, Example 37 (20.0 g, g, 74.2 mmol) was added in two portions over 15 min. The resulting suspension was stirred for 3 h at rt. The suspension was then diluted with a mixture of pH=4 buffer (500 mL) and 1.0 M HCl (41 mL) and extracted with EtOAc (3×150 mL). The organic extracts were combined and washed with pH=4 buffer (75 mL) and then with brine (50 mL). The organic was then extracted with a mixture of 1.0M NaOH (30 mL) and water (50 mL) twice, and the combined basic extracts were washed with EtOAc (30 mL). The aqueous basic extracts were treated with 1.0M HCl (approximately 60 mL) until pH=4 was achieved, and the desired product was then extracted into EtOAc (3×100 mL). The extracts were combined, dried over MgSO$_4$ and filtered. The filtrate was evaporated in vacuo to dryness to give a foamy solid. The desired product (13.2 g, 92.7% yield) was isolated after purification by silica gel column chromatography (step gradient DCM, then 40:1 DCM:MeOH, then 10:1 DCM:MeOH) as a glassy solid. LC-MS, MS m/z 549 (M$^+$+H).

Step 5:

A mixture of the product of Step 4, Example 37 (12.3 g, 22.4 mmol), NMM (6.80 g, 67.3 mmol) and cyclopropanesulfonic acid (1-(R)-amino-2-(S)-vinyl-cyclopropanecarbonyl)-amide HCl salt (6.28 g, 23.5 mmol) in DCM (250 mL) was treated with HATU (10.23 g, 26.9 mmol), and the resulting solution was stirred at rt overnight. Solvent was removed in vacuo, and the residue was taken up in EtOAc (700 mL) and washed with pH=4 buffer (4×200 mL) and with brine (75 mL). The organic was dried over MgSO$_4$, filtered and concentrated in vacuo. The product (13.5 g, 79.1% yield) was isolated after purification by silica gel column chromatography (1:1 hexanes:EtOAc) as a white glassy solid. LC-MS, MS m/z 761 (M$^+$+H).

Step 6:

To a solution of the product of Step 5, Example 37 (15.0 g, 19.6 mmol) in a mixture of DCM (50 mL) and 1,2-DCE (50 mL) was added TFA (100 mL). The mixture was stirred at rt for 1.5 h and was then concentrated in vacuo. The residue was determined to be less than 85% pure by LCMS. The crude product (15.1 g) was purified by silica gel column chromatography (step gradient DCM+0.5% TEA followed by 50:1 DCM:MeOH+0.5% TEA followed by 40:1 DCM:MeOH+

Scheme 3

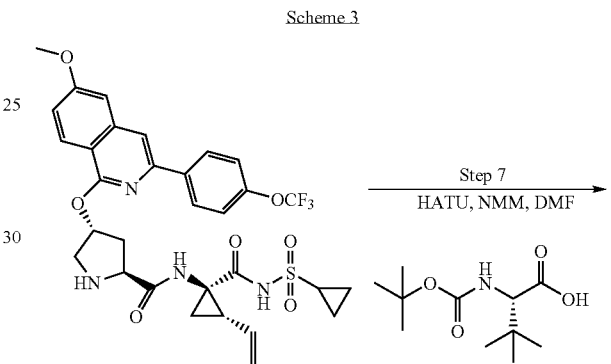

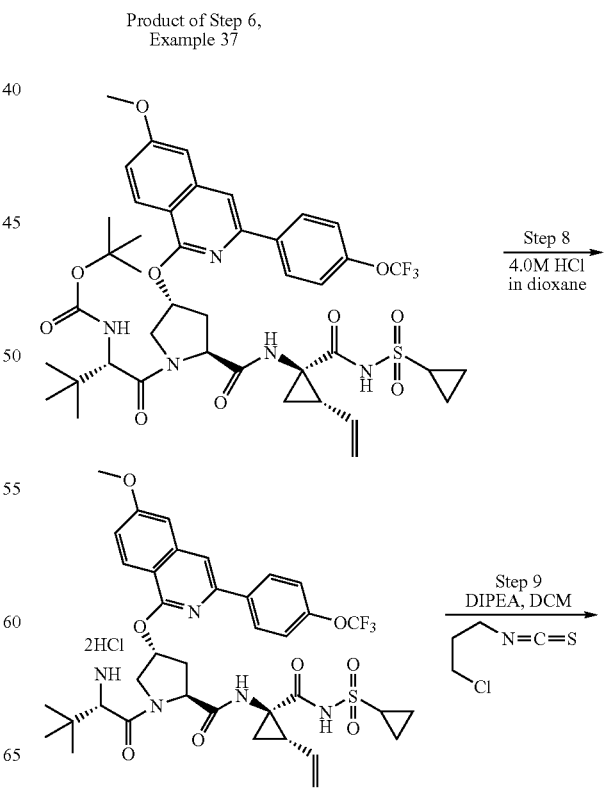

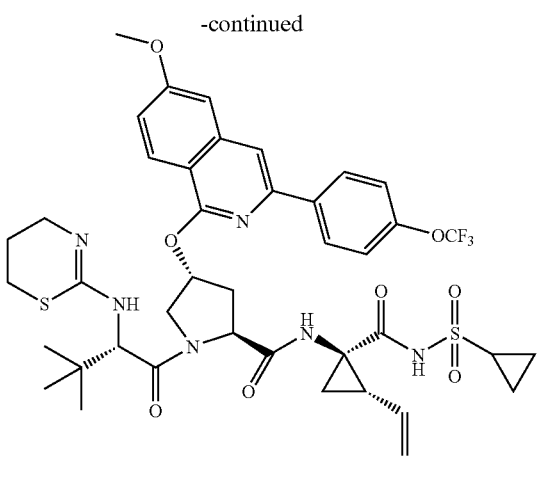

Compound 37

Step 7:

The product of Step 6, Example 37 (6.00 g, 6.95 mmol) was combined with N-Boc-tert-leucine (1.77 g, 7.65 mmol) and HATU (3.17 g, 8.34 mmol) in DCM (75 mL), and the resulting suspension was treated with NMM (1.48 g, 14.6 mmol), and the mixture was stirred at rt for 3 days. The reaction mixture was concentrated in vacuo to a residue, redissolved in EtOAc (250 mL) and washed with a 1:1 mixture of pH=4 buffer and brine (4×100 mL). The combined organics were dried over anhydrous MgSO$_4$, filtered and concentrated in vacuo to a beige foam. Purification by silica gel column chromatography (1:1 hexanes: EtOAc) afforded pure product as an off-white foam (4.62 g, 76.1% yield). LC-MS, MS m/z 874 (M$^+$+H).

Step 8:

The product of Step 7, Example 37 (4.61 g, 5.28 mmol) was treated with a mixture of 1,4-dioxane (50 mL) and 4.0M HCl in 1,4-dioxane (50 mL) for 2.5 h, resulting in a sticky gel sitting at the bottom of the flask. The mixture was concentrated in vacuo, then the resulting foamy solid was redissolved with DCM (25 mL) and the solution was added dropwise to a rapidly stirred mixture of diethyl ether (100 mL) and 2.0M HCl in ether (100 mL). A white powder precipitated and was isolated by filtration, rinsed with ether and dried under high vacuum. Total recovery was 3.95 g (88.4% yield) of white powder bis HCl salt product. $^1$H NMR (500 MHz, MeOD) δ ppm 1.09-1.15 (m, 2H) 1.20 (s, 9H) 1.23-1.32 (m, 2H) 1.46 (dd, J=9.46, 5.49 Hz, 1H) 1.94 (dd, J=8.24, 5.49 Hz, 1H) 2.31 (q, J=8.75 Hz, 1H) 2.42 (ddd, J=13.96, 10.15, 4.27 Hz, 1H) 2.77 (dd, J=13.89, 7.17 Hz, 1H) 2.98 (ddd, J=12.67, 8.09, 4.88 Hz, 1H) 3.99 (s, 3H) 4.12 (s, 1H) 4.25 (dd, 1H) 4.32 (d, 1H) 4.74 (dd, J=10.22, 7.17 Hz, 1H) 5.17 (dd, J=10.68, 1.22 Hz, 1H) 5.33 (dd, J=16.94, 1.07 Hz, 1H) 5.77 (ddd, J=17.17, 10.15, 9.00 Hz, 1H) 6.15 (s, 1H) 7.21 (dd, J=9.16, 2.44 Hz, 1H) 7.34 (d, J=2.14 Hz, 1H) 7.40 (d, J=8.24 Hz, 2H) 7.88 (s, 1H) 8.15 (d, J=9.16 Hz, 1H) 8.29 (d, J=8.55 Hz, 2H) 9.25 (s, 1H); LC-MS, MS m/z 774 (M$^+$+H).

Step 9:

To a mixture of the product of step 8, example 37 (0.271 g, 0.320 mmol) and DIEA (0.083 g, 0.641 mmol) in DCM (5 mL) was added 3-chloropropyl isothiocyanate (0.046 g, 0.336 mmol). The mixture was heated to 45° C. for 3 h then left to stand at rt overnight. The reaction mixture was diluted with DCM (50 mL) and washed with 0.1N HCl (3 mL). The aqueous layer was extracted with DCM (25 mL) and the combined organic layer was washed with 10% aqueous Na$_2$CO$_3$ (3 mL), brine, dried over MgSO$_4$ and concentrated to a yellow foam solid. The product was purified by reverse phase preparative HPLC to give Compound 37 as light yellow bis-HCl salt solid. $^1$H NMR (500 MHz, MeOD) δ ppm 1.11 (s, 9H), 1.15 (d, J=1.8 Hz, 1H), 1.22-1.29 (m, 2H), 1.45-1.51 (m, 1H), 1.78-1.87 (m, J=8.9 Hz, 1H), 1.91-1.98 (m, 2H), 2.31 (q, J=8.6 Hz, 1H), 2.37-2.45 (m, 1H), 2.70-2.84 (m, 2H), 2.93-3.01 (m, 1H), 3.98-4.02 (m, J=1.5 Hz, 3H), 4.18 (d, J=11.3 Hz, 1H), 4.28 (s, 1H), 4.34-4.42 (m, 1H), 4.71-4.78 (m, 1H), 5.17 (d, J=10.4 Hz, 1H), 5.35 (d, J=17.1 Hz, 1H), 5.75-5.83 (m, 1H), 6.15 (s, 1H), 7.24 (d, J=9.2 Hz, 1H), 7.37 (s, 1H), 7.42 (d, J=7.9 Hz, 1H), 7.91 (s, 1H), 8.10 (d, J=9.2 Hz, 1H), 8.31 (dd, J=8.9, 1.8 Hz, 2H); LC-MS, MS m/z 873 (M$^+$+H).

Compound 38 Isomers 3-methyl-N-(6-methyl-2-pyridinyl)-L-valyl-(4R)—N-((1R,2S)-1-((cyclopropylsulfonyl)carbamoyl)-2-vinylcyclopropyl)-4-((3-(dimethylamino)-5-methoxy-1-isoquinolinyl)oxy)-L-prolinamide and 3-methyl-N-(6-methyl-2-pyridinyl)-D-valyl-(4R)—N-((1R,2S)-1-((cyclopropylsulfonyl)carbamoyl)-2-vinylcyclopropyl)-4-((3-(dimethylamino)-5-methoxy-1-isoquinolinyl)oxy)-L-prolinamide Example 38

Preparation of Compounds 38A and 38B

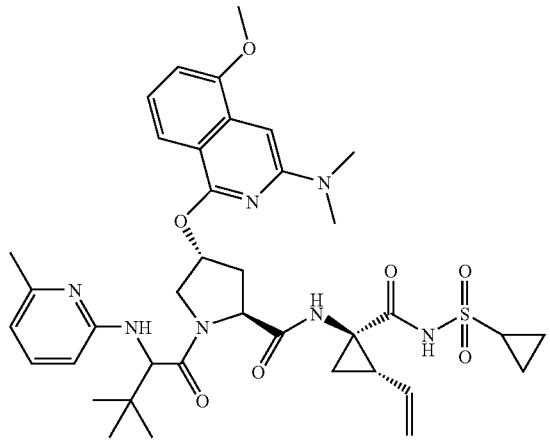

Compound 38A and 38B

Compounds 38A and 38B were prepared by a similar procedure as that described for the preparation of compound 17, but with the following exceptions: In Step 1,3-methoxy-2-methylbenzoic acid was used in place of 4-methoxy-2-methylbenzoic acid. In Step 2, LDA was replaced with KHMDS. And in Step 7, the product of step 1, example 28 was used in place of commercially available 2-(4,6-dimethylpyridin-2-ylamino)-3-methyl butanoic acid. Two isomeric compounds were isolated from Step 7: the first isomer to elute from a preparative HPLC column was compound 38A, and the second isomer to elute from the preparative HPLC column was compound 38B.

Product of Step 1, Example 38: Slightly yellow solid (100% yield). $^1$H NMR (500 MHz, CHLOROFORM-D) δ ppm 2.42 (s, 3H) 2.96 (s, 12H) 3.80 (s, 3H) 6.81 (d, J=7.93 Hz, 1H) 7.11 (t, J=7.93 Hz, 1H) 7.25 (d, J=6.71 Hz, 1H); LC-MS, MS m/z 264 (M$^+$+H).

Product of Step 2, Example 38: Yellow solid (89% yield). $^1$H NMR (500 MHz, CHLOROFORM-D) δ ppm 3.04 (s, 6H) 3.92 (s, 3H) 5.89 (s, 1H) 6.92 (d, J=7.63 Hz, 1H) 7.09 (t, J=7.93 Hz, 1H) 7.82 (d, J=7.93 Hz, 1H) 10.69 (s, 1H); LC-MS, MS m/z 219 (M$^+$+H).

Product of Step 3, Example 38: Yellow solid (95% yield). $^1$H NMR (300 MHz, CHLOROFORM-D) δ ppm 3.12 (s, 6H) 3.93 (s, 3H) 6.77 (d, J=7.32 Hz, 1H) 6.83 (s, 1H) 7.09 (dd, J=8.42, 7.68 Hz, 1H) 7.62 (d, J=8.42 Hz, 1H); LC-MS, MS m/z 237 (M$^+$+H).

Product of Step 4, Example 38: Yellow solid (92% yield). LC-MS, MS m/z 432 (M$^+$+H).

Product of Step 5, Example 38: Yellow/green solid (73% yield). LC-MS, MS m/z 644 (M$^+$+H).

Product of Step 6, Example 38: Yellow solid (95% yield). LC-MS, MS m/z 544 (M$^+$+H).

Compound 38A (Product of Step 7, Example 38): $^1$H NMR (500 MHz, MeOD) δ ppm 1.07-1.14 (m, 2H), 1.15 (s, 9H), 1.27 (dd, J=4.6, 2.7 Hz, 2H), 1.43-1.49 (m, 1H), 1.94 (dd, J=8.1, 5.3 Hz, 1H), 2.25-2.36 (m, 2H), 2.41 (s, 3H), 2.67 (dd, J=13.9, 7.5 Hz, 2H), 2.95-3.02 (m, 2H), 3.16 (s, 6H), 3.18-3.20 (m, 1H), 3.99 (s, 3H), 4.10 (dd, J=12.1, 3.2 Hz, 1H), 4.38 (d, J=11.9 Hz, 1H), 4.50 (s, 1H), 4.69 (dd, J=10.1, 7.3 Hz, 1H), 5.17 (dd, J=10.4, 1.5 Hz, 1H), 5.34 (dd, J=17.1, 1.2 Hz, 1H), 5.73-5.82 (m, 1H), 5.98 (s, 1H), 6.64 (dd, J=9.8, 7.3 Hz, 2H), 6.90 (d, J=6.7 Hz, 1H), 6.95 (t, J=7.9 Hz, 1H), 7.30 (dd, J=9.0, 7.5 Hz, 1H), 7.33 (d, J=7.3 Hz, 1H); LC-MS, MS m/z 748 (M$^+$+H).

Compound 38B (Product of Step 7, Example 38): $^1$H NMR (500 MHz, MeOD) δ ppm 0.98 (s, 9H), 1.05-1.10 (m, 2H), 1.15 (s, 1H), 1.15-1.19 (m, 1H), 1.23-1.28 (m, 1H), 1.40 (dd, J=9.6, 5.0 Hz, 1H), 1.91 (dd, J=8.1, 5.3 Hz, 1H), 2.31 (q, J=8.7 Hz, 1H), 2.40-2.47 (m, 1H), 2.54 (s, 3H), 2.68 (dd, J=13.9, 7.5 Hz, 2H), 2.89-2.95 (m, 2H), 3.15 (s, 6H), 3.18-3.20 (m, 1H), 3.98 (s, 3H), 4.21 (dd, J=12.1, 3.5 Hz, 1H), 4.44 (d, J=12.2 Hz, 1H), 4.65 (s, 1H), 4.66-4.69 (m, 1H), 5.16 (dd, J=10.4, 1.8 Hz, 1H), 5.36 (dd, J=17.2, 1.4 Hz, 1H), 5.74-5.83 (m, 1H), 6.02 (s, 1H), 6.84 (d, J=7.3 Hz, 1H), 6.94 (d, J=7.3 Hz, 1H), 7.04-7.09 (m, 2H), 7.47 (dd, J=8.2, 0.9 Hz, 1H), 7.96 (dd, J=9.2, 7.3 Hz, 1H); LC-MS, MS m/z 748 (M$^+$+H).

Compound 200 Isomers

N-(3-fluorophenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(3-fluorophenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 200

Preparation of Compounds 200A and 200B

Compounds 200A and 200B

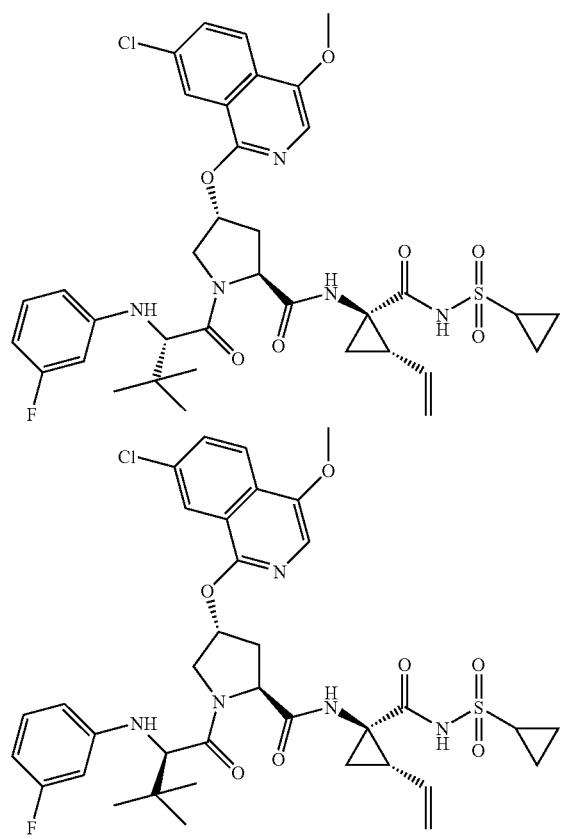

Scheme 1

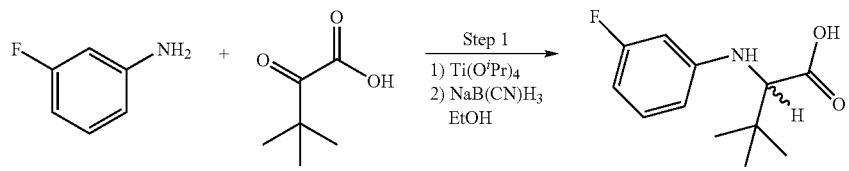

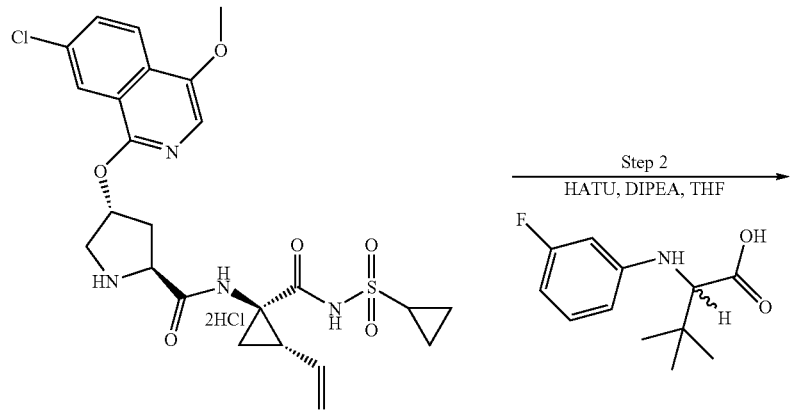

Product of
Example 22, Step 5

→ Step 2
HATU, DIPEA, THF

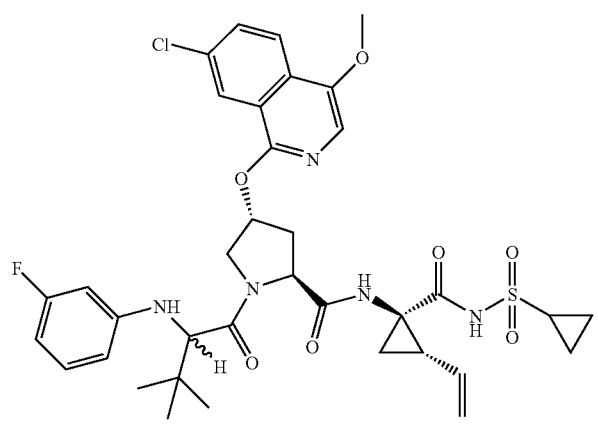

Compounds 200A and 200B
Mixture of isomers

Step 1:

To a mixture of 3-fluoroaniline (160 mg, 1.299 mmol) and 3,3-dimethyl-2-oxobutanoic acid (220 mg, 1.690 mmol) in a 100 mL round bottom flask (RBF) at RT was added tetraisopropoxytitanium (2 ml,) via a pipet. The color of the mixture soon changed into a characteristic canary color. The solution was warmed to 75° C. for about 15 minutes and the color remained the same. The solution was diluted with absolute ethanol (8 ml) at RT, followed by the addition of 1.5× of sodium cyanotrihydroborate (136 mg, 2.16 mmol), and the remaining half after the bubbling and sizzling was over. The color of the solution became lighter. The solution was mixed with 4 mL of water, forming a suspension. The white PPT was removed by centrifuge, organic residue was extracted into ethyl acetate and the organic phase was dried over $Na_2SO_4$. Evaporation to dryness under high vacuum (20-40 micronHg) at RT gave a white foam which was used in the next step without further purification. LC-MS, MS m/z 226 ($M^+$+H).

Step 2:

To the yellow solution of 2-(3-fluorophenylamino)-3,3-dimethylbutanoic acid (0.20 g, 0.888 mmol, from step 1, example 200) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.10 g, 0.187 mmol, from step 5, example 22) in THF (4 mL) at 0° C. was added HATU (0.175 g, 0.46 mmol) followed by diisopropylethyl amine (400 µL, excess). A pale yellow solution was formed after addition of the base. The mixture was stirred at room temperature overnight. The reaction mixture was diluted with ethyl acetate (25 ml), washed with water (pH~6), and brine. The organic was dried over sodium sulfate, filtered and concentrated, and the residue was purified by reverse phase preparative HPLC to give two separate products with identical MS (m/z 226 for [M+H]$^+$) as observed by LCMS. Compound 200A (0.022 g, 16% yield, not optimized) was the first of the two isomers to elute out by reverse phase preparative HPLC. Compound 200B (0.010 g, 7% yield, not optimized) was the second of the two isomers to be eluted by reverse phase preparative HPLC.

Compound 200A $^1$H NMR (400 MHz, CD$_3$OD) δ ppm 1.12 (s, 9H), 1.26-1.31 (m, 2H), 1.39 (dd, J=6.71, 4.27 Hz, 2H), 1.45 (dd, J=9.46, 5.49 Hz, 1H), 1.90 (dd, J=7.93, 5.49 Hz, 1H), 2.19-2.32 (m, 2H), 2.55 (dd, J=13.73, 7.02 Hz, 1H), 2.93-3.03 (m, 1H), 3.69-3.78 (m, 1H), 4.04 (s, 3H), 4.05 (dd, J=8.85, 3.35 Hz, 1H), 4.31 (d, J=12.21 Hz, 1H), 4.55 (dd, J=10.38, 7.02 Hz, 1H), 5.14 (d, J=10.38 Hz, 1H), 5.32 (d, J=17.09 Hz, 1H), 5.71-5.83 (m, 2H), 5.89-5.98 (m, 1H), 6.21 (dd, J=8.09, 1.98 Hz, 1H), 6.25-6.32 (m, 1H), 6.42-6.50 (m, 1H), 7.57 (s, 1H), 7.70 (dd, J=8.85, 2.14 Hz, 1H), 7.83 (d, J=1.83 Hz, 1H), 8.11 (d, J=8.85 Hz, 1H), 9.19 (br. s, 1H); LC-MS, MS m/z 743 [M+H]$^+$.

Compound 200B

LC-MS, MS m/z 743 [M+H]$^+$.

Compound 201 Isomers

N-(3-methoxyphenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide N-(3-methoxyphenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 201

Preparation of Compounds 201A and 201B

Compounds 201A and 201B

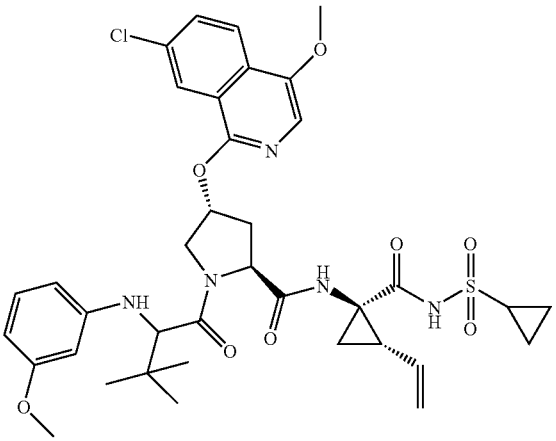

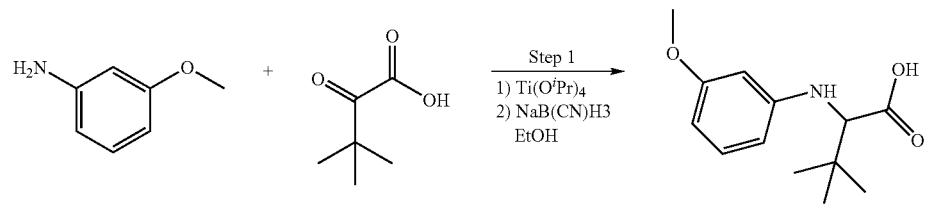

Scheme 1

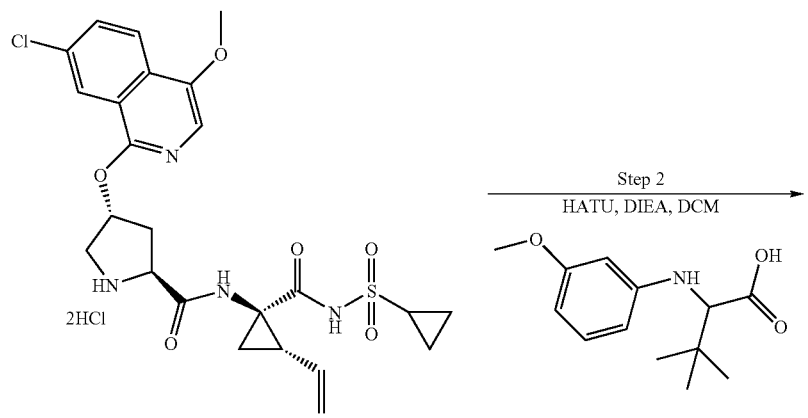

Product of
Example 22, Step 5

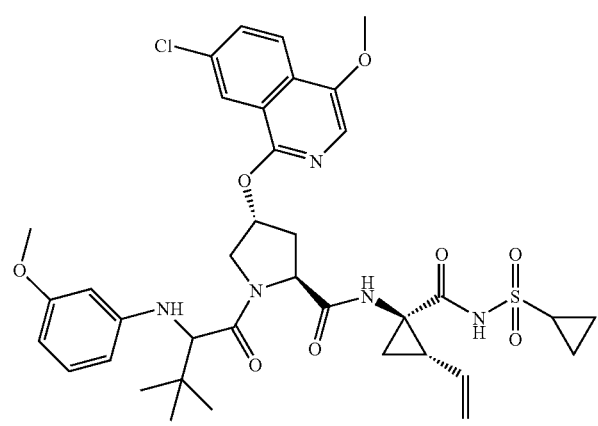

Compounds 201A and 201B
Mixture of isomers

Step 1:

To a mixture of 3-methoxyaniline (160 mg, 1.299 mmol) and 3,3-dimethyl-2-oxobutanoic acid (220 mg, 1.690 mmol) in a 100 mL RBF at RT was added tetraisopropoxytitanium (2 ml,) via a pipet. The color of the mixture soon changed into a characteristic canary color. The solution was warmed to 75° C. for about 15 minutes and the color remained the same. The solution was diluted with absolute ethanol (8 ml) at RT, followed by the addition of 1.5× of sodium cyanotrihydroborate (245 mg, 3.90 mmol), and the remaining half after the bubbling and sizzling was over. The color of the solution became lighter. The solution was mixed with 4 mL of water, forming a suspension, the white PPT was removed by centrifuge. The organic was extracted into ethyl acetate, and the organic phase was dried over $Na_2SO_4$, filtered and evaporated to dryness to give a white foam. This material was carried on to the next step without further purification. LC-MS, MS m/z 238 ($M^+$+H).

Step 2:

To the yellow solution of 2-(3-methoxyphenylamino)-3,3-dimethylbutanoic acid (0.045 g, 0.189 mmol, step 1, example 201) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.101 g, 0.189 mmol, step 5, example 22) in $CH_2Cl_2$ at 0° C. was added HATU (0.144 g, 0.378 mmol) followed by diisopropylethyl amine (0.061 g, 0.473 mmol). A light yellow solution was formed after addition of the base. The mixture was stirred at room temperature overnight. The reaction mixture was diluted with ethyl acetate (25 ml) and then washed with water (pH~6) and brine. The organic was dried over sodium sulfate, concentrated, and the residue was purified by reverse phase preparative HPLC to give two separate products with identical MS m/z as observed by LCMS. Compound 201A (0.045 g, 32% yield) was the first of the two isomers to elute by reverse phase preparative HPLC. Compound 201B (0.024 g, 16.2% yield) was the second of the two isomers to elute by reverse phase preparative HPLC.

Compound 201A $^1$H NMR (400 MHz, $CD_3OD$) δ ppm 1.03-1.14 (m, 11H) 1.21-1.32 (m, 2H) 1.41 (dd, J=9.44, 5.41 Hz, 1H) 1.87 (dd, J=8.06, 5.54 Hz, 1H) 2.16-2.26 (m, 2H) 2.48 (dd, J=13.60, 6.80 Hz, 1H) 2.95 (ddd, J=12.78, 8.12, 4.78 Hz, 1H) 3.95-4.07 (m, 5H) 4.48 (dd, J=10.58, 7.05 Hz, 1H) 5.11 (d, J=10.32 Hz, 1H) 5.29 (d, J=17.12 Hz, 1H) 5.65-5.73 (m, 2H) 5.73-5.79 (m, 1H) 6.15-6.21 (m, 1H) 6.27 (d, J=2.01 Hz, 1H) 6.36-6.42 (m, 1H) 7.50 (s, 1H) 7.68 (d, J=9.06 Hz, 1H) 7.74 (s, 1H) 8.08 (d, J=8.81 Hz, 1H); LC-MS, MS m/z 753 ($M^+$+H).

Compound 201B

LC-MS, MS m/z 753 ($M^+$+H).

Compound 202 Isomers 3-methyl-N-(3-(methylcarbamoyl)phenyl)-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and 3-methyl-N-(3-(methylcarbamoyl)phenyl)-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 202

Preparation of Compounds 202A and 202B

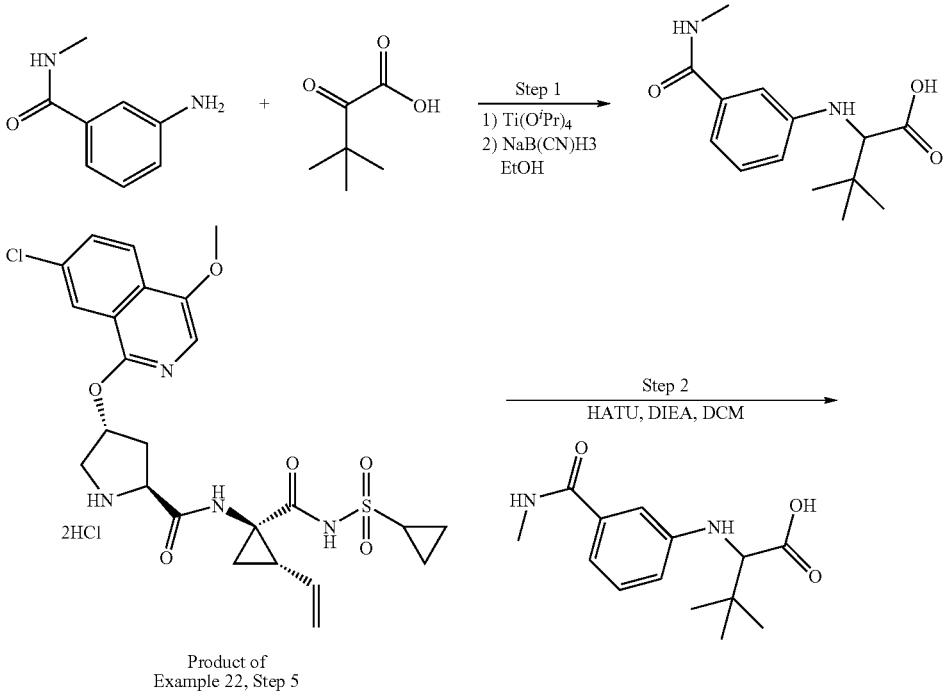

Compounds 202A and 202B

Scheme 1

Product of Example 22, Step 5

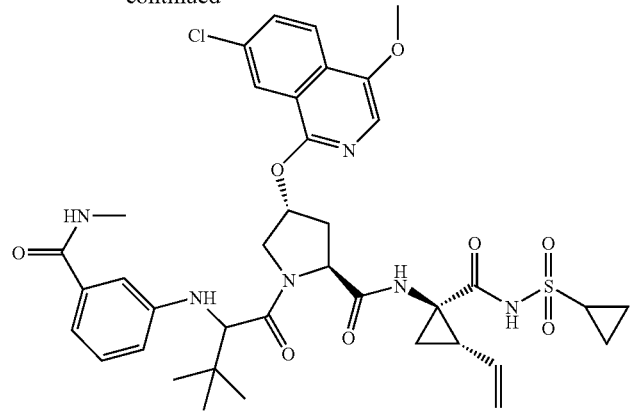

Compounds 202A and 202B
Mixture of isomers

Step 1:

To a mixture of 3-amino-N-methylbenzamide (230 mg, 1.532 mmol) and 3,3-dimethyl-2-oxobutanoic acid (199 mg, 1.532 mmol) in a 100 mL RBF at RT was added tetraisopropoxytitanium (2 ml,) via a pipet, The color of the mixture soon changed into a characteristic canary color. The solution was warmed to 75° C. for about 15 minutes and the color remained the same. The solution was diluted with absolute ethanol (8 ml) at RT, followed by the addition of 1.5× of sodium cyanotrihydroborate (245 mg, 3.90 mmol), and the remaining half after the bubbling and sizzling was over. The color of the solution became lighter. The solution was mixed with 4 mL of water, forming a suspension, the white PPT was removed by centrifuge, organic was extracted into ethyl acetate, dried over Na$_2$SO$_4$. Evaporated into dryness, white foam was obtained and used in the next step without further purification. LC-MS, MS m/z 265 (M$^+$+H).

Step 2:

To the yellow solution of (S)-3,3-dimethyl-2-(3-(methylcarbamoyl)phenylamino)butanoic acid (0.050 g, 0.189 mmol, step 1, example 202) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.101 g, 0.189 mmol, step 5, example 22) in CH$_2$Cl$_2$ at 0° C. was added HATU (0.144 g, 0.378 mmol) followed by diisopropylethyl amine (0.061 g, 0.473 mmol). A light yellow solution was formed after addition of the base. The mixture was stirred at room temperature overnight. The reaction mixture was diluted with ethyl acetate (25 ml) and was washed with water (pH~6) and brine. The organic was dried over sodium sulfate, then concentrated, and the residue was purified by reverse phase preparative HPLC to give two separate products with identical MS m/z as observed by LCMS. Compound 202A (0.061 g, 41% yield) was the first of the two isomers to elute by reverse phase preparative HPLC. Compound 202B (0.015 g, 10.2% yield) was the second of the two isomers to elute by reverse phase preparative HPLC.

Compound 202A $^1$H NMR (400 MHz, CD$_3$OD) δ ppm 1.02-1.13 (m, 11H) 1.20-1.30 (m, 2H) 1.42 (dd, J=9.44, 5.41 Hz, 1H) 1.87 (dd, J=8.06, 5.54 Hz, 1H) 2.14-2.25 (m, 2H) 2.47 (dd, J=13.72, 6.92 Hz, 1H) 2.77 (s, 3H) 2.95 (ddd, J=12.65, 7.99, 4.78 Hz, 1H) 3.94 (dd, J=12.21, 3.15 Hz, 1H) 3.98 (s, 4H) 4.22 (d, J=12.09 Hz, 1H) 4.51 (dd, J=10.32, 7.05 Hz, 1H) 5.11 (d, J=10.32 Hz, 1H) 5.28 (d, J=17.12 Hz, 1H) 5.69-5.79 (m, 2H) 6.63-6.73 (m, 3H) 7.01 (s, 1H) 7.48 (s, 1H) 7.64 (dd, J=8.94, 2.14 Hz, 1H) 7.71 (d, J=2.01 Hz, 1H) 8.05 (d, J=8.81 Hz, 1H); LC-MS, MS m/z 781 (M$^+$+H).

Compound 202B

LC-MS, MS m/z 781 (M$^+$+H).

Compound 203 Isomers

N-(3-cyanophenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(3-cyanophenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 203

Preparation of Compounds 203A and 203B

Compounds 203A and 203B

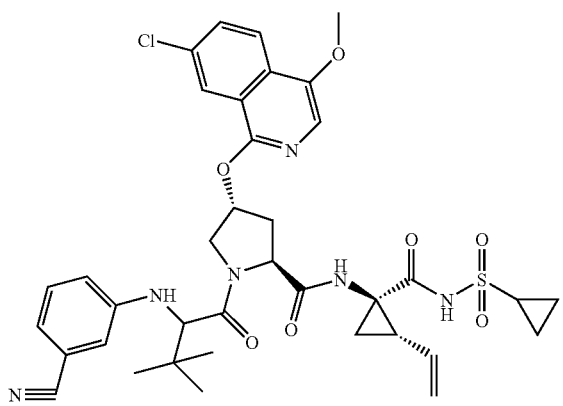

Scheme 1

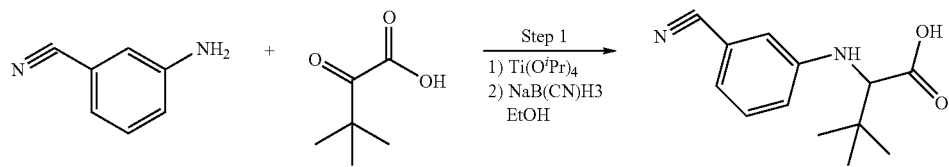

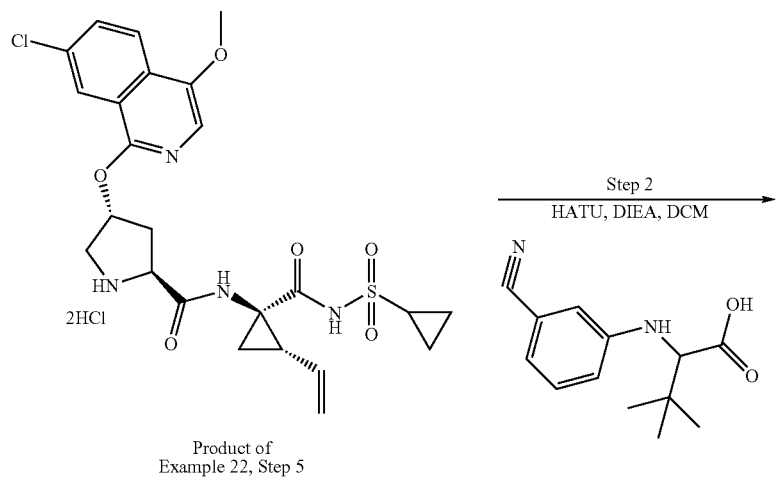

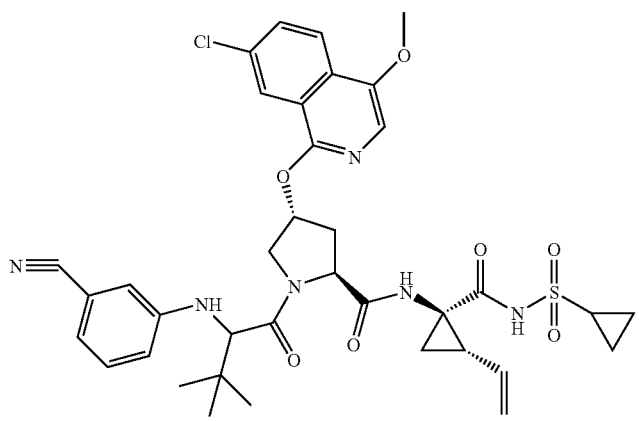

Compounds 203A and 203B
Mixture of isomers

Step 1:

To a mixture of 3-aminobenzonitrile (180 mg, 1.524 mmol) and 3,3-dimethyl-2-oxobutanoic acid (198 mg, 1.524 mmol) in a 100 mL RBF at RT was added tetraisopropoxytitanium (2 ml,) via a pipet. The color of the mixture soon changed into a characteristic canary color. The solution was warmed to 75° C. for about 15 minutes and the color remained the same. The solution was diluted with absolute ethanol (8 ml) at RT, followed by the addition of 1.5× of sodium cyanotrihydroborate (245 mg, 3.90 mmol), and the remaining half after the bubbling and sizzling was over. The color of the solution became lighter. The solution was mixed with 4 mL of water, forming a suspension, the white PPT was removed by centrifuge, organic was extracted into ethyl acetate, and the organic phase was dried over $Na_2SO_4$, filtered, and evaporated into dryness. A yellow oil was obtained and used in the next step without further purification. LC-MS, MS m/z 233 ($M^+$+H).

Step 2:

To the yellow solution (s)-2-(3-cyanophenylamino)-3,3-dimethylbutanoic acid (0.044 g, 0.189 mmol, step 1, example 203) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.101 g, 0.189 mmol, step 5, example 22) in CH$_2$Cl$_2$ at 0° C. was added HATU (0.144 g, 0.378 mmol) followed by diisopropylethyl amine (0.061 g, 0.473 mmol). A light yellow solution was formed after addition of the base. The mixture was stirred at room temperature overnight. The reaction mixture was diluted with ethyl acetate (25 ml) and then washed with water (pH~6) and brine. The organic was dried over sodium sulfate, filtered, concentrated, and the residue was purified by reverse phase preparative HPLC to give two separate products with identical MS m/z as observed by LCMS. Compound 203A (0.025 g, 17.7% yield) was the first of the two isomers to elute by reverse phase preparative HPLC. Compound 203B (0.014 g, 10.0% yield) was the second of the two isomers to elute by reverse phase preparative HPLC.

Compound 203A $^1$H NMR (400 MHz, CD$_3$OD) δ ppm 1.07 (s, 11H) 1.19-1.31 (m, 2H) 1.41 (dd, J=9.44, 5.41 Hz, 1H) 1.87 (dd, J=8.06, 5.54 Hz, 1H) 2.17-2.26 (m, 2H) 2.51 (dd, J=13.60, 6.80 Hz, 1H) 2.88-2.98 (m, 1H) 3.95-4.02 (m, 4H) 4.02-4.05 (S, 1H) 4.21 (d, J=12.09 Hz, 1H) 4.53 (dd, J=10.32, 7.05 Hz, 1H) 5.11 (d, J=10.32 Hz, 1H) 5.28 (d, J=17.12 Hz, 1H) 5.68-5.78 (m, 2H) 6.46 (d, J=7.30 Hz, 1H) 6.57 (t, J=7.93 Hz, 1H) 6.63-6.68 (m, 1H) 6.86 (s, 1H) 7.50 (s, 1 H) 7.64 (dd, J=8.94, 1.38 Hz, 1H) 7.69 (s, 1H) 8.05 (d, J=8.81 Hz, 1H); LC-MS, MS m/z 749 (M$^+$+H).

Compound 203B

LC-MS, MS m/z 749 (M$^+$+H).

Compound 204 Isomers

N-(4-(tert-butoxycarbonyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide N-(4-(tert-butoxycarbonyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 204

Preparation of Compounds 204A and 204B

Compounds 204A and 204B

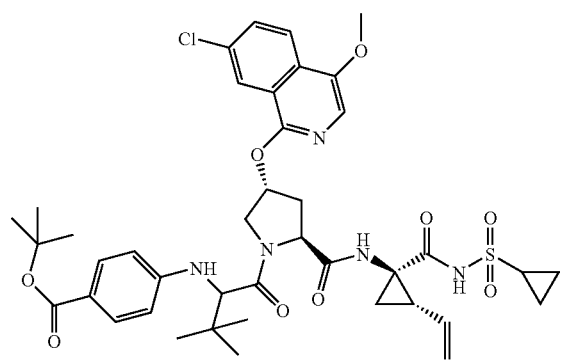

Scheme 1

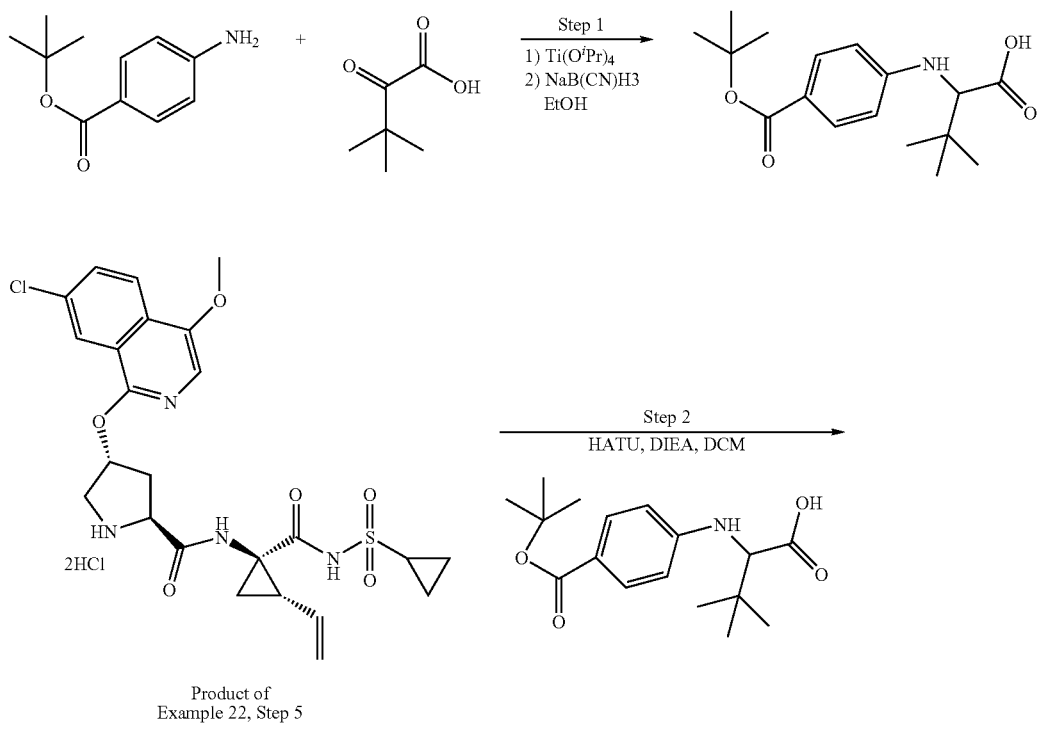

Product of Example 22, Step 5

-continued

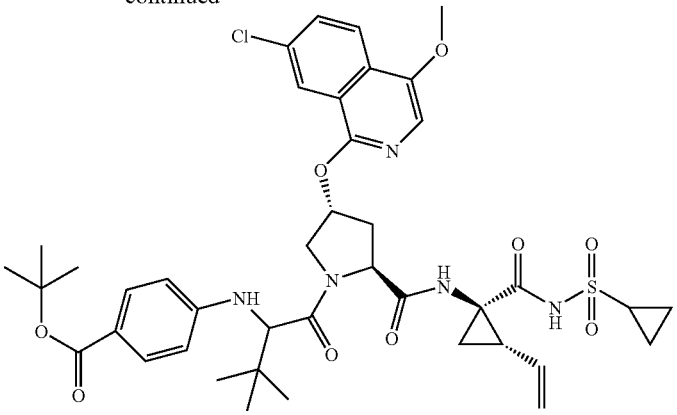

Compounds 204A and 204B
Mixture of isomers

Step 1:

To a mixture of tert-butyl 4-aminobenzoate (230 mg, 1.190 mmol) and 3,3-dimethyl-2-oxobutanoic acid (155 mg, 1.190 mmol) in a 100 mL RBF at RT was added tetraisopropoxytitanium (2 ml,) via a pipet. The color of the mixture soon changed into a characteristic canary color. The solution was warmed to 75° C. for about 15 minutes and the color remained the same. The solution was diluted with absolute ethanol (8 ml) at RT, followed by the addition of 1.5x of sodium cyanotrihydroborate (245 mg, 3.90 mmol), and the remaining half after the bubbling and sizzling was over. The color of the solution became lighter. The solution was mixed with 4 mL of water, forming a suspension, the white PPT was removed by centrifuge. The organic was extracted into ethyl acetate, and the organic phase was dried over $Na_2SO_4$, filtered and evaporated to dryness. A yellow oil was obtained and used in the next step without further purification. LC-MS, MS m/z 308 ($M^+$+H).

Step 2:

To the yellow solution (S)-2-(4-(tert-butoxycarbonyl)phenylamino)-3,3-dimethylbutanoic acid (0.058 g, 0.189 mmol, step 1, example 204) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.101 g, 0.189 mmol, step 5, example 22) in $CH_2Cl_2$ at 0° C. was added HATU (0.144 g, 0.378 mmol) followed by diisopropylethyl amine (0.061 g, 0.473 mmol). A light yellow solution was formed after addition of the base. The mixture was stirred at room temperature overnight. The reaction mixture was diluted with ethyl acetate (25 ml), washed with water (pH~6) and brine. The organic was dried over sodium sulfate, concentrated, and the residue was purified by reverse phase preparative HPLC to give two separate products with identical MS m/z as observed by LCMS. Compound 204A (0.024 g, 15.4% yield) was the first of the two isomers to elute by reverse phase preparative HPLC. Compound 204B (0.020 g, 12.8% yield) was the second of the two isomers to elute by reverse phase preparative HPLC.

Compound 204A $^1$H NMR (400 MHz, $CD_3OD$) δ ppm 1.02-1.11 (m, 11H) 1.19-1.30 (m, 2H) 1.41 (dd, J=9.19, 5.41 Hz, 1H) 1.46-1.54 (S, 9H) 1.86 (dd, J=8.06, 5.54 Hz, 1H) 2.17-2.27 (m, 2H) 2.54 (dd, J=13.60, 6.80 Hz, 1H) 2.95 (ddd, J=12.65, 7.99, 4.78 Hz, 1H) 3.96-4.04 (m, 4H) 4.12 (s, 1H) 4.37 (d, J=12.09, 1H) 4.55 (dd, J=10.07, 7.30 Hz, 1H) 5.10 (d, J=10.58 Hz, 1H) 5.28 (d, J=17.58 Hz, 1H) 5.75 (m, 1H) 5.78 (S, 1H) 6.42 (d, J=8.81 Hz, 2H) 7.28 (d, J=8.56 Hz, 2H) 7.52 (s, 1H) 7.59 (dd, J=8.94, 2.14 Hz, 1H) 7.75 (d, J=1.76 Hz, 1H) 8.03 (d, J=8.81 Hz, 1H); LC-MS, MS m/z 824 ($M^+$+H).

Compound 204B

LC-MS, MS m/z 824 ($M^+$+H).

Compound 205 Isomers

N-(4-cyanophenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(4-cyanophenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 205

Preparation of Compounds 205A and 205B

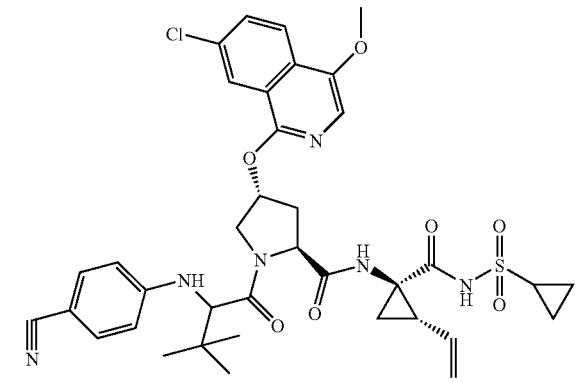

Compounds 205A and 205B

Scheme 1
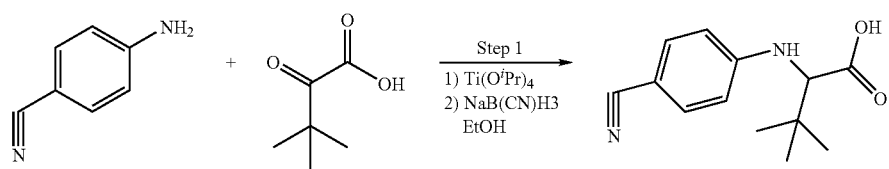
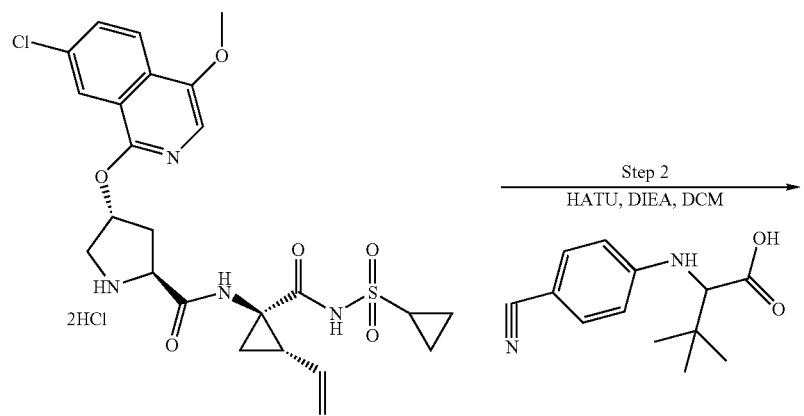
Product of
Example 22, Step 5
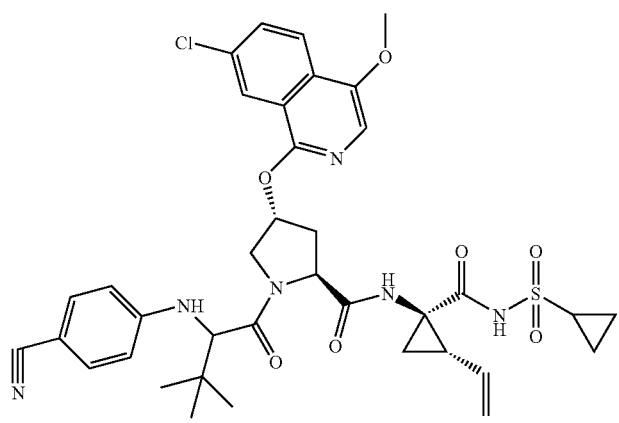
Compounds 205A and 205B
Mixture of isomers Step 1:

To a mixture of 4-aminobenzonitrile (180 mg, 1.524 mmol) and 3,3-dimethyl-2-oxobutanoic acid (198 mg, 1.524 mmol) in a 100 mL RBF at RT was added tetraisopropoxytitanium (2 ml,) via a pipet. The color of the mixture soon changed into a characteristic canary color. The solution was warmed to 75° C. for about 15 minutes and the color remained the same. The solution was diluted with absolute ethanol (8 ml) at RT, followed by the addition of 1.5× of sodium cyanotrihydroborate (245 mg, 3.90 mmol), and the remaining half after the bubbling and sizzling was over. The color of the solution became lighter. The solution was mixed with 4 mL of water, forming a suspension, the white PPT was removed by centrifuge. The organic was extracted into ethyl acetate, and the organic phase was dried over $Na_2SO_4$, filtered, and evaporated into dryness. A yellow oil was obtained and was used in the next step without further purification. LC-MS, MS m/z 233 ($M^+$+H).

Step 2:

To the yellow solution of 2-(4-cyanophenylamino)-3,3-dimethylbutanoic acid (0.044 g, 0.189 mmol, step 1, example 205) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.101 g, 0.189 mmol, step 5, example 22) in $CH_2Cl_2$ at 0° C. was added HATU (0.144 g, 0.378 mmol) followed by diisopropylethyl amine (0.061 g, 0.473 mmol). A light yellow solution was formed after addition of the base. The mixture was stirred at room temperature overnight. The reaction mixture was diluted with ethyl acetate (25 ml), washed with water (pH~6) and brine. The organic was dried over sodium sulfate, filtered, and concentrated, and the residue was purified by reverse phase preparative HPLC to give two separate products with identical MS m/z as observed by LCMS. Compound 205A (0.052 g, 37% yield) was the first of the two isomers to elute by reverse phase preparative HPLC. Compound 205B (0.013 g, 9% yield) was the second of the two isomers to elute by reverse phase preparative HPLC.

Compound 205A $^1$H NMR (400 MHz, $CD_3OD$) δ ppm 0.99-1.09 (m, 11H) 1.17-1.26 (m, 2H) 1.35-1.45 (m, 1H) 1.87 (dd, J=8.06, 5.29 Hz, 1H) 2.17-2.28 (m, 2H) 2.56 (dd, J=13.85, 7.05 Hz, 1H) 2.94 (ddd, J=12.84, 8.06, 4.78 Hz, 1H) 3.95-4.04 (m, 4H) 4.08 (s, 1H) 4.28-4.37 (m, 1H) 4.56 (dd, J=10.32, 7.05 Hz, 1H) 5.05-5.13 (m, 1H) 5.28 (d, J=17.12 Hz, 1H) 5.66-5.75 (m, 1H) 5.78 (s, 1H) 6.44 (d, J=8.81 Hz, 2H) 6.80 (d, J=8.56 Hz, 2H) 7.46-7.54 (s, 1H) 7.63-7.73 (m, 1H) 7.74-7.81 (s, 1H) 8.02-8.10 (m, 1H); LC-MS, MS m/z 749 ($M^+$+H).

Compound 205B

LC-MS, MS m/z 749 ($M^+$+H).

Compound 206 Isomers

N-(3-(tert-butylsulfamoyl)phenyl)-3-methyl-L-valyl-(4R)-4-((7-chloro-4-methoxy-1-isoquinolinyl)oxy)-N-((1R,2S)-1-(((cyclopropylsulfonyl)carbamoyl)-2-vinylcyclopropyl)-L-prolinamide and N-(3-(tert-butylsulfamoyl)phenyl)-3-methyl-D-valyl-(4R)-4-((7-chloro-4-methoxy-1-isoquinolinyl)oxy)-N-((1R,2S)-1-(((cyclopropylsulfonyl)carbamoyl)-2-vinylcyclopropyl)-L-prolinamide Example 206

Preparation of Compounds 206A and 206B

Compounds 206A and 206B

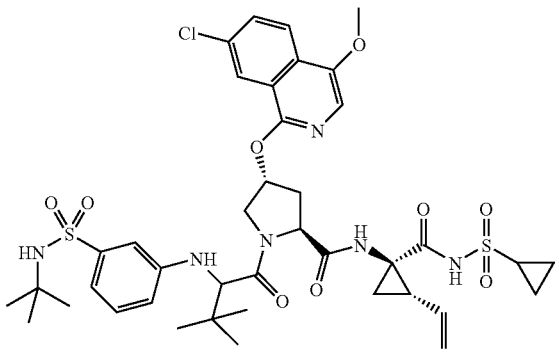

Scheme 1

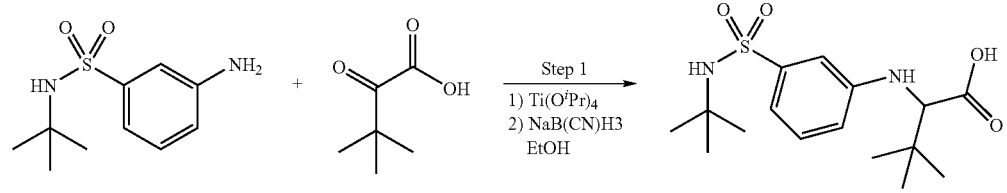

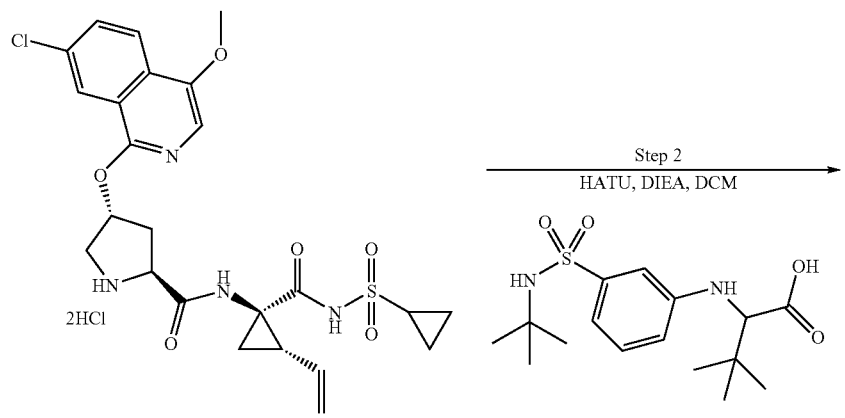

Product of
Example 22, Step 5

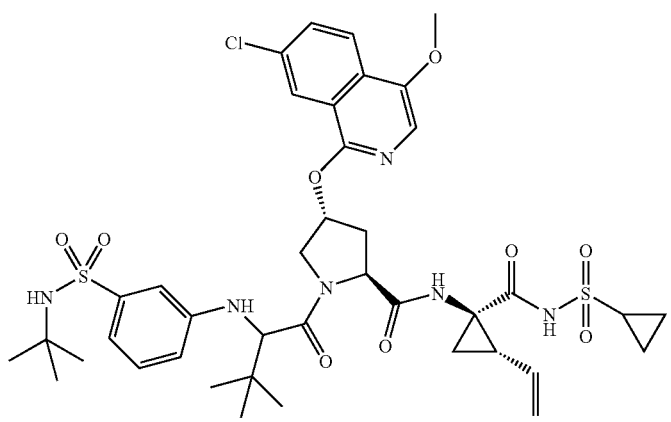

Compounds 206A and 206B
Mixture of isomers

Step 1:

To a mixture of 3-amino-N-tert-butylbenzenesulfonamide (180 mg, 0.788 mmol) and 3,3-dimethyl-2-oxobutanoic acid (308 mg, 2.365 mmol) in a 100 mL RBF at RT was added tetraisopropoxytitanium (2 ml,) via a pipet. The color of the mixture soon changed into a characteristic canary color. The solution was warmed to 75° C. for about 15 minutes and the color remained the same. The solution was diluted with absolute ethanol (8 ml) at RT, followed by the addition of 1.5× of sodium cyanotrihydroborate (245 mg, 3.90 mmol), and the remaining half after the bubbling and sizzling was over. The color of the solution became lighter. The solution was mixed

187 with 4 mL of water, forming a suspension, the white PPT was removed by centrifuge. The organic was extracted into ethyl acetate, and the organic phase was dried over $Na_2SO_4$, filtered, and evaporated to dryness. A yellow oil was obtained and used in the next step without further purification. LC-MS, MS m/z 343 ($M^++H$).

Step 2:

To the yellow solution of 2-(3-(N-tert-butylsulfamoyl)phenylamino)-3,3-dimethylbutanoic acid (0.065 g, 0.189 mmol step 1, example 206) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.101 g, 0.189 mmol, step 5, example 22) in $CH_2Cl_2$ at 0° C. was added HATU (0.144 g, 0.378 mmol) followed by diisopropylethyl amine (0.061 g, 0.473 mmol). A light yellow solution was formed after addition of the base. The mixture was stirred at room temperature overnight. The reaction mixture was diluted with ethyl acetate (25 ml) and was washed with water (pH~6) and brine. The organic was dried over sodium sulfate, filtered, concentrated, and the residue was purified by reverse phase preparative HPLC to give two separate products with identical MS m/z as observed by LCMS. Compound 206A (0.025 g, 15.4% yield) was the first of the two isomers to elute by reverse phase preparative HPLC. Compound 206B (0.013 g, 8% yield) was the second of the two isomers to elute by reverse phase preparative HPLC.

188

Compound 206A $^1H$ NMR (400 MHz, $CD_3OD$) δ ppm 0.97-1.06 (m, 9H) 1.06-1.18 (m, 11H) 1.18-1.29 (m, 2H) 1.36-1.46 (m, 1H) 1.86 (dd, J=8.06, 5.54 Hz, 1H) 2.18-2.29 (m, 2H) 2.55 (m, 1H) 2.95 (ddd, J=12.84, 8.06, 4.78 Hz, 1H) 3.95-4.01 (s, 3H) 4.02-4.12 (m, 2H) 4.26 (d, J=12.09 Hz, 1H) 4.51 (dd, J=10.07, 7.05 Hz, 1H) 5.10 (dd, J=10.32, 1.51 Hz, 1H) 5.24-5.32 (m, 1H) 5.73 (m, 2H) 6.52 (m, 1H) 6.62 (m, 1H) 6.86 (m, 1H) 7.15 (d, J=2.01 Hz, 1H) 7.50-7.56 (s, 1 H) 7.62-7.70 (m, 1H) 7.83 (s, 1H) 8.01-8.09 (m, 1H); LC-MS, MS m/z 859 ($M^++H$).

Compound 206B

LC-MS, MS m/z 859 ($M^++H$).

Compound 207 Isomers 3-methyl-N-(3-sulfamoylphenyl)-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and 3-methyl-N-(3-sulfamoylphenyl)-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 207

Preparation of Compounds 207A and 207B

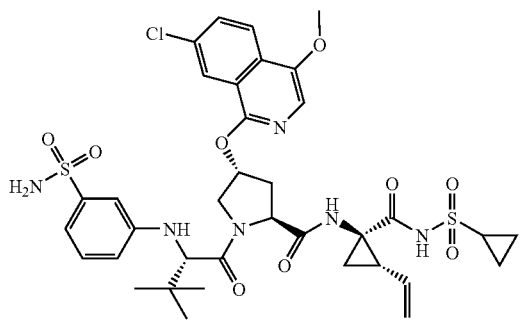 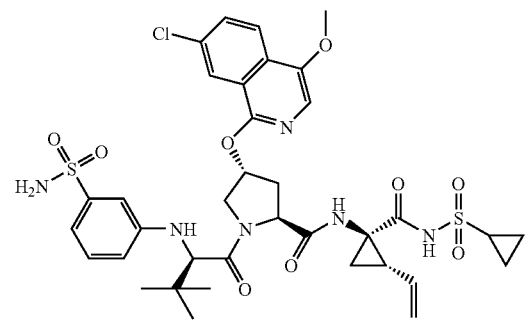

Compounds 207A and 207B

-continued

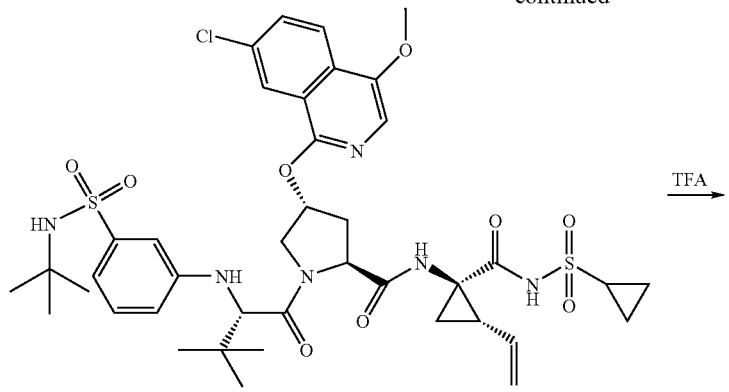

↓ TFA

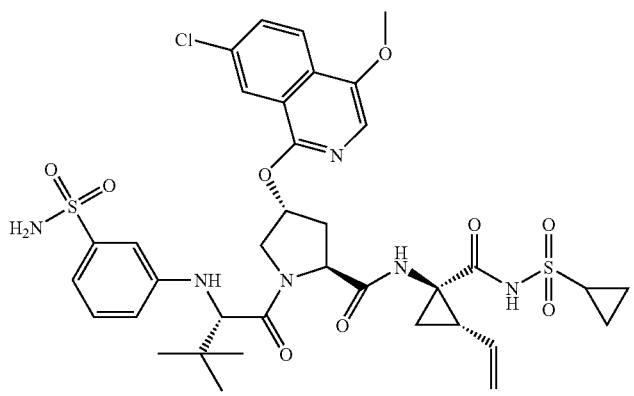

(2S,4R)-1-((S)-2-(3-(N-tert-butylsulfamoyl)phenylamino)-3,3-dimethylbutanoyl)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (compound 206A) was dissolved in 1 ml of 2,2,2-trifluoroacetic acid at 25° C. The mixture was stirred overnight. The TFA was removed and the residue was purified by preparative HPLC. Compound 207A was thus obtained as a white powder (0.012 g, 64% yield). $^1$H NMR (400 MHz, CD$_3$OD) δ ppm 1.05-1.14 (m, 11H) 1.19-1.29 (m, 2H) 1.41 (dd, J=9.44, 5.41 Hz, 1H) 1.87 (dd, J=8.18, 5.41 Hz, 1H) 2.17-2.26 (m, 2H) 2.52 (dd, J=13.85, 7.05 Hz, 1H) 2.95 (ddd, J=12.78, 8.12, 4.78 Hz, 1H) 3.96-4.02 (s, 3H) 4.02-4.10 (m, 2H) 4.30 (d, J=12.09 Hz, 1H) 4.52 (dd, J=10.07, 7.05 Hz, 1H) 5.11 (dd, J=10.32, 1.51 Hz, 1H) 5.24-5.32 (m, 1H) 5.69-5.79 (m, 2H) 6.49-6.55 (m, 1H) 6.60 (t, J=7.81 Hz, 1H) 6.87 (d, J=7.55 Hz, 1H) 7.16 (s, 1H) 7.51-7.55 (s, 1H) 7.67 (dd, J=8.94, 2.14 Hz, 1H) 7.85 (d, J=2.01 Hz, 1H) 8.07 (d, J=8.81 Hz, 1H); LC-MS, MS m/z 803 (M$^+$+H).

Compound 207B was made from compound 206B by the same procedure as was used for the preparation of compound 207A. LC-MS, MS m/z 803 (M$^+$+H).

Compound 208 Isomers

N-(2,3-difluorophenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(2,3-difluorophenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 208

Preparation of Compounds 208A and 208B

Compounds 208A and 208B

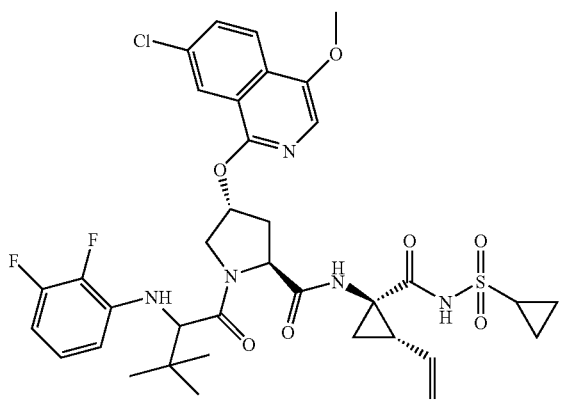

Scheme 1
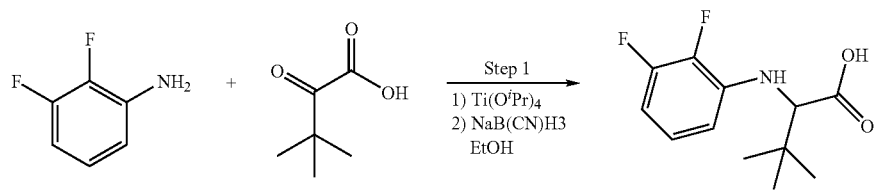
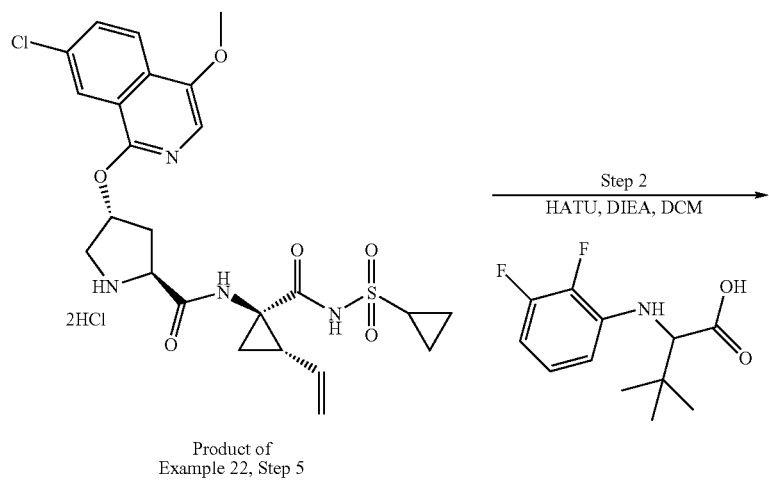
Product of
Example 22, Step 5
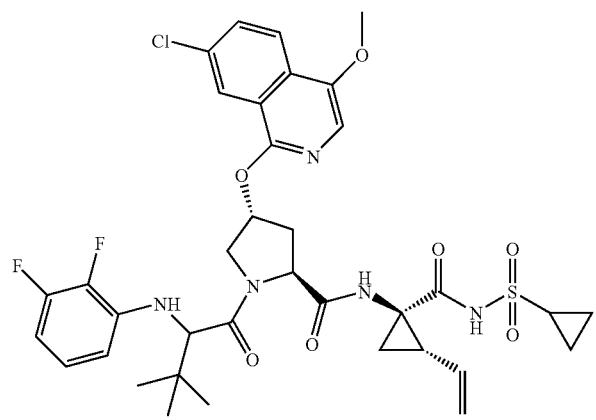
Compounds 208A and 208B
Mixture of isomers Step 1:

To a mixture of 2,3-difluoroaniline (180 mg, 1.394 mmol) and 3,3-dimethyl-2-oxobutanoic acid (500 mg, 3.84 mmol) in a 100 ml RBF at RT was added tetraisopropoxytitanium (2 ml,) via a pipet. The color of the mixture soon changed into a characteristic canary color. The solution was warmed to 75° C. for about 15 minutes and the color remained the same. The solution was diluted with absolute ethanol (8 ml) at RT, followed by the addition of 1.5× of sodium cyanotrihydroborate (245 mg, 3.90 mmol), and the remaining half after the bubbling and sizzling was over. The color of the solution became lighter. The solution was mixed with 4 mL of water, forming a suspension, the white PPT was removed by centrifuge. The organic was extracted into ethyl acetate, and the organic phase was dried over $Na_2SO_4$, filtered and evaporated into dryness. A yellow oil was obtained and was used in the next step without further purification. LC-MS, MS m/z 244 ($M^+$+H).

Step 2:

To the yellow solution of 2-(2,3-difluorophenylamino)-3,3-dimethylbutanoic acid (0.046 g, 0.189 mmol step 1, example 208) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.101 g, 0.189 mmol, step 5, example 22) in $CH_2Cl_2$ at 0° C. was added hatu (0.144 g, 0.378 mmol) followed by diisopropylethyl amine (0.061 g, 0.473 mmol). A light yellow solution was formed after addition of the base. The mixture was stirred at room temperature overnight. The reaction mixture was diluted with ethyl acetate (25 ml), and the organic was washed with water (pH~6) and brine. The organic was dried over sodium sulfate, filtered, concentrated, and purified by reverse phase preparative HPLC to give two separate products with identical MS m/z as observed by LCMS. Compound 208A (0.026 g, 18.4% yield) was the first of the two isomers to elute by reverse phase preparative HPLC. Compound 208B (0.012 g, 9% yield) was the second of the two isomers to elute by reverse phase preparative HPLC.

Compound 208A $^1$H NMR (400 MHz, $CD_3OD$) δ ppm 1.03-1.12 (m, 11H) 1.21-1.26 (m, 2H) 1.41 (dd, J=9.44, 5.41 Hz, 1H) 1.86 (dd, J=8.06, 5.54 Hz, 1H) 2.17-2.28 (m, 2H) 2.53 (dd, J=13.60, 7.05 Hz, 1H) 2.94 (ddd, J=12.72, 8.06, 4.66 Hz, 1H) 3.96-4.02 (m, 4H) 4.02-4.07 (s, 1H) 4.27 (d, J=12.09 Hz, 1H) 4.53 (dd, J=10.45, 7.18 Hz, 1H) 5.10 (d, J=10.32 Hz, 1H) 5.28 (d, J=17.12 Hz, 1H) 5.68-5.75 (m, 1H) 5.77 (s, 1H) 6.02-6.10 (m, 2H) 6.21-6.28 (m, 1H) 7.55 (s, 1H) 7.68 (dd, J=8.81, 2.01 Hz, 1H) 7.76 (d, J=2.01 Hz, 1H) 8.09 (d, J=8.81 Hz, 1H);

LC-MS, MS m/z 760 ($M^+$+H).

Compound 208B

LC-MS, MS m/z 760 ($M^+$+H).

Compound 209 Isomers

N-(4-carboxyphenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide N-(4-carboxyphenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 209

Preparation of Compounds 209A and 209B

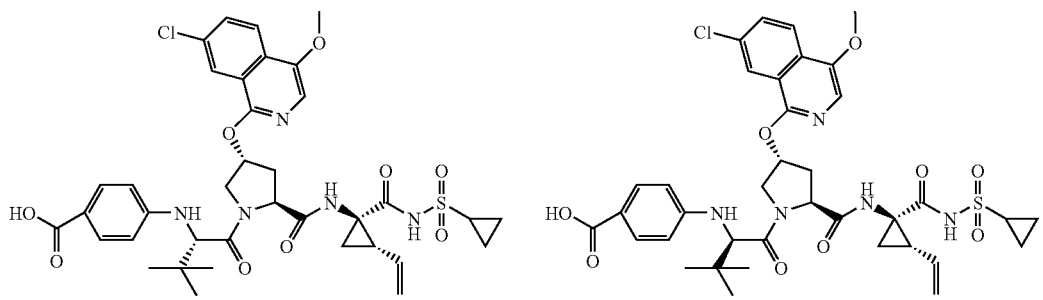

Compounds 209A and 209B

-continued

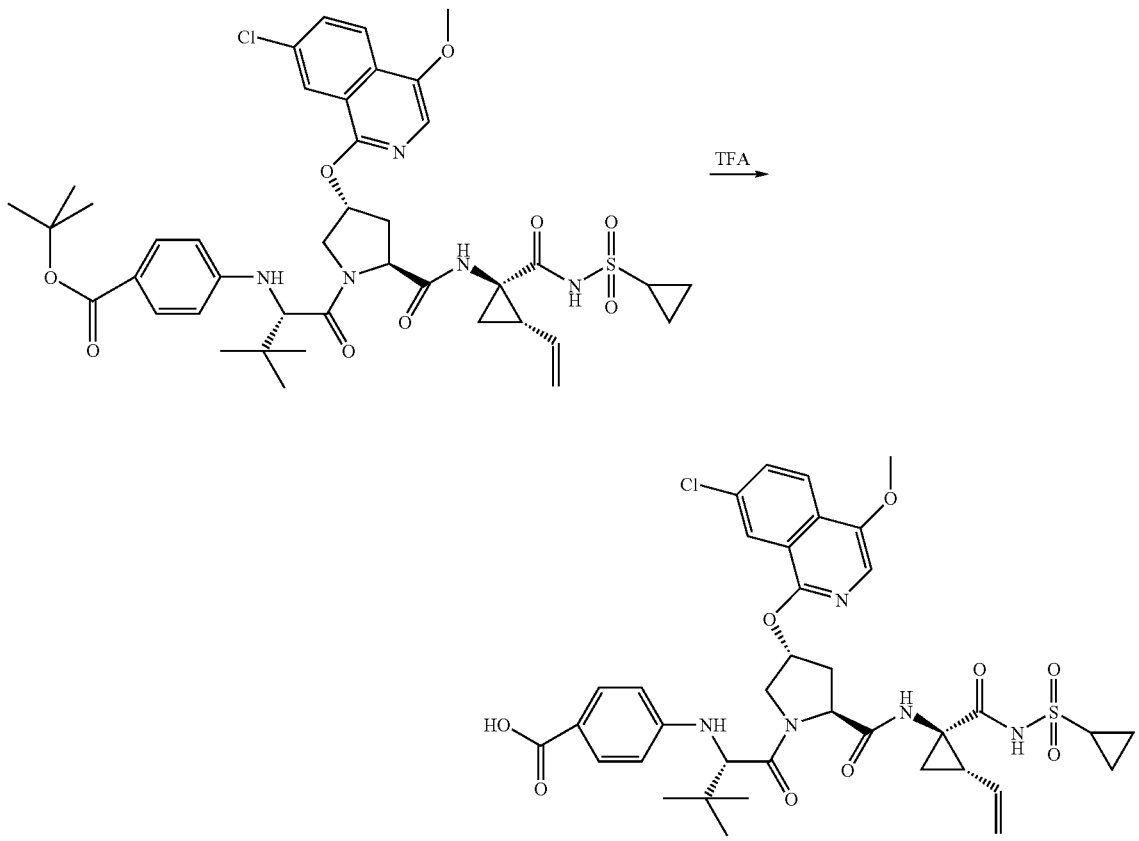

tert-butyl 4-((S)-1-((2S,4R)-4-(7-chloro-4-methoxyisoquinolin-1-yloxy)-2-((1R,2S)-1-(cyclopropylsulfonylcarbamoyl)-2-vinylcyclopropylcarbamoyl)pyrrolidin-1-yl)-3,3-dimethyl-1-oxobutan-2-ylamino)benzoate (20 mg, 0.024 mmol, compound 204A) was dissolved in CH$_2$Cl$_2$ (2 ml) at 25° C. TFA (0.019 ml, 0.243 mmol) was added dropwise. The mixture was stirred overnight. The TFA was removed and the residue was purified by preparative HPLC. Compound 209A was thus obtained as a white powder (0.018 g, 95% yield). $^1$H NMR (400 MHz, CD$_3$OD) δ ppm 1.05-1.14 (m, 11H) 1.18-1.29 (m, 2H) 1.42 (dd, J=9.32, 5.29 Hz, 1H) 1.87 (dd, J=8.06, 5.54 Hz, 1H) 2.19-2.28 (m, 2H) 2.55 (dd, J=13.72, 7.18 Hz, 1H) 2.95 (ddd, J=12.78, 8.12, 4.78 Hz, 1H) 3.96-4.03 (m, 4H) 4.06-4.10 (s, 1H) 4.36 (d, J=12.34 Hz, 1H) 4.58 (dd, J=10.32, 7.05 Hz, 1H) 5.07-5.15 (m, 1H) 5.29 (d, J=17.12 Hz, 1H) 5.68-5.78 (m, 2H) 6.38 (d, J=8.81 Hz, 2H) 7.22 (d, J=8.81 Hz, 2H) 7.51 (s, 1H) 7.61 (dd, J=8.81, 2.27 Hz, 1H) 7.79 (d, J=2.01 Hz, 1H) 8.04 (d, J=9.06 Hz, 1H); LC-MS, MS m/z 768 (M$^+$+H).

Compound 209B was made from compound 204B by same procedure as was used for the preparation of compound 209A. LC-MS, MS m/z 768 (M$^+$+H).

Compound 210 Isomers

N-(3-(tert-butoxycarbonyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide N-(3-(tert-butoxycarbonyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 210

Preparation of Compounds 210A and 210B

Compounds 210A and 210B

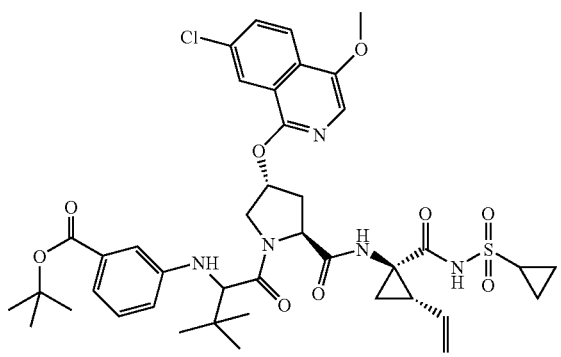

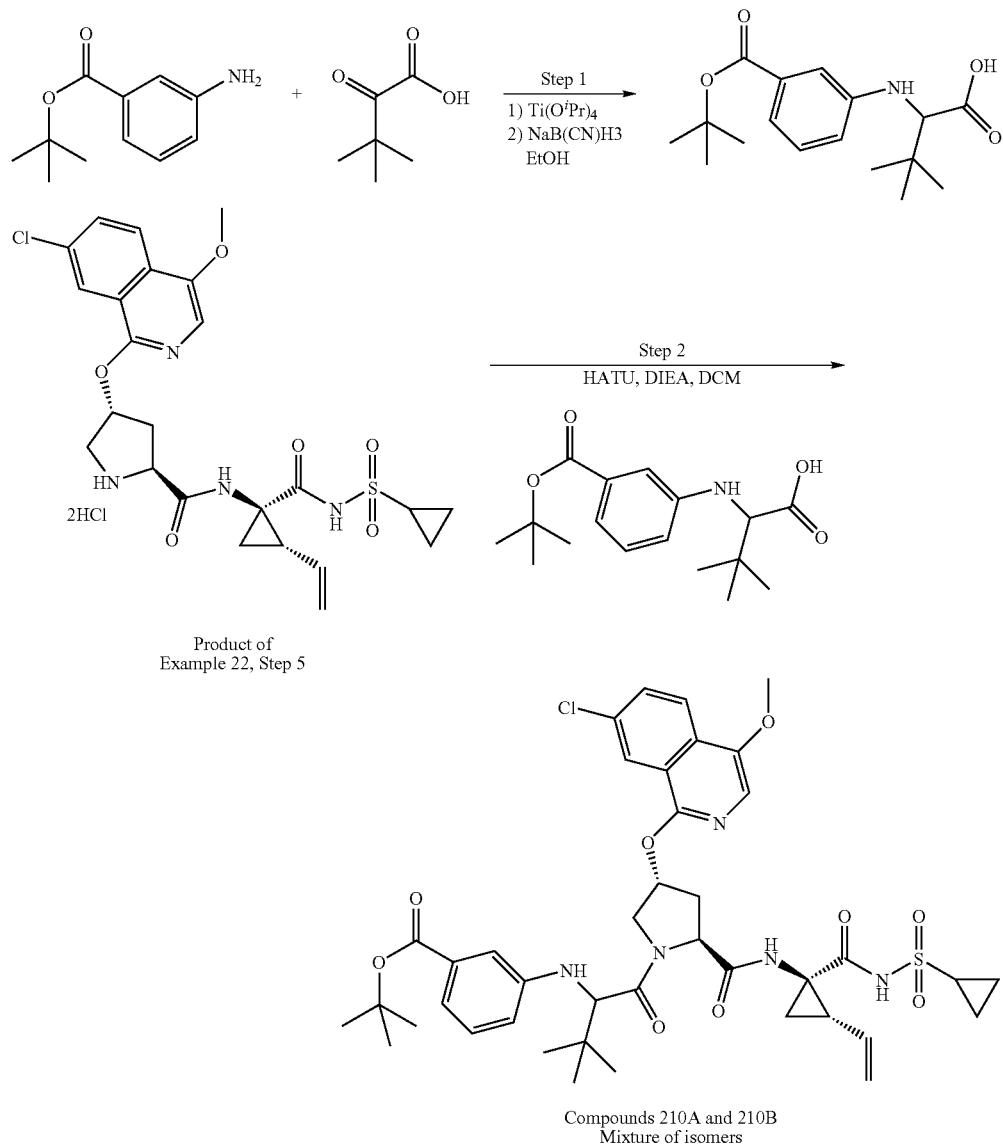

Scheme 1

Compounds 210A and 210B
Mixture of isomers

Step 1:

To a mixture of 3-amino-N-tert-butylbenzenesulfonamide (180 mg, 0.788 mmol) and 3,3-dimethyl-2-oxobutanoic acid (308 mg, 2.365 mmol) in a 100 mL RBF at RT was added tetraisopropoxytitanium (2 ml,) via a pipet. The color of the mixture soon changed into a characteristic canary color. The solution was warmed to 75° C. for about 15 minutes and the color remained the same. The solution was diluted with absolute ethanol (8 ml) at RT, followed by the addition of 1.5× of sodium cyanotrihydroborate (245 mg, 3.90 mmol), and the remaining half after the bubbling and sizzling was over. The color of the solution became lighter. The solution was mixed with 4 mL of water, forming a suspension, and the white PPT was removed by centrifuge. The organic was extracted into ethyl acetate, and the organic phase was dried over $Na_2SO_4$, filtered, and evaporated to dryness. A yellow oil was obtained and was used in the next step without further purification. LC-MS, MS m/z 308 ($M^+$+H).

Step 2:

To the yellow solution of 2-(3-(N-tert-butylsulfamoyl)phenylamino)-3,3-dimethylbutanoic acid (0.065 g, 0.189 mmol step 1, example 210) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.101 g, 0.189 mmol, step 5, example 22) in $CH_2Cl_2$ at 0° C. was added HATU (0.144 g, 0.378 mmol) followed by diisopropylethyl amine (0.061 g, 0.473 mmol). A light yellow solution was formed after addition of the base. The mixture was stirred at room temperature overnight. The reaction mixture was diluted with ethyl acetate (25 ml) and was washed with water (pH~6) and brine. The organic was dried over sodium sulfate, filtered, concentrated, and purified by reverse phase preparative HPLC to give two separate products with identical MS m/z as observed by LCMS. Compound 210A (0.021 g, 13.5% yield) was the first of the two isomers to elute by reverse phase preparative HPLC. Compound 210B (0.020 g, 13.3% yield) was the second of the two isomers to elute by reverse phase preparative HPLC.

Compound 210A

¹H NMR (400 MHz, CD₃OD) δ ppm 1.04-1.14 (m, 11H) 1.19-1.31 (m, 2H) 1.38-1.48 (m, 9H) 1.50-1.60 (m, 1H)) 1.86 (m, 1H) 2.15-2.24 (m, 2H) 2.47 (m, 1H) 2.94 (m, 1H) 3.92-4.04 (m, 4H) 4.11 (s, 1H) 4.18 (m, 1H) 4.46 (m, 1H) 5.06-5.15 (m, 1H) 5.29 (m, 1H) 5.67-5.77 (m, 2H) 6.54 (m, 1H) 6.75 (ddd, J=19.83, 7.62, 2.01 Hz, 1H) 6.89 (m, 1H) 7.31 (s, 1H) 7.49 (s, 1H) 7.59-7.68 (m, 2H) 8.04 (t, J=8.44 Hz, 1H); LC-MS, MS m/z 824 (M⁺+H).

Compound 210B

LC-MS, MS m/z 824 (M⁺+H).

Compound 211 Isomers

N-(3-carboxyphenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(3-carboxyphenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 211

Preparation of Compounds 211A and 211B

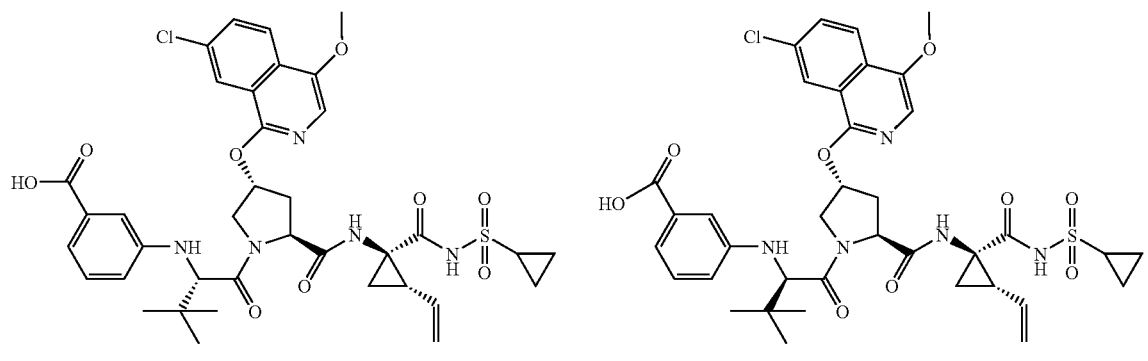

Compounds 211A and 211B

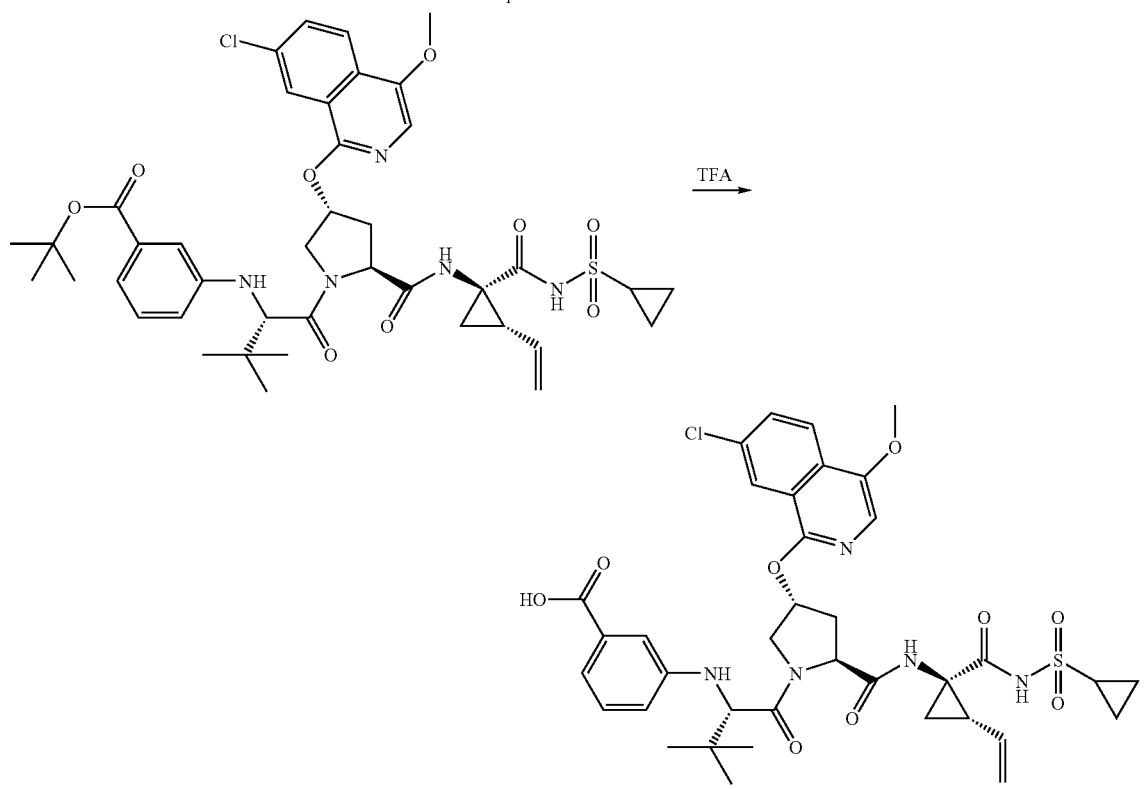

tert-butyl 3-((S)-1-((2S,4R)-4-(7-chloro-4-methoxyisoquinolin-1-yloxy)-2-((1R,2S)-1-(cyclopropylsulfonylcarbamoyl)-2-vinylcyclopropylcarbamoyl)pyrrolidin-1-yl)-3,3-dimethyl-1-oxobutan-2-ylamino)benzoate (20 mg, 0.024 mmol, compound 210A) was dissolved in CH2Cl2 (2 ml) at 25° C. TFA (0.019 ml, 0.243 mmol) was added dropwise. The mixture was stirred overnight. The TFA was removed and the residue was purified by preparative HPLC. Compound 211A was obtained as a white powder (0.005 g, 26.8% yield). $^1$HNMR (400 MHz, CD$_3$OD) δ ppm 1.04-1.14 (m, 11H) 1.19-1.30 (m, 2H) 1.38-1.46 (m, 1H) 1.86 (dd, J=8.18, 5.41 Hz, 1H) 2.21 (ddd, J=13.91, 9.76, 3.78 Hz, 2H) 2.48 (dd, J=13.72, 6.92 Hz, 1H) 2.95 (ddd, J=12.84, 8.06, 4.78 Hz, 1H) 3.94-4.02 (m, 5H) 4.15 (d, J=12.09 Hz, 1H) 4.46-4.56 (m, 1H) 5.10 (dd, J=10.32, 1.51 Hz, 1H) 5.28 (dd, J=17.25, 1.39 Hz, 1H) 5.68-5.78 (m, 2H) 6.48-6.56 (m, 1H) 6.63 (dd, J=7.81, 2.01 Hz, 1H) 6.84 (d, J=7.81 Hz, 1H) 7.17-7.28 (m, 1H) 7.42-7.49 (m, 1H) 7.62 (td, J=8.56, 2.01 Hz, 2H) 7.97-8.05 (m, 1H); LC-MS, MS m/z 768 (M$^+$+H).

Compound 211B was made from compound 210B by the same procedure as was used for the preparation of compound 211A. LC-MS, MS m/z 768 (M$^+$+H).

Compound 212 Isomers

N-(3-(tert-butylcarbamoyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(3-(tert-butylcarbamoyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 212

Preparation of Compounds 212A and 212B

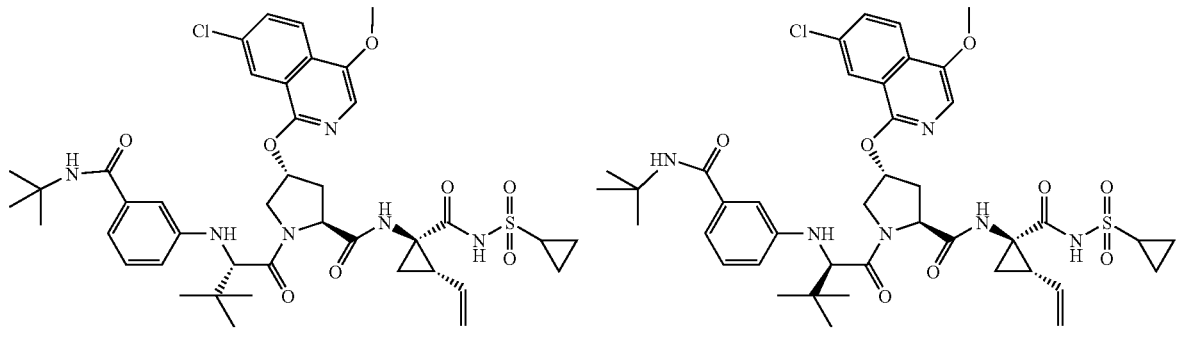

Compounds 212A and 212B

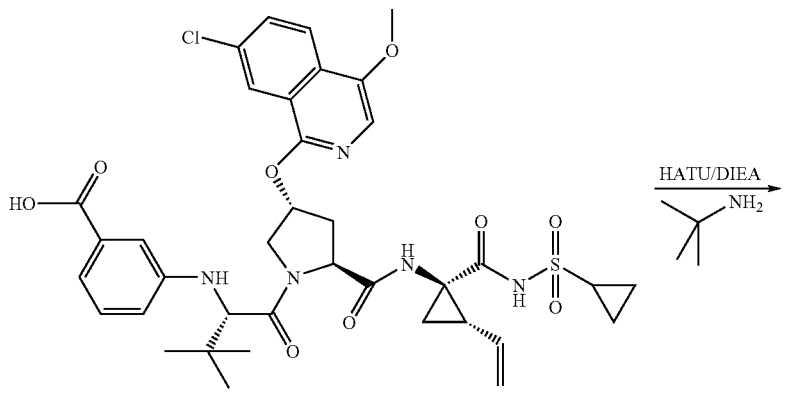

-continued

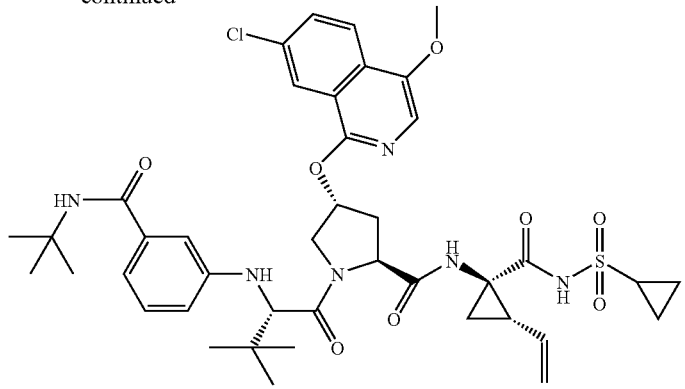

To the solution of 3-((S)-1-((2S,4R)-4-(7-chloro-4-methoxyisoquinolin-1-yloxy)-2-((1R,2S)-1-(cyclopropylsulfonylcarbamoyl)-2-vinylcyclopropylcarbamoyl)pyrrolidin-1-yl)-3,3-dimethyl-1-oxobutan-2-ylamino)benzoic acid (60 mg, 0.078 mmol, compound 211A) and 2-methylpropan-2-amine (11.42 mg, 0.156 mmol) in methylene chloride at 0° C. was added HATU (59.4 mg, 0.156 mmol) followed by diisopropylethyl amine (25.2 mg, 0.195 mmol). A light yellow solution was formed after addition of the base. The mixture was stirred at room temperature for two hours. The reaction mixture was diluted with ethyl acetate (25 ml), washed with water (pH~6) and brine. The organic was dried over sodium sulfate, filtered, and concentrated. A yellow oil was obtained. Purification by preparative HPLC gave Compound 212A as a white powder (0.036 g, 56% yield). $^1$H NMR (400 MHz, CD$_3$OD) δ ppm 1.04-1.14 (m, 11H) 1.23-1.34 (m, 11H) 1.41 (ddd, J=14.73, 5.29, 5.16 Hz, 1H) 1.86 (dd, J=8.18, 5.41 Hz, 1H) 2.16-2.25 (m, 2H) 2.48 (dd, J=13.72, 6.92 Hz, 1H) 2.95 (ddd, J=12.84, 8.06, 4.78 Hz, 1H) 3.97-4.00 (m, 3H) 4.02-4.11 (m, 2H) 4.26 (d, J=12.34 Hz, 1H) 4.46 (dd, J=10.20, 6.92 Hz, 1H) 5.10 (dd, J=10.20, 1.64 Hz, 1H) 5.23-5.31 (m, 1H) 5.68-5.78 (m, 2H) 6.51-6.60 (m, 2H) 6.69-6.78 (m, 1H) 7.09 (d, J=2.01 Hz, 1H) 7.50-7.55 (m, 1H) 7.63-7.73 (m, 2H) 8.07 (d, J=9.06 Hz, 1H); LC-MS, MS m/z 823 (M$^+$+H).

Compound 212B was made from compound 211B by the same procedure used for preparation of compound 212A. LC-MS, MS m/z 768 (M$^+$+H).

Compound 213 Isomers 3-methyl-N-phenyl-L-valyl-(4R)-4-((7-chloro-4-methoxy-1-isoquinolinyl)oxy)-N-((1R,2S)-1-((cyclopropylsulfonl)carbamoyl)-2-vinylcyclopropyl)-L-prolinamide and 3-methyl-N-phenyl-D-valyl-(4R)-4-((7-chloro-4-methoxy-1-isoquinolinyl)oxy)-N-((1R,2S)-1-((cyclopropylsulfonl)carbamoyl)-2-vinylcyclopropyl)-L-prolinamide Example 213

Preparation of Compounds 213A and 213B

Compounds 213A and 213B

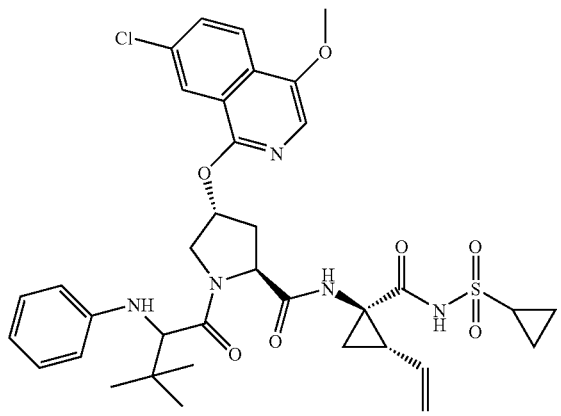

Scheme 1

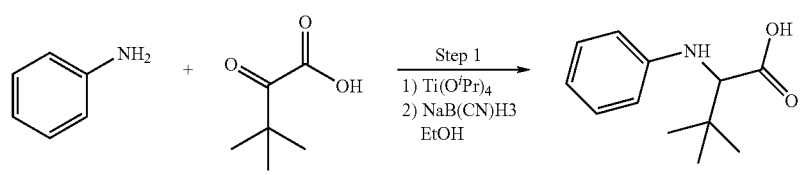

-continued

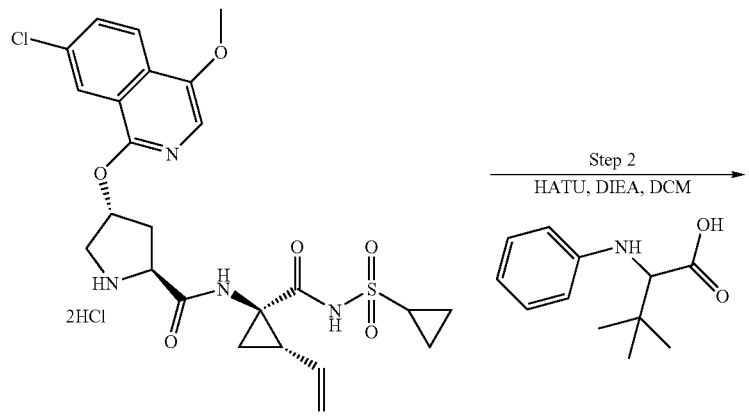

Product of
Example 22, Step 5

→ Step 2
HATU, DIEA, DCM

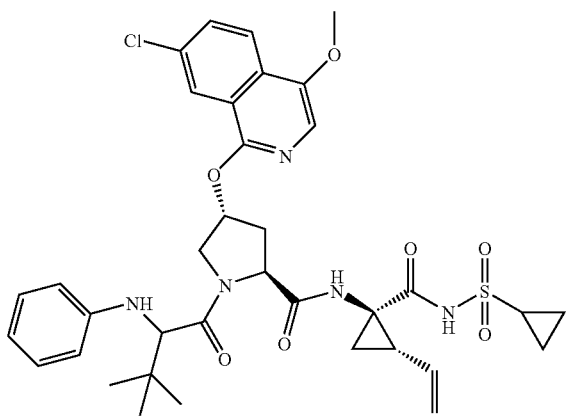

Compounds 213A and 213B
Mixture of isomers

Step 1:

To a mixture of aniline (180 mg, 1.94 mmol) and 3,3-dimethyl-2-oxobutanoic acid (500 mg, 3.84 mmol) in a 100 ml RBF at RT was added tetraisopropoxytitanium (2 ml,) via a pipet. The color of the mixture soon changed into a characteristic canary color. The solution was warmed to 75° C. for about 15 minutes and the color remained the same. The solution was diluted with absolute ethanol (8 ml) at RT, followed by the addition of 1.5× of sodium cyanotrihydroborate (245 mg, 3.90 mmol), and the remaining half after the bubbling and sizzling was over. The color of the solution became lighter. The solution was mixed with 4 mL of water, forming a suspension, and the white PPT was removed by centrifuge. The organic was extracted into ethyl acetate, and the organic phase was dried over $Na_2SO_4$, filtered, and evaporated to dryness. A yellow oil was obtained and was used in the next step without further purification. LC-MS, MS m/z 208 ($M^+$+H).

Step 2:

To the yellow solution of 2-phenylamino-3,3-dimethylbutanoic acid (0.039 g, 0.189 mmol step 1, example 213) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.101 g, 0.189 mmol, step 5, example 22) in CH$_2$Cl$_2$ at 0° C. was added HATU (0.144 g, 0.378 mmol) followed by diisopropylethyl amine (0.061 g, 0.473 mmol). A light yellow solution was formed after addition of the base. The mixture was stirred at room temperature overnight. The reaction mixture was diluted with ethyl acetate (25 ml), washed with water (pH~6) and brine. The organic was dried over sodium sulfate, filtered, concentrated, and the residue was purified by reverse phase preparative HPLC to give two separate products with identical MS m/z as observed by LCMS. Compound 213A (0.0032 g, 2.3% yield) was the first of the two isomers to elute by reverse phase preparative HPLC. Compound 213B (0.0035 g, 2.3% yield) was the second of the two isomers to elute by reverse phase preparative HPLC.

Compound 213A $^1$H NMR (400 MHz, CD$_3$OD) δ ppm 1.01-1.10 (m, 2H) 1.11-1.21 (m, 9H) 1.21-1.32 (m, 2H) 1.35-1.46 (m, 1H) 1.87 (dd, J=8.18, 5.41 Hz, 1H) 2.16-2.26 (m, 2H) 2.49 (dd, J=13.85, 6.80 Hz, 1H) 2.95 (ddd, J=12.84, 8.06, 4.78 Hz, 1H) 3.94-4.02 (m, 4H) 4.04-4.10 (m, 2H) 4.46 (dd, J=10.70, 6.92 Hz, 1H) 5.11 (dd, J=10.32, 1.51 Hz, 1H) 5.29 (dd, J=17.12, 1.26 Hz, 1H) 5.67-5.78 (m, 2H) 6.23 (t, J=7.30 Hz, 1H) 6.58-6.63 (m, 2H) 6.65-6.70 (m, 1H) 7.49-7.56 (m, 1H) 7.67-7.76 (m, 2H) 8.11 (d, J=8.81 Hz, 1H); LC-MS, MS m/z 724 (M$^+$+H).

Compound 213B

LC-MS, MS m/z 724 (M$^+$+H).

Compound 214 Isomers

N-(4-(tert-butylsulfamoyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(4-(tert-butylsulfamoyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide

Example 214

Preparation of Compounds 214A and 214B

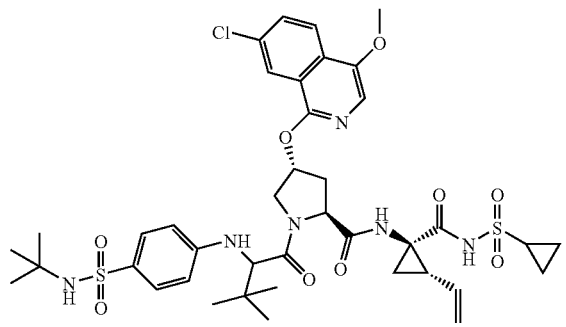

Compounds 214A and 214B

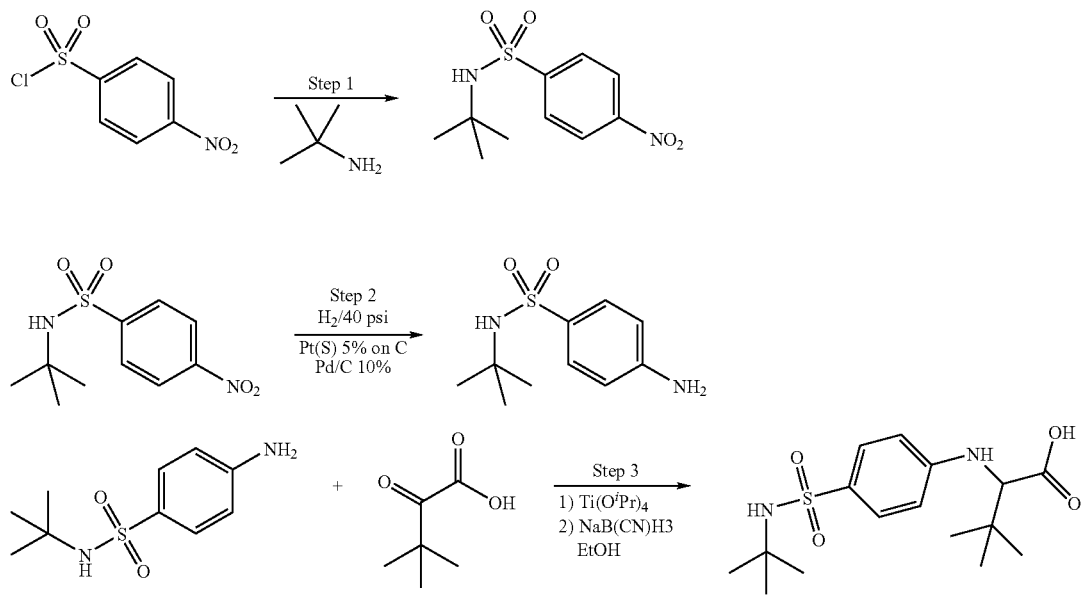

Scheme 1

-continued

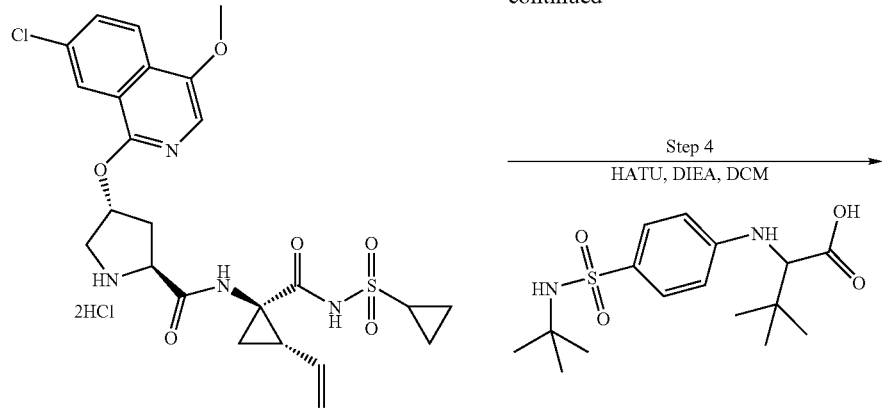

Product of
Example 22, Step 5

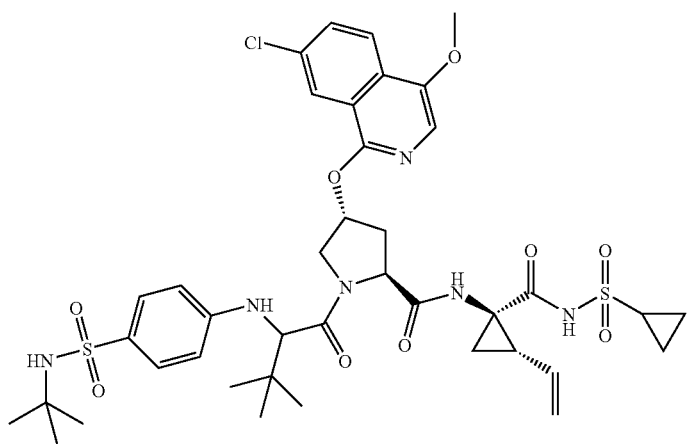

Compounds 214A and 214B
Mixture of isomers

Step 1:

To 4-nitrobenzene-1-sulfonyl chloride (500 mg, 2.256 mmol) in CH$_2$Cl$_2$ (20 ml) at 0-25° C. was added 2-methyl-propan-2-amine (825 mg, 11.28 mmol). The mixture was stirred over the weekend. A light brown suspension formed. LC-MS, MS m/z 208 (M$^+$+H). showed the reaction was complete. Diluted the reaction mixture with ethyl acetate (20 ml), washed with water, brine. The organic layer was dried and concentrated to dryness. The residue was used in the next step without further purification.

Step 2:

N-tert-butyl-4-nitrobenzenesulfonamide (500 mg, 1.936 mmol) from step 1 was dissolved in methanol (30 ml). Pd—C was added under nitrogen. The flask was pressurized with hydrogen gas to 40 PSI and shaken on a Parr apparatus overnight. Pd—C was filtered away, evaporated solvent to dryness. The residue was used directly in the next step without further purification. LC-MS, MS m/z 229 (M$^+$+H).

Step 3

To a mixture of 4-amino-N-tert-butylbenzenesulfonamide (180 mg, 0.788 mmol, from step 2) and 3,3-dimethyl-2-oxobutanoic acid (308 mg, 2.4 mmol) in a 100 ml RBF at RT was added tetraisopropoxytitanium (2 ml,) via a pipet. The color of the mixture soon changed into a characteristic canary color. The solution was warmed to 75° C. for about 15 minutes and the color remained the same. The solution was diluted with absolute ethanol (8 ml) at RT, followed by the addition of 1.5× of sodium cyanotrihydroborate (245 mg, 3.90 mmol), and the remaining half after the bubbling and sizzling was over. The color of the solution became lighter. The solution was mixed with 4 mL of water, forming a suspension, and the white PPT was removed by centrifuge. The organic was extracted into ethyl acetate, and the organic phase was dried over Na$_2$SO$_4$, filtered, and evaporated to dryness. A yellow oil was obtained and was used directly in the next step without further purification. LC-MS, MS m/z 343 (M$^+$+H).

Step 4:

To the yellow solution of 2-(4-(N-tert-butylsulfamoyl)phenylamino)-3,3-dimethylbutanoic acid (0.066 g, 0.189 mmol step 1, example 214) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.101 g, 0.189 mmol, step 5, example 22) in CH$_2$Cl$_2$ at 0° C. was added HATU (0.144 g, 0.378 mmol) followed by diisopropylethyl amine (0.061 g, 0.473 mmol). A light yellow solution was formed after addition of the base. The mixture was stirred at room temperature overnight. The reaction mixture was diluted with ethyl acetate (25 ml) and was washed with water (pH~6) and brine. The organic was dried over sodium sulfate, filtered, concentrated, and the residue was purified by reverse phase preparative HPLC to give two separate products with identical MS m/z as observed by LCMS. Compound 214A (0.021 g, 13.0% yield) was the first of the two isomers to elute by reverse phase preparative HPLC. Compound 214B (0.0022 g, 13.5.0% yield) was the second of the two isomers to elute by reverse phase preparative HPLC.

Compound 214A $^1$H NMR (500 MHz, CD$_3$OD) δ ppm 0.98-1.06 (m, 9H) 1.08-1.16 (m, 12H) 1.27-1.36 (m, 2H) 1.46 (dd, J=9.46, 5.49 Hz, 1H) 1.91 (dd, J=7.93, 5.49 Hz, 1H) 2.24-2.33 (m, 2H) 2.60 (d, J=6.10 Hz, 1H) 2.96-3.01 (m, 1 H) 4.03 (s, 3H) 4.09-4.13 (m, 2H) 4.47 (d, J=11.90 Hz, 1H) 4.63 (dd, J=10.22, 7.17 Hz, 1H) 5.15 (d, J=10.38 Hz, 1H) 5.30-5.35 (m, 1H) 5.74-5.80 (m, 2H) 6.52 (d, J=8.85 Hz, 2H) 7.16 (d, J=8.85 Hz, 2H) 7.60 (s, 1H) 7.71 (dd, J=8.85, 2.14 Hz, 1H) 7.98 (d, J=1.83 Hz, 1H) 8.14 (d, J=8.85 Hz, 1H); LC-MS, MS m/z 859 (M$^+$+H).

Compound 214B

LC-MS, MS m/z 859 (M$^+$+H).

Compound 215 Isomers 3-methyl-N-(4-sulfamoylphenyl)-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and 3-methyl-N-(4-sulfamoylphenyl)-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 215

Preparation of Compounds 215A and 215B

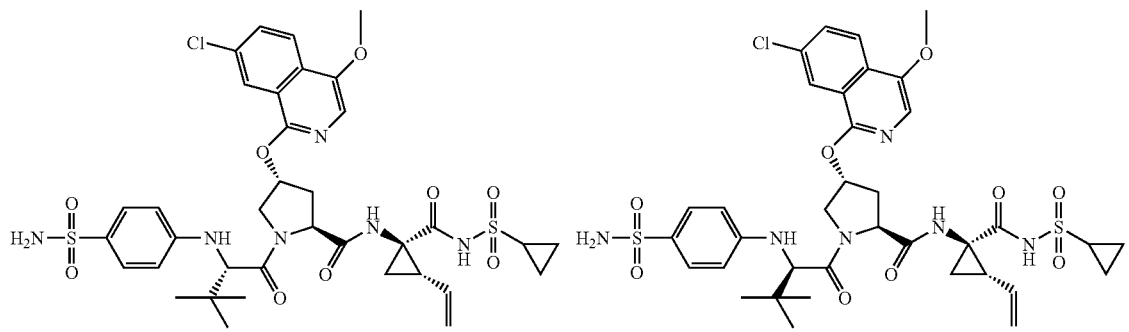

Compounds 215A and 215B

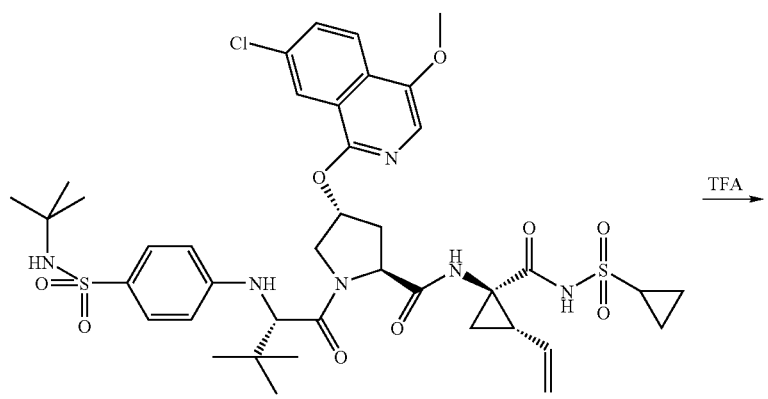

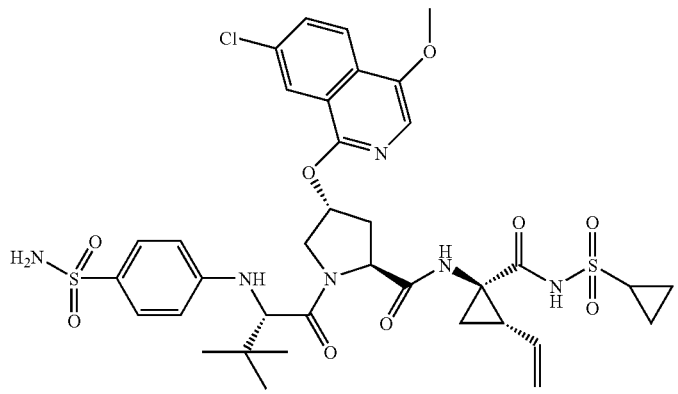

(2S,4R)-1-((S)-2-(3-(N-tert-butylsulfamoyl)phenylamino)-3,3-dimethylbutanoyl)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (20 mg, 0.024 mmol, compound 214A) was dissolved in TFA (2 ml) at 25° C. the mixture was stirred overnight. The TFA was removed and the residue was purified by preparative HPLC. Compound 215A was thus obtained as a white powder (0.013 g, 69.5% yield). $^1$H NMR (400 MHz, CD$_3$OD) 6) 1.01-1.13 (m, 11H) 1.27-1.37 (m, 2H) 1.40-1.44 (m, 1H) 1.87 (dd, J=8.18, 5.41 Hz, 1H) 2.20-2.28 (m, 2H) 2.57 (dd, J=13.72, 7.18 Hz, 1H) 2.92-2.98 (m, 1H) 3.98-4.06 (m, 4H) 4.09 (s, 1H) 4.37 (d, J=12.09 Hz, 1H) 4.58 (dd, J=10.07, 7.05 Hz, 1H) 5.11 (dd, J=10.32, 1.51 Hz, 1H) 5.32 (m, 1H) 5.69-5.78 (m, 2H) 6.48-6.53 (m, 2H) 7.19-7.26 (m, 2H) 7.53-7.56 (s, 41H) 7.65 (dd, J=8.94, 2.14 Hz, 1H) 7.90 (d, J=2.01 Hz, 1H) 8.07 (d, J=8.81 Hz, 1H); LC-MS, MS m/z 803 (M$^+$+H).

Compound 215B was made from compound 214B by the same procedure as was used for the preparation of compound 215A. LC-MS, MS m/z 803 (M$^+$+H).

Compound 216 Isomers 3-methyl-N-(3-((1-methyl-1-phenylethyl)carbamoyl)phenyl)-L-valyl-(4R)-4-((7-chloro-4-methoxy-1-isoquinolinyl)oxy)-N-((1R,2S)-1-((cyclopropylsulfonl)carbamoyl)-2-vinylcyclopropyl)-L-prolinamide
and 3-methyl-N-(3-((1-methyl-1-phenylethyl)carbamoyl)phenyl)-D-valyl-(4R)-4-((7-chloro-4-methoxy-1-isoquinolinyl)oxy)-N-((1R,2S)-1-((cyclopropylsulfonl)carbamoyl)-2-vinylcyclopropyl)-L-prolinamide Example 216

Preparation of Compounds 216A and 216B

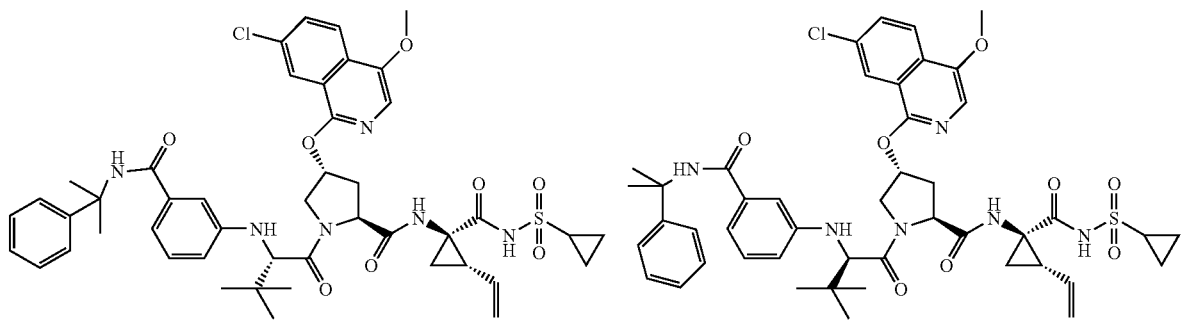

Compounds 216A and 216B

-continued

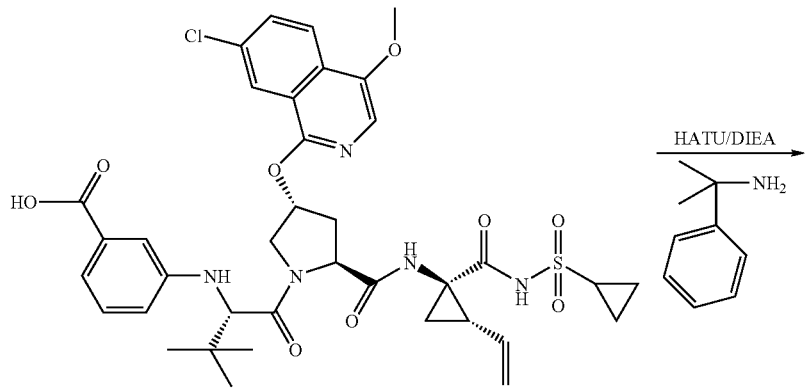

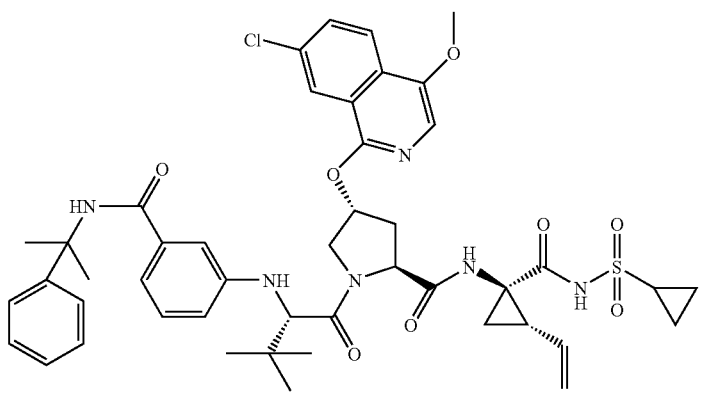

To the solution of 3-((S)-1-((2S,4R)-4-(7-chloro-4-methoxyisoquinolin-1-yloxy)-2-((1R,2S)-1-(cyclopropylsulfonylcarbamoyl)-2-vinylcyclopropylcarbamoyl)pyrrolidin-1-yl)-3,3-dimethyl-1-oxobutan-2-ylamino)benzoic acid (60 mg, 0.078 mmol, compound 211A) and 2-phenylpropan-2-amine (21.12 mg, 0.156 mmol) in methylenechloride at 0° C. was added HATU (59.4 mg, 0.156 mmol) followed by diisopropylethyl amine (25.2 mg, 0.195 mmol). A light yellow solution was formed after addition of the base. The mixture was stirred at room temperature for two hours. The reaction mixture was diluted with ethyl acetate (25 ml) and was washed with water (pH~6) and brine. The organic was dried over sodium sulfate, filtered, and concentrated to a yellow oil.

217

Purification by preparative gave Compound 216A as a white powder (0.056 g, 81% yield). $^1$H NMR (400 MHz, CD$_3$OD) δ ppm 1.03-1.13 (m, 11H) 1.19-1.30 (m, 2H) 1.41 (dd, J=9.44, 5.41 Hz, 1H) 1.63 (d, J=5.79 Hz, 6H) 1.85 (dd, J=8.06, 5.54 Hz, 1H) 2.16-2.25 (m, 2H) 2.49 (dd, J=13.72, 6.92 Hz, 1H) 2.91-2.98 (m, 1H) 3.99 (s, 3H) 4.06 (dd, J=12.09, 3.53 Hz, 1H) 4.10 (s, 1H) 4.30 (d, J=12.09 Hz, 1H) 4.46 (dd, J=10.07, 7.05 Hz, 1H) 5.10 (dd, J=10.45, 1.64 Hz, 1H) 5.25-5.29 (dd, J=17.12, J=1.51 Hz, 1H) 5.68-5.79 (m, 2H) 6.52-6.59 (m, 2H) 6.82 (dd, J=6.42, 1.89 Hz, 1H) 7.10-7.13 (m, 2H) 7.17-7.23 (m, 2H) 7.29-7.34 (m, 2H) 7.54 (s, 1H) 7.67 (dd, J=8.94, 2.14 Hz, 1H) 7.74 (d, J=2.01 Hz, 1H) 8.09 (d, J=8.81 Hz, 1H); LC-MS, MS m/z 886 (M$^+$+H).

Compound 216B was made from compound 211B by the same procedure as was used for the preparation of compound 216A. LC-MS, MS m/z 886 (M$^+$+H).

218

Compound 217 Isomers

N-(3-carbamoylphenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(3-carbamoylphenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 217

Preparation of Compounds 217A and 217B

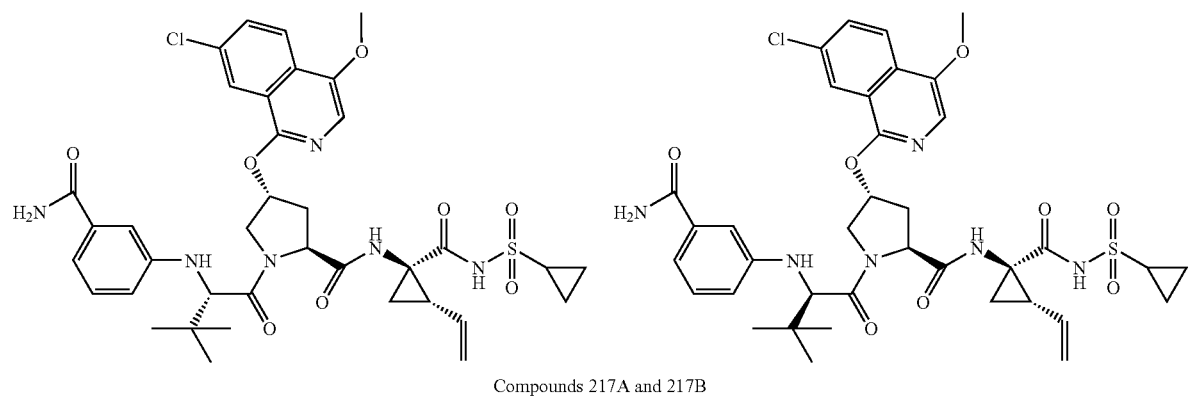

Compounds 217A and 217B

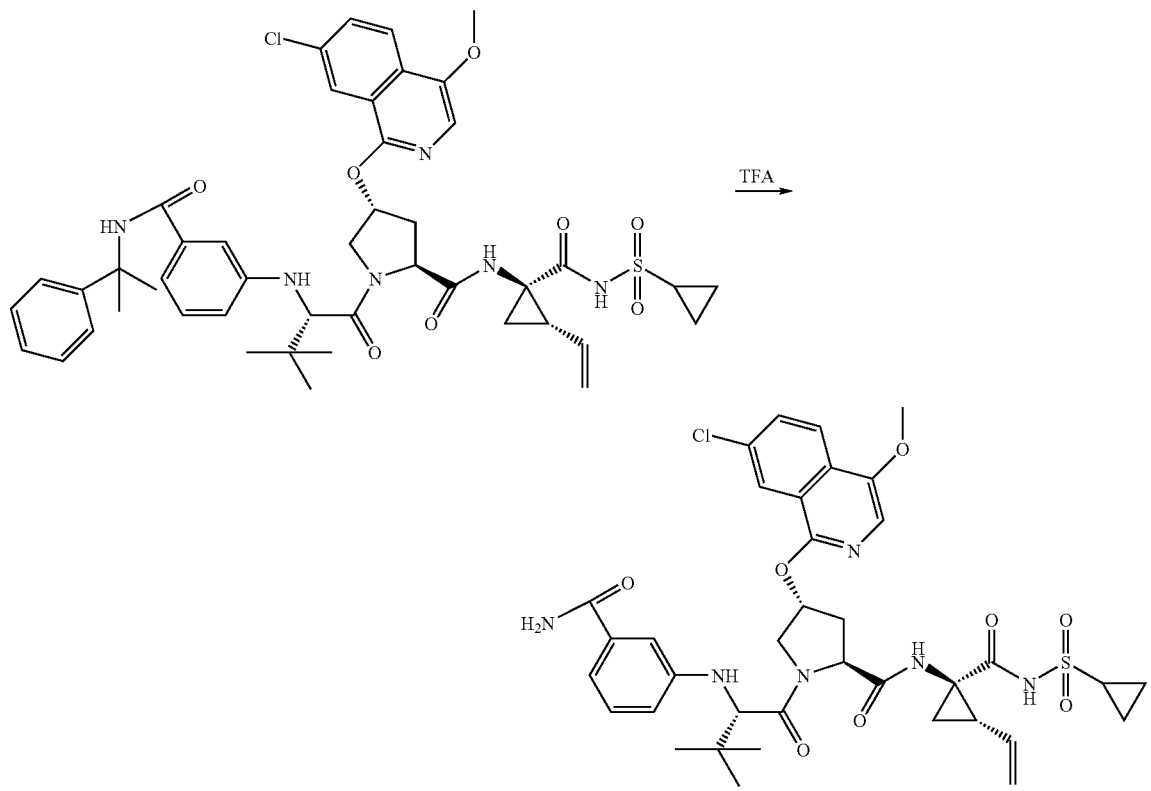

(2S,4R)-4-(7-chloro-4-methoxyisoquinolin-1-yloxy)-N-((1R,2S)-1-(cyclopropylsulfonylcarbamoyl)-2-vinylcyclopropyl)-1-((S)-3,3-dimethyl-2-(3-(2-phenylpropan-2-ylcarbamoyl)phenylamino)butanoyl)pyrrolidine-2-carboxamide (50 mg, 0.056 mmol compound 216A) was dissolved in 1 ml of 2,2,2-trifluoroacetic acid at 25° C. The resulting solution was stirred overnight. The TFA was removed and the residue was purified by preparative HPLC to give Compound 217A as a white powder (0.023 g, 46% yield). $^1$H NMR (400 MHz, CD$_3$OD) δ ppm 1.03-1.12 (m, 11H) 1.19-1.30 (m, 2H) 1.42 (dd, J=9.44, 5.41 Hz, 1H) 1.87 (dd, J=8.06, 5.54 Hz, 1H) 2.16-2.26 (m, 2H) 2.49 (dd, J=13.72, 6.92 Hz, 1H) 2.92-2.99 (m, 1H) 3.96-4.05 (m, 5H) 4.20 (t, J=11.83 Hz, 1H) 4.51 (dd, J=10.58, 7.05 Hz, 1H) 5.11 (dd, J=10.32, 1.76 Hz, 1H) 5.29 (dd, J=17.25, 1.39 Hz, 1H) 5.69-5.79 (m, 2H) 6.56-6.66 (m, 2H) 6.76 (d, J=7.55 Hz, 1H) 7.11 (d, J=1.76 Hz, 1H) 7.47-7.52 (s, 1H) 7.66 (dd, J=8.81, 2.27 Hz, 1H) 7.74 (d, J=1.76 Hz, 1H) 8.07 (d, J=8.81 Hz, 1H); LC-MS, MS m/z 767 (M$^+$+H).

Compound 217B was made from compound 216B by the same procedure as was used for the preparation of compound 217A. LC-MS, MS m/z 767 (M$^+$+H).

Compound 218 Isomers

N-(3-(dimethylcarbamoyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(3-(dimethylcarbamoyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 218

Preparation of Compounds 218A and 218B

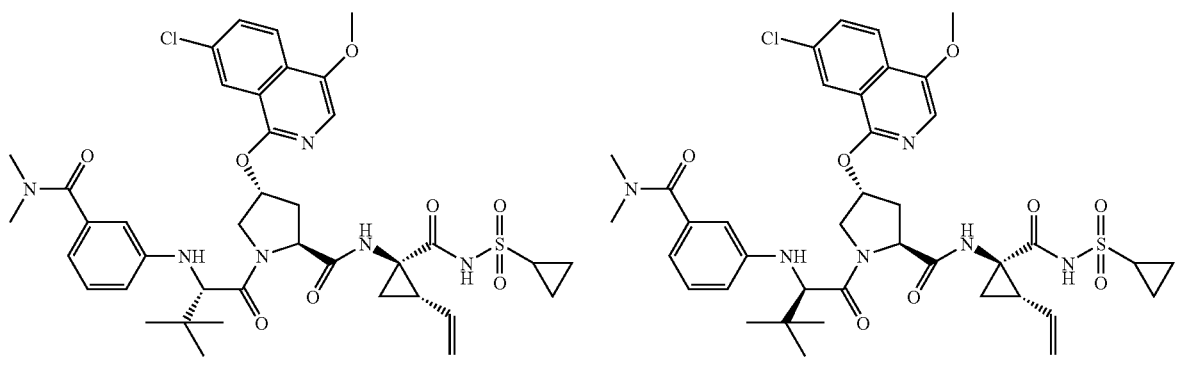

Compounds 218A and 218B

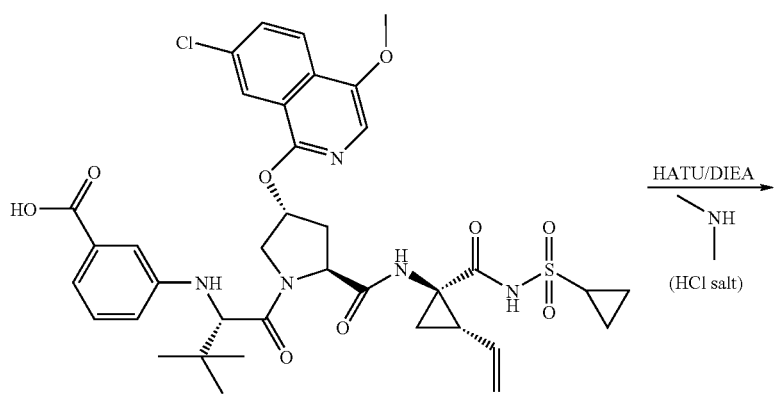

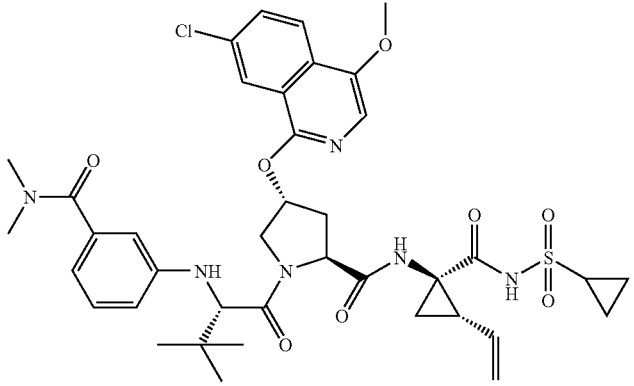

To the solution of 3-((S)-1-((2S,4R)-4-(7-chloro-4-methoxyisoquinolin-1-yloxy)-2-((1R,2S)-1-(cyclopropylsulfonylcarbamoyl)-2-vinylcyclopropylcarbamoyl)pyrrolidin-1-yl)-3,3-dimethyl-1-oxobutan-2-ylamino)benzoic acid (60 mg, 0.078 mmol, compound 211A) and dimethylaminehydrochloride (12.6 mg, 0.156 mmol) in methylenechloride at 0° C. was added HATU (59.4 mg, 0.156 mmol) followed by diisopropylethyl amine (25.2 mg, 0.195 mmol). A light yellow solution was formed after addition of the base. The mixture was stirred at room temperature for two hours. The reaction mixture was diluted with ethyl acetate (25 ml) and was washed with water (pH~6) and brine. The organic was dried over sodium sulfate, filtered, and concentrated to a yellow oil. Purification by preparative HPLC afforded Compound 218A as a white powder (0.035 g, 58% yield). $^1$H NMR (400 MHz, CD$_3$OD) δ ppm 1.03-1.13 (m, 11H) 1.16-1.28 (m, 2H) 1.38-1.45 (m, 1H) 1.86 (dd, J=8.18, 5.41 Hz, 1H) 2.18-2.27 (m, 2H) 2.51 (dd, J=13.72, 6.92 Hz, 1H) 2.77-2.87 (m, 3H) 2.91-3.00 (m, 4H) 3.96-4.07 (m, 5H) 4.23 (d, J=12.34 Hz, 1H) 4.48 (dd, J=10.32, 7.05 Hz, 1H) 5.11 (dd, J=10.32, 1.51 Hz, 1H) 5.28 (dd, J=17.12, 1.51 Hz, 1H) 5.69-5.79 (m, 2H) 6.30-6.36 (m, 1H) 6.47-6.54 (m, 2H) 6.76 (d, J=1.26 Hz, 1H) 7.52-7.56 (m, 1H) 7.68 (dd, J=8.94, 2.14 Hz, 1H) 7.81 (d, J=2.01 Hz, 1H) 8.04-8.11 (m, 1H); LC-MS, MS m/z 795 (M$^+$+H).

Compound 218B was made from compound 211B by the same procedure as was used for the preparation of compound 218A. LC-MS, MS m/z 795 (M$^+$+H).

Compound 219 Isomers

N-(3-(dimethylsulfamoyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(3-(dimethylsulfamoyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 219

Preparation of Compounds 219A and 219B

Compounds 219A and 219B

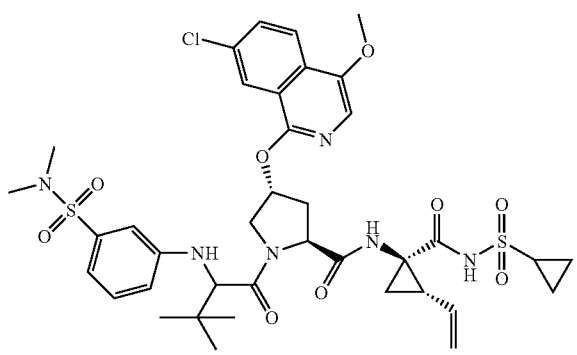

Scheme 1

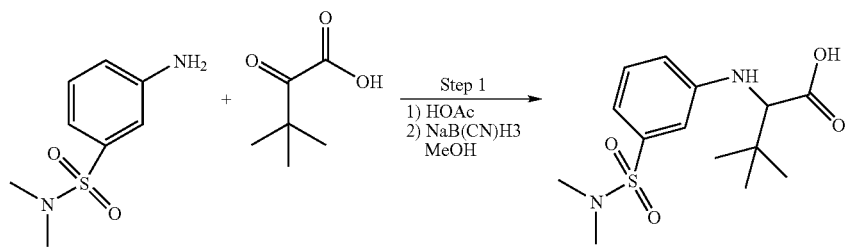

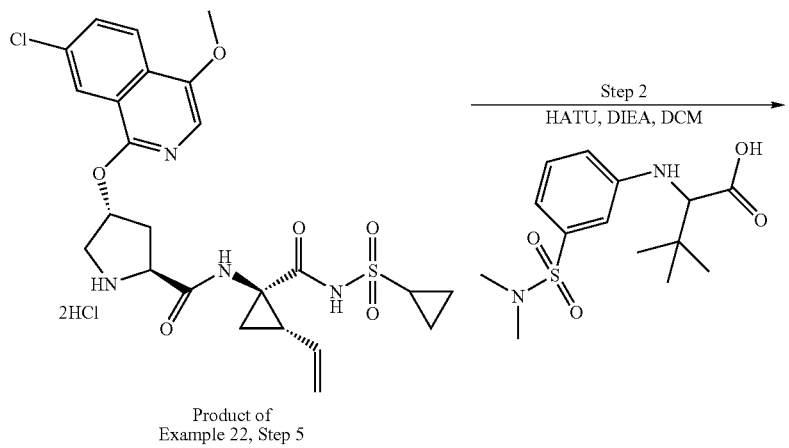

Product of
Example 22, Step 5

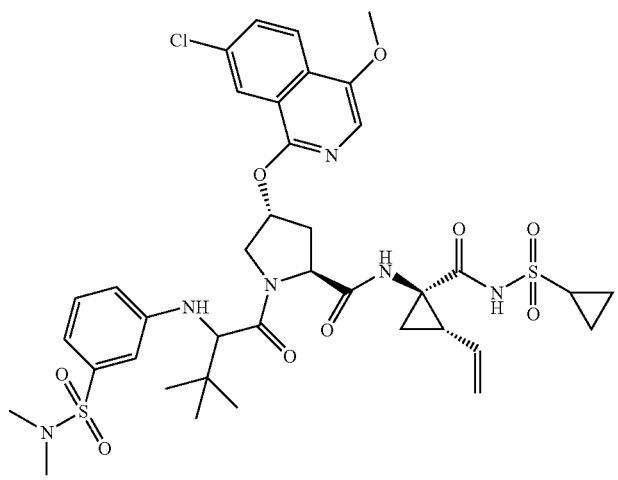

Compounds 219A and 219B
Mixture of isomers

Step 1:

To a mixture of 3-amino-N,N-dimethylbenzenesulfonamide (203 mg, 1.014 mmol) and 3,3-dimethyl-2-oxobutanoic acid (264 mg, 2.027 mmol)) in a 100 ml RBF at RT was added acetic acid (2 ml,) via a pipet. The color of the mixture soon changed into a characteristic canary color. The solution was warmed to 75° C. for about 120 minutes and the color remained the same. The solution was diluted with methanol (2 ml) at RT, followed by the addition of 1.5× of sodium cyanotrihydroborate (245 mg, 3.90 mmol), and the remaining half after the bubbling and sizzling was over. The color of the solution became lighter. Added 30 ml of water to the mixture, then extracted it with 10 ml of ethyl acetate (adjust pH to 4). Then the organic was washed by sodium bicarbonate at pH=8. The organic layer was dried over $Na_2SO_4$, filtered, and concentrated. The oily residue was dried under high vacuum. A yellow oil was obtained and was used directly in the next step without further purification. LC-MS, MS m/z 315 ($M^+$+H).

Step 2:

To the yellow solution of 2-(3-(N,N-dimethylsulfamoyl)phenylamino)-3, 3-dimethylbutanoic acid (59.4 mg, 0.189 mmol, step 1, example 219) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.150 g, 0.28 mmol, step 5, example 22) in $CH_2Cl_2$ at 0° C. was added HATU (0.144 g, 0.378 mmol) followed by diisopropylethyl amine (0.061 g, 0.473 mmol). A light yellow solution was formed after addition of the base. The mixture was stirred at room temperature overnight. The reaction mixture was diluted with ethyl acetate (25 ml) and was washed with water (pH~6) and brine. The organic was dried over sodium sulfate, filtered, concentrated, and the residue was purified by reverse phase preparative HPLC to give two separate products with identical MS m/z as observed by LCMS. Compound 219A (0.062 g, 39.5% yield) was the first of the two isomers to elute by reverse phase preparative HPLC. Compound 219B (0.038 g, 24.2% yield) was the second of the two isomers to elute by reverse phase preparative HPLC.

Compound 219A $^1$H NMR (400 MHz, $CD_3OD$) δ ppm 1.02-1.12 (m, 9H) 1.17-1.20 (m, 2H) 1.22-1.29 (m, 2H) 1.32-1.44 (m, 1H) 1.87 (dt, J=8.25, 5.57 Hz, 1H) 2.16-2.28 (m, 2H) 2.46-2.57 (m, 7H) 2.90-2.98 (m, 1H) 3.96-4.00 (s, 3H) 4.03-4.10 (m, 2H) 4.30 (t, J=11.96 Hz, 1H) 4.47-4.58 (m, 1H) 5.10 (dd, J=10.32, 1.76 Hz, 1H) 5.29 (ddd, J=17.12, 7.93, 1.39 Hz, 1H) 5.68-5.79 (m, 2H) 6.55-6.67 (m, 3H) 7.02 (s, 1H) 7.50-7.55 (m, 1H) 7.63-7.69 (m, 1H) 7.81 (d, J=2.01 Hz, 1H) 8.02-8.09 (m, 1H); LC-MS, MS m/z 831 ($M^+$+H).

Compound 219B

LC-MS, MS m/z 831 ($M^+$+H).

Compound 220 Isomers

N-(3, 4-difluorophenyl)-3-methyl-L-valyl-(4R)-4-((7-chloro-4-methoxy-1-isoquinolinyl)oxy)-N-((1R, 2S)-1-((cyclopropylsulfonyl)carbamoyl)-2-vinylcyclopropyl)-L-prolinamide and N-(3, 4-difluorophenyl)-3-methyl-D-valyl-(4R)-4-((7-chloro-4-methoxy-1-isoquinolinyl)oxy)-N-((1R, 2S)-1-((cyclopropylsulfonyl)carbamoyl)-2-vinylcyclopropyl)-L-prolinamide Example 220

Preparation of Compounds 220A and 220B

Compounds 220A and 220B

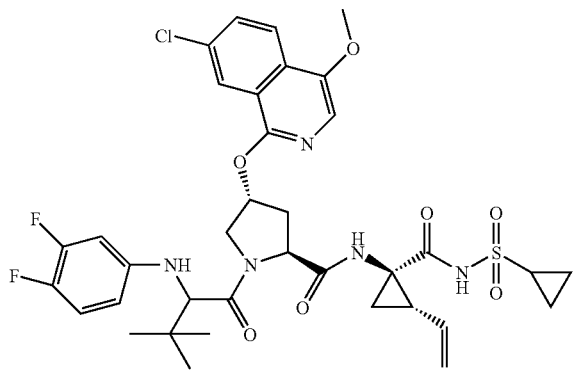

Scheme 1

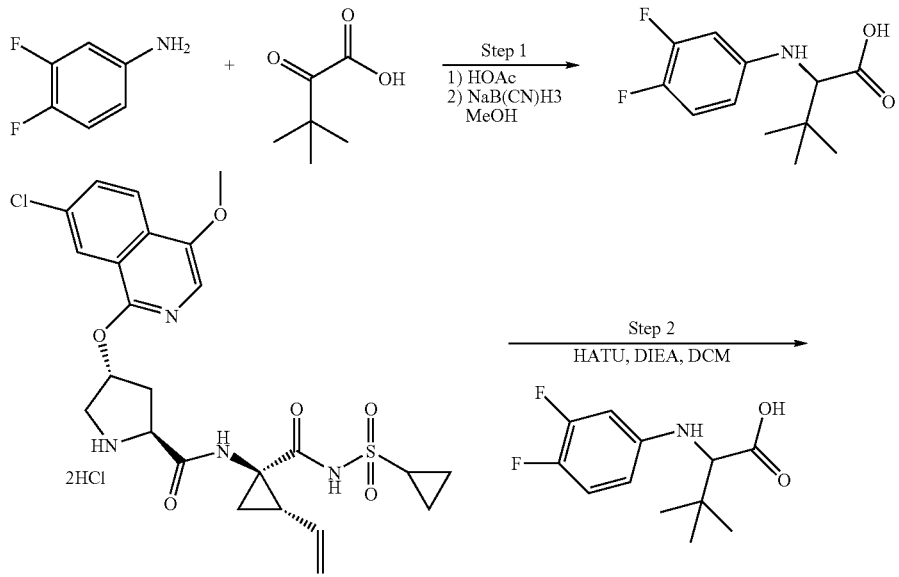

Product of Example 22, Step 5

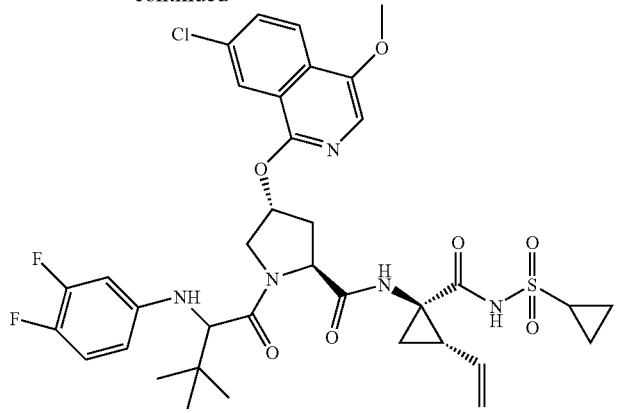

Compounds 220A and 220B
Mixture of isomers

Step 1:

To a mixture of 3,4-difluoroaniline (180 mg, 1.394 mmol) and 3,3-dimethyl-2-oxobutanoic acid (500 mg, 3.84 mmol) in a 25 ml RBF at RT was added 2 ml of acetic acid. The solution was warmed to 75° C. for about 120 minutes. The solution was diluted with methanol (2 ml) at RT, followed by the addition of 1.5× of sodium cyanotrihydroborate (245 mg, 3.90 mmol), and the remaining half after the bubbling and sizzling was over. The color of the solution became lighter. Added 30 ml of water to the mixture, then extracted it with 10 ml of ethyl acetate (adjust pH to 4). The organic was washed with sodium bicarbonate at PH=8. The organic layer was dried over $Na_2SO_4$, filtered, and concentrated. The resulting oily residue was dried under high vacuum. A yellow oil was thus obtained and was used directly in the next step without further purification. LC-MS, MS m/z 244 ($M^+$+H).

Step 2:

To the yellow solution of 2-(3,4-difluorophenylamino)-3,3-dimethylbutanoic acid (0.046 g, 0.189 mmol, step 1, example 208) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.101 g, 0.189 mmol, step 5, example 22) in $CH_2Cl_2$ at 0° C. was added HATU (0.144 g, 0.378 mmol) followed by diisopropylethyl amine (0.061 g, 0.473 mmol). A light yellow solution was formed after addition of the base. The mixture was stirred at room temperature overnight. The reaction mixture was diluted with ethyl acetate (25 ml) and was washed with water (pH~6) and brine. The organic was dried over sodium sulfate, filtered, concentrated, and the residue was purified by reverse phase preparative HPLC to give two separate products with identical MS m/z as observed by LCMS. Compound 220A (0.033 g, 23.0% yield) was the first of the two isomers to elute by reverse phase preparative HPLC. Compound 220B (0.026 g, 19% yield) was the second of the two isomers to elute by reverse phase preparative HPLC.

Compound 220A $^1$H NMR (500 MHz, $CD_3OD$) δ ppm 1.07-1.16 (m, 11 H) 1.23-1.31 (m, 2H) 1.41-1.49 (m, 1H) 1.90 (dd, J=8.24, 5.49 Hz, 1H) 2.21-2.29 (m, 2H) 2.55 (dd, J=13.58, 6.56 Hz, 2H) 2.92-3.00 (m, 1H) 3.88-3.95 (s, 1H) 3.97-4.04 (m, 4H) 4.27 (d, J=12.21 Hz, 1H) 4.57 (dd, J=10.53, 7.17 Hz, 1H) 5.14 (d, J=10.38 Hz, 1H) 5.32 (d, J=17.40 Hz, 1H) 5.73-5.81 (m, 2H) 6.15 (d, J=8.85 Hz, 1H) 6.26-6.34 (m, 1H) 6.44 (ddd, J=13.12, 6.71, 2.75 Hz, 1H) 7.55 (s, 1H) 7.66-7.73 (m, 1H) 7.80 (d, J=2.14 Hz, 1H) 8.07-8.14 (m, 1H); LC-MS, MS m/z 760 ($M^+$+H).

Compound 220B

LC-MS, MS m/z 760 ($M^+$+H).

Compound 221 Isomers

N-(4-(dimethylcarbamoyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(4-(dimethylcarbamoyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 221

Preparation of Compounds 221A and 221B

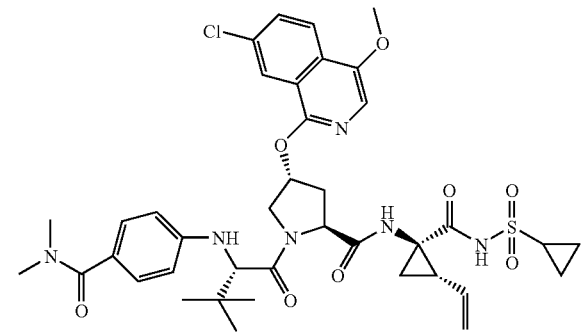

Compounds 221A and 221B

-continued

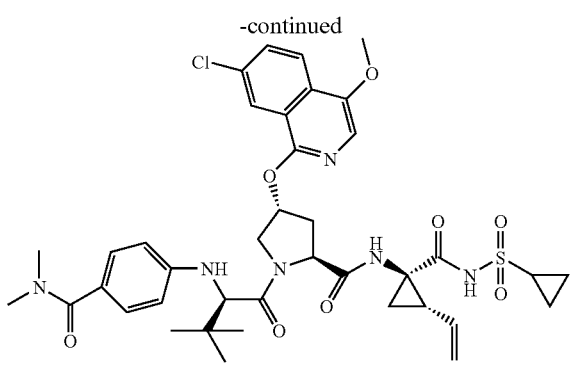

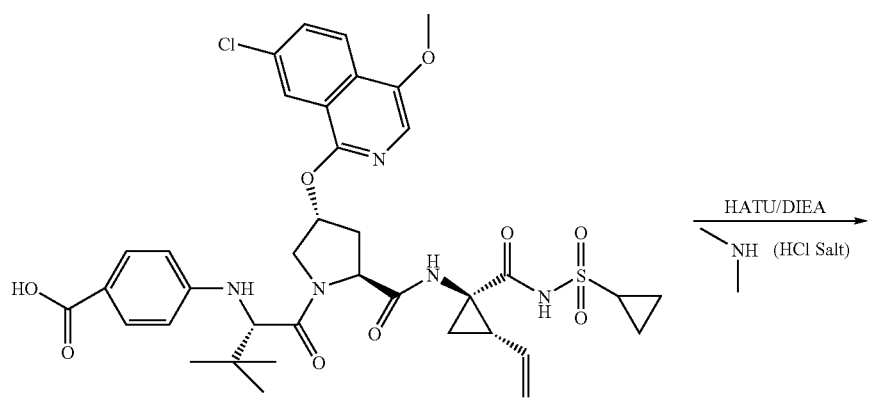

To the solution of 4-((S)-1-((2S,4R)-4-(7-chloro-4-methoxyisoquinolin-1-yloxy)-2-((1R,2S)-1-(cyclopropylsulfonylcarbamoyl)-2-vinylcyclopropylcarbamoyl)pyrrolidin-1-yl)-3,3-dimethyl-1-oxobutan-2-ylamino)benzoic acid (20 mg, 0.026 mmol, compound 209A) and dimethylaminehydrochloride (4.2 mg, 0.052 mmol) in methylene chloride at 0° C. was added HATU (20 mg, 0.052 mmol) followed by diisopropylethyl amine (8.4 mg, 0.065 mmol). A light yellow solution was formed after addition of the base. The mixture was stirred at room temperature for two hours. The reaction mixture was diluted with ethyl acetate (25 ml) and was washed with water (pH~6) and brine. The organic was dried over sodium sulfate, filtered, and concentrated to a yellow oil. Purification by preparative HPLC afforded Compound 221A as a white powder (0.04 g, 19% yield). $^1$H NMR (400 MHz, CD$_3$OD) δ ppm 1.02-1.13 (m, 11H) 1.20-1.33 (m, 2H) 1.41 (dd, J=9.44, 5.41 Hz, 1H) 1.86 (dd, J=8.06, 5.54 Hz, 1H) 2.18-2.30 (m, 2H) 2.57 (dd, J=13.72, 7.18 Hz, 1H) 2.77-2.89 (s, 3H) 2.89-3.00 (m, 4H) 3.99-4.09 (m, 5H) 4.48 (d, J=12.84 Hz, 1H) 4.55 (dd, J=10.58, 7.05 Hz, 1H) 5.11 (dd, J=10.32, 1.51 Hz, 1H) 5.28 (dd, J=17.12, 1.26 Hz, 1H) 5.68-5.80 (m, 2H) 6.41 (d, J=8.81 Hz, 2H) 6.66 (d, J=8.81 Hz, 2H) 7.61 (s, 1H) 7.69 (dd, J=8.94, 2.14 Hz, 1H) 7.92 (d, J=2.01 Hz, 1H) 8.12 (d, J=9.07 Hz, 1H); LC-MS, MS m/z 795 (M$^+$+H).

Compound 221B was made from compound 209B by the same procedure as was used for the preparation of compound 221A. LC-MS, MS m/z 795 (M$^+$+H).

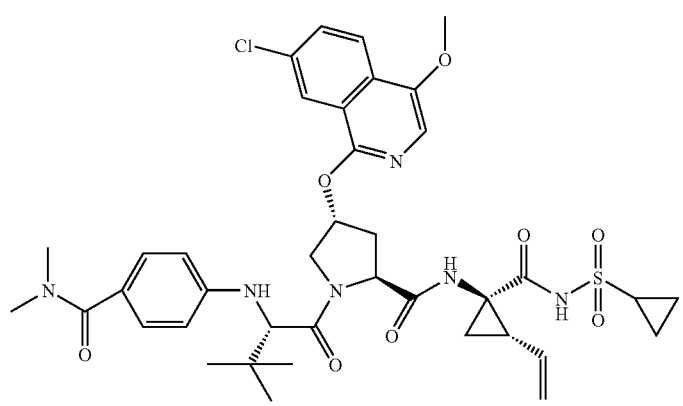

Compound 222 Isomers 3-methyl-N-(4-((1-methyl-1-phenylethyl)carbamoyl)
  phenyl)-L-valyl-(4R)-4-((7-chloro-4-methoxy-1-
  isoquinolinyl)oxy)-N-((1R2S)-1-((cyclopropylsul-
  fonl)carbamoyl)-2-vinylcyclopropyl)-L-prolinamide
  and 3-methyl-N-(4-((1-methyl-1-phenylethyl)carbamoyl)
  phenyl)-L-valyl-(4R)-4-((7-chloro-4-methoxy-1-
  isoquinolinyl)oxy)-N-((1R,2S)-1-((cyclopropylsul-
  fonl)carbamoyl)-2-vinylcyclopropyl)-L-prolinamide

Example 222

Preparation of Compounds 222A and 222B

Compounds 222A and 222B

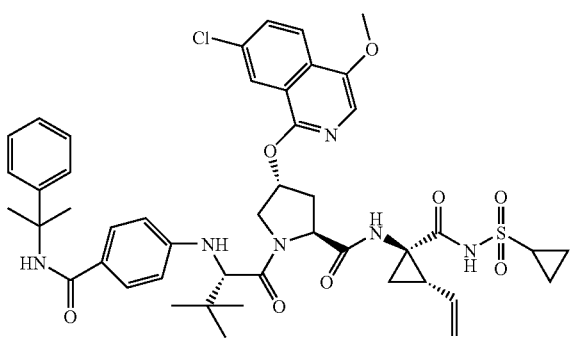

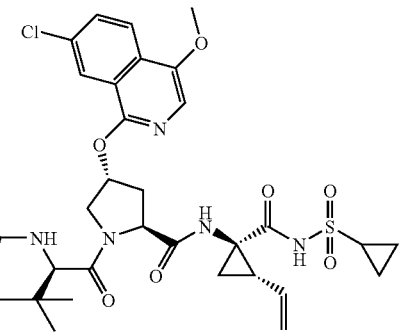

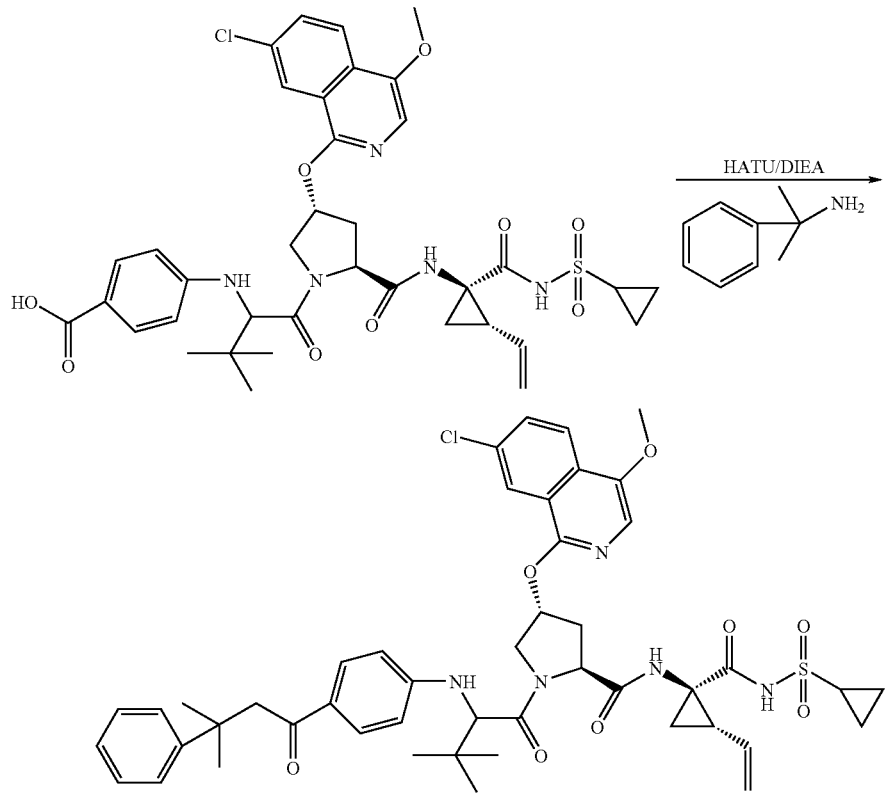

Compounds 222A and 222B
Mixture of isomers

To the solution of 4-((S)-1-((2S,4R)-4-(7-chloro-4-methoxyisoquinolin-1-yloxy)-2-((1R,2S)-1-(cyclopropylsulfonylcarbamoyl)-2-vinylcyclopropylcarbamoyl)pyrrolidin-1-yl)-3,3-dimethyl-1-oxobutan-2-ylamino)benzoic acid (60 mg, 0.078 mmol, compound 209A) and 2-phenylpropane-2-amine (10.56 mg, 0.078 mmol) in methylene chloride at 0° C. was added HATU (60 mg, 0.156 mmol) followed by diisopropylethyl amine (25 mg, 0.21 mmol). A light yellow solution was formed after addition of the base. The mixture was stirred at room temperature for two hours. The reaction mixture was diluted with ethyl acetate (25 ml). and was washed with water (pH~6) and brine. The organic was dried over sodium sulfate, filtered, and concentrated to a yellow oil. Purification by preparative HPLC gave two separate products with identical MS m/z as observed by LCMS.

Compound 222A

White powder (0.01 g, 14.6% yield). $^1$H NMR (400 MHz, CD$_3$OD) δ ppm 1.03-1.12 (m, 11H) 1.20-1.26 (m, 2H) 1.41 (dd, J=9.44, 5.41 Hz, 1H) 1.70 (d, J=3.02 Hz, 6H) 1.87 (dd, J=8.18, 5.41 Hz, 1H) 2.18-2.27 (m, 2H) 2.54 (dd, J=13.72, 6.92 Hz, 1H) 2.92-2.98 (m, 1H) 3.95-4.06 (m, 4H) 4.11 (s, 1H) 4.38 (d, J=12.09 Hz, 1H) 4.55 (dd, J=10.07, 7.05 Hz, 1H) 5.11 (dd, J=10.45, 1.64 Hz, 1H) 5.26-5.30 (dd, J=17.12, J=1.26 Hz, 1H)) 5.69-5.80 (m, 2H) 6.49 (d, J=8.81 Hz, 2H) 7.12-7.17 (m, 1H) 7.22-7.28 (m, 3H) 7.33-7.40 (m, 2H) 7.54 (s, 1H) 7.60 (dd, J=8.94, 2.14 Hz, 1H) 7.83 (d, J=2.27 Hz, 1H) 8.04 (d, J=9.06 Hz, 1H); LC-MS, MS m/z 886 (M$^+$+H).

Compound 222B

LC-MS, MS m/z 886 (M$^+$+H).

Compound 223 Isomers

N-(4-(ethylsulfamoyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(4-(ethylsulfamoyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 223

Preparation of Compounds 223A and 223B

Compounds 223A and 223B

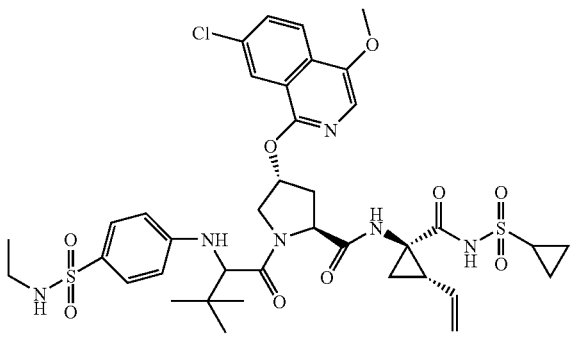

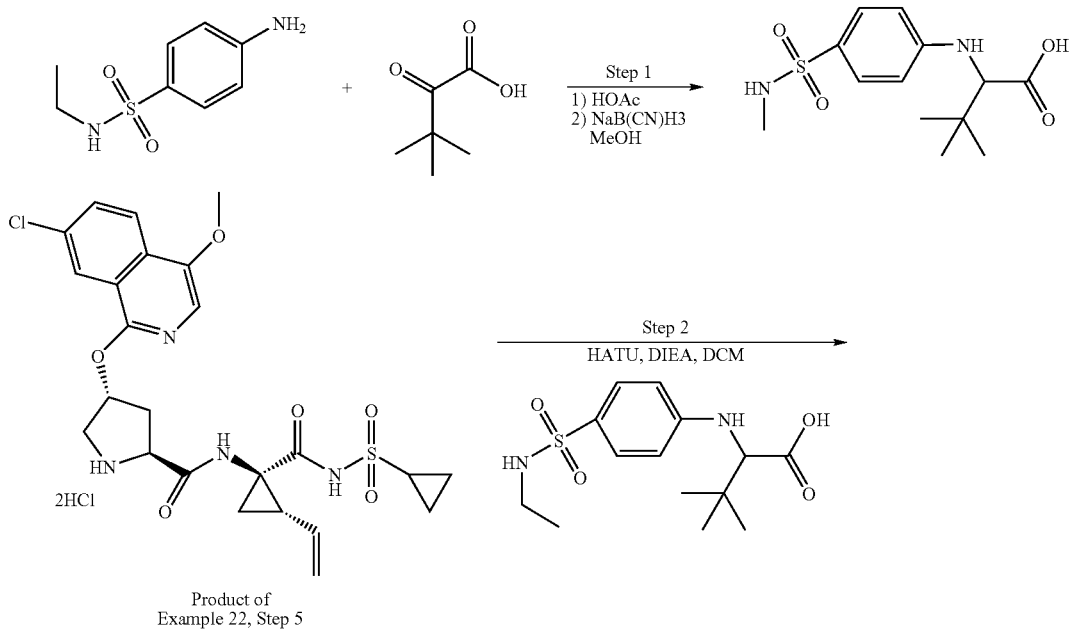

Scheme 1

-continued

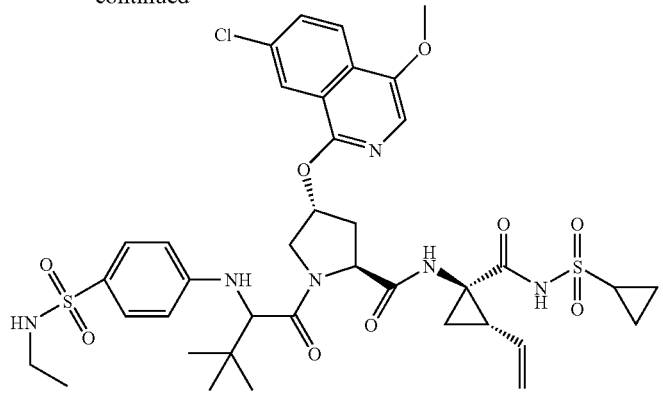

Compounds 223A and 223B
Mixture of isomers

Step 1

To a mixture of 4-amino-N-ethylbenzenesulfonamide (203 mg, 1.014 mmol) and 3,3-dimethyl-2-oxobutanoic acid (264 mg, 2.027 mmol) in a 25 ml RBF at RT was added acetic acid (2 ml,) via a pipet. The color of the mixture soon changed into a characteristic canary color. The solution was warmed to 75° C. for about 120 minutes and the color remained the same. The solution was diluted with methanol (2 ml) at RT, followed by the addition of 1.5× of sodium cyanotrihydroborate (245 mg, 3.90 mmol), and the remaining half after the bubbling and sizzling was over. The color of the solution became lighter. Added 30 ml of water to the mixture, then extracted it with 10 ml of ethyl acetate (adjust pH to 4). The organic was washed with sodium bicarbonate at pH=8. The organic layer dried over $Na_2SO_4$, filtered, and concentrated to an oily residue which was dried under high vacuum. The yellow oil thus obtained was used directly in the next step without further purification. LC-MS, MS m/z 315 ($M^+$+H).

Step 2:

To the yellow solution of 2-(4-(N-ethylsulfamoyl)phenylamino)-3,3-dimethylbutanoic acid (0.059 g, 0.189 mmol step 1, example 223) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.101 g, 0.189 mmol, step 5, example 22) in $CH_2Cl_2$ at 0° C. was added HATU (0.144 g, 0.378 mmol) followed by diisopropylethyl amine (0.061 g, 0.473 mmol). A light yellow solution was formed after addition of the base. The mixture was stirred at room temperature overnight. The reaction mixture was diluted with ethyl acetate (25 ml) and was washed with water (pH~6) and brine. The organic was dried over sodium sulfate, filtered, concentrated, and the residue was purified by reverse phase preparative HPLC to give two separate products with identical MS m/z as observed by LCMS. Compound 223A (0.033 g, 21.0% yield) was the first of the two isomers to elute by reverse phase preparative HPLC. Compound 223B (0.024 g, 15.3.0% yield) was the second of the two isomers to elute by reverse phase preparative HPLC.

Compound 223A $^1$H NMR (400 MHz, $CD_3OD$) δ ppm 0.92 (t, J=7.30 Hz, 3H) 1.02-1.11 (m, 11H) 1.19-1.29 (m, 2H) 1.42 (dd, J=9.44, 5.41 Hz, 1H) 1.87 (dd, J=8.18, 5.41 Hz, 1H) 2.20-2.29 (m, 2H) 2.54-2.64 (m, 3H) 2.95 (ddd, J=12.84, 8.06, 4.78 Hz, 1H) 3.96-4.01 (s, 3H) 4.01-4.09 (m, 2H) 4.45 (d, J=12.09 Hz, 1H) 4.59 (dd, J=10.07, 7.05 Hz, 1H) 5.11 (dd, J=10.32, 1.76 Hz, 1H) 5.29 (dd, J=17.25, 1.39 Hz, 1H) 5.68-5.78 (m, 2H) 6.45-6.50 (m, 2H) 7.04-7.09 (m, 2H) 7.55 (s, 1H) 7.65 (dd, J=8.81, 2.27 Hz, 1H) 7.90 (d, J=1.76 Hz, 1H) 8.08 (d, J=9.06 Hz, 1H); LC-MS, MS m/z 831 ($M^+$+H).

Compound 223B

LC-MS, MS m/z 831 ($M^+$+H).

Compound 224 Isomers

N-(4-(dimethylsulfamoyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(4-(dimethylsulfamoyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 224

Preparation of Compounds 224A and 224B

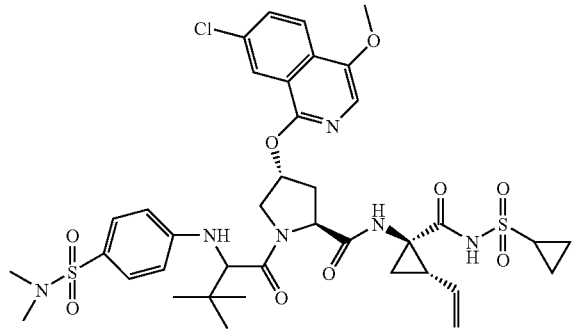

Compounds 224A and 224B

Scheme 1

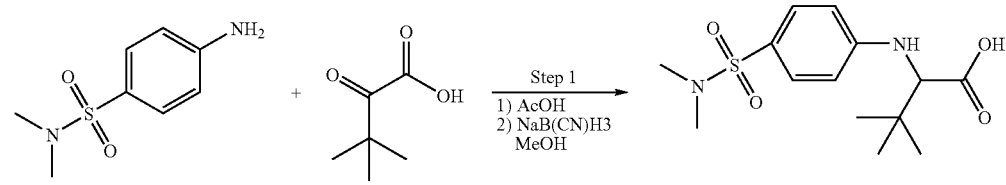

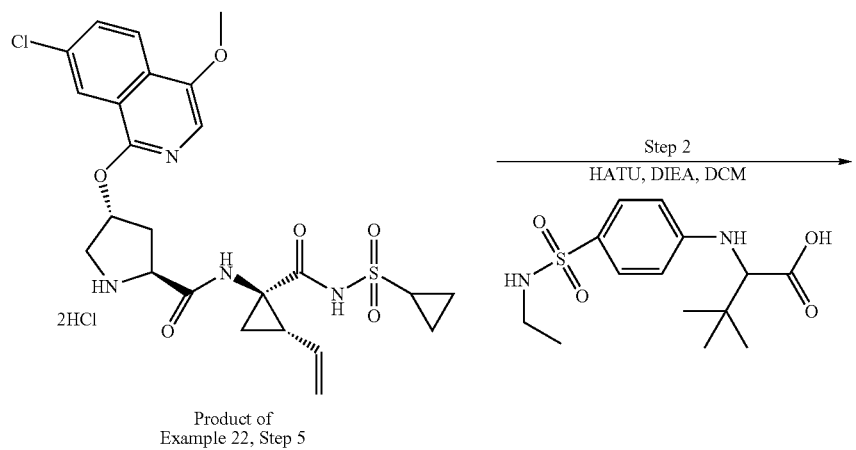

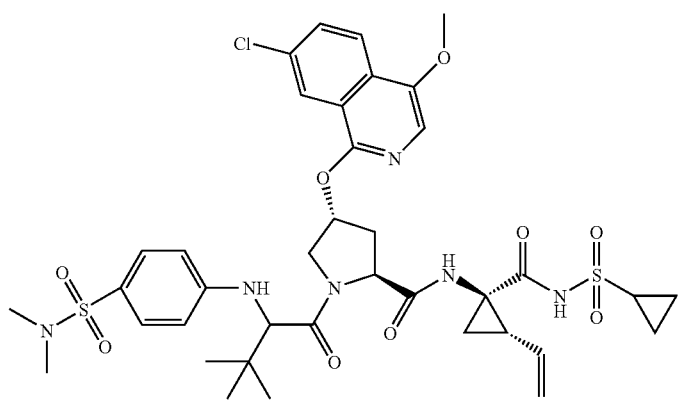

Compounds 224A and 224B
Mixture of isomers

Step 1

To a mixture of 4-amino-N-ethylbenzenesulfonamide (203 mg, 1.014 mmol) and 3,3-dimethyl-2-oxobutanoic acid (264 mg, 2.027 mmol) in a 100 ml RBF at RT was added 2 ml of acetic acid. The solution was warmed to 75° C. for about 120 minutes. The solution was diluted with methanol (2 ml) at RT, followed by the addition of 1.5× of sodium cyanotrihydroborate (245 mg, 3.90 mmol), and the remaining half after the bubbling and sizzling was over. The color of the solution became lighter. Added 30 ml of water to the mixture, then extracted it with 10 ml of ethyl acetate (adjust pH to 4). The organic was washed with sodium bicarbonate at pH=8. The organic layer was dried over Na$_2$SO$_4$, filtered, and concentrated to a yellow oil which was dried under high vacuum. This material was used directly in the next step without further purification. LC-MS, MS m/z 315 (M$^+$+H).

Step 2:

To the yellow solution of 2-(4-(N,N-dimethylsulfamoyl)phenylamino)-3,3-dimethylbutanoic acid (0.059 g, 0.189 mmol step 1, example 224) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.101 g, 0.189 mmol, step 5, example 22) in CH$_2$Cl$_2$ at 0° C. was added HATU (0.144 g, 0.378 mmol) followed by diisopropylethyl amine (0.061 g, 0.473 mmol). A light yellow solution was formed after addition of the base. The mixture was stirred at room temperature overnight. The reaction mixture was diluted with ethyl acetate (25 ml) and was washed with water (pH~6) and brine. The organic was dried over sodium sulfate, filtered, concentrated, and the residue was purified by reverse phase preparative HPLC to give two separate products with identical MS m/z as observed by LCMS. Compound 224A (0.020 g, 13.0% yield) was the first of the two isomers to elute by reverse phase preparative HPLC. Compound 224B (0.014 g, 9.0% yield) was the second of the two isomers to elute by reverse phase preparative HPLC.

Compound 224A $^1$H NMR (400 MHz, CD$_3$OD) δ ppm 1.03-1.12 (m, 11H) 1.22-1.26 (m, 2H) 1.42 (dd, J=9.32, 5.54 Hz, 1H) 1.88 (dd, J=8.18, 5.41 Hz, 1H) 2.20-2.31 (m, 2H) 2.35-2.40 (m, 6H) 2.53-2.64 (m, 1H) 2.91-3.00 (m, 1H) 3.95-4.00 (s, 3H) 4.03-4.09 (m, 2H) 4.51 (d, J=12.09 Hz, 1H) 4.57-4.67 (m, 1H) 5.11 (dd, J=10.32, 1.51 Hz, 1H) 5.29 (dd, J=17.12, 1.26 Hz, 1H) 5.68-5.79 (m, 2H) 6.47 (d, J=9.06 Hz, 2H) 6.93 (d, J=8.81 Hz, 2H) 7.53-7.57 (s, 1H) 7.63-7.69 (m, 1H) 7.91 (d, J=2.01 Hz, 1H) 8.03-8.12 (m, 1H); LC-MS, MS m/z 831 (M$^+$+H).

Compound 224B

LC-MS, MS m/z 831 (M$^+$+H).

Compound 226 Isomers

N-(4-carbamoylphenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(4-carbamoylphenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 226

Preparation of Compounds 226A and 226B

Compounds 226A and 226B

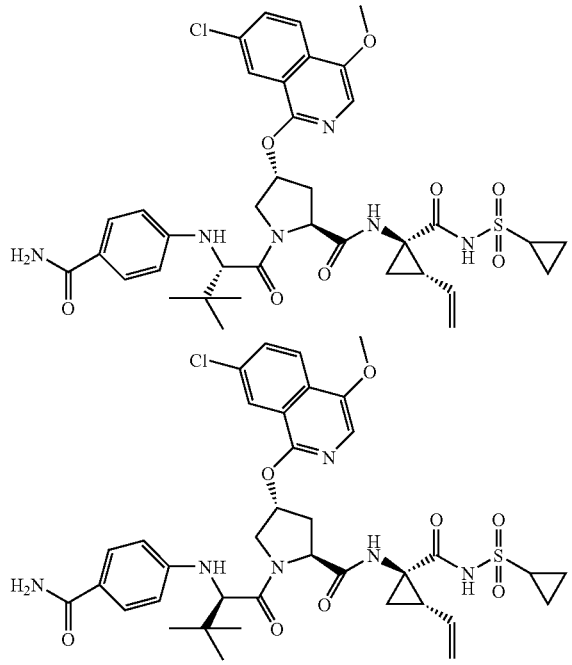

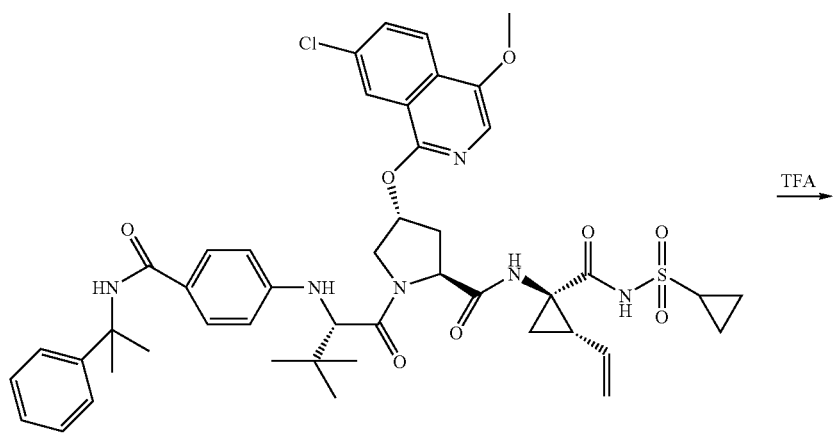

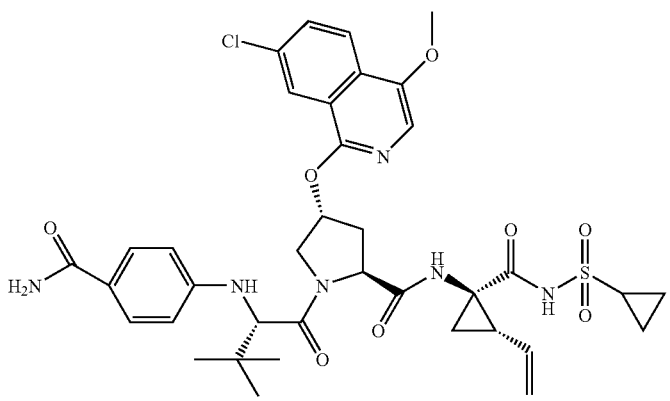

(2S,4R)-4-(7-chloro-4-methoxyisoquinolin-1-yloxy)-N-((1R,2S)-1-(cyclopropylsulfonylcarbamoyl)-2-vinylcyclopropyl)-1-((S)-3,3-dimethyl-2-(4-(2-phenylpropan-2-ylcarbamoyl)phenylamino)butanoyl)pyrrolidine-2-carboxamide (8 mg, 0.009 mmol, compound 222A) was dissolved in 1 ml of 2,2,2-trifluoroacetic acid at 25° C. The resulting mixture was stirred overnight. The TFA was removed and the residue was purified by preparative HPLC to afford Compound 226A as a white powder (0.005 g, 81% yield). $^1$H NMR (400 MHz, CD$_3$OD) δ ppm 1.04-1.12 (m, 11 H) 1.23-1.33 (m, 2H) 1.42 (dd, J=9.57, 5.29 Hz, 1H) 1.87 (dd, J=8.18, 5.41 Hz, 1H) 2.19-2.27 (m, 2H) 2.54 (dd, J=13.72, 7.43 Hz, 1H) 2.92-2.98 (m, 1H) 3.98-4.05 (m, 4H) 4.12 (s, 1H) 4.33 (d, J=12.59 Hz, 1H) 4.55 (dd, J=10.32, 7.05 Hz, 1H) 5.11 (dd, J=10.32, 1.76 Hz, 1H) 5.27 (m, 2H) 5.72-5.79 (m, 2H) 6.45-6.49 (m, 2H) 7.22-7.25 (2, 4H) 7.52 (s, 1H) 7.62 (dd, J=8.94, 2.14 Hz, 1H) 7.79 (d, J=2.01 Hz, 1H) 8.05 (d, J=8.81 Hz, 1H); LC-MS, MS m/z 767 (M$^+$+H).

Compound 226B was made from compound 222B by the same procedure as was used for the preparation of compound 226A. LC-MS, MS m/z 767 (M$^+$+H).

Compound 227 Isomers 3-methyl-N-(3-(methylsulfamoyl)phenyl)-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and 3-methyl-N-(3-(methylsulfamoyl)phenyl)-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 227

Preparation of Compounds 227A and 227B

Compounds 227A and 227B

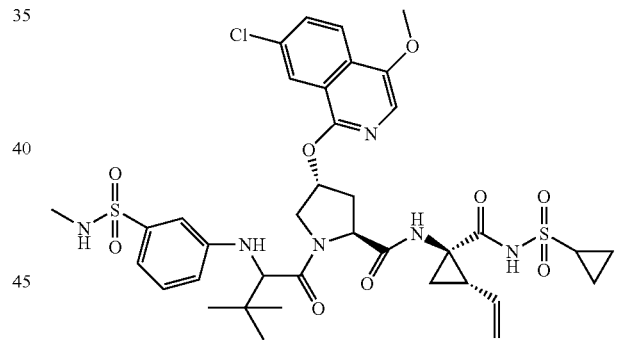

Scheme 1

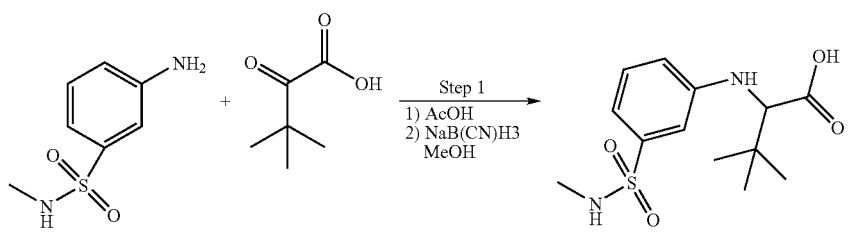

-continued

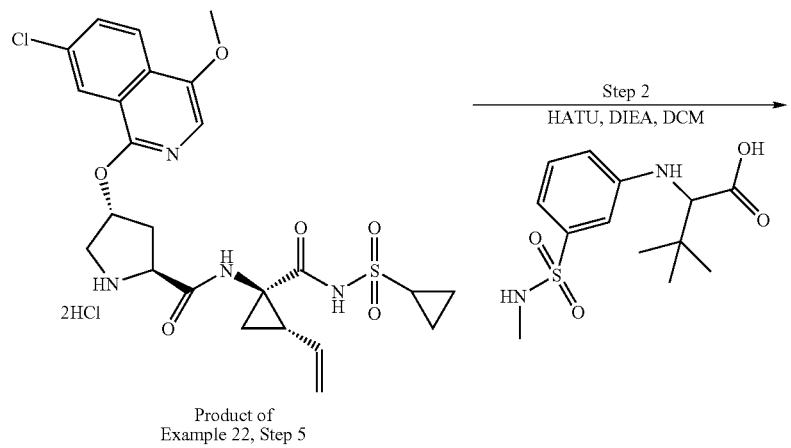

Product of
Example 22, Step 5

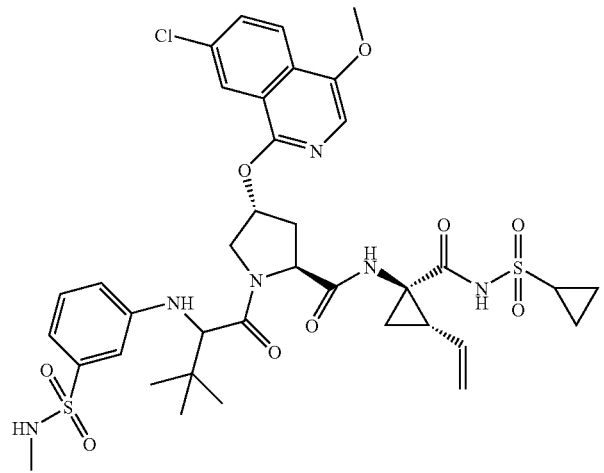

Compounds 227A and 227B
Mixture of isomers

Step 1

To a mixture of 3-amino-N-methylbenzenesulfonamide (203 mg, 1.09 mmol) and 3,3-dimethyl-2-oxobutanoic acid (264 mg, 2.027 mmol) in a 25 ml RBF at RT was added 2 ml of acetic acid. The solution was warmed to 75° C. for about 120 minutes. The solution was diluted with methanol (2 ml) at RT, followed by the addition of 1.5× of sodium cyanotrihydroborate (245 mg, 3.90 mmol), and the remaining half after the bubbling and sizzling was over. The color of the solution became lighter. Added 30 ml of water to the mixture, then extracted it with 10 ml of ethyl acetate (adjust pH to 4). The organic was washed with sodium bicarbonate at pH=8. The organic layer was dried over $Na_2SO_4$, filtered, and concentrated to a yellow oil which was dried under high vacuum. This material was used directly in the next step without further purification. LC-MS, MS m/z 301 ($M^+$+H).

Step 2:

To the yellow solution of 2-(3-(N,-methylsulfamoyl)phenylamino)-3,3-dimethylbutanoic acid (0.034 g, 0.114 mmol step 1, example 227) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.101 g, 0.189 mmol, step 5, example 22) in $CH_2Cl_2$ at 0° C. was added HATU (0.087 g, 0.228 mmol) followed by diisopropylethyl amine (0.061 g, 0.473 mmol). A light yellow solution was formed after addition of the base. The mixture was stirred at room temperature overnight. The reaction mixture was diluted with ethyl acetate (25 ml) and was washed with water (pH~6) and brine. The organic was dried over sodium sulfate, filtered, concentrated, and the residue was purified by reverse phase preparative HPLC to give two separate products with identical MS m/z as observed by LCMS. Compound 227A (0.013 g, 14.0% yield) was the first of the two isomers to elute by reverse phase preparative HPLC. Compound 227B (0.009 g, 9.0% yield) was the second of the two isomers to elute by reverse phase preparative HPLC.

Compound 227A $^1$H NMR (400 MHz, $CD_3OD$) δ ppm 1.04-1.12 (m, 11 H) 1.17-1.27 (m, 2H) 1.42 (dd, J=9.44, 5.41 Hz, 1H) 1.87 (dd, J=8.18, 5.41 Hz, 1H) 2.18-2.27 (m, 2H) 2.38 (s, 3H) 2.52 (dd, J=13.47, 6.92 Hz, 1H) 2.95 (ddd, J=12.78, 8.12, 4.78 Hz, 1H) 3.97-4.01 (s, 3H) 4.03-4.11 (m, 2H) 4.30 (d, J=12.09 Hz, 1H) 4.52 (dd, J=10.07, 7.05 Hz, 1H) 5.11 (dd, J=10.32, 1.51 Hz, 1H) 5.28 (dd, J=17.25, 1.38 Hz, 1H) 5.69-5.79 (m, 2H) 6.53-6.63 (m, 2H) 6.77 (d, J=7.55 Hz, 1H) 7.08 (t, J=1.89 Hz, 1H) 7.53-7.57 (m, 1H) 7.65-7.69 (m, 1H) 7.84 (d, J=1.76 Hz, 1H) 8.08 (d, J=8.81 Hz, 1H); LC-MS, MS m/z 817 ($M^+$+H).

Compound 227B

LC-MS, MS m/z 817 ($M^+$+H).

Compound 231 Isomers

N-(3-(isopropoxycarbonyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(3-(isopropoxycarbonyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 231

Preparation of Compounds 231A and 231B

Compounds 231A and 231B

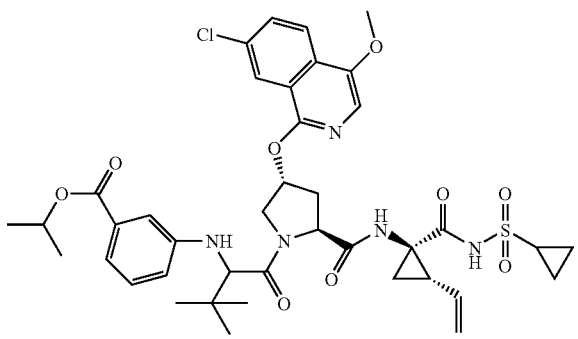

Scheme 1

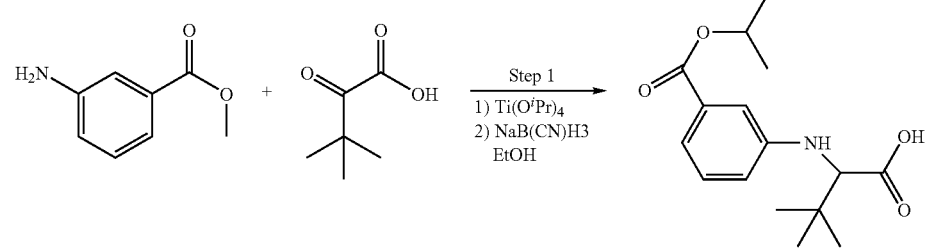

-continued

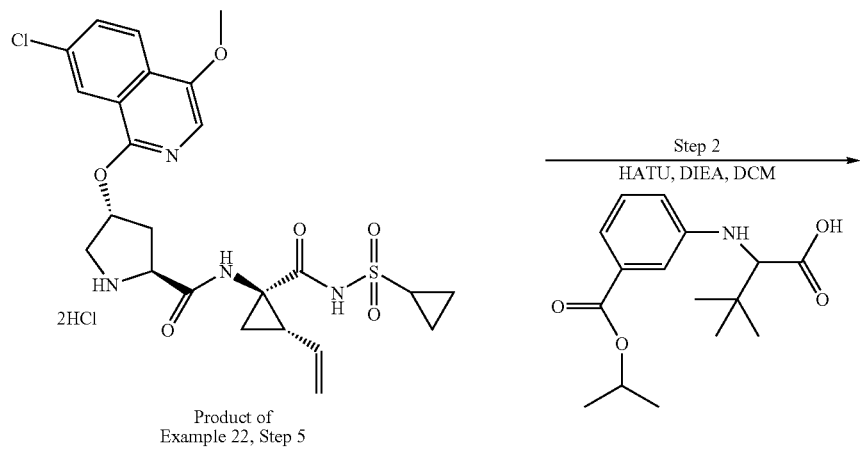

Product of
Example 22, Step 5

Step 2
HATU, DIEA, DCM

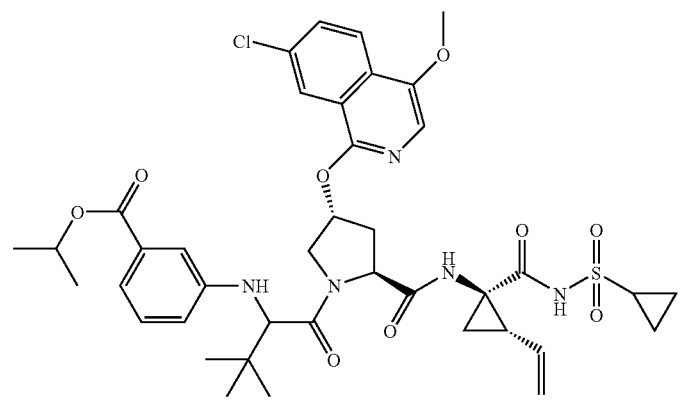

Compounds 231A and 231B
Mixture of isomers

Step 1:

To a mixture of methyl 3-benzoate (230 mg, 1.52 mmol) and 3,3-dimethyl-2-oxobutanoic acid (198 mg, 1.52 mmol) in a 100 mL RBF at RT was added tetraisopropoxytitanium (2 ml,) via a pipet. The color of the mixture soon changed into a characteristic canary color. The solution was warmed to 75° C. for about 15 minutes and the color remained the same. The solution was diluted with absolute ethanol (8 ml) at RT, followed by the addition of 1.5× of sodium cyanotrihydroborate (245 mg, 3.90 mmol), and the remaining half after the bubbling and sizzling was over. The color of the solution became lighter. The solution was mixed with 4 mL of water, forming a suspension, the white PPT was removed by centrifuge. The organic was extracted into ethyl acetate, and the organic phase was dried over $Na_2SO_4$, filtered, and evaporated to a white foam. This material was used directly in the next step without further purification. LC-MS, MS m/z 294 ($M^+$+H)

Step 2:

To the yellow solution of 2-(3-(isopropoxycarbonyl)phenylamino)-3,3-dimethylbutanoic acid (0.055 g, 0.189 mmol, step 1, example 231) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.101 g, 0.189 mmol, step 5, example 22) in $CH_2Cl_2$ at 0° C. was added HATU (0.144 g, 0.378 mmol) followed by diisopropylethyl amine (0.061 g, 0.473 mmol). A light yellow solution was formed after addition of base. The mixture was stirred at room temperature overnight. The reaction mixture was diluted with ethyl acetate (25 ml) and was washed with water (pH~6) and brine. The organic was dried over sodium sulfate, filtered, concentrated, and the residue was purified by reverse phase preparative HPLC to give two separate products with identical MS m/z as observed by LCMS. Compound 231A (0.0235 g, 15.3.0% yield) was the first of the two isomers to elute by reverse phase preparative HPLC. Compound 231B (0.0175 g, 11.6% yield) was the second of the two isomers to elute by reverse phase preparative HPLC.

Compound 231A $^1$H NMR (400 MHz, $CD_3OD$) δ ppm 1.04-1.14 (m, 11H) 1.19-1.29 (m, 6H) 1.29-1.38 (m, 2H) 1.38-1.43 (m, 1H) 1.81-1.89 (m, 1H) 2.16-2.25 (m, 2H) 2.47 (dd, J=13.60, 7.05 Hz, 1H) 2.95 (ddd, J=12.78, 8.12, 4.78 Hz, 1H) 3.96-4.02 (m, 4H) 4.02-4.08 (m, 1H) 4.14-4.24 (m, 1H) 4.42-4.53 (m, 1H) 4.93-5.03 (m, J=6.24, 6.24, 6.24, 6.24, 6.24 Hz, 1H) 5.06-5.16 (m, 1H) 5.20-5.32 (m, 1H) 5.68-5.78 (m, 2H) 6.54 (t, J=7.81 Hz, 1H) 6.60-6.69 (m, 1H) 6.87 (d, J=7.55 Hz, 1H) 7.20-7.26 (m, 1H) 7.45-7.52 (m, 1H) 7.58-7.68 (m, 2H) 7.97-8.06 (m, 1H); LC-MS, MS m/z 810 ($M^+$+H).

Compound 231B

LC-MS, MS m/z 810 ($M^+$+H).

Compound 232 Isomers

N-(3-(methoxycarbonyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide and N-(3-(methoxycarbonyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide Example 232

Preparation of Compounds 232A and 232B

Compounds 232A and 232B

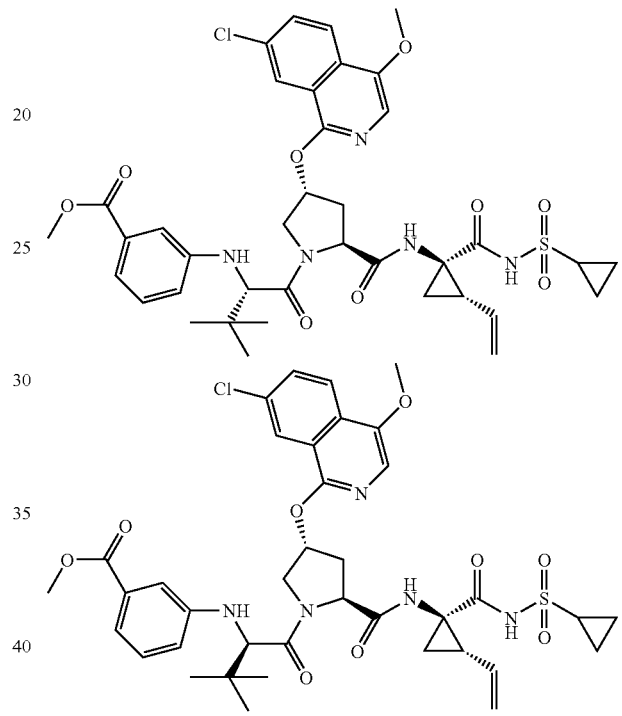

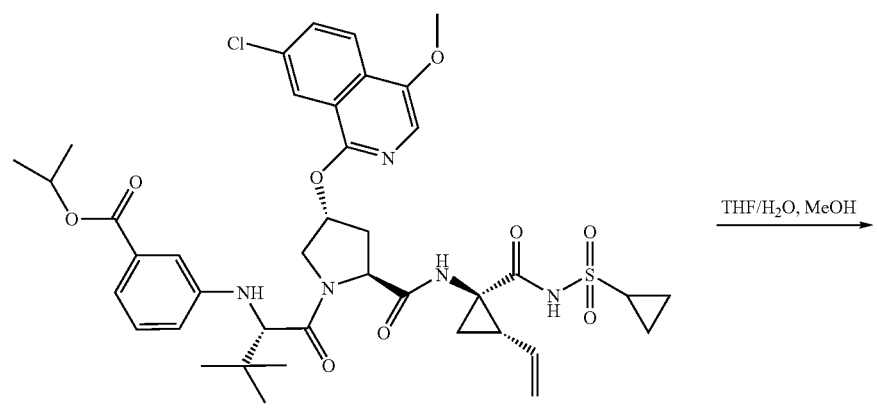

Compound 231A

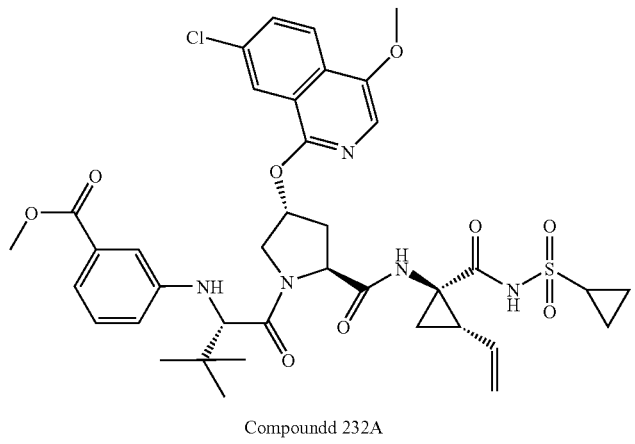

Compoundd 232A isopropyl 3-((S)-1-((2S,4R)-4-(7-chloro-4-methoxyisoquinolin-1-yloxy)-2-((1R,2S)-1-(cyclopropylsulfonylcarbamoyl)-2-vinylcyclopropylcarbamoyl)pyrrolidin-1-yl)-3,3-dimethyl-1-oxobutan-2-ylamino)benzoate (20 mg, 0.025 mmol, compound 231A) was dissolved in THF (0.200 ml) and MeOH (0.2 ml) at 25° C. 10M aqueous lithium hydroxide (0.049 ml, 0.049 mmol) was added dropwise, and the mixture was stirred for 4 hours. The reaction mixture was diluted with ethyl acetate (25 ml) and was washed with water (pH~4) and brine. The organic was dried over sodium sulfate, filtered, concentrated, and the residue was purified by reverse phase preparative HPLC to give Compound 232A (0.005 g, 25.6%). $^1$H NMR (400 MHz, CD$_3$OD) δ ppm 0.89-1.02 (m, 2H) 1.04-1.12 (m, 11H) 1.29-1.36 (m, 2H) 1.42 (dd, J=9.44, 5.41 Hz, 1H) 1.87 (dd, J=8.06, 5.54 Hz, 1H) 2.16-2.25 (m, 2H) 2.46 (d, J=6.55 Hz, 1H) 2.91-2.99 (m, 1H) 3.63-3.71 (m, 3H) 3.93-4.03 (m, 4H) 4.08 (m, 1H) 4.21 (s, 1H) 4.51 (dd, J=10.32, 7.05 Hz, 1H) 5.06-5.16 (m, 1H) 5.28 (d, J=17.37 Hz, 1H) 5.70-5.79 (m, 2H) 6.58 (t, J=7.81 Hz, 1H) 6.69 (dd, J=8.06, 1.51 Hz, 1H) 6.80 (d, J=7.55 Hz, 1H) 7.18 (s, 1H) 7.50 (s, 1H) 7.61-7.69 (m, 2H) 8.04-8.11 (m, 1H); LC-MS, MS m/z 782 (M$^+$+H).

Compound 232B was made from compound 231B by same method as described for the preparation of compound 232A. LC-MS, MS m/z 782 (M$^+$+H).

Compound 233 Isomers (4R)-4-((7-chloro-4-methoxy-1-isoquinolinyl)oxy)-N-((1R,2S)-1-(((cyclopropylsulfonyl)carbamoyl)-2-vinylcyclopropyl)-1-((2S)-2-((4-ethoxy-1,2,5-thiadiazol-3-yl)amino)butanoyl)-L-prolinamide and (4R)-4-((7-chloro-4-methoxy-1-isoquinolinyl)oxy)-N-((1R,2S)-1-(((cyclopropylsulfonyl)carbamoyl)-2-vinylcyclopropyl)-1-((2R)-2-((4-ethoxy-1,2,5-thiadiazol-3-yl)amino)butanoyl)-L-prolinamide Example 233

Preparation of Compounds 233A and 233B

Compounds 233A and 233B

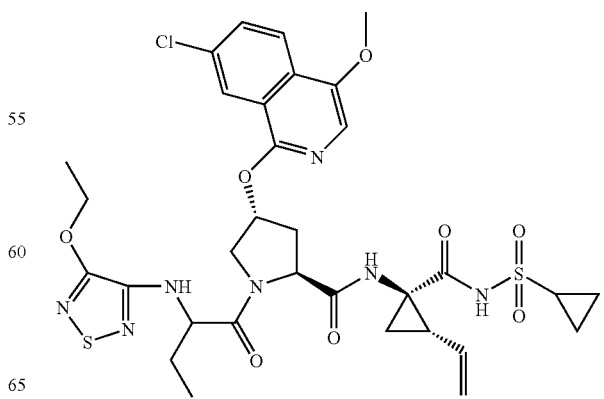

253 254

Step 1

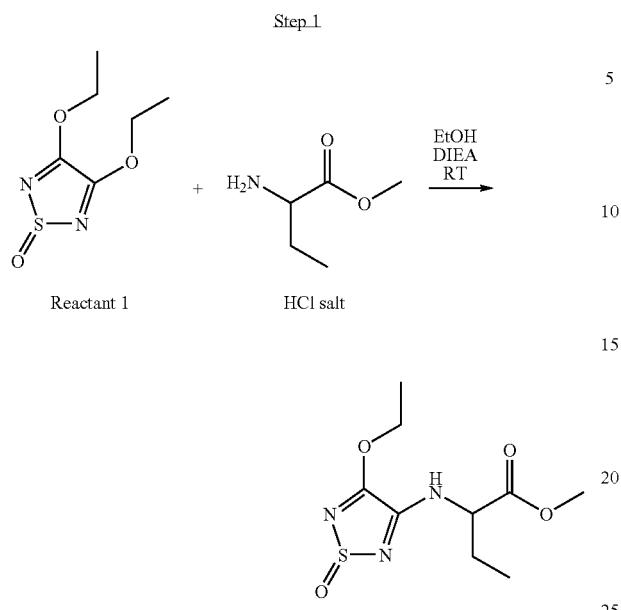

Reactant 1      HCl salt

Step 1:

To a solution of Reactant 1 (0.114 g, 0.6 mmol) in EtOH (5 ml) at 25° C. was added methyl 2-aminobutanoate (0.070 g, 0.600 mmol) followed by DIEA (0.210 ml, 1.200 mmol). The mixture was stirred overnight at room temperature. Solvent was removed, and the material was dried under high vacuum. This material was used directly in the next step without further purification.

step 2

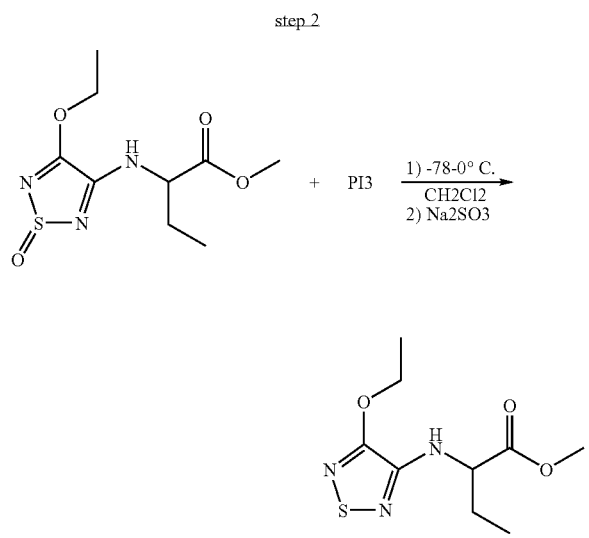

Step 2:

To a yellow solution of the product of example 233, step 1 (0.157 g, 0.6 mmol) in CH$_2$Cl$_2$ (8 ml) at −78° C. was added triiodophosphine (0.247 g, 0.600 mmol). An orange suspension was obtained. The mixture was allowed to warm up to 0° C. over 2 h. A dark brown solution formed. The reaction mixture was diluted with ethyl acetate (15 ml) and washed with sodium bisulfite (2 g in 10 ml of water), H$_2$O, and sat NaCl. The organic was dried over Na$_2$SO$_4$, filtered and concentrated. The crude product was purified by silica gel column (elution with 5-15% ethyl acetate in hexanes). A colorless oil was thus obtained.

step 3

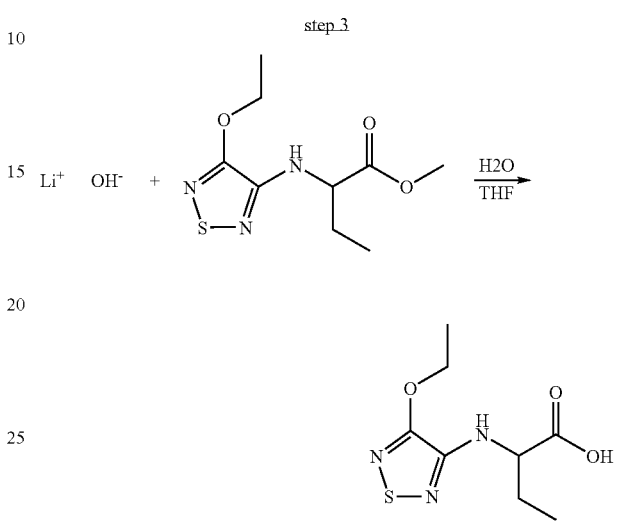

Step 3:

To the solution of methyl 2-(4-ethoxy-1,2,5-thiadiazol-3-ylamino)butanoate (57 mg, 0.232 mmol) in 4 ml of THF at rt was added lithium hydroxide (6.68 mg, 0.279 mmol) and water (0.6 ml). The mixture was stirred for 2 h. The mixture was adjusted to pH4 and was extracted with ethyl acetate (10 ml×2). The organic layers were combined and washed with water (1×10 mL). The organic was dried over Na$_2$SO$_4$, filtered and concentrated to afford a white solid.

step 4

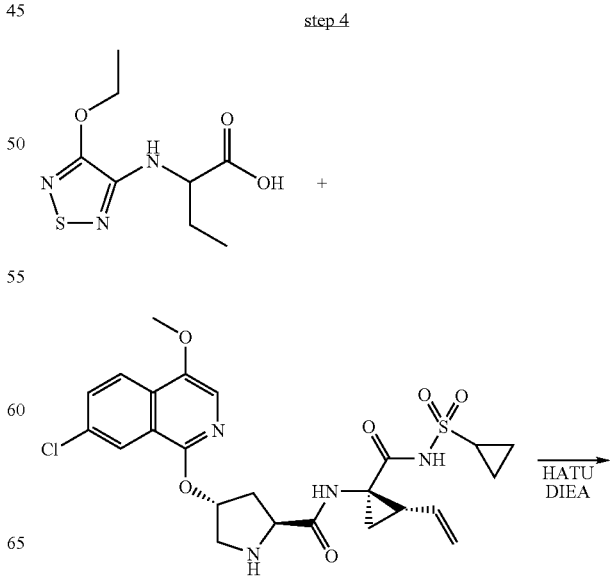

-continued

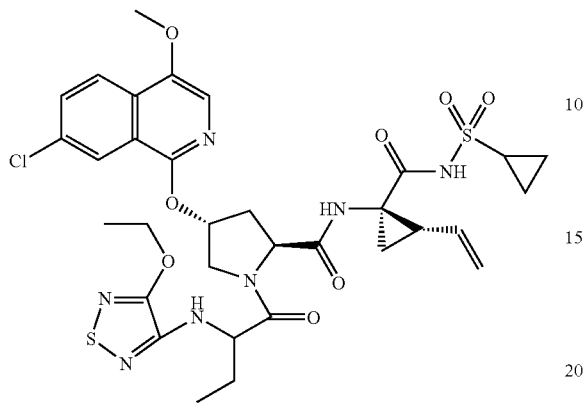

compound 233A and
compound 233B

Step 4:

To the yellow solution of 2-(4-ethoxy-1,2,5-thiadiazol-3-ylamino)butanoic acid (23.34 mg, 0.101 mmol) and (2S,4R)-4-(7-chloro-4-methoxyisoquinolin-1-yloxy)-N-((1R,2S)-1-(cyclopropylsulfonylcarbamoyl)-2-vinylcyclopropyl) pyrrolidine-2-carboxamide (54 mg, 0.101 mmol) at 0° C. was added HATU (77 mg, 0.202 mmol) followed by diisopropylethyl amine (32.6 mg, 0.252 mmol). A yellow solution was formed. The mixture was stirred overnight at room temperature. The reaction mixture was diluted with ethyl acetate (15 ml) and was washed with H$_2$O (pH=6) and brine. The organic was dried over Na$_2$SO$_4$, filtered and concentrated. The crude material was purified by preparative HPLC to give two separate products with identical MS m/z as observed by LCMS. Compound 233A (0.046 g, 5.3% yield) was the first of the two isomers to elute by reverse phase preparative HPLC. Compound 233B (0.085 g, 10% yield was the second of the two isomers to elute by reverse phase preparative HPLC.

Compound 233A

LC-MS, MS m/z 748 (M$^+$+H).

Compound 233B

LC-MS, MS m/z 748 (M$^+$+H).

Compound 234 Isomers

N-(2-fluorophenyl)-3-methyl-D-valyl-(4R)-4-[(7-chloro-4-methoxy-1-isoquinolinyl)oxy]-N-((1R,2S)-1-{[(cyclopropylsulfonyl)amino]carbonyl}-2-vinyl-cyclopropyl)-L-prolinamide and N-(2-fluorophenyl)-3-methyl-L-valyl-(4R)-4-[(7-chloro-4-methoxy-1-isoquinolinyl)oxy]-N-((1R,2S)-1-{[(cyclopropylsulfonyl)amino]carbonyl}-2-vinyl-cyclopropyl)-L-prolinamide Example 234

Preparation of Compounds 234A and 234B

Compounds 234A and 234B

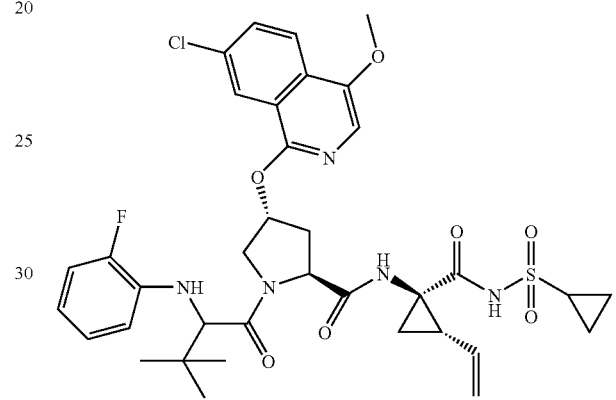

Scheme 1

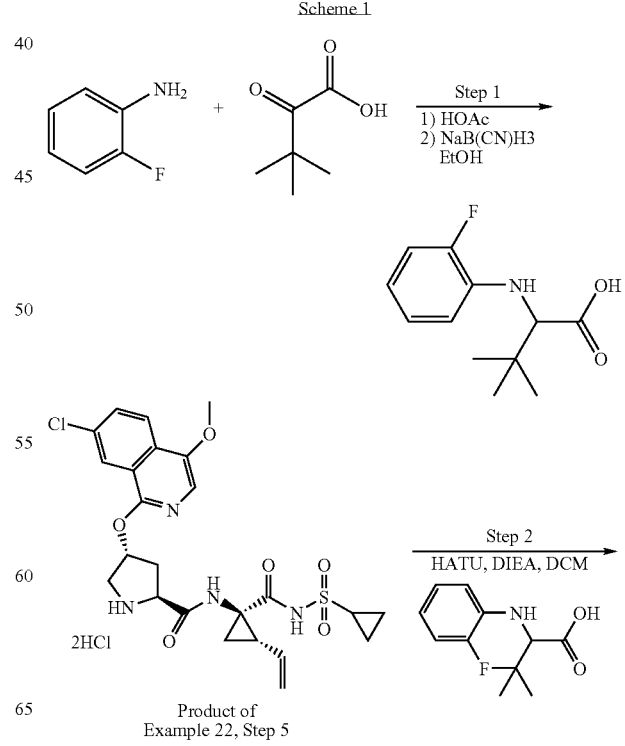

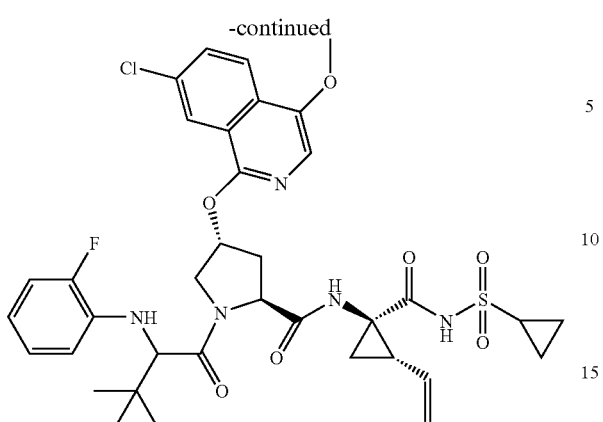

Compounds 234A and 234B
Mixture of isomers

Step 1:

To a mixture of 2-fluoroaniline (203 mg, 1.827 mmol) and 3,3-dimethyl-2-oxobutanoic acid (476 mg, 3.65 mmol) in a 100 ml RBF at RT was added acetic acid (2 ml) via a pipet. The color of the mixture soon changed into a characteristic canary color. The solution was warmed to 75° C. for about 120 minutes and the color remained the same. The solution was diluted with methanol (2 ml) at RT, followed by the addition of 0.5× of sodium cyanotrihydroborate (230 mg, 3.65 mmol)), and the remaining half after the bubbling and sizzling was over. The color of the solution became lighter. Added 30 ml of water to the mixture, then extracted it with 10 ml of ethyl acetate (adjust pH to 4). Then the organic was washed with sodium bicarbonate at pH=8. The organic layer dried over $Na_2SO_4$, filtered, and concentrated to a yellow oil. The material was purified by preparative HPLC and carried into the next step. LC-MS, MS m/z 226 ($M^++H$).

Step 2:

To the yellow solution of 2-(2-fluorophenylamino)-3,3-dimethylbutanoic acid (63.2 mg, 0.280 mmol, step 1, example 234) and (2S,4R)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide (0.150 g, 0.28 mmol, step 5, example 22) in $CH_2Cl_2$ at 0° C. was added HATU (0.213 g, 0.561 mmol) followed by diisopropylethyl amine (0.091 g, 0.701 mmol). A light yellow solution was formed after addition of the base. The mixture was stirred at room temperature overnight. The reaction mixture was diluted with ethyl acetate (25 ml) and was washed with water (pH~6) and brine. The organic was dried over sodium sulfate, filtered, concentrated, and the residue was purified by reverse phase preparative HPLC to give two separate products with identical MS m/z as observed by LCMS. Compound 234A (0.050 g, 24% yield) was the first of the two isomers to elute by reverse phase preparative HPLC. Compound 234B (0.038 g, 18.2% yield) was the second of the two isomers to elute by reverse phase preparative HPLC.

Compound 234A $^1$H NMR (400 MHz, $CD_3OD$) δ ppm 0.99-1.08 (m, 2H) 1.09-1.17 (m, 9H) 1.20-1.29 (m, 2H) 1.40 (dd, J=9.44, 5.41 Hz, 1H) 1.86 (dd, J=8.06, 5.54 Hz, 1H) 2.17-2.27 (m, 2H) 2.52 (dd, J=13.72, 6.92 Hz, 1H) 2.94 (ddd, J=12.78, 8.12, 4.78 Hz, 1H) 3.97-4.04 (m, 5H) 4.27 (d, J=12.09 Hz, 1H) 4.50 (dd, J=10.45, 6.92 Hz, 1H) 5.11 (dd, J=10.32, 1.51 Hz, 1H) 5.28 (dd, J=17.12, 1.51 Hz, 1H) 5.67-5.77 (m, 2H) 6.08-6.14 (m, 1H) 6.14-6.20 (m, 1H) 6.40-6.47 (m, 1H) 6.58 (ddd, J=11.96, 8.06, 1.39 Hz, 1H) 7.56 (s, 1H) 7.69 (dd, J=8.81, 2.01 Hz, 1H) 7.77 (d, J=2.01 Hz, 1H) 8.10 (d, J=8.81 Hz, 1H); LC-MS, MS m/z 742 ($M^++H$).

Compound 234B

LC-MS, MS m/z 742 ($M^++H$).

Compound 235 Isomers

N-(3, 4-difluorophenyl)-3-methyl-L-valyl-(4R)—N-((1R,2S)-1-((cyclopropylsulfonyl)carbamoyl)-2-vinylcyclopropyl)-4-((9-methoxy-4-methyl-3,4-dihydro-2H-[1,4]oxazino[3,2-c]isoquinolin-6-yl)oxy)-L-prolinamide and N-(3, 4-difluorophenyl)-3-methyl-D-valyl-(4R)—N-((1R,2S)-1-((cyclopropylsulfonyl)carbamoyl)-2-vinylcyclopropyl)-4-((9-methoxy-4-methyl-3,4-dihydro-2H-[1,4]oxazino[3,2-c]isoquinolin-6-yl)oxy)-L-prolinamide Example 235

Preparation of Compounds 235A and 235B

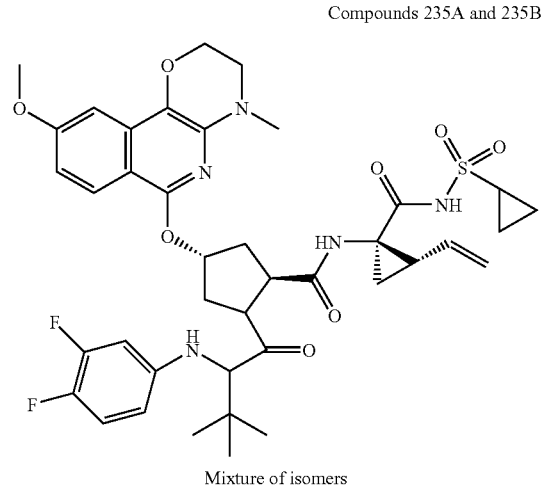

Compounds 235A and 235B

Mixture of isomers scheme 1

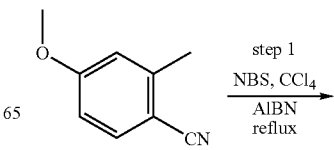

step 1
NBS, $CCl_4$
AIBN
reflux

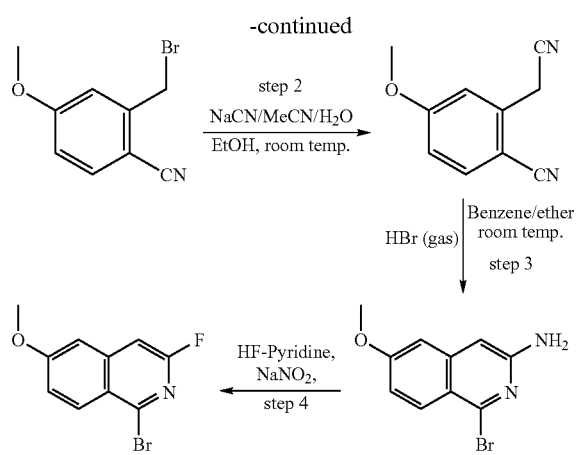

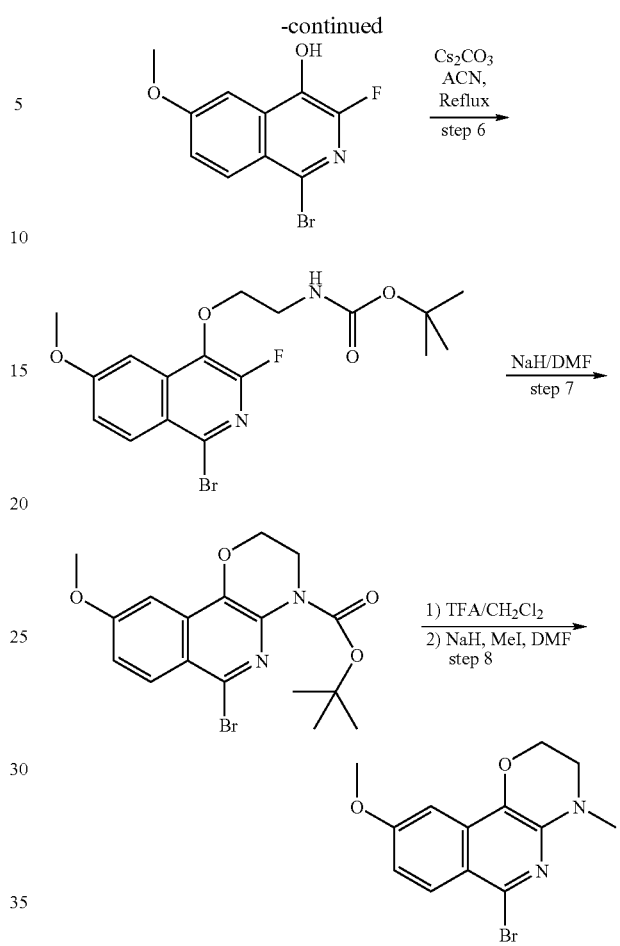

Step 1

4-methoxy-2-methylbenzonitrile (50 g, 340 mmole) and NBS (62 g, 350 mmole) were suspended in $CCl_4$ (500 ml) and AIBN (5 g, 10% wt) was added. The mixture was heated at flux overnight. Filtered off precipitate and removed the solvent. The brown oil was purified by flash column (2-5% acetone:hexanes). White crystal (36 g) were obtained.

Step 2

2-(Bromomethyl)-4-methoxybenzonitrile (36 g, example 235, step 1) was suspended in 200 ml of ethanol, 200 ml of acetonitrile was added followed by KCN (8.3 g) and 150 ml of water. Mixture was stirred and the colorless solution turned to yellow. The reaction was complete after 4 hours of stirring. The volatiles were removed under vacuum, and the residual solid was redissolved in ethyl acetate (200 ml) and washed with water (100 ml) and brine (100 ml). The organics were then dried over sodium sulfate. Ethyl acetate was removed and the residue was recrystallized from ethyl acetate and dichloride methane to provide 17 g of 2-(cyanomethyl)-4-methoxybenzonitrile.

Step 3

See J. Med. Chem., 1970, Vol. 13, No. 4, pp 613 for preparation of 1-bromo-6-methoxyisoquinolin-3-amine.

Step 4

1-bromo-6-methoxyisoquinolin-3-amine (1.5 g, example 235, step 3) was dissolved in HF-Py (12.5 ml) at −10° C., and $NaNO_2$ (600 mg) was added. A yellow solid was observed to form. The reaction mixture was suspended in large amount of water, adjusted PH to 5, extracted with ethyl acetate (3×30 ml), washed with water and brine, then dried over sodium sulfate. Light yellow solid (1.2 g) was obtained after flash column purification.

scheme 2

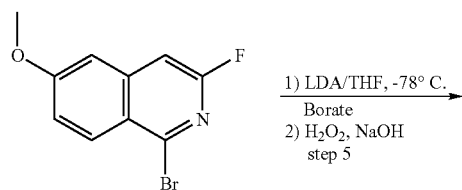

Step 5

1-bromo-3-fluoro-6-methoxyisoquinoline (322 mg, 1.26 mmol, example 235, step 4) was dissolved in THF (7 ml) at −78° C., LDA (1.5 M, 2.52 ml) was added dropwise, stirred for 30 min, then isopropyl borate (477 mg, 585 ul) was added. 30 minutes later, the reaction was quenched by sat. $NH_4Cl$ and 1 N HCl, extracted with ethyl acetate (3×30 ml). Removed solvent to dryness. The residue was dissolved in $CH_2Cl_2$ (8 ml), NaOH (1 N, 4 ml) was added followed by $H_2O_2$ (1.2 ml, 50%). Gas evolution was observed. Stirred for 30 min. Yellow paste formed. The mixture was taken up in 50 ml of ethyl acetate, the organic layer was washed with sodium bisulfite solution, and brine, then dried over sodium sulfate. Purified by silica gel (eluted with 5-10% ethyl acetate:hexane). 200 mg of yellow solid obtained.

Step 6

1-bromo-3-fluoro-6-methoxyisoquinolin-4-ol (160 mg, example 235, step 5) was dissolved in acetonitrile (10 ml) at rt, $Cs_2CO_3$ (215 mg) and tert-butyl 2-bromoethylcarbamate (60 ul) were added. The resulted mixture was brought to reflux for 2 hours. The solvent was removed and the residue was taken up in 30 ml of ethyl acetate, washed with water and brine, dried over sodium sulfate. The residue was purified by flash column with 5% acetone:hexanes. White solid (169 mg) was obtained.

Step 7

Tert-butyl 2-(1-bromo-3-fluoro-6-methoxyisoquinolin-4-yloxy)ethylcarbamate (169 mg, example 235, step 6) was dissolved in 10 ml of DMF at 0° C., 24 mg of sodium hydride (95%) was added, stirred overnight. The reaction mixture was diluted with 50 ml of water, extracted with ethyl acetate (3×20 ml). The organic was combined and washed with water (2×10 ml), brine (20 ml), dried over sodium sulfate. The solvent was removed and the residue was purified by flash column with 2.5-10% acetone:hexanes. White solid (100 mg) was obtained.

Step 8

Tert-butyl 6-bromo-9-methoxy-2H-[1,4]oxazino[3,2-c]isoquinoline-4(3H)-carboxylate (20 mg, example 235, step 7) was dissolved in 5 ml of $CH_2Cl_2$ at 0° C., 2 ml of TFA added, stirred for 2 hours. The reaction mixture was dried under vacuum, the residue was redissolved in ethyl acetate and washed with water (PH~5), brine, dried over sodium sulfate. Solvent was removed to dryness and the solid obtained was dissolved in DMF (5 ml) at room temperature, treated with NaH (10 mg), followed by MeI (10 ul). Stirred for 60 min. The reaction mixture was diluted with 50 ml of water, extracted with ethyl acetate (3×20 ml). The organic was combined and washed with water (2×10 ml), brine (20 ml), dried over sodium sulfate. The solvent was removed and the residue was purified by flash column with 5-15% acetone:hexanes. White solid (10 mg) was obtained. NMR 1H NMR (400 MHz, CHLOROFORM-D) δ ppm 2.89 (s, 3H) 3.16-3.21 (m, 2H) 4.40-4.44 (m, 2H) 7.05 (dd, J=9.32, 2.52 Hz, 1H) 7.20 (d, J=2.52 Hz, 1H) 8.04 (d, J=9.32 Hz, 1H)

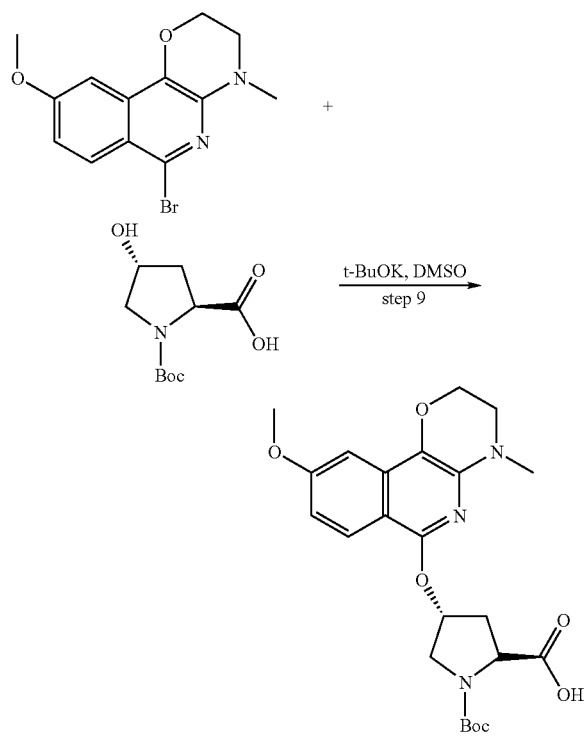

scheme 3

Step 9

A solution of 6-bromo-9-methoxy-4-methyl-3,4-dihydro-2H-[1,4]oxazino[3,2-c]isoquinoline (62 mg, 0.2 mmol, example 235, step 8), Boc-L-Hyp-OH (50.8 mg, 0.22 mmol), t-BuOK (82 m g, 0.60 mmol) in DMSO (2 mL) was stirred for 3 h. The reaction was quenched with water (5 mL) at 0° C. and neutralized with 1 N HCl to pH 5, extracted with EtOAc (40 mL), washed with brine (10 mL) and water (15 mL×2), dried over $MgSO_4$, concentrated to give a crude product (90 mg) as a solid, which was used in the next step without further purification.

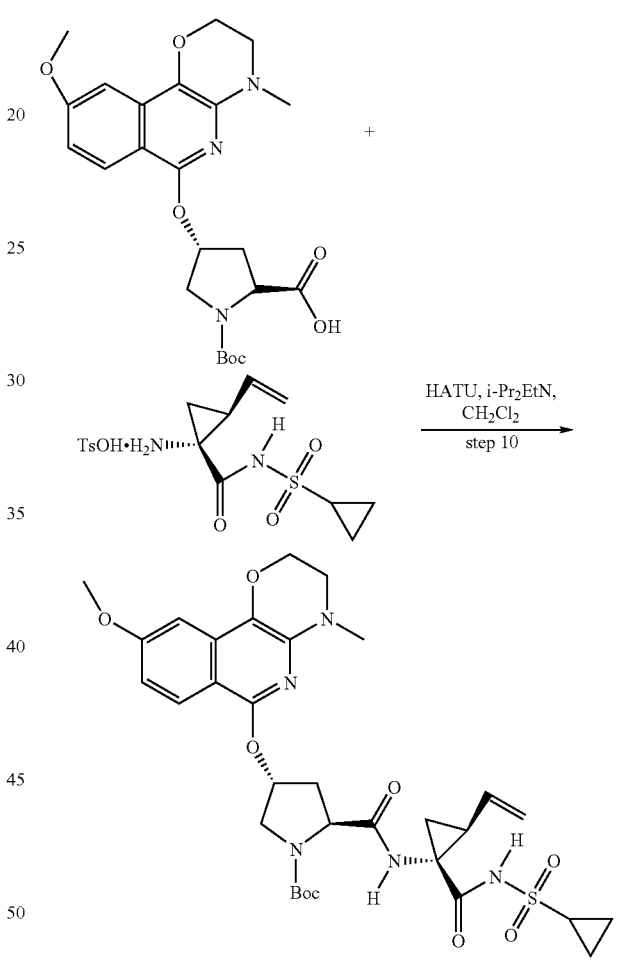

scheme 4

Step 10

To a solution of (2S,4R)-1-(tert-butoxycarbonyl)-4-(9-methoxy-4-methyl-3,4-dihydro-2H-[1,4]oxazino[3,2-c]isoquinolin-6-yloxy)pyrrolidine-2-carboxylic acid (90 mg, example 235, step 9), (1R,2S)-1-amino-N-(cyclopropylsulfonyl)-2-vinylcyclopropanecarboxamide TsOH salt (90 mg), i-$Pr_2EtN$ (0.5 mL) in $CH_2Cl_2$ (5 mL) was added HATU (112 mg). The resulting mixture was stirred for 16 h. After concentration, the residue was extracted with EtOAc (30 mL), washed with 1 N HCl (10 mL×3), water (10 mL×2), and brine (10 ml×2), dried over $MgSO_4$, concentrated, purified by prep HPLC. 113 mg solid obtained scheme 5

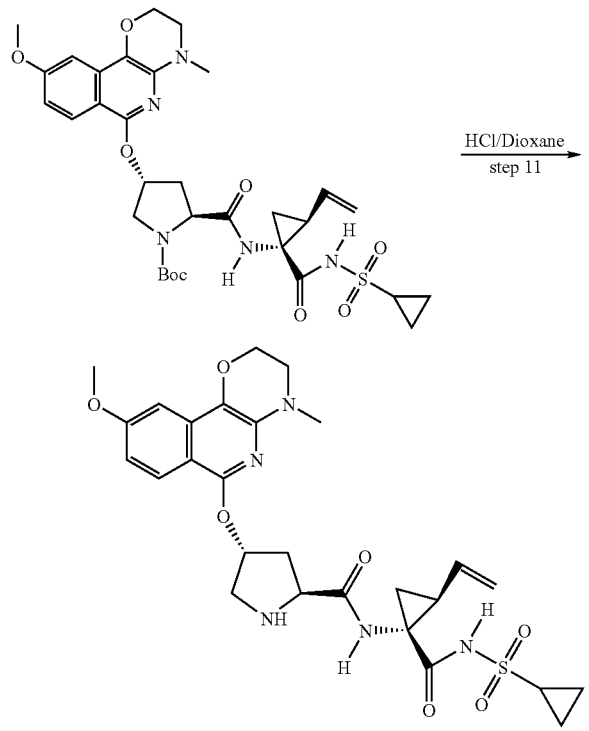

Step 11

(2S,4R)-tert-butyl 2-((1R,2S)-1-(cyclopropylsulfonylcarbamoyl)-2-vinylcyclopropylcarbamoyl)-4-(9-methoxy-4-methyl-3,4-dihydro-2H-[1,4]oxazino[3,2-c]isoquinolin-6-yloxy)pyrrolidine-1-carboxylate (50 mg, example 235, step 10) was dissolved in 2 ml of 4N HCl in dioxane, stirred for 2 hours. The solvent was removed to dryness, the resulted brown solid was ued as is.

scheme 6

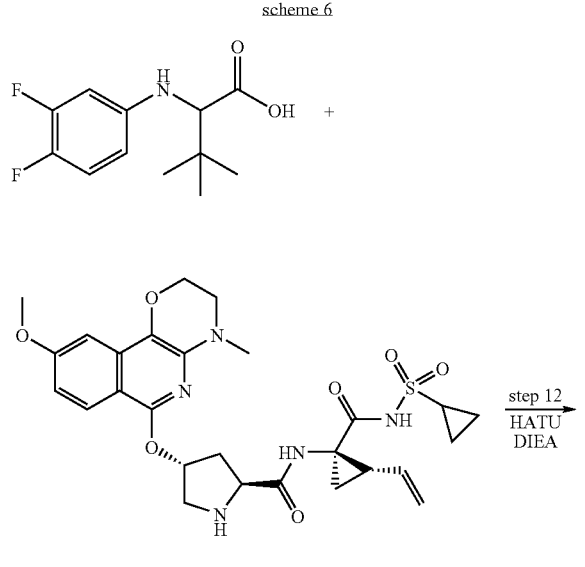

Step 12

To the yellow solution of 2-(3,4-difluorophenylamino)-3,3-dimethylbutanoic acid (0.043 g, 0.175 mmol, from example 220, step 1) and (2S,4R)—N-((1R,2S)-1-(cyclopropylsulfonylcarbamoyl)-2-vinylcyclopropyl)-4-(9-methoxy-4-methyl-3,4-dihydro-2H-[1,4]oxazino[3,2-c]isoquinolin-6-yloxy)pyrrolidine-2-carboxamide (20 mg, example 235, step 11) at 0° C. was added HATU (0.133 g, 0.350 mmol) followed by diisopropylethyl amine (0.057 g, 0.437 mmol). brown solution was formed after addition of base. The mixture was stirred at room temperature.

The reaction mixture was diluted with ethyl acetate. Washed with water and brine. Dried over sodium sulfate. Purified by prep HPLC to give two separate products with identical MS m/z as observed by LCMS. Compound 235A (0.0008 g, 3.0% yield) was the first of the two isomers to elute by reverse phase preparative HPLC. Compound 235B (0.003 g, 11.0% yield) was the second of the two isomers to elute by reverse phase preparative HPLC. Compound 235A: LC-MS, MS m/z 798 ($M^+$+H)

1H NMR (400 MHz, MeOD) δ ppm 1.01-1.10 (m, 11H) 1.41 (m, 2H) 1.86 (dd, J=8.18, 5.41 Hz, 1H) 2.13-2.24 (m, 2H) 2.50 (d, J=6.80 Hz, 1H) 2.90-3.01 (m, 1H) 3.02-3.09 (m, 3H) 3.42 (d, J=2.52 Hz, 2H) 3.91-4.01 (m, 5H) 4.22-4.32 (m, 1H) 4.42-4.48 (m, 1H) 4.50-4.59 (m, 2H) 5.11 (dd, J=10.32, 1.76 Hz, 1H) 5.28 (dd, J=17.25, 1.39 Hz, 1H) 5.67-5.78 (m, 2H) 6.19-6.24 (m, 1H) 6.35-6.40 (m, 1H) 6.49-6.56 (m, 1H) 6.87 (dd, J=9.07, 2.27 Hz, 1H) 7.13-7.17 (m, 1H) 7.60 (d, J=2.27 Hz, 1H) Compound 235: LC-MS, MS m/z 798 ($M^+$+H)

Compounds 236, 237, 238, 239, 240, 241, 242, 243 were prepared using the methods described herein.

Example 236

Compound 236

Example 237
Compound 237
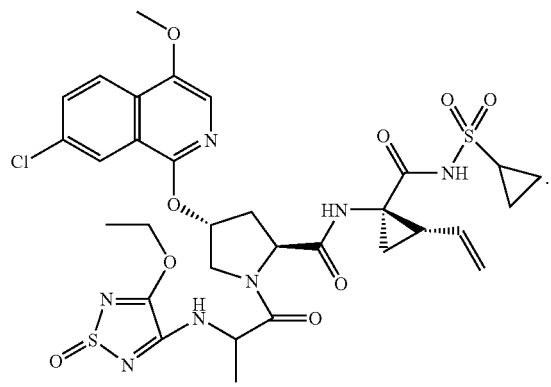
Example 238
Compound 238
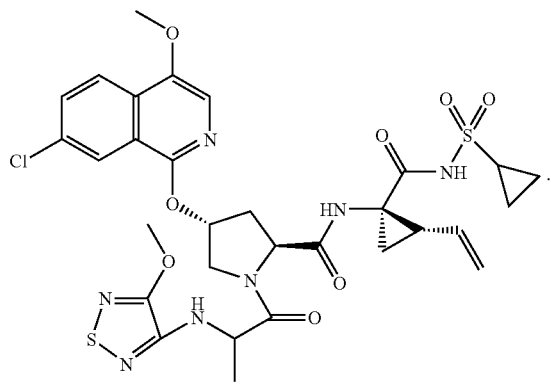
Example 239
Compound 239
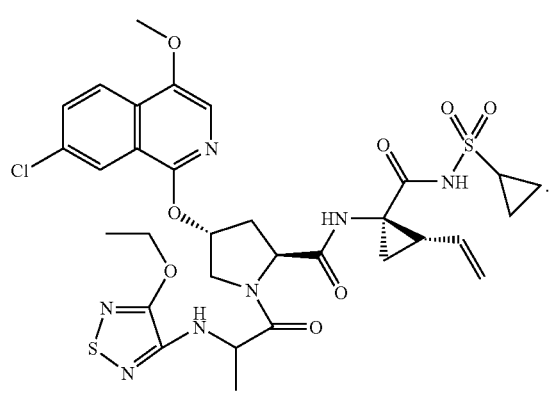
Example 240
Compound 240
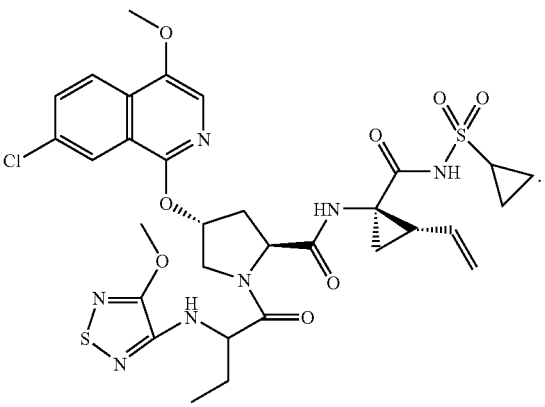
Example 241
Compound 241
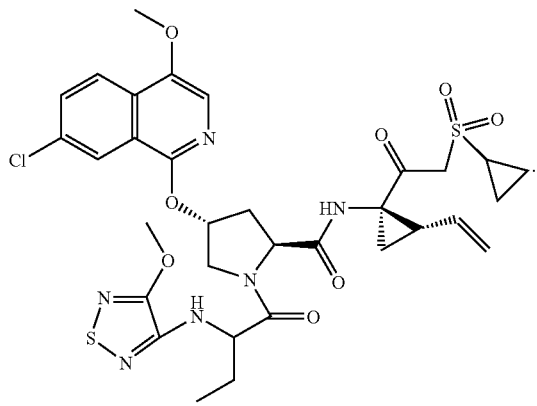
Example 242
Compound 242
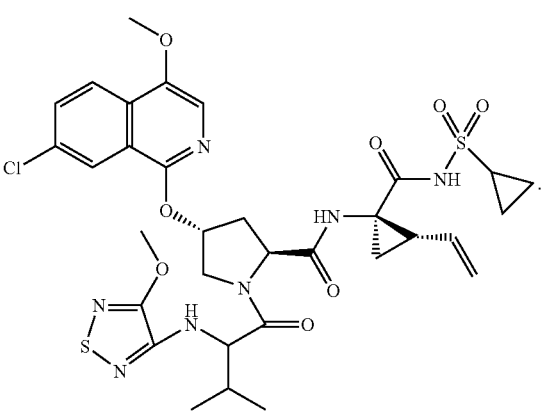

Example 243

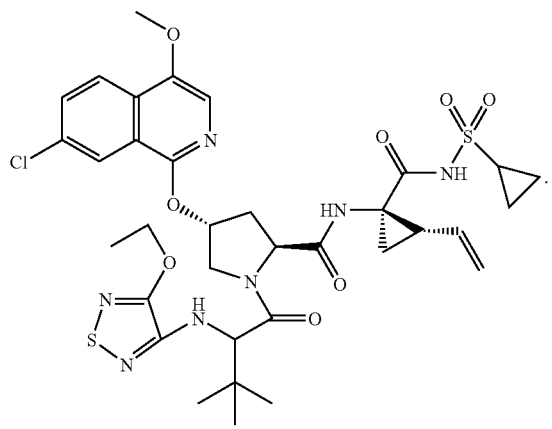

Compound 243

Example 407

Preparation of Compounds 407

Scheme 1

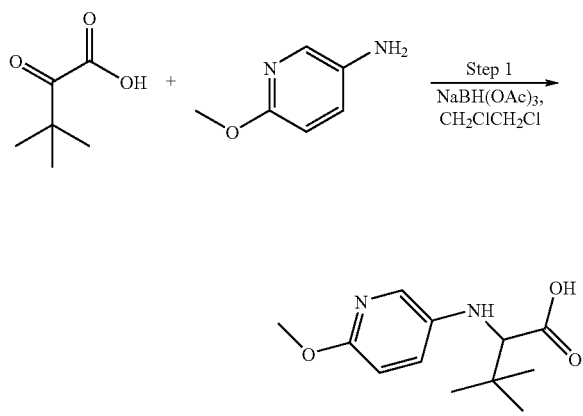

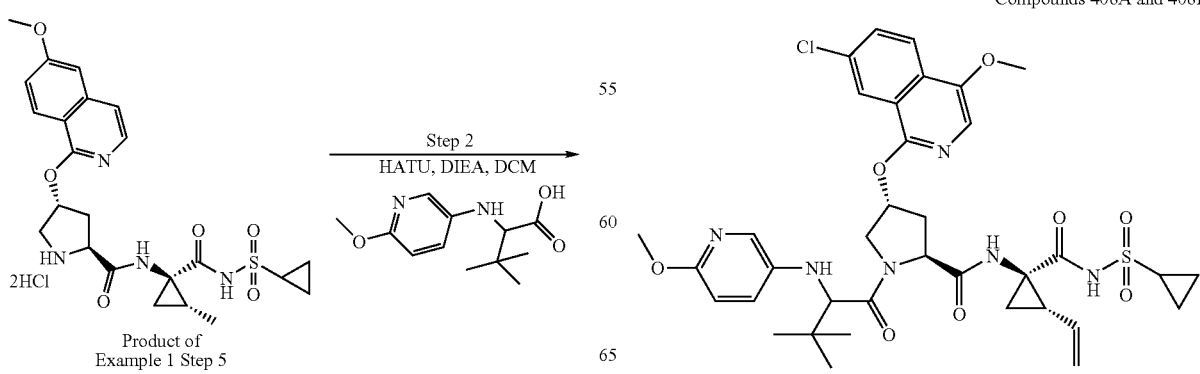

Compounds 407

Step 1:

A mixture of 6-methoxypyridin-3-amine (372 mg, 3 mmol), 3,3-dimethyl-2-oxobutanoic acid (781 mg, 6.00 mmol), and sodium triacetoxyhydroborate (1907 mg, 9.00 mmol) in CH$_2$ClCH$_2$Cl (5 ml) was stirred for 24 h. The reaction was quenched with saturated NH$_4$Cl (20 mL), diluted with EtOAc (50 mL), washed with brine (20 ml), dried over MgSO$_4$, filtrated, concentrated. Concentration gave 0.71 g (99%) of a crude desired product which was used in the next step without further purification. purification. $^1$H NMR (400 MHz, CCl$_3$D) δ ppm 1.09 (s, 9H), 3.63 (s, 1H), 3.85 (s, 3 H), 6.63 (d, J=8.81 Hz, 1H), 7.07 (dd, J=8.81, 3.02 Hz, 1H), 7.63 (d, J=3.02 Hz, 1H); LC-MS, MS m/z 239 (M$^+$+H).

Step 2:

To a mixture of the product of Step 5, Example 1 (150 mg, 0.3 mmol), was added the product of Step 1, Example 407 (71 mg, 0.3 mmol), and Hunig's Base (0.524 ml, 3 mmol) in CH$_2$Cl$_2$ (5 ml) was added HATU (171 mg, 0.45 mmol). After stirring for 16 h and concentration, purification of the residue by reverse phase preparative HPLC gave two products with identical m/z by LCMS. Compound 407A was the first of the two isomers to elute by reverse phase preparative HPLC and was obtained as a solid (37 mg, 18% yield). Compound 407B was the second of the two isomers to elute by reverse phase preparative HPLC and was obtained as a solid (31 mg, 14% yield). Compound 407: LC-MS, MS m/z 721 (M$^+$+H). Compound 407B: LC-MS, MS m/z 721 (M$^+$+H).

Example 408

Preparation of Compounds 408A and 408B

Compounds 408A and 408B

Compounds 408 were prepared by the same procedure as that described for the preparation of Compound 407, except that the product of Step 5 of Scheme 2 in Example 22 (182 mg, 0.299 mmol) was used in the synthesis of Compound 408. Compound 408A was the first of the two isomers to elute by reverse phase preparative HPLC and was obtained as a solid (66 mg, 29% yield). Compound 408B was the second of the two isomers to elute by reverse phase preparative HPLC and was obtained as a solid (46 mg, 20% yield). Compound 408A: LC-MS, MS m/z 755 ($M^+$+H). Compound 408B: LC-MS, MS m/z 755 ($M^+$+H).

Example 409

Preparation of Compounds 409A and 409B

Compounds 409A and 409B

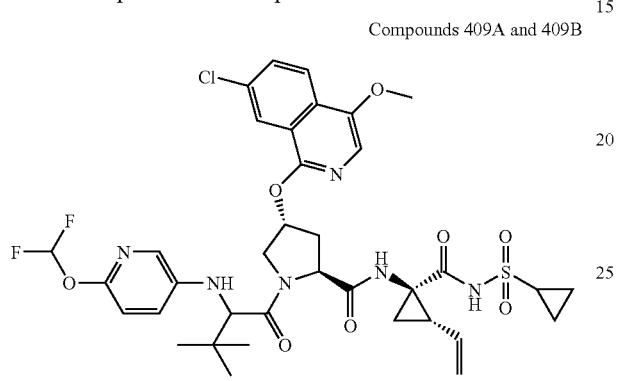

Compounds 409 were prepared by the same procedure as that described for the preparation of Compound 407, except 6-(difluoromethoxy)pyridin-3-amine was used in Step 1 and the product of Step 5 of Scheme 2 in Example 22 (182 mg, 0.299 mmol) was used in Step 2. Compound 409A was the first of the two isomers to elute by reverse phase preparative HPLC and was obtained as a solid (45 mg, 33% yield). Compound 409B was the second of the two isomers to elute by reverse phase preparative HPLC and was obtained as a solid (50 mg, 37% yield). Compound 409A: LC-MS, MS m/z 791 ($M^+$+H). Compound 409B: LC-MS, MS m/z 791 ($M^+$+H).

Compounds 410 and 411 were prepared according to the methods described herein.

Example 410

Preparation of Compounds 410

Compound 410

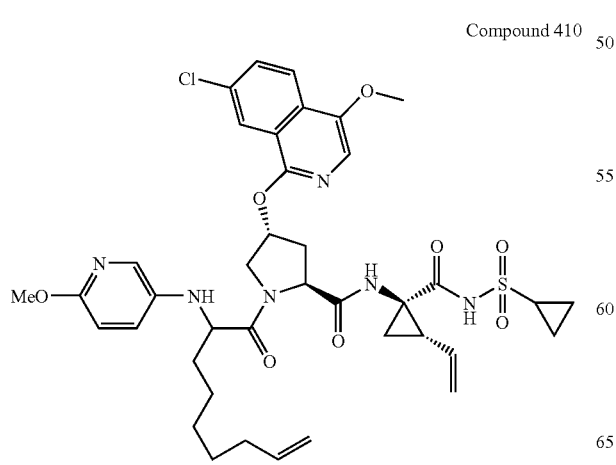

Example 411

Preparation of Compounds 411

Compound 411

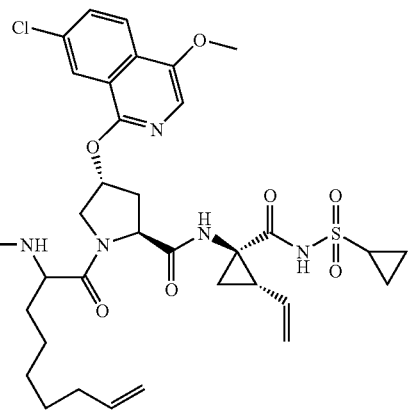

Example 412

Preparation of Intermediates

Example of preparations of P2 isoquinoline intermediates for incorporation into compounds of Formula 1

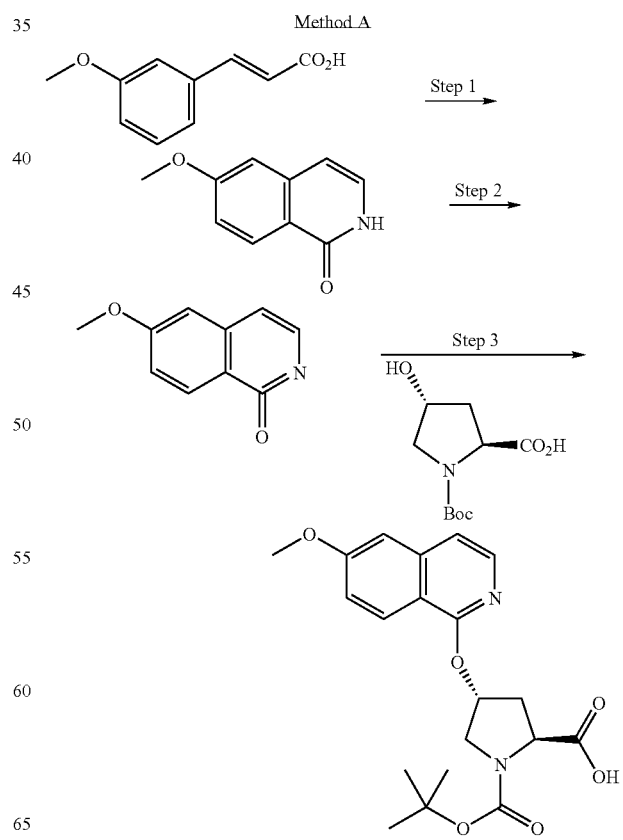

Step 1:

To a solution of 3-methoxy cinnamic acid (11.04 g, 62 mmol) and triethylamine (12.52 g, 124 mmol) in acetone (80 mL) was added ethyl chloroformate (approximately 1.5 equivalents) dropwise at 0° C. After stirring at this temperature for 1 h, aqueous $NaN_3$ (6.40 g, 100 mmol in 35 mL $H_2O$; appropriate precautions must be taken when using sodium azide) was added dropwise and the reaction mixture was stirred for 16 h at the ambient temperature. Water (100 mL) was added to the mixture and the volatile was removed in vacuo. The resulting slurry was extracted with toluene (3×50 mL) and the combined organic layers were dried over $MgSO_4$. This dried solution was added dropwise to a heated solution of diphenylmethane (50 mL) and tributylamine (30 mL) at 190° C. The toluene was distilled off as added. After complete addition, the reaction temperature was raised to 210° C. for 2 h. After cooling, the precipitated product was collected by filtration, washed with hexane (2×50 mL), and dried to yield the desired product as a white solid (5.53 g, 51%) (Nicolas Briet at el, Tetrahedron, 2002, 5761-5766). MS m/z 176 ($M^++H$).

An alternative procedure to the above employs diphenylphosphoryl azide for the conversion of the carboxylic acid to the corresponding acylazide. In a one pot procedure here the acid is converted to the corresponding quinolone. The process is described below for the preparation of 4-methyl-2H-isoquinolin-1-one from 3-phenyl-but-2-enoic acid:

A solution of 3-phenyl-but-2-enoic acid (16.2 g), diphenylphosphoryl azide (27.5 g), and triethylamine (10.1 g) in benzene (100 mL) was stirred for 1 h. After filtration through a silica gel plug washing with benzene and concentration, the residue was dissolved in diphenylmethane (80 mL) and refluxed for 3 h. After cooling to rt, solids were collected through a plug washing with benzene and dried to give 10 g (63%) of the desired 4-methyl-2H-isoquinolin-1-one as a solid. $^1$H NMR (400 MHz, $CD_3OD$) δ ppm 2.30 (s, 3H), 7.00 (s, 1H), 7.54 (m, 1H), 7.77 (m, 2H), 8.33 (d, J=7.34 Hz, 1H).

Step 2:

6-Methoxy-2H-isoquinolin-1-one (5.0 g, 28.4 mmol) in $POCl_3$ (10 mL) was heated to gentle reflux for 3 h the evaporated in vacuo (Nicolas Briet at el, Tetrahedron, 2002, 5761-5766). The residue was poured into iced water (20 mL) and neutralized to pH 10 with 10 M NaOH. Extracted with $CHCl_3$. The organic layer was washed with brine, dried over $MgSO_4$, filtered, evaporated. The residue was purified by flash chromatography (1:1 hexane-EtOAc) to afford 4.41 g (80%) of the desired product as a white solid.

$^1$H NMR ($CD_3OD$) δ 3.98 (s, 3H), 7.34-7.38 (m, 2H), 7.69 (d, J=5.5 Hz, 1H), 8.10 (d, J=6.0 Hz, 1H), 8.23 (d, J=9.5 Hz, 1H). MS m/z 194 ($M^++H$).

Step 3:

To a solution of N—BOC-3-(R)-hydroxy-L-proline (892 mg, 3.89 mmol) in DMSO (40 mL) at the ambient temperature was added potassium tert-butoxide (1.34 g, 12.0 mmol) in one portion. The formed suspension was stirred at this temperature for 30 min before being cooled to 10° C. 1-chloro-6-methoxy-isoquinoline (example 11, Step 2) (785 mg, 4.05 mmol) was added as solid in one portion and the final mixture was stirred at the ambient temperature for 12 h. Quenched with iced 5% citric acid (aq), extracted with EtOAC (100 mL). The aqueous phase was extracted with EtOAC again. The combined organic layers were washed with 5% citric acid (aq) and brine respectively, dried over $MgSO_4$, filtered. The filtrate was evaporated in vacuo to dryness to yield 1.49 g (99%) of the desired product as an off-white foam. This material was used in the next step reaction as crude without further purification. $^1$H NMR ($CD_3OD$) δ 1.42, 1.44 (rotamers, 9H), 2.38-2.43 (m, 1H), 2.66-2.72 (m, 1H), 3.80-3.87 (m, 2H), 3.92 (s, 3H), 4.44-4.52 (m, 1H), 5.73 (b, 1H), 7.16-7.18 (m, 2H), 7.24-7.25 (m, 1H), 7.87-7.88 (m, 1H), 8.07 (d, J=8.5 Hz, 1H). MS m/z 389 ($M^++H$).

The following intermediates were prepared as described herein and can be incorporated into compounds of Formula 1

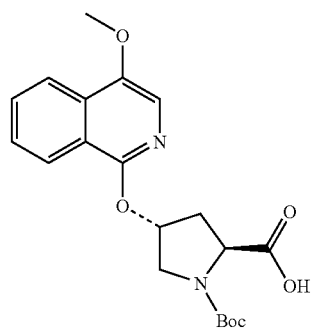

Step 1:

Modifications: 15 g 3-methoxy-3-phenyl-acrylic acid used, 250 mg product obtained (2% yield).

Product:

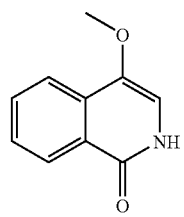

$^1$H NMR (400 MHz, $CD_3COCD_3$) δ ppm 3.85 (s, 3H), 6.96 (s, 1H), 7.54 (m, 1H), 7.71 (m, 1H), 7.86 (d, J=8.07 Hz, 1H), 8.31 (d, J=8.07 Hz, 1H).

Step 2:

Modifications: 200 mg 4-methoxy-2H-isoquinolin-1-one used, 150 mg product obtained (68% yield).

Product:

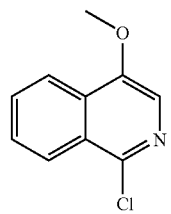

$^1$H NMR (400 MHz, $CDCl_3$) δ ppm 4.05 (s, 2H), 7.71 (m, 1H), 7.72 (m, 2H), 7.80 (s, 1H), 8.23 (dd, J=18.71, 7.70 Hz, 2H).

Step 3:

Modifications: 122 mg 1-chloro-4-methoxy-isoquinoline used, 218 mg product obtained (89% yield).

Product:

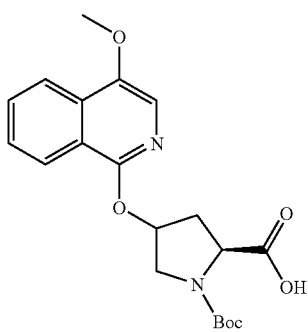

MS: (M+Na)⁺ 411.

The following intermediates were prepared as described herein and can be incorporated into compounds of Formula 1

Product:

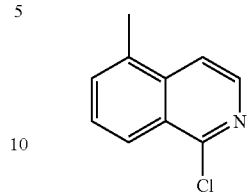

Data: ¹H NMR (400 MHz, CDCl₃) δ ppm 2.67 (s, 3H), 7.55 (m, 2H), 7.70 (dd, J=5.9, 1.0 Hz, 1H), 8.19 (m, 1H), 8.28 (d, J=5.9 Hz, 1H); MS: (M+H)⁺ 178.

Step 3:

Modifications: 533 mg 1-chloro-5-methyl-isoquinoline used, 1116 mg product obtained (100% yield).

Product:

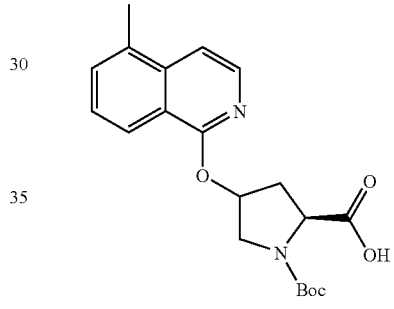

Data: MS: (M+H)⁺ 373.

The following intermediates were prepared as described herein and can be incorporated into compounds of Formula 1

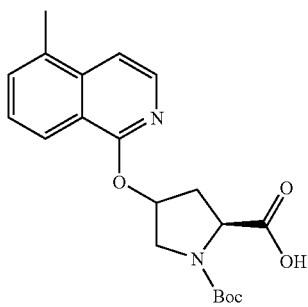

Step 1:

Modifications: 20 g 2-methylcinnamic acid used, 14.3 g product obtained (72% yield)

Product:

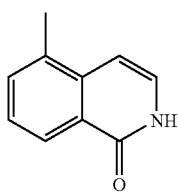

Data: ¹H NMR (400 MHz, CD₃OD) δ ppm 2.54 (s, 1H), 6.69 (d, J=7.3 Hz, 1H), 7.23 (d, J=7.3 Hz, 1H), 7.39 (t, J=7.8 Hz, 1H), 7.50 (d, J=7.1 Hz, 1H), 8.30 (d, J=8.1 Hz, 1H), 11.62 (s, 1H); MS: (M+H)⁺ 160.

Step 2:

Modifications: 14.4 g 5-methyl-2H-isoquinolin-1-one used, 10.6 g product obtained (66% yield).

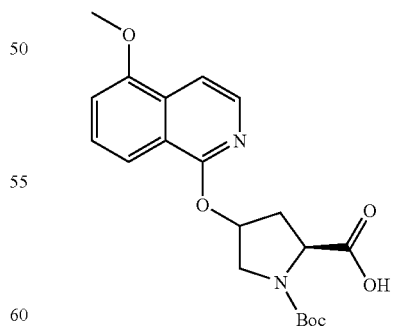

Step 1:

Modifications: 10 g 2-methoxy cinnamic acid used, 5.3 g product obtained (53% yield).

Product:

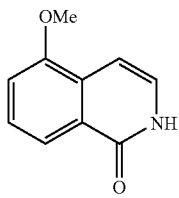

Data: ¹H NMR (400 MHz, CD₃OD) δ ppm 3.95 (s, 3H), 6.94 (d, J=7.3 Hz, 1H), 7.08 (d, J=8.1 Hz, 1H), 7.14 (d, J=7.3 Hz, 1H), 7.43 (t, J=8.1 Hz, 1H), 7.99 (d, J=8.1 Hz, 1H), 10.92 (s, 1H); MS: (M+H)⁺ 176.

Step 2:

Modifications: 5.3 g 5-methoxy-2H-isoquinolin-1-one used, 5.38 g product obtained (92% yield).

Product:

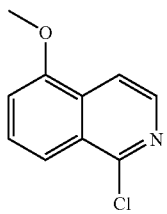

Data: ¹H NMR (400 MHz, CDCl₃) δ ppm 4.01 (s, 3H), 7.04 (d, J=7.8 Hz, 1H), 7.57 (t, J=8.1 Hz, 1H), 7.88 (d, J=8.6 Hz, 1H), 7.97 (d, J=5.9 Hz, 1H), 8.25 (d, J=5.9 Hz, 1H); MS: (M+H)⁺ 194.

Step 3:

Modifications: 581 mg 1-chloro-5-methoxy-isoquinoline used, 1163 mg product obtained (100% yield).

Product:

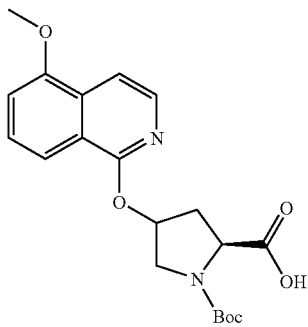

Data: MS: (M+H)⁺ 389.

The following intermediates were prepared as described herein and can be incorporated into compounds of Formula 1

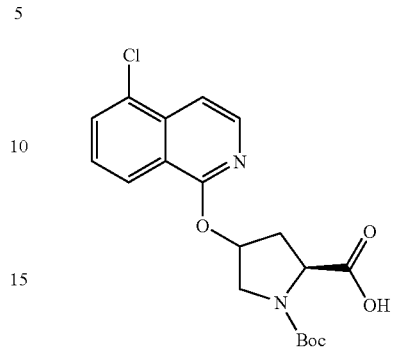

Step 1:

Modifications: 25 g 2-chlorocinnamic acid used, 14.6 g product obtained (59% yield).

Product:

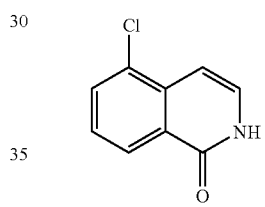

Data: ¹H NMR (400 MHz, CD₃OD) δ ppm 7.22 (d, J=7.3 Hz, 1H), 7.42 (t, J=7.8 Hz, 1H), 7.73 (d, J=7.8 Hz, 1H), 8.34 (d, J=8.1 Hz, 1H), 10.61 (s, 1H); MS: (M+H)⁺ 180.

Step 2:

Modifications: 14.2 g 5-chloro-2H-isoquinolin-1-one used, 8.28 g product obtained (53% yield).

Product:

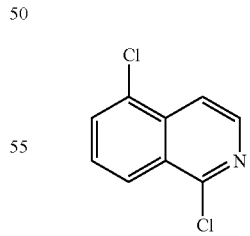

Data: ¹H NMR (400 MHz, CDCl₃) δ ppm 7.60 (dd, J=8.6, 7.6 Hz, 1H), 7.83 (m, 1H), 8.00 (d, J=5.9 Hz, 1H), 8.29 (dt, J=8.9, 1.0 Hz, 1H), 8.38 (d, J=5.9 Hz, 1H); MS: (M+H)⁺ 198.

Step 3:

Modifications: 594 mg 1,5-dichloro-isoquinoline used, 1174 mg product obtained (100% yield).

Product:

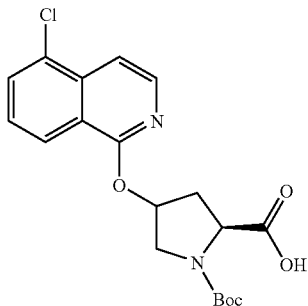

Data: MS: (M+H)+ 393.

The following intermediates were prepared as described herein and can be incorporated into compounds of Formula 1

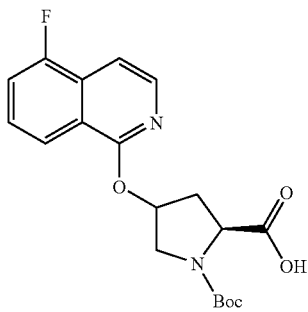

Step 1:
Modifications: 16.6 g 2-fluorocinnamic acid used, 8.55 g product obtained (51% yield).

Product:

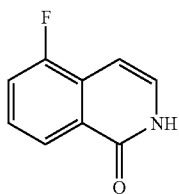

Data: ¹H NMR (400 MHz, CD₃COCD₃) δ ppm 6.62 (d, J=7.3 Hz, 1H), 7.32 (d, J=7.3 Hz, 1H), 7.47 (m, 2H), 8.09 (m, 1H).

Step 2:
Modifications: 8.4 g 5-fluoro-2H-isoquinolin-1-one used, 7.5 g product obtained (80% yield).

Product:

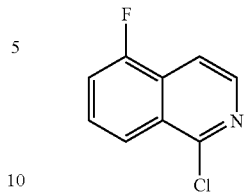

Data: ¹H NMR (400 MHz, CDCl₃) δ ppm 7.43 (ddd, J=9.7, 7.8, 0.9 Hz, 1H), 7.62 (td, J=8.2, 5.4 Hz, 1H), 7.84 (d, J=5.6 Hz, 1H), 8.14 (d, J=8.6 Hz, 1H), 8.33 (d, J=5.9 Hz, 1H); MS: (M+H)+ 182.

Step 3:
Modifications: 203 mg 1-chloro-5-fluoro-isoquinoline used, 384 mg product obtained (90% yield).

Product:

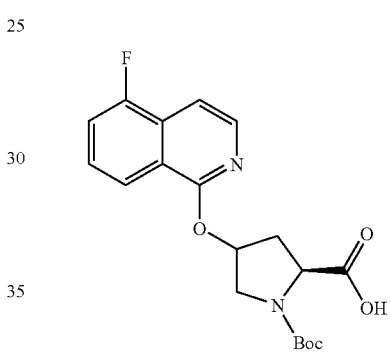

Data: ¹H NMR (400 MHz, CD₃SOCD₃) δ ppm 1.34, 1.36 (2s, 9H, rotamers), 2.35 (m, 1H), 2.61 (m, 1H), 3.65 (d, J=12.23 Hz, 1H), 3.80 (m, 1H), 4.35 (m, 1H), 5.70 (s, 1H), 7.48 (d, J=6.11 Hz, 1H), 7.63 (m, 2H), 7.99 (m, 1H), 8.10 (d, J=5.87 Hz, 1 H); MS: (M+Na)+ 399.

The following intermediates were prepared as described herein and can be incorporated into compounds of Formula 1

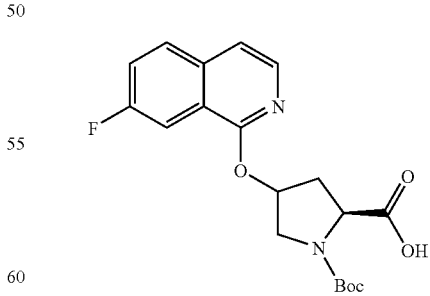

Step 1:
Modifications: 16.6 g 4-fluorocinnamic acid used, 8.2 g product obtained (49% yield).

Product:

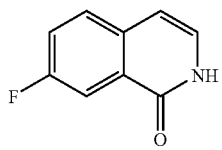

Data: $^1$H NMR (400 MHz, CD$_3$COCD$_3$) δ ppm 6.57 (d, J=7.09 Hz, 1H), 7.21 (d, J=7.09 Hz, 1H), 7.50 (m, 1H), 7.72 (dd, J=8.68, 5.26 Hz, 1H), 7.90 (dd, J=9.54, 2.93 Hz, 1H).

Step 2:
Modifications: 8.15 g 7-fluoro-2H-isoquinolin-1-one used, 7.6 g product obtained (84% yield).

Product:

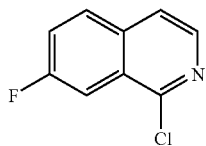

Data: $^1$H NMR (400 MHz, CDCl$_3$) δ ppm 7.52 (td, J=8.6, 2.6 Hz, 1H), 7.59 (d, J=5.6 Hz, 1H), 7.86 (dd, J=9.1, 5.4 Hz, 1H), 7.95 (dd, J=9.5, 2.5 Hz, 1H), 8.26 (d, J=5.6 Hz, 1H); MS: (M+H)$^+$ 182.

Step 3:
Modifications: 191 mg 1-chloro-7-fluoro-isoquinoline used, 350 mg product obtained (93% yield).

Product:

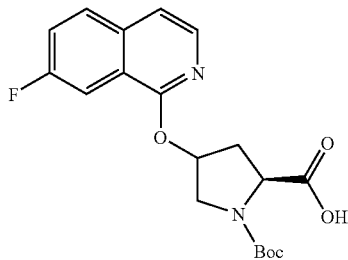

Data: MS: (M+Na)$^+$ 399.

The following intermediates were prepared as described herein and can be incorporated into compounds of Formula 1

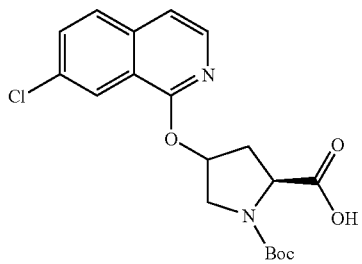

Step 1:
Modifications: 9.13 g 4-chlorocinnamic acid used, 4 g product obtained (44% yield).

Product:

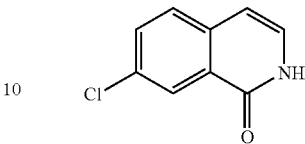

Data: $^1$H NMR (400 MHz, CD$_3$SOCD$_3$) δ ppm 6.58 (d, J=7.1 Hz, 1H), 7.20 (dd, J=7.1, 5.9 Hz, 1H), 7.72 (m, 2H), 8.10 (m, 1H).

Step 2:
Modifications: 3.5 g 7-chloro-2H-isoquinolin-1-one used, 2.8 g product obtained (72% yield).

Product:

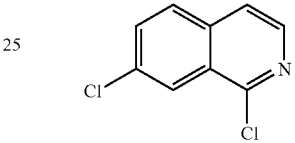

Data: $^1$H NMR (500 MHz, CDCl$_3$) δ ppm 7.59 (d, J=5.5 Hz, 1H), 7.69 (dd, J=8.9, 2.1 Hz, 1H), 7.80 (d, J=8.6 Hz, 1H), 8.29 (d, J=5.5 Hz, 1H), 8.34 (s, 1H); MS: (M+H)$^+$ 198.

Step 3:
Modifications: 208 mg 1,7-dichloro-isoquinoline used, 350 mg product obtained (89% yield).

Product:

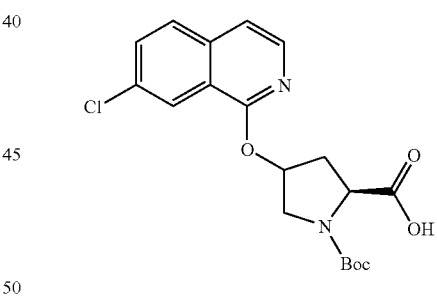

Data: MS: (M+Na)+415.

The following intermediates were prepared as described herein and can be incorporated into compounds of Formula 1

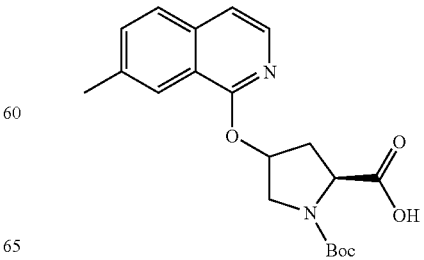

281

Step 1:

Modifications: 25 g 4-methylcinnamic acid used, 15.3 g product obtained (62% yield).

Product:

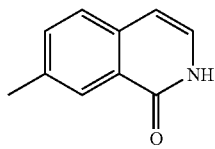

Data: ¹H NMR (400 MHz, CD₃OD) δ ppm 2.50 (s, 3H), 6.54 (d, J=7.1 Hz, 1H), 7.13 (d, J=7.1 Hz, 1H), 7.49 (m, 2H), 8.22 (s, 1H), 11.49 (s, 1H); MS: (M+H)⁺ 160.

Step 2:

Modifications: 15.3 g 7-methyl-2H-isoquinolin-1-one used, 5.15 g product obtained (30% yield).

Product:

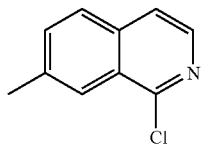

Data: ¹H NMR (400 MHz, CDCl₃) δ ppm 2.58 (s, 3H), 7.56 (m, 2H), 7.73 (d, J=8.3 Hz, 1H), 8.09 (s, 1H), 8.20 (d, J=5.6 Hz, 1H); MS: (M+H)⁺ 178.

Step 3:

Modifications: 205 mg 1-chloro-7-methyl-isoquinoline used, 350 mg product obtained (89% yield).

Product:

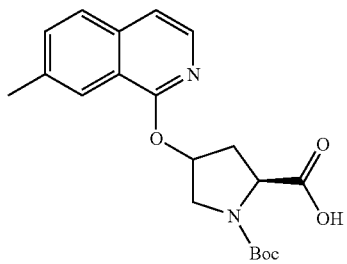

Data: MS: (M+H)⁺ 373.

The following intermediates were prepared as described herein and can be incorporated into compounds of Formula 1

282

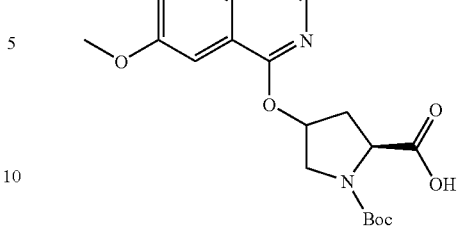

Step 1:

Modifications: 33 g using 4-methoxycinnamic acid used, 7 g product obtained (33% yield).

Product:

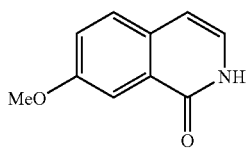

Data: ¹H NMR (500 MHz, CD₃COCD₃) δ ppm 3.90 (s, 3H), 6.49 (d, J=7.0 Hz, 1H), 7.10 (d, J=7.3 Hz, 1H), 7.28 (dd, J=8.6, 2.8 Hz, 1H), 7.57 (d, J=8.9 Hz, 1H), 7.71 (d, J=2.8 Hz, 1H).

Step 2:

Modifications: 4 g 7-methoxy-2H-isoquinolin-1-one used, 3 g product obtained (68% yield).

Product:

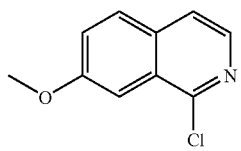

Data: ¹H NMR (400 MHz, CDCl₃) δ ppm 3.98 (s, 3H), 7.38 (dd, J=8.9, 2.6 Hz, 1H), 7.52 (m, 2H), 7.73 (d, J=8.8 Hz, 1H), 8.16 (d, J=5.4 Hz, 1H).

Step 3:

Modifications: 533 mg 1-chloro-7-methoxy-isoquinoline used, 1115 mg product obtained (100% yield).

Product:

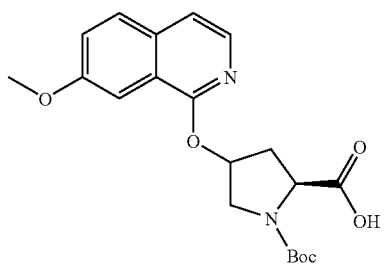

The following intermediates were prepared as described herein and can be incorporated into compounds of Formula 1

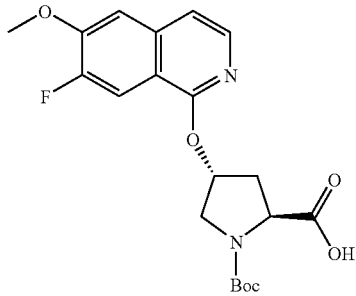

Step 1:
Modifications: 19.6 g 4-fluoro-3-methoxycinnamic acid used, 9.5 g product obtained (48% yield).

Product:

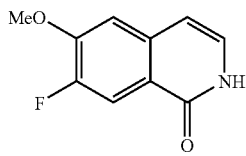

Data: ¹H NMR (400 MHz, CD₃COCD₃) δ ppm 4.00 (s, 1H), 6.49 (d, J=7.34 Hz, 1H), 7.19 (d, J=7.09 Hz, 1H), 7.29 (d, J=8.07 Hz, 1H), 7.86 (d, J=11.74 Hz, 1H).

Step 2:
Modifications: 9 g 7-fluoro-6-methoxy-2H-isoquinolin-1-one used, 7 g product obtained (70% yield).

Product:

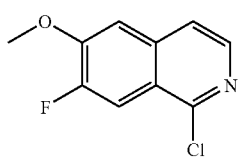

Data: ¹H NMR (400 MHz, CDCl₃) δ ppm 4.04 (s, 3H), 7.17 (d, J=8.07 Hz, 1H), 7.48 (d, J=5.62 Hz, 1H), 7.94 (d, J=11.49 Hz, 1H), 8.20 (d, J=5.62 Hz, 1H).

Step 3:
Modifications: 222 mg 1-chloro-7-fluoro-6-methoxy-isoquinoline used, 406 mg of desired product obtained.

Desired Product:

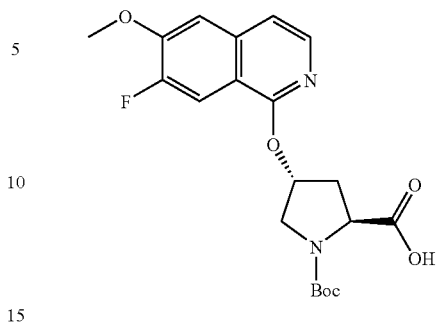

The following intermediates were prepared as described herein and can be incorporated into compounds of Formula 1

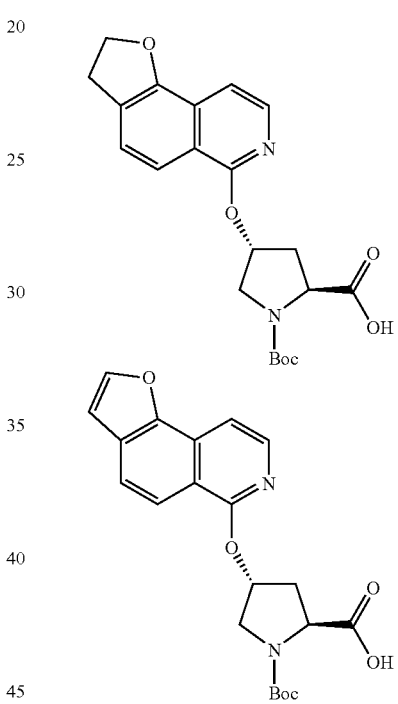

Step 1:
Modifications: 3.8 g 3-(2,3-dihydro-benzofuran-7-yl)-acrylic acid used, 2 g product obtained (53% yield).

Product:

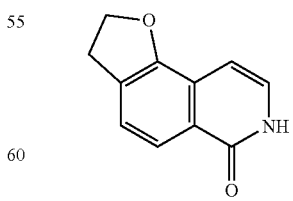

Data: ¹H NMR (400 MHz, CD₃OD) δ ppm 3.37 (t, J=9.05 Hz, 1H), 4.73 (t, J=9.05 Hz, 2H), 6.67 (d, J=7.09 Hz, 1H), 7.10 (d, J=7.09 Hz, 1H), 7.37 (d, J=8.07 Hz, 1H), 7.81 (d, J=8.07 Hz, 1H); MS: (M+H)⁺ 188.

Step 2:
Modifications: 1.87 g 2,3-dihydro-7H-furo[2,3-f]isoquinolin-6-one used, 1.84 g product obtained (90% yield).

Product:

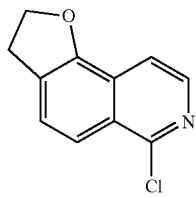

Data: ¹H NMR (400 Hz, CDCl₃) δ ppm 3.43 (t, J=9.05 Hz, 2H), 4.82 (t, J=9.05 Hz, 2H), 7.52 (d, J=8.56 Hz, 1H), 7.66 (d, J=5.62 Hz, 1H), 7.84 (d, J=8.31 Hz, 1H), 8.19 (d, J=5.62 Hz, 1H); MS (M+H)⁺ 206.

Step 3

Modifications: 206 mg 6-chloro-2,3-dihydro-furo[2,3-f]isoquinoline used, 300 mg products mixture obtained.

Products:

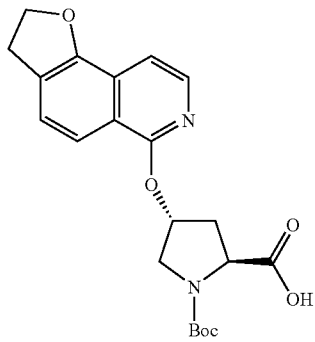

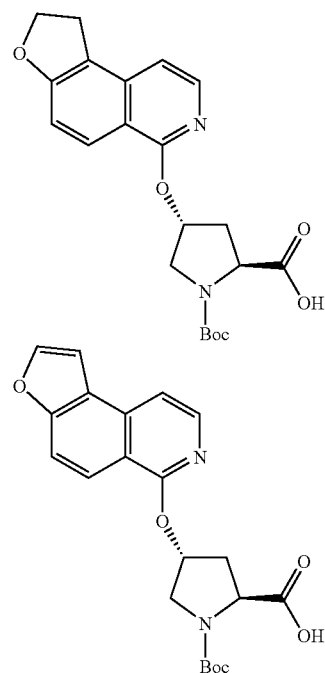

Step 1:
Modifications: 1.14 g 3-(2,3-dihydro-benzofuran-4-yl)-acrylic acid used, 600 mg product obtained (52% yield).

Product:

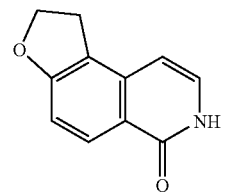

Data: ¹H NMR (400 MHz, CD₃OD) δ ppm 3.35 (t, J=8.93 Hz, 2H), 4.74 (t, J=8.93 Hz, 2H), 6.49 (d, J=7.09 Hz, 1H), 6.95 (d, J=8.56 Hz, 1H), 7.25 (d, J=7.09 Hz, 1H), 8.13 (d, J=8.80 Hz, 1H); MS (M+H)⁺ 188.

Step 2:
Modifications: 560 mg 1,7-dihydro-2H-furo[3,2-f]isoquinolin-6-one used, 380 mg product obtained (48% yield).

Product:

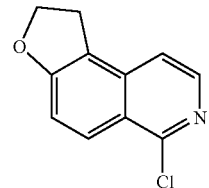

The following intermediates were prepared as described herein and can be incorporated into compounds of Formula 1

Data: ¹H NMR (400 Hz, CDCl₃) δ ppm 3.47 (t, J=9.05 Hz, 2H), 4.84 (t, J=9.05 Hz, 2H), 7.24 (d, J=8.56 Hz, 1H), 7.33 (d, J=5.87 Hz, 1H), 8.20 (m, 2H); MS (M+H)⁺ 206.

Step 3:

Modifications: 105 mg 6-chloro-1,2-dihydro-furo[3,2-f]isoquinoline used, 390 mg products mixture obtained.

Products:

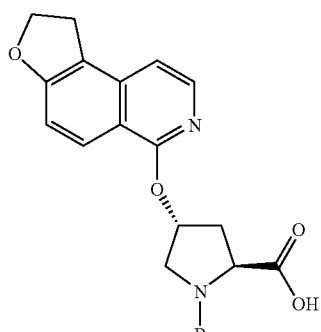

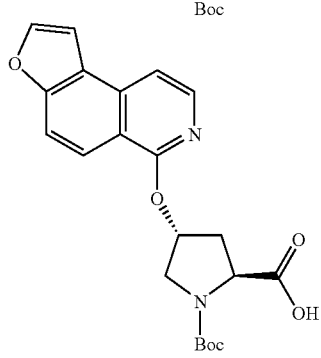

The following intermediates were prepared as described herein and can be incorporated into compounds of Formula 1

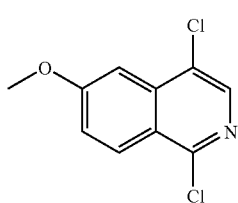

Step 1:

Modifications: A mixture of 6-methoxy-2H-isoquinolin-1-one (700 mg) and NCS (532 mg) in MeCN (10 mL) was refluxed for 3 h. Filtration gave 600 mg (72%) of the desired product as a solid.

Product:

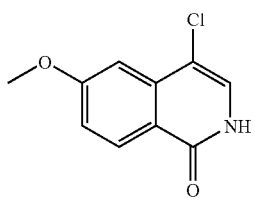

Data: $^1$H NMR (400 MHz, CD$_3$OD) δ ppm 3.96 (s, 1H), 7.19 (dd, J=8.80, 2.45 Hz, 1H), 7.28 (d, J=2.45 Hz, 1H), 7.34 (s, 1H), 8.25 (d, J=9.05 Hz, 1H); MS: (M+H)$^+$ 210.

Step 2:

Modifications: 500 mg 4-chloro-6-methoxy-2H-isoquinolin-1-one used, 400 mg product obtained.

Product:

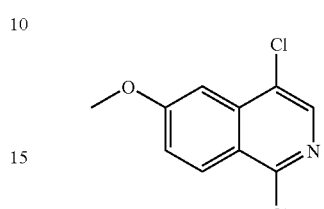

Data: $^1$H NMR (400 Hz, CDCl$_3$) δ ppm 4.01 (s, 3H), 7.35 (d, J=2.45 Hz, 1H), 7.41 (d, J=2.45 Hz, 1H), 8.24 (d, J=9.29 Hz, 1H), 8.27 (s, 1H); MS: (M+H)$^+$ 229.

Method B

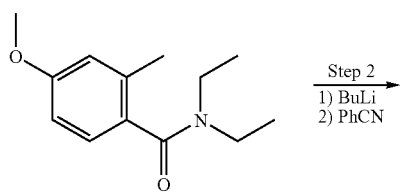 Step 1
1) SOCl$_2$
2) NHEt$_2$

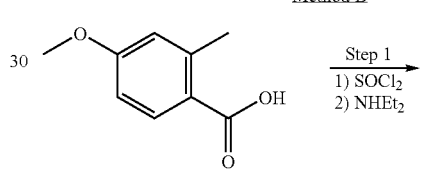 Step 2
1) BuLi
2) PhCN

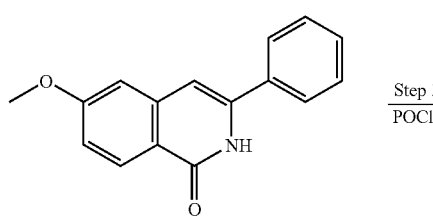 Step 3
POCl$_3$

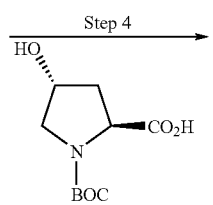 Step 4

-continued

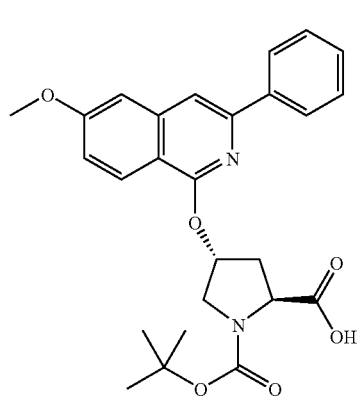

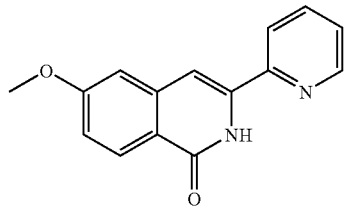

Step 1:

A mixture of 4-methoxy-2-methyl-benzoic acid (5.00 g, 30.1 mmol) and thionyl chloride (20.0 g, 0.17 mol) was heated to reflux for 30 min. Removed the volatile in vacuo. After pumping overnight, the viscous oily acid chloride was used as crude for the next reaction without any purification.

To a solution of 4-methoxy-2-methyl-benzoyl chloride in $CH_2Cl_2$ (60 mL) at 0° C. was added diethylamine dropwise. The formed mixture was allowed to warm up to the ambient temperature for 2 h with stirring. Removed the volatiles in vacuo. The residue was triturated with EtOAc (100 mL) and filtered. The filtrate was washed with 1M HCl, 1M NaOH and brine, dried over $MgSO_4$. Evaporation of the solvent yielded 6.51 g (98%) of the desired product as a viscous oil. MS m/z 222 ($M^+$+H).

Step 2:

To a solution of N,N-diethyl-4-methoxy-2-methyl-benzamide (221 mg, 1.0 mmol) in THF (2 mL) at −78° C. was added n-BuLi (0.84 mL of 2.5 M in hexane, 2.10 mmol) dropwise. The formed orange solution was kept at this temperature for additional 30 min before dropwise addition of benzonitrile (103 mg, 1.0 mmol). The final solution was allowed to warm up to the ambient temperature over night with stirring. Quenched with iced 5% citric acid. Filtered, washed with water, dried. Trituration with 2:1 hexane-EtOAc (5 mL) yielded 205 mg (82%) of the desired product as a white solid.

$^1$H NMR ($d_6$-DMSO) δ 3.89 (s, 3H), 6.84 (s, 1H), 7.05-7.07 (m, 1H), 7.18 (d, J=2.5 Hz, 1H), 7.44-7.51 (m, 3H), 7.78 (d, J=7.0 Hz, 1H), 8.11 (d, J=9.0 Hz, 1H). MS m/z 252 ($M^+$+H).

Step 3:

This product, 1-chloro-6-methoxy-3-phenyl-isoquinoline, was prepared by the same method as described above except using 6-methoxy-3-phenyl-2H-isoquinolin-1-one instead.

$^1$H NMR ($CDCl_3$) δ 3.97 (s, 3H), 7.12 (d, J=2.5 Hz, 1H), 7.23-7.26 (m, 1H), 7.40-7.42 (m, 1H), 7.46-7.50 (m, 2H), 7.89 (s, 1H), 8.08 (d, J=7.0 Hz, 2H), 8.21 (d, J=9.0 Hz, 1H). MS m/z 270, 271 ($M^+$+H).

The following intermediates were prepared as described herein and can be incorporated into compounds of Formula 1

To a solution of N,N-Diethyl-4-methoxy-2-methyl-benzamide (332 mg, 1.5 mmol) in THF (15 mL) at −78° C., t-BuLi (1.7 M solution in pentane, 1.3 mL, 2.25 mmol) was added. The resulting red solution was stirred at −78° C. for 10 min, then 2-cyanopyridine (156 mg, 1.5 mmol) was added. The reaction mixture was then warmed to rt and stirred for overnight. The reaction was quenched with saturated $NH_4Cl$ solution and extracted with ethyl acetate twice. The combined organic layers were dried ($MgSO_4$) and concentrated. The crude product was purified by Prep. HPLC to give yellowish solid as TFA salt. (85 mg, 15% yield)

$^1$H NMR (400 MHz, $CD_3OD$) δ 3.91 (m, 3H), 7.09 (dd, J=9.05, 2.45 Hz, 1H), 7.17 (d, J=2.45 Hz, 1H), 7.37 (s, 1H), 7.42 (m, 1H), 7.92 (m, 1H), 8.08 (d, J=8.07 Hz, 1H), 8.18 (d, J=9.05 Hz, 1H), 8.65 (d, J=4.89 Hz, 1H). MS m/z 253 ($MH^+$).

Step 2 (Scheme 3, Step 1):

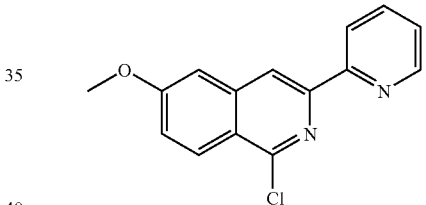

6-Methoxy-3-pyridin-2-yl-2H-isoquinolin-1-one TFA salt (85 mg, 0.232 mmol) was heated under reflux with $POCl_3$ (3.0 mL) for 2 days. Then $POCl_3$ was distilled off and the residue was quenched with ice. It was then neutralized with 10 N NaOH solution and the brown solid was collected as pure product. (62 mg, 99% yield). MS m/z 271 ($MH^+$).

The following intermediates were prepared as described herein and can be incorporated into compounds of Formula 1

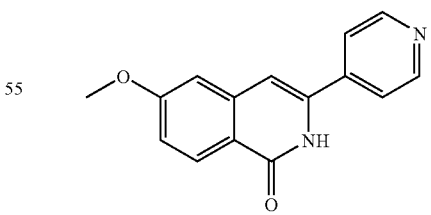

To a solution of N,N-Diethyl-4-methoxy-2-methyl-benzamide (332 mg, 1.5 mmol) in THF (15 mL) at −78° C., t-BuLi (1.7 M solution in pentane, 1.3 mL, 2.25 mmol) was added. The resulting red solution was stirred at −78° C. for 10 min, then 4-cyanopyridine (164 mg, 1.575 mmol) was added. The reaction mixture was then warmed to rt and stirred for overnight. The reaction was quenched with saturated NH₄Cl solution and the yellow precipitate was collected as pure product. (145 mg, 38% yield)

¹H NMR (CD₃OD, 400 MHz) δ3.91 (s, 3H), 7.18 (dd, J=8.8 Hz, 2.8 Hz, 1H), 7.26 (m, 2H), 8.06 (d, J=6.0 Hz, 2H), 8.16 (d, J=8.8 Hz, 1H), 8.84 (d, J=6.0 Hz, 2H). MS m/z 253 (MH⁺).

Step 2 (Scheme 3, Step 1):

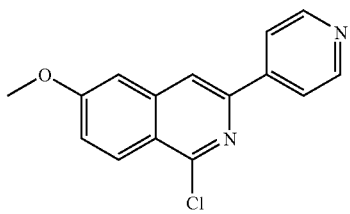

6-Methoxy-3-pyridin-4-yl-2H-isoquinolin-1-one (134 mg, 0.531 mmol) was heated under reflux with POCl₃ (6.0 mL) for 5 days. Then POCl₃ was distilled off and the residue was quenched with ice. It was then neutralized with saturated NaHCO₃ solution and the brown solid was collected as pure product. (125 mg, 87% yield) ¹H NMR (DMSO-d⁶, 400 MHz) δ3.99 (s, 3H), 7.53 (dd, J=9.04 Hz, 2.44 Hz, 1H), 7.59 (d, J=2.69 Hz, 1H), 8.26 (d, J=9.05 Hz, 1H), 8.30 (d, J=5.38 Hz, 2H), 8.73 (s, 1H), 8.85 (d, J=6.36 Hz, 2H). MS m/z 271 (MH⁺).

The following intermediates were prepared as described herein and can be incorporated into compounds of Formula 1

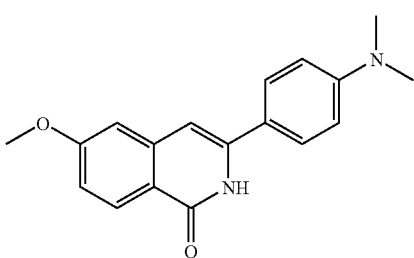

To a solution of N,N-Diethyl-4-methoxy-2-methyl-benzamide (332 mg, 1.5 mmol) in THF (15 mL) at −78° C., t-BuLi (1.7 M solution in pentane, 1.3 mL, 2.25 mmol) was added. The resulting red solution was stirred at −78° C. for 10 min, then 4-dimethylamino benzonitrile (219 mg, 1.5 mmol) was added. The reaction mixture was then warmed to rt and stirred for overnight. The reaction was quenched with saturated NH₄Cl solution and the yellow precipitate was collected and triturated with ether to give an off-white solid as pure product. (247 mg, 56% yield)

¹H NMR (DMSO-d⁶, 400 MHz) δ2.97 (s, 6H), 3.87 (s, 3H), 6.72 (s, 1H), 6.78 (d, J=8.80 Hz, 2H), 6.97 (dd, J=8.80, 2.45 Hz, 1H), 7.10 (d, J=2.45 Hz, 1H), 7.65 (d, J=8.80 Hz, 2H), 8.05 (d, J=8.80 Hz, 1H), 11.11 (s, 1H). MS m/z 295 (MH⁺).

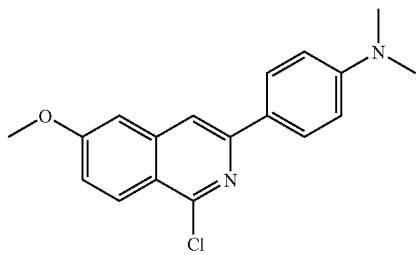

3-(4-Dimethylamino-phenyl)-6-methoxy-2H-isoquinolin-1-one (245 mg, 0.83 mmol) was heated under reflux with POCl₃ (10.0 mL) for 2 days. Then POCl₃ was distilled off and the residue was quenched with ice. It was then neutralized with 10 N NaOH solution and extracted with ethyl acetate twice. The organic layers were combined and dried (MgSO4). Evaporation of solvent gave an orange solid as product (215 mg, 83% yield)

¹H NMR (400 MHz, CD₃OD) δ 3.01 (s, 6H), 3.96 (s, 3H), 6.88 (d, J=9.05 Hz, 2H), 7.20 (dd, J=9.17, 2.57 Hz, 1H), 7.28 (d, J=2.45 Hz, 1H), 7.94 (s, 1H), 7.96 (d, J=9.05 Hz, 2H), 8.13 (d, J=9.29 Hz, 1H). MS m/z 313 (MH⁺).

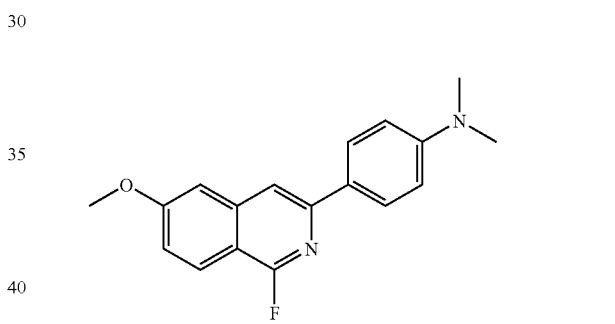

A mixture of [4-(1-Chloro-6-methoxy-isoquinolin-3-yl)-phenyl]-dimethyl-amine (110 mg, 0.35 mmol) and tetrabutyl phosphonium hydrogen difluoride (0.5 g) was heated at 140° C. in Smith microwave reactor for 20 min. Then it was added water and extracted with ethyl acetate. The organic layer was separated, washed with water and dried (MgSO₄). Evaporation of solvent gave a brownish solid as product. (85 mg, 82% yield). MS m/z 297 (MH⁺).

Method C

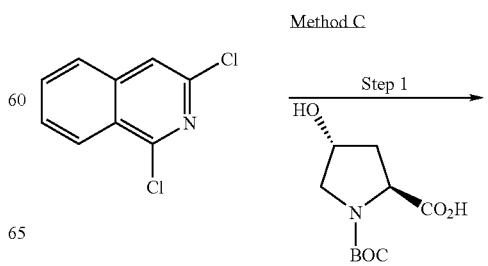

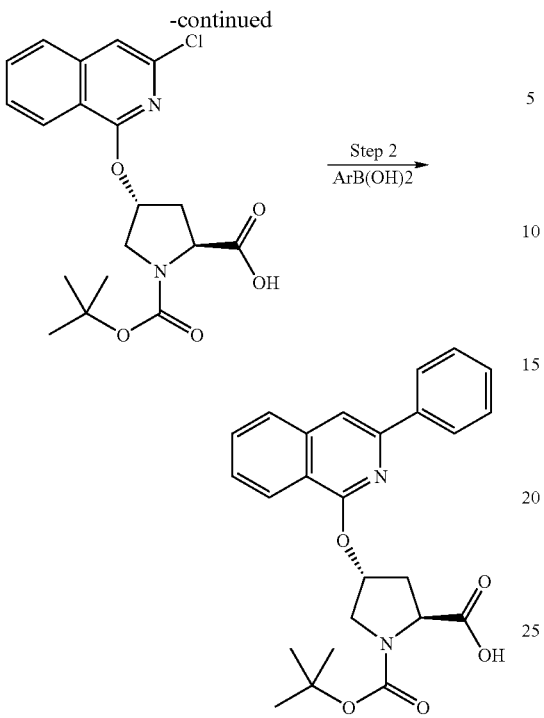

Step 1:

To a solution of N—BOC-3-(R)-hydroxy-L-proline (6.22 g, 26.9 mmol) in DMF (250 mL) at 0° C. was added NaH (60%, 3.23 g, 80.8 mmol) by several portions. The formed suspension was stirred at this temperature for 30 min. 1,3-dichloro-isoquinoline (5.33 g, 26.9 mmol) was added as solid in one portion and the final mixture was stirred at the ambient temperature for 12 h. Quenched with iced 5% citric acid (aq), extracted with EtOAC (300 mL). The aqueous phase was extracted with EtOAC again. The combined organic layers were washed with 5% citric acid (aq) and brine respectively, dried over MgSO$_4$, filtered. The filtrate was evaporated in vacuo to dryness to yield 10.53 g (99.8%) of 4-(6-methoxy-isoquinolin-1-yloxy)-pyrrolidine-1,2-dicarboxylic acid 1-tert-butyl ester as an off-white foam. This material was used in the next step reaction as crude without further purification.

$^1$H NMR (CD$_3$OD) δ 1.43, 1.44 (rotamers, 9H), 2.39-2.44 (m, 1H), 2.68-2.72 (m, 1H), 3.80-3.90 (m, 2H), 4.44-4.52 (m, 1H), 5.77 (b, 1H), 7.39 (s, 1H), 7.58 (t, J=7.3 Hz, 1H), 7.71-7.78 (m, 2H), 8.16 (d, J=7.5 Hz, 1H). MS m/z 392 (M$^+$+H).

Step 2:

A mixture of 4-(6-methoxy-isoquinolin-1-yloxy)-pyrrolidine-1,2-dicarboxylic acid 1-tert-butyl ester (39 mg, 0.10 mmol), phenylboronic acid (14.6 mg, 0.12 mmol), sodium tert-butoxide (38 mg, 0.40 mmol) and ((t-Bu)$_2$POH)$_2$PdCl$_2$ (POPd) (5 mg, 0.01 mmol) in THF (2 mL) was heated to reflux for 4 h. After cooling down, the formed mixture was quenched with 5% citric acid (aq) and extracted with EtOAc (20 mL). The organic layer was washed with brine, dried over MgSO$_4$, filtered, evaporated. The residue was purified by prep-HPLC to yield 36 mg (83%) of the desired product as an off-white foam.

$^1$H NMR (CD$_3$OD) δ 1.43, 1.45 (rotamers, 9H), 2.51-2.56 (m, 1H), 2.74-2.82 (m, 1H), 3.88-3.92 (m, 1H), 3.98-4.01 (m, 1H), 4.50-4.57 (m, 1H), 5.95 (b, 1H), 7.36-7.39 (m, 1H), 7.45-7.48 (m, 2H), 7.55 (t, J=7.3 Hz, 1H), 7.70 (t, J=7.5 Hz, 1H), 7.84-7.89 (m, 2H), 8.14-8.17 (m, 3H), 9.05 (b, 1H). MS m/z 435 (M$^+$+H).

The following intermediates were prepared as described herein and can be incorporated into compounds of Formula 1

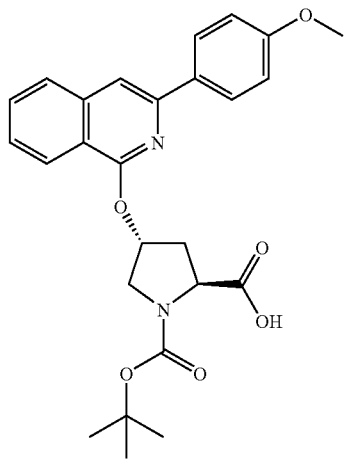

Prepared using 4-methoxyphenylboronic Acid $^1$H NMR (CD$_3$OD) δ 1.40, 1.45 (rotamers, 9H), 2.50-2.55 (m, 1H), 2.73-2.81 (m, 1H), 3.81-3.89 (m, 4H), 3.98-4.01 (m, 1H), 4.50-4.57 (m, 1H), 5.93 (b, 1H), 7.02 (d, J=9.0 Hz, 2H), 7.50 (t, J=7.3 Hz, 1H), 7.67 (t, J=7.5 Hz, 1H), 7.73 (s, 1H), 7.83 (d, J=8.5 Hz, 1H), 8.09 (d, J=8.5 Hz, 2H), 8.15 (d, J=8.0 Hz, 1H). MS m/z 465 (M$^+$+H).

The following intermediate was prepared as described above:

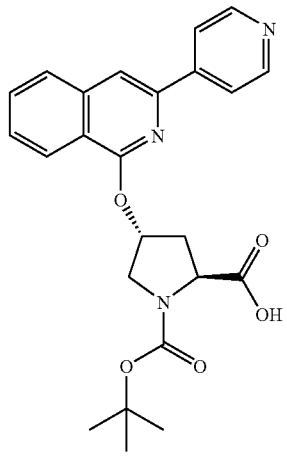

Prepared using 4-pyridylboronic Acid $^1$H NMR (CD$_3$OD) δ 1.43, 1.46 (rotamers, 9H), 2.53-2.56 (m, 1H), 2.80-2.89 (m, 1H), 3.90-3.93 (m, 1H), 4.00-4.05 (m, 1H), 4.50-4.57 (m, 1H), 6.00, 6.05 (rotamers, 1H), 7.80 (t, J=7.3 Hz, 1H), 7.87 (t, J=7.5 Hz, 1H), 8.08 (d, J=8.5 Hz, 1H), 8.32 (d, J=8.0 Hz, 1H), 8.49 (s, 1H), 8.84 (d, J=6.0 Hz, 2H), 8.84 (d, J=6.5 Hz, 2H. MS m/z 436 (M$^+$+H).

The following intermediates were prepared as described herein and can be incorporated into compounds of Formula 1

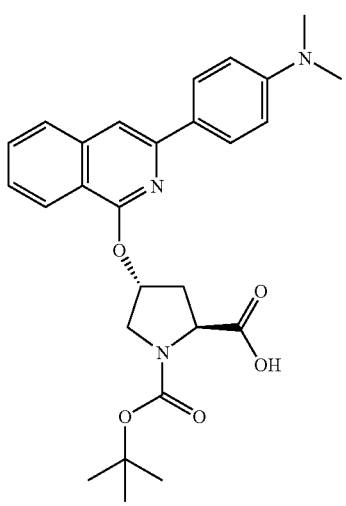

Prepared using 4-N,N-dimethylamino-phenylboronic Acid

MS m/z 478 (M⁺+H).

Method D

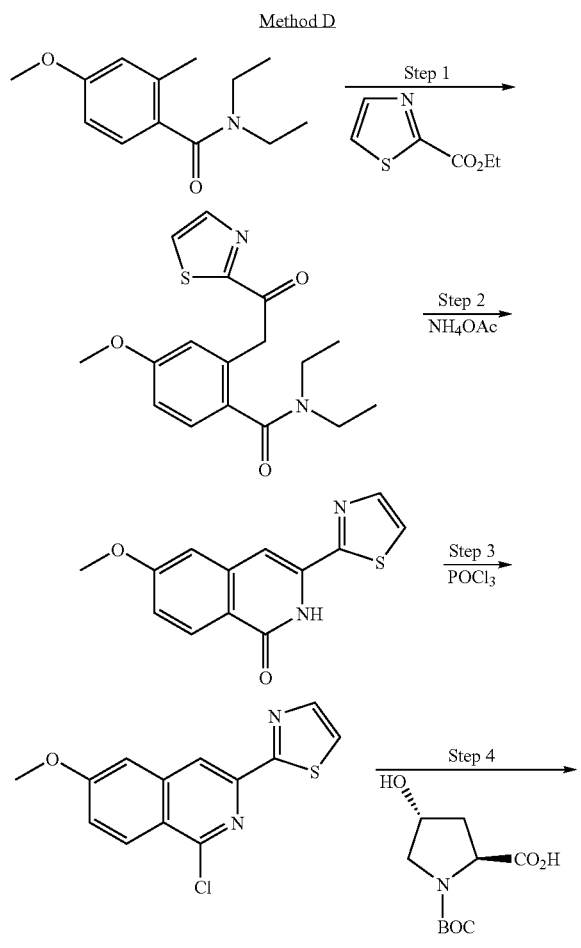

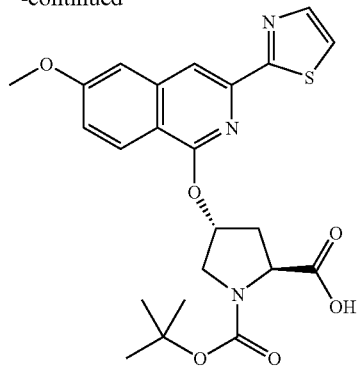

Step 1:

To a solution of N,N-diethyl-4-methoxy-2-methyl-benzamide (633 mg, 2.9 mmol) in THF (15 mL) at −78° C. was added n-BuLi (2.3 mL of 2.5 M in hexane, 5.74 mmol) dropwise. The formed red solution was kept at this temperature for additional 30 min before being cannulated to a solution of thiazole-2-carboxylic acid ethyl ester (A. Medici et al, Tetrahedron Lett. 1983, p 2901) (450 mg, 2.9 mmol) in THF (5 mL) at −78° C. The final dark green solution was kept to this temperature for 2 h with stirring. Quenched with sat. NH₄Cl (aq) and extracted with EtOAc (50 mL). The organic layer was washed with sat. NH₄Cl (aq) and brine, dried, purified by flash column chromatography, eluting with 2:1 EtOAc:hexane to provide 405 mg (45%) of the desired product as an off-white viscous oil.

$^1$H NMR (CDCl$_3$) δ 1.08 (t, J=7.0 Hz, 6H), 3.22 (b, 2H), 3.44 (b, 2H), 3.79 (s, 3H), 4.59 (s, 2H), 6.79-6.81 (m, 1H), 6.86 (d, J=2.5 Hz, 1H), 7.16 (d, J=8.5 Hz, 1H), 7.66 (d, J=3.0 Hz, 1H), 8.00 (d, J=3.0 Hz, 1H).

MS m/z 333 (M⁺+H).

Step 2:

A mixture of N,N-diethyl-4-methoxy-2-(2-oxo-2-thiazol-2-yl-ethyl)-benzamide (405 mg, 1.22 mmol) and NH₄OAc (3.0 g, 38.9 mmol) was heated to 140° C. in a sealed tube for 1 h. The melted solution was poured into iced water, filtered, washed the cake thoroughly with water. The dried brownish solid (240 mg, 76%) was used as crude for the next reaction without further purification. MS m/z 259 (M⁺+H).

Step 3:

This product, 1-chloro-6-methoxy-3-thiazol-2-yl-isoquinoline, was prepared as described above except using 6-methoxy-3-thiazol-2-yl-2H-isoquinolin-1-one instead.

$^1$H NMR (CDCl$_3$) δ 3.97 (s, 3H), 7.16 (d, J=4.0 Hz, 1H), 7.27-7.31 (m, 1H), 7.46 (d, J=5.0 Hz, 1H), 7.93 (d, J=5.5 Hz, 1H), 8.22 (d, J=15.5 Hz, 1H), 8.39 (s, 1H). MS m/z 277 (M⁺+H).

Step 4:

This product was prepared by the same method as described above using 1-chloro-6-methoxy-3-thiazol-2-yl-isoquinoline instead.

$^1$H NMR (CD$_3$OD) δ 0.97-1.09 (m, 12H), 1.24-1.29 (m, 10H), 1.44-1.46 (m, 1H), 1.87-1.90 (m, 1H), 2.20-2.26 (m, 1H), 2.30-2.36 (m. 1H), 2.65-2.71 (m, 1H), 2.93-2.96 (m, 1H), 3.96 (s, 3H), 4.12-4.27 (m, 2H), 4.38-4.52 (m, 2H), 5.12 (d, J=10.5 Hz, 1H), 5.29 (d, J=17.5 Hz, 1H), 5.69-5.74 (m, 1H), 5.99 (b, 1H), 7.14 (d, J=9.0 Hz, 1H), 7.33 (s, 1H), 7.66

(d, J=3.5 Hz, 1H), 7.93 (d, J=3.0 Hz, 1H), 8.05 (s, 1H), 8.11 (d, J=9.0 Hz, 1H), 9.14 (b, 1H).

MS m/z 797 (M⁺+H).

The following intermediates were prepared as described herein and can be incorporated into compounds of Formula 1

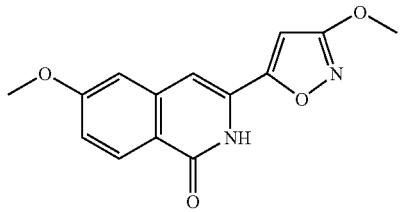

6-methoxy-3-(3-methoxy-isoxazol-5-yl)-2H-isoquinolin-1-one was prepared using N,N-diethyl-4-methoxy-2-[2-(3-methoxy-isoxazol-5-yl)-2-oxo-ethyl]-benzamide.

¹H NMR (DMSO-d₆) δ 3.89 (s, 3H), 3.97 (s, 3H), 7.01 (s, 1H), 7.14-7.16 (m, 2H), 7.43 (s, 1H), 8.13 (d, J=8.5 Hz, 1H).

MS m/z 273 (M⁺+H).

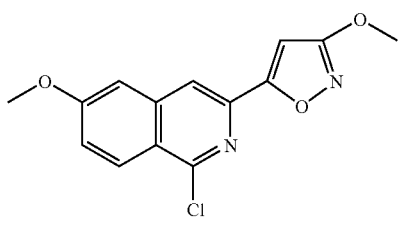

1-chloro-6-methoxy-3-(3-methoxy-isoxazol-5-yl)-isoquinoline was prepared using 6-methoxy-3-(3-methoxy-isoxazol-5-yl)-2H-isoquinolin-1-one ¹H NMR (CDCl₃) δ 3.97 (s, 3H), 4.04 (s, 3H), 6.60 (s, 1H), 7.17 (d, J=2.5 Hz, 1H), 7.31-7.33 (m, 1H), 8.02 (s, 1H), 8.23 (d, J=9.0 Hz, 1H).

MS m/z 291, 293 (M⁺+H)

The following intermediates were prepared as described herein and can be incorporated into compounds of Formula 1

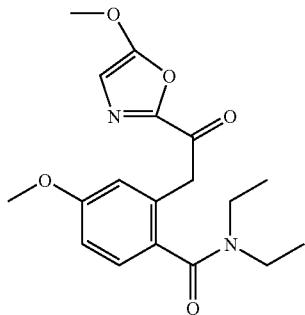

N,N-diethyl-4-methoxy-2-[2-(5-methoxy-oxazol-2-yl)-2-oxo-ethyl]-benzamide, was prepared using 5-methoxy-oxazole-2-carboxylic acid ethyl ester.

MS m/z 347 (M⁺+H).

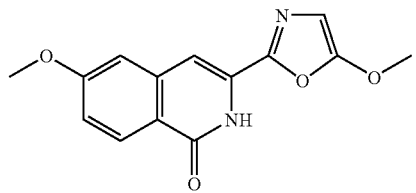

6-methoxy-3-(5-methoxy-oxazol-2-yl)-2H-isoquinolin-1-one, was prepared using N,N-diethyl-4-methoxy-2-[2-(5-methoxy-oxazol-2-yl)-2-oxo-ethyl]-benzamide. ¹H NMR (DMSO-d₆) δ 3.94 (s, 3H), 4.01 (s, 3H), 6.34 (s, 1H), 6.99 (d, J=2.0 Hz, 1H), 7.12-7.14 (m, 1H), 7.25 (s, 1H), 8.32 (d, J=9.0 Hz, 1H).

MS m/z 274 (M⁺+H).

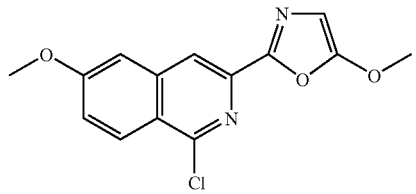

1-chloro-6-methoxy-3-(5-methoxy-oxazol-2-yl)-isoquinoline, was prepared using 6-methoxy-3-(5-methoxy-oxazole-2-yl)-2H-isoquinolin-1-one.

¹H NMR (CDCl₃) δ 3.96 (s, 3H), 4.00 (s, 3H), 6.34 (s, 1H), 7.12 (d, J=2.5 Hz, 1H), 7.28-7.31 (m, 1H), 8.13 (s, 1H), 8.23 (d, J=9.0 Hz, 1H).

MS m/z 291, 293 (M⁺+H).

The following intermediates were prepared as described herein and can be incorporated into compounds of Formula 1

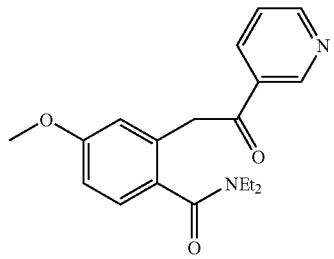

To a solution of N,N-Diethyl-4-methoxy-2-methyl-benzamide (332 mg, 1.5 mmol) in THF (15 mL) at −78° C., t-BuLi (1.7 M solution in pentane, 2.12 mL, 3.6 mmol) was added. The resulting red solution was stirred at −78° C. for 10 min, then methyl nicotinate (206 mg, 1.5 mmol) was added. The reaction mixture was stirred at −78° C. for 2 h. Then the reaction was quenched with saturated NH₄Cl solution and extracted with ethyl acetate twice. The combined organic layers were dried (MgSO₄) and concentrated. The crude product was purified by Prep. HPLC to give yellowish thick oil as TFA salt. (124 mg, 19% yield).

MS m/z 349 (M+Na⁺).

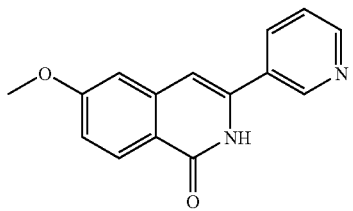

N,N-Diethyl-4-methoxy-2-(2-oxo-2-pyridin-3-yl-ethyl)-benzamide (120 mg, 0.272 mmol) was heated with ammonium acetate (1 g) for 3 hr. Then it was cooled down and added water. Extracted with ethyl acetate and the organic layer was separated. It was then dried (MgSO$_4$) and concentrated to give a brownish solid as product. (65 mg, 95% yield)

$^1$H NMR (400 MHz, DMSO-d$^6$) δ 3.89 (s, 3H), 6.93 (s, 1H), 7.10 (dd, J=8.80, 2.45 Hz, 1H), 7.19 (d, J=2.45 Hz, 1H), 7.52 (dd, J=7.46, 4.77 Hz, 1H), 8.15 (m, 2H), 8.64 (dd, J=4.89, 1.47 Hz, 1H), 8.96 (d, J=1.71 Hz, 1H), 11.51 (s, 1H).

MS m/z 253 (MH$^+$).

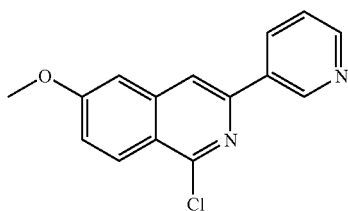

6-Methoxy-3-pyridin-3-yl-2H-isoquinolin-1-one (65 mg, 0.258 mmol) was heated under reflux with POCl$_3$ (2.5 mL) for 7 days. Then POCl$_3$ was distilled off and the residue was quenched with ice. It was then neutralized with 10 N NaOH solution and extracted with ethyl acetate twice. The combined organic layers were dried (MgSO$_4$) and concentrated to give yellow solid as product. (27 mg, 39% yield).

MS m/z 271 (MH$^+$).

The following intermediates were prepared as described herein and can be incorporated into compounds of Formula 1

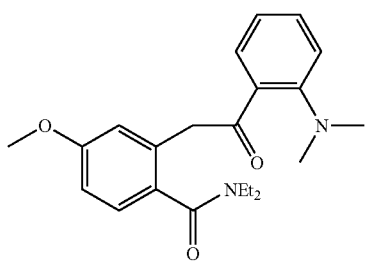

To a solution of N,N-Diethyl-4-methoxy-2-methyl-benzamide (332 mg, 1.5 mmol) in THF (15 mL) at −78° C., t-BuLi (1.7 M solution in pentane, 2.2 mL, 3.75 mmol) was added. The resulting red solution was stirred at −78° C. for 10 min, then N,N-dimethylanthranilic acid methyl ester (269 mg, 1.5 mmol) was added. The reaction mixture was stirred at −78° C. for 2 h. Then the reaction was quenched with saturated NH$_4$Cl solution and extracted with ethyl acetate twice. The combined organic layers were dried (MgSO$_4$) and concentrated. The crude product was purified by Prep. HPLC to give yellowish thick oil as product. (256 mg, 46% yield)

$^1$H NMR (400 MHz, CD$_3$OD) δ 0.99-1.13 (m, 6H), 3.23-3.31 (m, 8H), 3.39 (m, 2 H), 3.82 (s, 3H), 4.35 (s, 2H), 6.91 (dd, J=8.44, 2.57 Hz, 1H), 6.99 (d, J=2.45 Hz, 1H), 7.22 (d, J=8.56 Hz, 1H), 7.69 (t, J=7.70 Hz, 1H), 7.84 (m, 1H), 7.96 (d, J=8.31 Hz, 1H), 8.18 (d, J=7.83 Hz, 1H).

MS m/z 369 (MH$^+$).

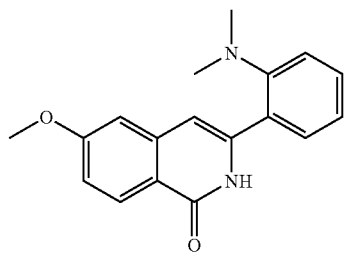

2-[2-(2-Dimethylamino-phenyl)-2-oxo-ethyl]-N,N-diethyl-4-methoxy-benzamide (250 mg, 0.678 mmol) was heated with ammonium acetate (1.5 g) for 2 hr. Then it was cooled down and added water. Extracted with ethyl acetate and the organic layer was separated. It was then dried (MgSO$_4$) and concentrated to give a yellowish solid as product. (125 mg, 63% yield)

$^1$H NMR (400 MHz, CD$_3$OD) δ 2.95 (s, 6H), 3.92 (s, 3H), 6.92 (s, 1H), 7.12 (dd, J=8.80, 2.45 Hz, 1H), 7.16 (d, J=2.45 Hz, 1H), 7.35 (m, 1H), 7.55 (m, 2H), 7.63 (d, J=7.83 Hz, 1H), 8.20 (d, J=9.05 Hz, 1H).

MS m/z 295 (MH$^+$).

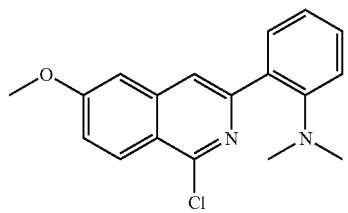

3-(2-Dimethylamino-phenyl)-6-methoxy-2H-isoquinolin-1-one (125 mg, 0.425 mmol) was heated under reflux with POCl$_3$ (4.0 mL) for one day. Then POCl$_3$ was distilled off and the residue was quenched with ice. It was then neutralized with 10 N NaOH solution and extracted with ethyl acetate twice. The organic layers were combined and dried (MgSO$_4$). Evaporation of solvent gave a brownish solid as product (82 mg, 62% yield)

MS m/z 313 (MH$^+$).

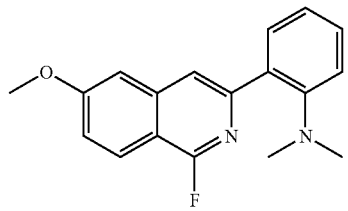

A mixture of [2-(1-Chloro-6-methoxy-isoquinolin-3-yl)-phenyl]-dimethyl-amine (82 mg, 0.262 mmol) and tetrabutyl phosphonium hydrogen difluoride (1.0 g) was heated at 140° C. in Smith microwave reactor for 20 min. Then it was added water and extracted with ethyl acetate. The organic layer was separated, washed with water and dried (MgSO$_4$). Evaporation of solvent gave the crude product which was purified by Prep. HPLC to afford a yellowish oil as product. (85 mg)

$^1$H NMR (400 MHz, CD$_3$OD) δ 3.41 (s, 6H), 4.00 (s, 3H), 7.42 (dd, J=9.05, 2.45 Hz, 1H), 7.53 (s, 1H), 7.71 (m, 2H), 7.99 (m, 1H), 8.16 (m, 2H), 8.31 (s, 1H). MS m/z 297 (MH$^+$).

The following intermediates were prepared as described herein and can be incorporated into compounds of Formula 1

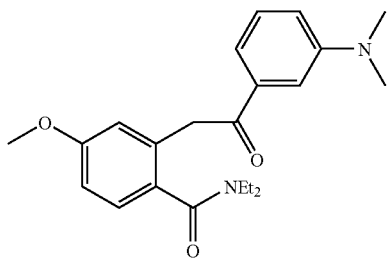

To a solution of N,N-Diethyl-4-methoxy-2-methyl-benzamide (332 mg, 1.5 mmol) in THF (15 mL) at −78° C., t-BuLi (1.7 M solution in pentane, 2.2 mL, 3.75 mmol) was added. The resulting red solution was stirred at −78° C. for 10 min, then (3-dimethylamino)benzoic acid methyl ester (269 mg, 1.5 mmol) was added. The reaction mixture was stirred at −78° C. for 2 h. Then the reaction was quenched with saturated NH$_4$Cl solution and extracted with ethyl acetate twice. The combined organic layers were dried (MgSO$_4$) and concentrated. The crude product was purified by Prep. HPLC to give yellowish thick oil as TFA salt. (245 mg, 33% yield) 1H NMR (400 MHz, CD$_3$OD) δ 1.01 (t, J=6.85 Hz, 3H), 1.09 (m, 3H), 3.11 (s, 6H), 3.21 (m, 2H), 3.40 (m, 2H), 3.79 (s, 3H), 4.39 (s, 2H), 6.84-6.91 (m, 2H), 7.19 (d, J=8.32 Hz, 1H), 7.35 (m, 1H), 7.49 (t, J=8.07 Hz, 1H), 7.66-7.71 (m, 2H).

MS m/z 369 (MH$^+$).

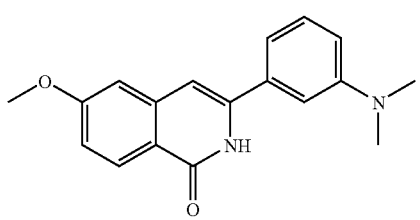

2-[2-(3-Dimethylamino-phenyl)-2-oxo-ethyl]-N,N-diethyl-4-methoxy-benzamide (240 mg, 0.497 mmol) was heated with ammonium acetate (2.0 g) for 2.5 hr. Then it was cooled down and added water. A brownish solid was collected as pure product. (95 mg, 65% yield)

1H NMR (400 MHz, CD$_3$OD) δ 2.98 (s, 6H), 3.88 (s, 3H), 6.74-6.87 (m, 2H), 7.01-7.07 (m, 3H), 7.18 (d, J=2.44 Hz, 1H), 7.28 (t, J=7.82 Hz, 1H), 8.10 (d, J=8.80 Hz, 1H). MS m/z 295 (MH$^+$).

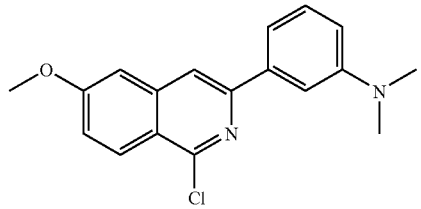

3-(3-Dimethylamino-phenyl)-6-methoxy-2H-isoquinolin-1-one (92 mg, 0.312 mmol) was heated under reflux with POCl$_3$ (3.0 mL) for 2 days. Then POCl$_3$ was distilled off and the residue was quenched with ice. It was then neutralized with saturated NaHCO$_3$ solution and extracted with ethyl acetate twice. The organic layers were combined and dried (MgSO$_4$). Evaporation of solvent gave a brownish thick oil as product. (72 mg, 74% yield). MS m/z 313 (MH$^+$).

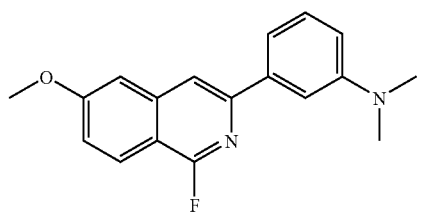

A mixture of [3-(1-Chloro-6-methoxy-isoquinolin-3-yl)-phenyl]-dimethylamine (72 mg, 0.23 mmol) and tetrabutyl phosphonium hydrogen difluoride (0.5 g) was heated at 140° C. in Smith microwave reactor for 20 min. Then it was added water and extracted with ethyl acetate. The organic layer was separated, washed with water and dried (MgSO$_4$). Evaporation of solvent gave a brownish oil as product. (58 mg, 85% yield).

MS m/z 297 (MH$^+$).

The following intermediates were prepared as described herein and can be incorporated into compounds of Formula 1

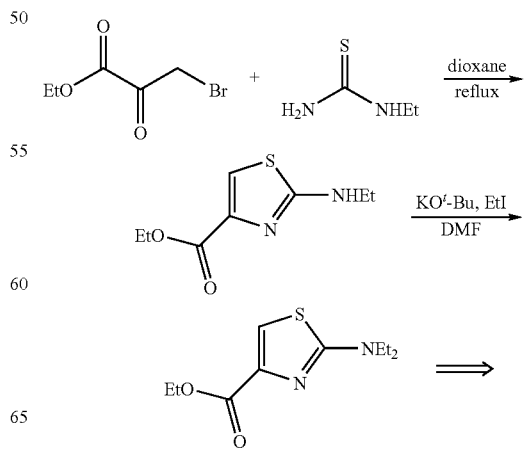

-continued

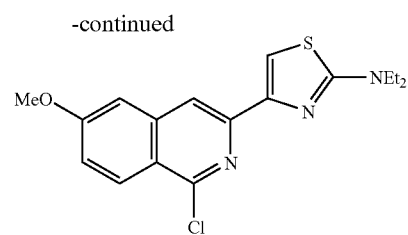

Condensation of ethyl bromopyruvate with ethyl thiourea in refluxing dioxane afforded the monoalkylamino thiazole as HBr salt in quantitative yield. Alkylation of 2-ethylamino-thiazole-4-carboxylic acid ethyl ester with EtI in DMF provided 2-diethylamino-thiazole-4-carboxylic acid ethyl ester.

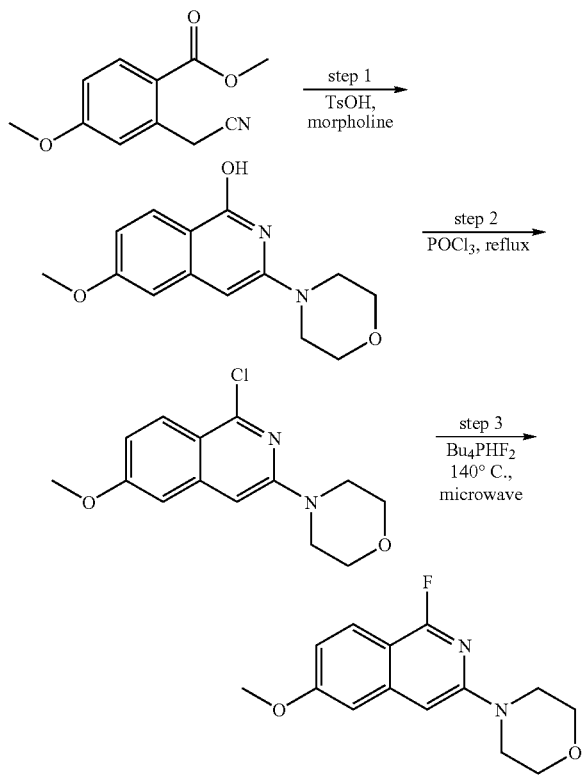

Step 1:

A suspension of 2-cyanomethyl-4-methoxy-benzoic acid methyl ester (1.9 g and TsOH. H₂O (0.15 g, mmol) in morpholine 5 mL) was refluxed for 4 h and removed the solvent in vacuo. The residue was recrystalyzed from EtOAc/hexanes with drops of MeOH to provide the product (0.43 g, 17%). MS m/z 266 (M$^+$+1).

Step 2:

A mixture of 6-methoxy-3-morpholin-4-yl-isoquinolin-1-ol (0.298 g, 1.15 mmol) in POCl₃ (20 mL) was refluxed for 2 h, removed the solvent in vacuo and cold water was added. The pH was adjusted to >11 by addition of 1.0 N NaOH. The aqueous layer was extracted with EtOAc. The extract was dried (MgSO₄), removed the solvent in vacuo to provide the product (0.299 g, 94%). MS m/z 279 (M$^+$+1).

Step 3:

A mixture of 1-Chloro-6-methoxy-3-morpholin-4-yl-isoquinoline (0.050 g, 0.18 mmol) and tetrabutyl phosphorium hydrogen difloride (0.8 g, 2.8 mmol) [Synlett 1992, (4), 345-6] was heated at 140° C. in microwave for 10 min. the reaction mixture was diluted with EtOAc and filtered through an ISCO 25 g precolumn with a layer of silicon gel on the top, removed the solvent to provide the product (0.037 mg, 77%): $^1$H NMR (CHLOROFORM-D) δ ppm 3.48 (m, 4H), 3.84 (m, 4H), 3.89 (s, 3H), 6.46 (d, J=1.22 Hz, 1H), 6.85 (s, 1H), 6.90 (dd, J=9.16, 2.44 Hz, 1H), 7.82 (d, J=8.85 Hz, 1H). MS m/z 263 (M$^+$+1).

Method F 6-fluoro and 6-alkyl isoquinolines used in the preparation of compounds of Formula 1 were prepared via a Pomeranz-Fritsch synthesis (Typical procedure: Preparation of optically active 8,8-disubstituted 1,1-biisoquinoline, K. Hirao, R. Tsuchiya, Y. Yano, H. Tsue, *Heterocycles* 42(1) 1996, 415-422) as outlined below. The products were converted into the 1-chloro derivatives via N-oxide intermediates.

General Synthetic Scheme

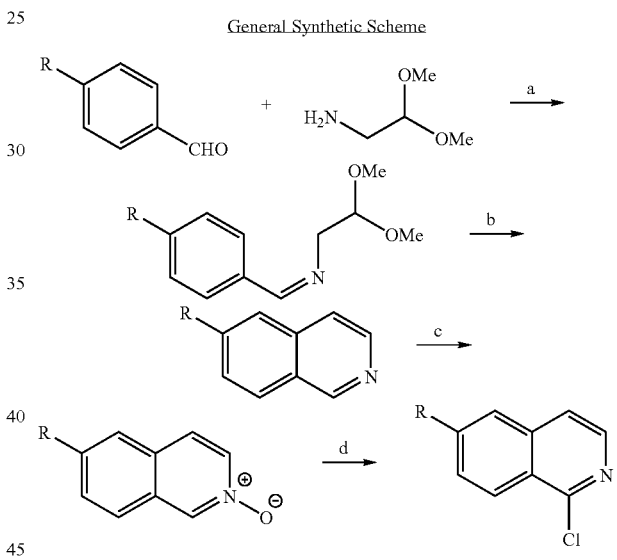

Reagents and reaction conditions: (a) reflux in benzene, azeotropic removal of water; (b) first step: ethyl chloroformate, trimethyl phosphite in THF, second step: titanium tetrachloride in chloroform; (c) MCPBA in CH₂Cl₂; (d) POCl₃ in benzene

| R | Isoquinoline, Yield | 1-Chloride, combined yield |
|---|---|---|
| F | 20 | 43 |
| Et | 76 | 65 |
| i-Pr | 14 | 18 |
| t-Bu | 47 | 55 |

Preparation of 6-isopropoxyl and 6-tert-butoxyl isoquinoline intermediates: Some 6-alkoxy-1-chloro isoquinolines were prepared by a direct, ipso displacement of the 6-fluoro-1-chloroisoquinoline with the corresponding alkoxide metal ions such as potassium tert-butoxide (53%) and sodium isopropoxide (54%).

General Synthetic Scheme

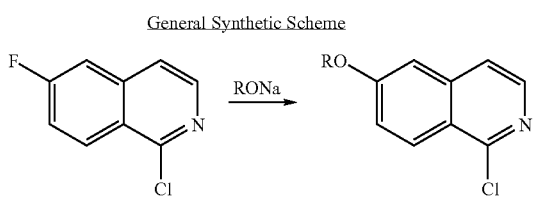

R=alkoxide anions such as tert-Bu, iso-Pr

The 6-fluoro-1-chloroisoquinoline was subjected to an aromatic nucleophilic displacement with sodium isopropoxide and potassium tert-butoxide in DMF to give the corresponding 6-isopropoxyl (54%): $^1$H NMR (400 MHz, CHLOROFORM-d) δ ppm 1.43 (d, J=6.11 Hz, 6H) 4.76 (m, J=6.11 Hz, 1H) 7.08 (d, J=2.45 Hz, 1H) 7.29 (dd, J=9.29, 2.45 Hz, 1H) 7.50 (d, J=5.62 Hz, 1H) 8.18 (d, J=5.87 Hz, 1H) 8.24 (d, J=9.29 Hz, 1H) and 6-tert-butoxyl-1-chloro isoquinolines (55%): $^1$H NMR (400 MHz, CHLOROFORM-d) δ ppm 1.48 (s, 9H) 7.31 (m, 2H) 7.47 (d, J=5.62 Hz, 1H) 8.18 (d, J=5.62 Hz, 1H) 8.21 (d, J=9.78 Hz, 1H) as the major product respectively. These 6-alkoxyl-1-chloro isoquinolines were incorporated into compounds of Formula 1 as described herein.

This synthesis made use of the technologies described, in part, in the following references:

(1) Hojo, Masaru; Masuda, Ryoichi; Sakaguchi, Syuhei; Takagawa, Makoto, *Synthesis* (1986), (12), 1016-17
(2) Rigby, James H.; Holsworth, Daniel D.; James, Kelly. Vinyl Isocyanates In Synthesis. [4+2] Cycloaddition Reactions With Benzyne Addends. *Journal Of Organic Chemistry* (1989), 54(17), 4019-20
(3) Uchibori, Y.; Umeno, M.; Yoshiokai, H.; *Heterocycles*, 1992, 34 (8), 1507-1510

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A

Method G
General Synthetic Scheme

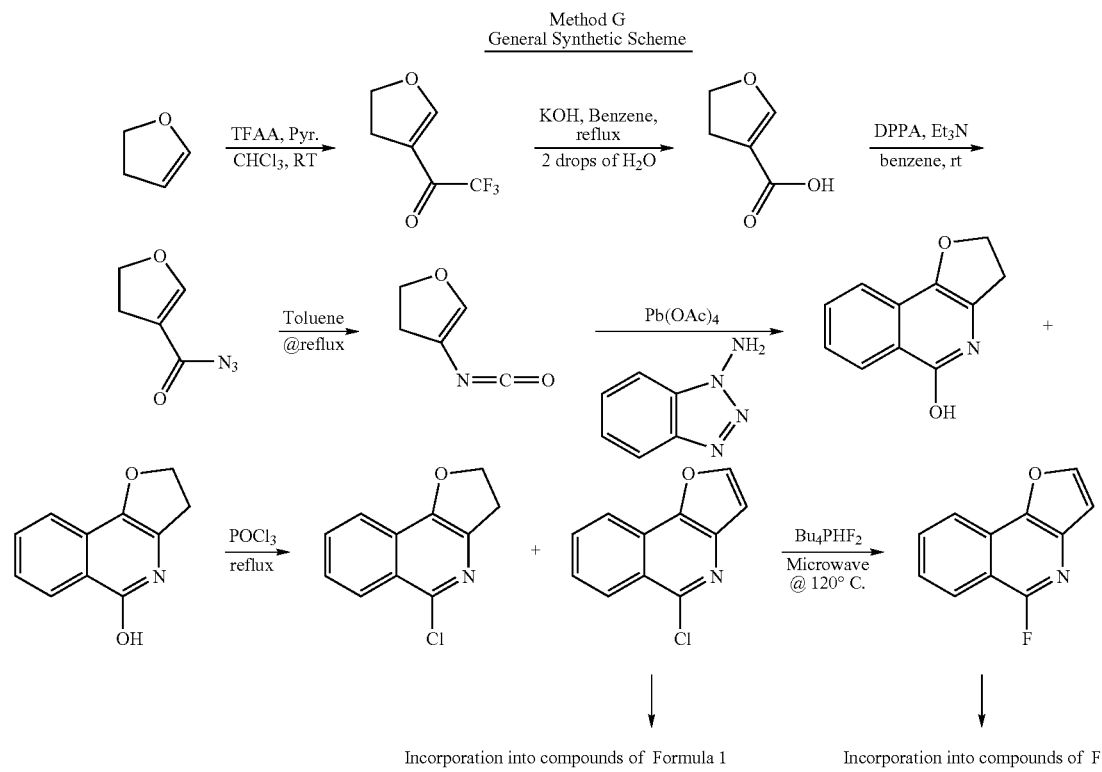

Follett, P L Yap and H Marsden, *J. Clin. Microbiol.*, 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, J. *Proc. Natl. Acad. Sci. U.S.A.* 94(16), 8738-8743 (1997); AF054247, see Yanagi, M., St Claire, M., Shapiro, M., Emerson, S. U., Purcell, R. H. and Bukh, J. *Virology* 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains was manipulated as described by P. Gallinari et al. (see Gallinari P, Paolini C, Brennan D, Nardi C, Steinkuhler C, De Francesco R. *Biochemistry* 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., *J. Virol.* 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)piperazine-N'-(2-Ethane Sulfonic acid) (HEPES), pH 7.5, 20% glycerol, 500 mM Sodium Chloride (NaCl), 0.5% Triton X-100, 1 microgram/milliliter ("μg/mL") lysozyme, 5 mM Magnesium Chloride (MgCl$_2$), 1 μg/ml DnaseI, 5 mM β-Mercaptoethanol (βME), Protease inhibitor-Ethylenediamine Tetraacetic acid (EDTA) free (Roche), homogenized and incubated for 20 minutes (min) at 4° C. The homogenate was sonicated and clarified by ultra-centrifugation at 235000 g for 1 hour at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat #22991) (FRET peptide), described by Taliani et al. in Anal. Biochem. 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 μM final concentration (from a 2 mM stock solution in DMSO stored at −20° C.). HCV NS3/4A protease type 1a (1b), 2-3 nM final concentration (from a 5 μM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 μg/ml Bovine Serum Albumin (Sigma) to the assay buffer and reducing the end protease concentration to 300 pM.

The assay was performed in a 96-well polystyrene black plate from Falcon. Each well contained 25 μl NS3/4A protease complex in assay buffer, 50 μl of a compound of the present disclosure in 10% DMSO/assay buffer and 25 μl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C.

Reactions were generally followed for approximately 15 minutes.

The percent inhibition was calculated with the following equation:

$$100-[(\delta F_{inh}/\delta F_{con})\times 100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, y=A+((B−A)/(1+((C/x)^D))).

Compounds of the present disclosure, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the in vitro selectivity of the compounds of the present disclosure in inhibiting HCV NS3/4A protease complex as compared to other serine or cysteine proteases.

The specificities of compounds of the present disclosure were determined against a variety of serine proteases: human neutrophil elastase (HNE), porcine pancreatic elastase (PPE) and human pancreatic chymotrypsin and one cysteine protease: human liver cathepsin B. In all cases a 96-well plate format protocol using either colorimetric p-nitroaniline (pNA) substrate or fluorometric Amino-Methyl-Coumarin (AMC) specific for each enzyme was used as described previously (PCT Patent Application No. WO 00/09543) with some modifications to the serine protease assays. All enzymes were purchased from Sigma, EMDbiosciences while the substrates were from Bachem, Sigma and EMDbiosciences.

The pNA assay for Chymotrypsin included a 1 h enzyme-inhibitor pre-incubation at room temperature followed by addition of substrate and hydrolysis to ~15% conversion as measured on a Spectramax Pro microplate reader. Compound concentrations varied from 100 to 0.4 µM depending on their potency. Cathepsin B, HNE, and PPE assays each was initiated by addition of substrate to enzyme-inhibitor pre-incubated for 10 min at room temperature and hydrolysis to 15% conversion as measured on cytofluor.

The final conditions for each assay were as follows:

50 mM Tris(hydroxymethyl)aminomethane hydrochloride (Tris-HCl) pH 8, 0.5 M Sodium Sulfate ($Na_2SO_4$), 50 mMNaCl, 0.1 mM EDTA, 3% DMSO, 0.01% Tween-20 with 100 µM succ-AAPF-pNA and 250 pM Chymotrypsin.

50 mM Tris-HCl, pH 8.0, 50 mM NaCl, 0.1 mM EDTA, 3% DMSO, 0.02% Tween-20, 5 µM succ-AAPV-AMC and 20 nM HNE or 8 nM PPE;

100 mM NaOAC (Sodium Acetate) pH 5.5, 3% DMSO, 1 mM TCEP (Tris(2-carboxyethyl)phosphine hydrochloride), 5 nM Cathepsin B (enzyme stock activated in buffer containing 20 mM TCEP before use), and 2 µM Z-FR-AMC diluted in $H_2O$.

The percentage of inhibition was calculated using the formula:

$[1-((UV_{inh}-UV_{blank})/(UV_{ctl}-UV_{blank}))] \times 100$

A non-linear curve fit was applied to the inhibition-concentration data, and the 50% effective concentration ($IC_{50}$) was calculated by the use of Excel XLfit software.

Generation of HCV Replicon

An HCV replicon whole cell system was established as described by Lohmann V, Korner F, Koch J, Herian U, Theilmann L, Bartenschlager R., Science 285(5424): 110-3 (1999). This system enabled us to evaluate the effects of our HCV Protease compounds on HCV RNA replication. Briefly, using the HCV strain 1b sequence described in the Lohmann paper (Assession number: AJ238799), an HCV cDNA was synthesized by Operon Technologies, Inc. (Alameda, Calif.), and the full-length replicon was then assembled in plasmid pGem9zf(+) (Promega, Madison, Wis.) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV 3' UTR. Plasmid DNAs were linearized with ScaI and RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

HCV Replicon FRET Assay

The HCV replicon FRET assay was developed to monitor the inhibitory effects of compounds described in the disclosure on HCV viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL). Cells were seeded the night before ($1.5 \times 10^4$ cells/well) in 96-well tissue-culture sterile plates. Compound and no compound controls were prepared in DMEM containing 4% FCS, 1:100 Penicillin/Streptomysin (Gibco-BRL), 1:100 L-glutamine and 5% DMSO in the dilution plate (0.5% DMSO final concentration in the assay). Compound/DMSO mixes were added to the cells and incubated for 4 days at 37° C. After 4 days, cells were first assessed for cytotoxicity using alamar Blue (Trek Diagnotstic Systems) for a $CC_{50}$ reading. The toxicity of compound ($CC_{50}$) was determined by adding $\frac{1}{10}^{th}$ volume of alamarBlue to the media incubating the cells. After 4 hours, the fluorescence signal from each well was read, with an excitation wavelength at 530 nm and an emission wavelength of 580 nm, using the Cytofluor Series 4000 (Perspective Biosystems). Plates were then rinsed thoroughly with Phosphate-Buffered Saline (PBS) (3 times 150 µl). The cells were lysed with 25 µl of a lysis assay reagent containing an HCV protease substrate (5× cell Luciferase cell culture lysis reagent (Promega #E153A) diluted to 1× with distilled water, NaCl added to 150 mM final, the FRET peptide substrate (as described for the enzyme assay above) diluted to 10 µM final from a 2 mM stock in 100% DMSO. The plate was then placed into the Cytofluor 4000 instrument which had been set to 340 nm excitation/490 nm emissions, automatic mode for 21 cycles and the plate read in a kinetic mode. $EC_{50}$ determinations were carried out as described for the $IC_{50}$ determinations.

HCV Replicon Luciferase Reporter Assay

As a secondary assay, $EC_{50}$ determinations from the replicon FRET assay were confirmed in a replicon luciferase reporter assay. Utilization of a replicon luciferase reporter assay was first described by Krieger et al (Krieger N, Lohmann V, and Bartenschlager R, *J. Virol.* 75(10):4614-4624 (2001)). The replicon construct described for our FRET assay was modified by inserting cDNA encoding a humanized form of the *Renilla* luciferase gene and a linker sequence fused directly to the 3'-end of the luciferase gene. This insert was introduced into the replicon construct using an AscI restriction site located in core, directly upstream of the neomycin marker gene. The adaptive mutation at position 1179 (serine to isoleucine) was also introduced (Blight K J, Kolykhalov, A A, Rice, C M, *Science* 290(5498):1972-1974). A stable cell line constitutively expressing this HCV replicon construct was generated as described above. The luciferase reporter assay was set up as described for the HCV replicon FRET assay with the following modifications. Following 4 days in a 37° C./5% $CO_2$ incubator, cells were analyzed for *Renilla* Luciferase activity using the Promega Dual-Glo Luciferase Assay System. Media (100 µl) was removed from each well containing cells. To the remaining 50 µl of media, 50 µl of Dual-Glo Luciferase Reagent was added, and plates rocked for 10 min to 2 h at room temperature. Dual-Glo Stop & Glo Reagent (50 µl) was then added to each well, and plates were rocked again for an additional 10 min to 2 h at room temperature. Plates were read on a Packard TopCount NXT using a luminescence program.

The percentage inhibition was calculated using the formula below:

$$\% \text{ control} = \frac{\text{average luciferase signal in experimental wells (+compound)}}{\text{average luciferase signal in } DMSO \text{ control wells (-compound)}}$$

The values were graphed and analyzed using XLfit to obtain the $EC_{50}$ value.

Representative compounds of the disclosure were assessed in the HCV enzyme assays, HCV replicon cell assay and/or in several of the outlined specificity assays. For example, Compound 18 was found to have an $IC_{50}$ of 3.4 nanomolar (nM) against the NS3/4A BMS strain in the enzyme assay. Similar potency values were obtained with the published H77 ($IC_{50}$ of 1.2 nM) and J4L6S ($IC_{50}$ of 0.9 nM) strains. The $EC_{50}$ value in the replicon FRET assay was 9 nM and 1.1 nM in the replicon Luciferase assay.

In the specificity assays, the same compound was found to have the following activity: HLE>1.56 µM; PPE>1.56 µM; Chymotrypsin >50 µM; Cathepsin B>50 µM. These results indicate this family of compounds is highly specific for the NS3 protease and many of these members inhibit HCV replicon replication.

It should be understood that the compounds of the present disclosure may inhibit all genotypes of HCV.

The compounds of the current disclosure were tested and found to have activities in the ranges as follow:

$IC_{50}$ Activity Range (NS3/4A BMS Strain): A is >0.2 µM; B is 0.02-0.2 µM; C is 0.6-20 nM.

$EC_{50}$ Activity Ranges (for compounds tested): A is >1 µM; B is 0.1-1 µM; C is 3-100 nM.

TABLE 2

| Compound Number | HCV Protease (IC50) | HCV Pro Replicon (EC50) |
| --- | --- | --- |
| 409 - first isomer | B | |
| 409 - second isomer | A | |
| 201A | 4.00 | 4.23 |
| 201B | B | C |
| 202A | C | C |
| 202B | 660.00 | 1298.00 |
| 203A | 4.00 | 1.54 |
| 203B | B | C |
| 204 first isomer | C | C |
| 204 second isomer | A | A |
| 205 first isomer | C | C |
| 205 second isomer | A | C |
| 206 first isomer | C | C |
| 206 second isomer | A | A |
| 207 first isomer | C | C |
| 207 second isomer | A | A |
| 208 first isomer | C | C |
| 208 second isomer | A | |
| 209 first isomer | C | C |
| 209 second isomer | A | A |
| 210 first isomer | C | C |
| 210 second isomer | B | B |
| 211 first isomer | C | C |
| 211 second isomer | A | C |
| 212 first isomer | A | B |
| 212 second isomer | C | C |
| 213 first isomer | A | B |
| 213 second isomer | C | C |
| 214 first isomer | C | B |
| 214 second isomer | A | |
| 215B | 830.00 | 5494.00 |
| 215A | C | C |
| 216 first isomer | C | C |
| 216 second isomer | A | |
| 217 first isomer | C | C |
| 217 second isomer | A | |
| 218 first isomer | C | C |
| 218 second isomer | A | A |
| 219 first isomer | A | A |
| 219 second isomer | C | C |
| 220 first isomer | C | C |
| 220 second isomer | A | B |
| 221 first isomer | C | B |
| 221 second isomer | B | A |

TABLE 2-continued

| Compound Number | HCV Protease (IC50) | HCV Pro Replicon (EC50) |
|---|---|---|
| 222 | C | C |
| 223 first isomer | C | B |
| 223 second isomer | A | A |
| 224 first isomer | C | B |
| 224 second isomer | A | B |
| 226 first isomer | C | C |
| 226 second isomer | A | |
| 227 first isomer | C | C |
| 227 second isomer | A | A |
| 231 first isomer | C | C |
| 231 second isomer | A | A |
| 232 first isomer | C | C |
| 232 second isomer | B | C |
| 233A | B | B |
| 233B | 1300.00 | 2628.00 |
| 234 first isomer | B | B |
| 234 second isomer | A | A |
| 235 first isomer | A | |
| 235 second isomer | C | C |
| 236 | A | A |
| 237 | A | A |
| 238 | B | B |
| 239 | A | B |
| 240 | C | B |
| 241 | A | A |
| 1B | 289.00 | 1639.00 |
| 1A | C | C |
| 2 | B | B |
| 3 | C | A |
| 4 | B | A |
| 5 | B | B |
| 6 first isomer | B | A |
| 6 second isomer | C | B |
| 16 | C | C |
| 17 | C | C |
| 21 | C | C |
| 35 | C | C |
| 36 | 73.00 | 1424.00 |
| 37 | C | C |
| 38A | C | C |
| 38B | 5000.00 | 7712.00 |
| 200A | C | C |
| 200B | 160.00 | 195.40 |
| 242 | C | C |
| 243 | C | C |
| 22 first isomer | C | C |
| 22 second isomer | C | B |
| 407 first isomer | C | B |
| 407 second isomer | C | B |
| 408 first isomer | C | C |
| 408 second isomer | A | B |
| 410 | A | C |
| 411 | A | B |
| 7 | B | C |
| 8 | B | C |
| 9 | C | C |
| 10 | C | C |
| 11 | C | C |
| 12 first isomer | C | C |
| 12 second isomer | B | B |
| 13 first isomer | B | C |
| 13B | 1200.00 | 5740.00 |
| 14 first isomer | C | C |
| 14 second isomer | A | B |
| 15 first isomer | C | C |
| 15B | 1900.00 | 3376.00 |
| 18 | C | C |
| 19 first isomer | C | C |
| 19B | 1000.00 | 1850.00 |
| 20 first isomer | C | C |
| 20 second isomer | B | B |
| 23 | C | C |
| 24A | 26.00 | 593.20 |
| 24 second isomer | A | A |
| 25 | C | C |
| 26 first isomer | C | C |
| 26B | 1300.00 | 3189.00 |
| 27A | 3.00 | 4.09 |
| 27 second isomer | B | C |
| 28 first isomer | C | C |
| 28 second isomer | B | B |
| 29A | C | B |
| 29B | 249.00 | 14890.00 |
| 32A | 1.00 | 3.59 |
| 32B | A | A |
| 33 | 2.00 | 8.19 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

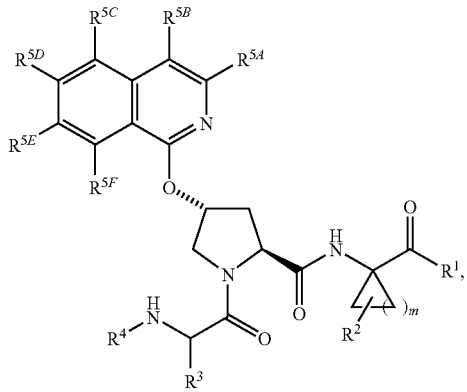

or a pharmaceutically acceptable salt thereof, wherein
m is 1, 2, or 3;
$R^1$ is selected from hydroxy and —$NHSO_2R^6$; wherein $R^6$ is selected from alkyl, aryl, cycloalkyl, (cycloalkyl)alkyl, heterocyclyl, and —$NR^aR^b$, wherein the alkyl, the cycloalkyl and the cycloalkyl part of the (cycloalkyl)alkyl are optionally substituted with one, two, or three substituents selected from alkenyl, alkoxy, alkoxyalkyl, alkyl, arylalkyl, arylcarbonyl, cyano, cycloalkenyl, (cycloalkyl)alkyl, halo, haloalkoxy, haloalkyl, and ($NR^eR^f$)carbonyl;
$R^2$ is selected from hydrogen, alkenyl, alkyl, and cycloalkyl, wherein the alkenyl, alkyl, and cycloalkyl are optionally substituted with halo;
$R^3$ is selected from alkenyl, alkoxyalkyl, alkoxycarbonylalkyl, alkyl, arylalkyl, carboxyalkyl, cyanoalkyl, cycloalkyl, (cycloalkyl)alkyl, haloalkoxy, haloalkyl, (heterocyclyl)alkyl, hydroxyalkyl, ($NR^cR^d$)alkyl, and ($NR^eR^f$)carbonylalkyl;
$R^4$ is selected from phenyl and a five- or six-membered partially or fully unsaturated ring optionally containing one, two, three, or four heteroatoms selected from nitrogen, oxygen, and sulfur; wherein each of the rings is optionally substituted with one, two, three, or four substitutents independently selected from alkoxy, alkoxycarbonyl, alkyl, alkylcarbonyl, alkylsulfanyl, carboxy, cyano, cycloalkyl, cycloalkyloxy, halo, haloalkyl, haloalkoxy, —$NR^cR^d$, ($NR^eR^f$)carbonyl, ($NR^eR^f$)sulfonyl, and oxo; provided that when $R^4$ is a six-membered substituted ring all substituents on the ring other than fluoro must be in the meta and/or para positions relative to the ring's point of attachment to the parent molecular moiety;
$R^{5A}$, $R^{5B}$, $R^{5C}$, $R^{5D}$, $R^{5E}$ and $R^{5F}$ are each independently selected from hydrogen, alkoxy, alkoxycarbonyl, alkyl, alkylcarbonyl, aryl, carboxy, cyano, cyanoalkyl, cycloalkyl, halo, haloalkyl, haloalkoxy, heterocyclyl, hydroxy, hydroxyalkyl, nitro, —$NR^cR^d$, ($NR^cR^d$)alkyl, ($NR^cR^d$)alkoxy, ($NR^eR^f$)carbonyl, and ($NR^eR^f$)sulfonyl; or
two adjacent $R^5$ groups, together with the carbon atoms to which they are attached, form a four- to seven-membered partially- or fully-unsaturated ring optionally containing one or two heteroatoms independently selected from nitrogen, oxygen, and sulfur, wherein the ring is optionally substituted with one, two, or three groups independently selected from alkoxy, alkyl, cyano, halo, haloalkoxy, and haloalkyl;
$R^a$ and $R^b$ are independently selected from hydrogen, alkoxy, alkyl, aryl, arylalkyl, cycloalkyl, (cycloalkyl)alkyl, heterocyclyl, and heterocyclylalkyl; or $R^a$ and $R^b$ together with the nitrogen atom to which they are attached form a four to seven-membered monocyclic heterocyclic ring;
$R^c$ and $R^d$ are independently selected from hydrogen, alkoxyalkyl, alkoxycarbonyl, alkyl, alkylcarbonyl, arylalkyl, and haloalkyl; and
$R^e$ and $R^f$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

2. A compound of claim 1, or a pharmaceutically acceptable salt thereof, wherein $R^1$ is —$NHSO_2R^6$.

3. A compound of claim 1, or a pharmaceutically acceptable salt thereof, wherein
m is 1 or 2;
$R^1$ is —$NHSO_2R^6$; wherein $R^6$ is selected from alkyl, aryl, cycloalkyl, (cycloalkyl)alkyl, heterocyclyl, and —$NR^aR^b$, wherein the alkyl, the cycloalkyl and the cycloalkyl part of the (cycloalkyl)alkyl are optionally substituted with one, two, or three substituents selected from alkenyl, alkoxy, alkoxyalkyl, alkyl, arylalkyl, arylcarbonyl, cyano, cycloalkenyl, (cycloalkyl)alkyl, halo, haloalkoxy, haloalkyl, and ($NR^eR^f$)carbonyl;
$R^2$ is selected from alkenyl, alkyl, and cycloalkyl, wherein the alkenyl, alkyl, and cycloalkyl are optionally substituted with halo;
$R^3$ is selected from alkenyl and alkyl;
$R^4$ is selected from phenyl and a five- or six-membered partially or fully unsaturated ring optionally containing one, two, three, or four heteroatoms selected from nitrogen, oxygen, and sulfur; wherein each of the rings is optionally substituted with one, two, three, or four substitutents independently selected from alkoxy, alkoxycarbonyl, alkyl, alkylcarbonyl, alkylsulfanyl, carboxy, cyano, cycloalkyl, cycloalkyloxy, halo, haloalkyl, haloalkoxy, —$NR^cR^d$, ($NR^eR^f$)carbonyl, ($NR^eR^f$)sulfonyl, and oxo; provided that when $R^4$ is a six-membered substituted ring all substituents on the ring other than fluoro must be in the meta and/or para positions relative to the ring's point of attachment to the parent molecular moiety;
$R^{5A}$, $R^{5B}$, $R^{5C}$, $R^{5D}$, $R^{5E}$ and $R^{5F}$ are each independently selected from hydrogen, alkoxy, alkoxycarbonyl, alkyl, alkylcarbonyl, aryl, carboxy, cyano, cyanoalkyl, cycloalkyl, halo, haloalkyl, haloalkoxy, heterocyclyl, hydroxy, hydroxyalkyl, nitro, —$NR^cR^d$, ($NR^cR^d$)alkyl, ($NR^cR^d$)alkoxy, ($NR^eR^f$)carbonyl, and ($NR^eR^f$)sulfonyl; or
two adjacent $R^5$ groups, together with the carbon atoms to which they are attached, form a four- to seven-membered partially- or fully-unsaturated ring optionally containing one or two heteroatoms independently selected from nitrogen, oxygen, and sulfur, wherein the ring is optionally substituted with one, two, or three groups independently selected from alkoxy, alkyl, cyano, halo, haloalkoxy, and haloalkyl;
$R^a$ and $R^b$ are independently selected from hydrogen, alkoxy, alkyl, aryl, arylalkyl, cycloalkyl, (cycloalkyl)alkyl, heterocyclyl, and heterocyclylalkyl; or $R^a$ and $R^b$ together with the nitrogen atom to which they are attached form a four- to seven-membered monocyclic heterocyclic ring;

$R^c$ and $R^d$ are independently selected from hydrogen, alkoxyalkyl, alkoxycarbonyl, alkyl, alkylcarbonyl, arylalkyl, and haloalkyl; and $R^e$ and $R^f$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

4. A compound of claim 3, or a pharmaceutically acceptable salt thereof, wherein $R^6$ is selected from unsubstituted cycloalkyl and —$NR^aR^b$.

5. A compound of claim 1, or a pharmaceutically acceptable salt thereof, wherein m is 1;

$R^1$ is —$NHSO_2R^6$; wherein $R^6$ is unsubstituted cycloalkyl;

$R^2$ is alkenyl;

$R^3$ is selected from alkenyl and alkyl;

$R^4$ is selected from phenyl and a five- or six-membered partially or fully unsaturated ring optionally containing one, two, three, or four heteroatoms selected from nitrogen, oxygen, and sulfur; wherein each of the rings is optionally substituted with one, two, or three substitutents independently selected from alkoxy, alkoxycarbonyl, alkyl, alkylcarbonyl, carboxy, cyano, cycloalkyl, cycloalkyloxy, halo, haloalkyl, haloalkoxy, —$NR^cR^d$, ($NR^eR^f$)carbonyl, ($NR^eR^f$)sulfonyl, and oxo; provided that when $R^4$ is a six-membered substituted ring all substituents on the ring other than fluoro must be in the meta and/or para positions relative to the ring's point of attachment to the parent molecular moiety;

$R^{5A}$, $R^{5B}$, $R^{5C}$, $R^{5D}$, $R^{5E}$ and $R^{5F}$ are each independently selected from hydrogen, alkoxy, aryl, and —$NR^cR^d$; or two adjacent $R^5$ groups, together with the carbon atoms to which they are attached, form a six-membered partially- or fully-unsaturated ring optionally containing one or two heteroatoms independently selected from nitrogen, oxygen, and sulfur, wherein the ring is optionally substituted with one, two, or three groups independently selected from alkoxy, alkyl, cyano, halo, haloalkoxy, and haloalkyl;

$R^c$ and $R^d$ are independently selected from hydrogen, alkoxycarbonyl, alkyl, alkylcarbonyl, and arylalkyl; and $R^e$ and $R^f$ are independently selected from hydrogen, alkyl, aryl, and arylalkyl.

6. A compound of claim 5, or a pharmaceutically acceptable salt thereof, wherein $R^4$ is phenyl optionally substituted with one, two, or three substitutents independently selected from alkoxy, alkoxycarbonyl, alkyl, alkylcarbonyl, carboxy, cyano, cycloalkyl, cycloalkyloxy, halo, haloalkyl, haloalkoxy, —$NR^cR^d$, ($NR^eR^f$)carbonyl, ($NR^eR^f$)sulfonyl, and oxo; provided that all substituents on the ring other than fluoro must be in the meta and/or para positions relative to the ring's point of attachment to the parent molecular moiety.

7. A compound of claim 5, or a pharmaceutically acceptable salt thereof, wherein $R^4$ is a six-membered fully unsaturated ring containing one nitrogen atom; wherein the ring is optionally substituted with one, two, or three substitutents independently selected from alkoxy, alkoxycarbonyl, alkyl, alkylcarbonyl, carboxy, cyano, cycloalkyl, cycloalkyloxy, halo, haloalkyl, haloalkoxy, —$NR^cR^d$, ($NR^eR^f$)carbonyl, ($NR^eR^f$)sulfonyl, and oxo; provided that all substituents on the ring other than fluoro must be in the meta and/or para positions relative to the ring's point of attachment to the parent molecular moiety.

8. A compound selected from

N-(4,6-dimethyl-2-pyridinyl)-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(4,6-dimethyl-2-pyridinyl)-D-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(5-(trifluoromethyl)-2-pyridinyl)valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(4,6-dimethoxy-1,3,5-triazin-2-yl)-3-methyl-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(4,6-dimethoxy-1,3,5-triazin-2-yl)valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(4,6-dimethoxy-2-pyrimidinyl)valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(4,6-dimethyl-2-pyrimidinyl)-D-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(4,6-dimethyl-2-pyrimidinyl)-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-2-pyridinylvalyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(4-methoxy-2-pyridinyl)valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(4-(trifluoromethyl)-2-pyridinyl)valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(4-methyl-2-pyridinyl)valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(4-cyano-2-pyridinyl)valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

3-methyl-N-2-pyridinyl-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

3-methyl-N-2-pyridinyl-D-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

3-methyl-N-3-pyridinyl-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

3-methyl-N-3-pyridinyl-D-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(4,6-dimethyl-2-pyridinyl)-3-methyl-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(4,6-dimethyl-2-pyridinyl)-3-methyl-D-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

3-methyl-N-phenyl-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

3-methyl-N-phenyl-D-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(4,6-dimethyl-2-pyridinyl)valyl-(4R)—N-((1R,2S)-1-((dimethylsulfamoyl)carbamoyl)-2-vinylcyclopropyl)-4-((6-methoxy-1-isoquinolinyl)oxy)-L-prolinamide;

N-(4,6-dimethyl-2-pyridinyl)valyl-(4R)—N-((1R,2S)-1-((cyclopropylsulfonyl)carbamoyl)-2-vinylcyclopropyl)-4-((3-(dimethylamino)-6-methoxy-1-isoquinolinyl)oxy)-L-prolinamide;

N-(4,6-dimethyl-2-pyridinyl)-3-methylvalyl-(4R)—N-((1R,2S)-1-((cyclopropylsulfonyl)carbamoyl)-2-vinylcyclopropyl)-4-((3-(dimethylamino)-6-methoxy-1-isoquinolinyl)oxy)-L-prolinamide;

3-methyl-N-phenyl-L-valyl-(4R)—N-((1R,2S)-1-((cyclopropylsulfonyl)carbamoyl)-2-vinylcyclopropyl)-4-((3-(dimethylamino)-6-methoxy-1-isoquinolinyl)oxy)-L-prolinamide;

3-methyl-N-phenyl-D-valyl-(4R)—N-((1R,2S)-1-((cyclopropylsulfonyl)carbamoyl)-2-vinylcyclopropyl)-4-((3-(dimethylamino)-6-methoxy-1-isoquinolinyl)oxy)-L-prolinamide;

3-methyl-N-(5-(trifluoromethyl)-3-pyridinyl)-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(5-(trifluoromethyl)-3-pyridinyl)-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(6-methyl-2-pyridinyl)-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(6-methyl-2-pyridinyl)-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(2,6-dimethyl-4-pyridinyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(2,6-dimethyl-4-pyridinyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(4,6-dichloro-2-pyridinyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(4,6-dichloro-2-pyridinyl)-3-methyl-D-valyl-(4R)-4-((7-chloro-4-methoxy-1-isoquinolinyl)oxy)-N-((1R, 2S)-1-((cyclopropylsulfonyl)carbamoyl)-2-vinylcyclopropyl)-L-prolinamide;

N-(5-chloro-3-pyridinyl)-3-methylvalyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(4-ethyl-1,3-thiazol-2-yl)-3-methyl-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(5,6-dihydro-4H-1,3-thiazin-2-yl)-3-methyl-L-valyl-(4R)—N-((1R,2S)-1-((cyclopropylsulfonyl)carbamoyl)-2-vinylcyclopropyl)-4-((6-methoxy-1-isoquinolinyl)oxy)-L-prolinamide;

N-(5,6-dihydro-4H-1,3-thiazin-2-yl)-3-methyl-L-valyl-(4R)—N-((1R,2S)-1-((cyclopropylsulfonyl)carbamoyl)-2-vinylcyclopropyl)-4-((6-methoxy-3-(4-(trifluoromethyl)phenyl)-1-isoquinolinyl)oxy)-L-prolinamide;

3-methyl-N-(6-methyl-2-pyridinyl)-L-valyl-(4R)—N-((1R,2S)-1-((cyclopropylsulfonyl)carbamoyl)-2-vinylcyclopropyl)-4-((3-(dimethylamino)-5-methoxy-1-isoquinolinyl)oxy)-L-prolinamide;

3-methyl-N-(6-methyl-2-pyridinyl)-D-valyl-(4R)—N-((1R,2S)-1-((cyclopropylsulfonyl)carbamoyl)-2-vinylcyclopropyl)-4-((3-(dimethylamino)-5-methoxy-1-isoquinolinyl)oxy)-L-prolinamide;

N-(3-fluorophenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(3-fluorophenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(3-methoxyphenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(3-methoxyphenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(3-(methylcarbamoyl)phenyl)-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(3-(methylcarbamoyl)phenyl)-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(3-cyanophenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(3-cyanophenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(4-(tert-butoxycarbonyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(4-(tert-butoxycarbonyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(4-cyanophenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(4-cyanophenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(3-(tert-butylsulfamoyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(3-(tert-butylsulfamoyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(3-sulfamoylphenyl)-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(3-sulfamoylphenyl)-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(2,3-difluorophenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(2,3-difluorophenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(4-carboxyphenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(4-carboxyphenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(3-(tert-butoxycarbonyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(3-(tert-butoxycarbonyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(3-carboxyphenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(3-carboxyphenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(3-(tert-butylcarbamoyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(3-(tert-butylcarbamoyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-phenyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-phenyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(4-(tert-butylsulfamoyl)phenyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(4-(tert-butylsulfamoyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-phenyl-L-valyl-(4R)—N-((1R,2S)-1-((cyclopropylsulfonyl)carbamoyl)-2-vinylcyclopropyl)-4-((3,6-dimethoxy-1-isoquinolinyl)oxy)-L-prolinamide;

3-methyl-N-phenyl-D-valyl-(4R)—N-((1R,2S)-1-((cyclopropylsulfonyl)carbamoyl)-2-vinylcyclopropyl)-4-((3,6-dimethoxy-1-isoquinolinyl)oxy)-L-prolinamide;

N-(4,6-dimethyl-2-pyridinyl)valyl-(4R)—N-((1R,2S)-1-((cyclopropylsulfonyl)carbamoyl)-2-vinylcyclopropyl)-4-((3,6-dimethoxy-1-isoquinolinyl)oxy)-L-prolinamide;

N-(4,6-dimethyl-2-pyridinyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(4,6-dimethyl-2-pyridinyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(4-methyl-5-nitro-2-pyridinyl)valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-5-pyrimidinyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-5-pyrimidinyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(5-methyl-3-pyridinyl)valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(6-methyl-3-pyridinyl)-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(6-methyl-3-pyridinyl)-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(4-sulfamoylphenyl)-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(4-sulfamoylphenyl)-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(3-((1-methyl-1-phenylethyl)carbamoyl)phenyl)-L-valyl-(4R)-4-((7-chloro-4-methoxy-1-isoquinolinyl)oxy)-N-((1R,2S)-1-((cyclopropylsulfonyl)car-
bamoyl)-2-vinylcyclopropyl)-L-prolinamide;
3-methyl-N-(3-((1-methyl-1-phenylethyl)carbamoyl)phe-
nyl)-D-valyl-(4R)-4-((7-chloro-4-methoxy-1-isoquino-
linyl)oxy)-N-((1R,2S)-1-((cyclopropylsulfonyl)car-
bamoyl)-2-vinylcyclopropyl)-L-prolinamide;
N-(3-carbamoylphenyl)-3-methyl-L-valyl-(4R)-4-((7-
chloro-4-methoxy-1-isoquinolinyl)oxy)-N-((1R,2S)-1-
((cyclopropylsulfonyl)carbamoyl)-2-vinylcyclopro-
pyl)-L-prolinamide;
N-(3-carbamoylphenyl)-3-methyl-D-valyl-(4R)-4-((7-
chloro-4-methoxy-1-isoquinolinyl)oxy)-N-((1R,2S)-1-
((cyclopropylsulfonyl)carbamoyl)-2-vinylcyclopro-
pyl)-L-prolinamide;
N-(3-(dimethylcarbamoyl)phenyl)-3-methyl-L-valyl-
(4R)-4-((7-chloro-4-methoxy-1-isoquinolinyl)oxy)-N-
((1R,2S)-1-((cyclopropylsulfonyl)carbamoyl)-2-vinyl-
cyclopropyl)-L-prolinamide;
N-(3-(dimethylcarbamoyl)phenyl)-3-methyl-D-valyl-
(4R)-4-((7-chloro-4-methoxy-1-isoquinolinyl)oxy)-N-
((1R,2S)-1-((cyclopropylsulfonyl)carbamoyl)-2-vinyl-
cyclopropyl)-L-prolinamide;
N-(3-(dimethylsulfamoyl)phenyl)-3-methyl-L-valyl-
(4R)-4-((7-chloro-4-methoxy-1-isoquinolinyl)oxy)-N-
((1R,2S)-1-((cyclopropylsulfonyl)carbamoyl)-2-vinyl-
cyclopropyl)-L-prolinamide;
N-(3-(dimethylsulfamoyl)phenyl)-3-methyl-D-valyl-
(4R)-4-((7-chloro-4-methoxy-1-isoquinolinyl)oxy)-N-
((1R,2S)-1-((cyclopropylsulfonyl)carbamoyl)-2-vinyl-
cyclopropyl)-L-prolinamide;
N-(3,4-difluorophenyl)-3-methyl-L-valyl-(4R)-4-((7-
chloro-4-methoxy-1-isoquinolinyl)oxy)-N-((1R,2S)-1-
((cyclopropylsulfonyl)carbamoyl)-2-vinylcyclopro-
pyl)-L-prolinamide;
N-(3,4-difluorophenyl)-3-methyl-D-valyl-(4R)-4-((7-
chloro-4-methoxy-1-isoquinolinyl)oxy)-N-((1R,2S)-1-
((cyclopropylsulfonyl)carbamoyl)-2-vinylcyclopro-
pyl)-L-prolinamide;
N-(4-(dimethylcarbamoyl)phenyl)-3-methyl-L-valyl-
(4R)-4-((7-chloro-4-methoxy-1-isoquinolinyl)oxy)-N-
((1R,2S)-1-((cyclopropylsulfonyl)carbamoyl)-2-vinyl-
cyclopropyl)-L-prolinamide;
N-(4-(dimethylcarbamoyl)phenyl)-3-methyl-D-valyl-
(4R)-4-((7-chloro-4-methoxy-1-isoquinolinyl)oxy)-N-
((1R,2S)-1-((cyclopropylsulfonyl)carbamoyl)-2-vinyl-
cyclopropyl)-L-prolinamide;
3-methyl-N-(4-((1-methyl-1-phenylethyl)carbamoyl)phe-
nyl)-L-valyl-(4R)-4-((7-chloro-4-methoxy-1-isoquino-
linyl)oxy)-N-((1R,2S)-1-((cyclopropylsulfonyl)car-
bamoyl)-2-vinylcyclopropyl)-L-prolinamide;
3-methyl-N-(4-((1-methyl-1-phenylethyl)carbamoyl)phe-
nyl)-L-valyl-(4R)-4-((7-chloro-4-methoxy-1-isoquino-
linyl)oxy)-N-((1R,2S)-1-((cyclopropylsulfonyl)car-
bamoyl)-2-vinylcyclopropyl)-L-prolinamide;
N-(4-(ethylsulfamoyl)phenyl)-3-methyl-L-valyl-(4R)-4-
((7-chloro-4-methoxy-1-isoquinolinyl)oxy)-N-((1R,
2S)-1-((cyclopropylsulfonyl)carbamoyl)-2-vinylcyclo-
propyl)-L-prolinamide;
N-(4-(ethylsulfamoyl)phenyl)-3-methyl-D-valyl-(4R)-4-
((7-chloro-4-methoxy-1-isoquinolinyl)oxy)-N-((1R,
2S)-1-((cyclopropylsulfonyl)carbamoyl)-2-vinylcyclo-
propyl)-L-prolinamide;
N-(4-(dimethylsulfamoyl)phenyl)-3-methyl-L-valyl-
(4R)-4-((7-chloro-4-methoxy-1-isoquinolinyl)oxy)-N-
((1R,2S)-1-((cyclopropylsulfonyl)carbamoyl)-2-vinyl-
cyclopropyl)-L-prolinamide;
N-(4-(dimethylsulfamoyl)phenyl)-3-methyl-D-valyl-
(4R)-4-((7-chloro-4-methoxy-1-isoquinolinyl)oxy)-N-
((1R,2S)-1-((cyclopropylsulfonyl)carbamoyl)-2-vinyl-
cyclopropyl)-L-prolinamide;
N-(4-carbamoylphenyl)-3-methyl-L-valyl-(4R)-4-((7-
chloro-4-methoxy-1-isoquinolinyl)oxy)-N-((1R,2S)-1-
((cyclopropylsulfonyl)carbamoyl)-2-vinylcyclopro-
pyl)-L-prolinamide;
N-(4-carbamoylphenyl)-3-methyl-D-valyl-(4R)-4-((7-
chloro-4-methoxy-1-isoquinolinyl)oxy)-N-((1R,2S)-1-
((cyclopropylsulfonyl)carbamoyl)-2-vinylcyclopro-
pyl)-L-prolinamide;
3-methyl-N-(3-(methylsulfamoyl)phenyl)-L-valyl-(4R)-
4-((7-chloro-4-methoxy-1-isoquinolinyl)oxy)-N-((1R,
2S)-1-((cyclopropylsulfonyl)carbamoyl)-2-vinylcyclo-
propyl)-L-prolinamide;
3-methyl-N-(3-(methylsulfamoyl)phenyl)-D-valyl-(4R)-
4-((7-chloro-4-methoxy-1-isoquinolinyl)oxy)-N-((1R,
2S)-1-((cyclopropylsulfonyl)carbamoyl)-2-vinylcyclo-
propyl)-L-prolinamide;
N-(3-(isopropoxycarbonyl)phenyl)-3-methyl-L-valyl-
(4R)-4-((7-chloro-4-methoxy-1-isoquinolinyl)oxy)-N-
((1R,2S)-1-((cyclopropylsulfonyl)carbamoyl)-2-vinyl-
cyclopropyl)-L-prolinamide;
N-(3-(isopropoxycarbonyl)phenyl)-3-methyl-D-valyl-
(4R)-4-((7-chloro-4-methoxy-1-isoquinolinyl)oxy)-N-
((1R,2S)-1-((cyclopropylsulfonyl)carbamoyl)-2-vinyl-
cyclopropyl)-L-prolinamide;
N-(3-(methoxycarbonyl)phenyl)-3-methyl-L-valyl-(4R)-
4-((7-chloro-4-methoxy-1-isoquinolinyl)oxy)-N-((1R,
2S)-1-((cyclopropylsulfonyl)carbamoyl)-2-vinylcyclo-
propyl)-L-prolinamide;
N-(3-(methoxycarbonyl)phenyl)-3-methyl-D-valyl-(4R)-
4-((7-chloro-4-methoxy-1-isoquinolinyl)oxy)-N-((1R,
2S)-1-((cyclopropylsulfonyl)carbamoyl)-2-vinylcyclo-
propyl)-L-prolinamide;
(4R)-4-((7-chloro-4-methoxy-1-isoquinolinyl)oxy)-N-
((1R,2S)-1-((cyclopropylsulfonyl)carbamoyl)-2-vinyl-
cyclopropyl)-1-((2S)-2-((4-ethoxy-1,2,5-thiadiazol-3-
yl)amino)butanoyl)-L-prolinamide;
(4R)-4-((7-chloro-4-methoxy-1-isoquinolinyl)oxy)-N-
((1R,2S)-1-((cyclopropylsulfonyl)carbamoyl)-2-vinyl-
cyclopropyl)-1-((2R)-2-((4-ethoxy-1,2,5-thiadiazol-3-
yl)amino)butanoyl)-L-prolinamide;
N-(2-fluorophenyl)-3-methyl-D-valyl-(4R)-4-[(7-chloro-
4-methoxy-1-isoquinolinyl)oxy]-N-((1R,2S)-1-{[(cy-
clopropylsulfonyl)amino]carbonyl}-2-vinylcyclopro-
pyl)-L-prolinamide;
N-(2-fluorophenyl)-3-methyl-L-valyl-(4R)-4-[(7-chloro-
4-methoxy-1-isoquinolinyl)oxy]-N-((1R,2S)-1-{[(cy-
clopropylsulfonyl)amino]carbonyl}-2-vinylcyclopro-
pyl)-L-prolinamide;
N-(3,4-difluorophenyl)-3-methyl-L-valyl-(4R)—N-((1R,
2S)-1-((cyclopropylsulfonyl)carbamoyl)-2-vinylcyclo-
propyl)-4-((9-methoxy-4-methyl-3,4-dihydro-2H-[1,4]
oxazino[3,2-c]isoquinolin-6-yl)oxy)-L-prolinamide;
N-(3,4-difluorophenyl)-3-methyl-D-valyl-(4R)—N-((1R,
2S)-1-((cyclopropylsulfonyl)carbamoyl)-2-vinylcyclo-
propyl)-4-((9-methoxy-4-methyl-3,4-dihydro-2H-[1,4]
oxazino[3,2-c]isoquinolin-6-yl)oxy)-L-prolinamide;
N-(6-methoxy-3-pyridinyl)-3-methyl-L-valyl-(4R)—N-
((1R,2S)-1-((cyclopropylsulfonyl)carbamoyl)-2-vinyl-
cyclopropyl)-4-((6-methoxy-1-isoquinolinyl)oxy)-L-
prolinamide;

N-(6-methoxy-3-pyridinyl)-3-methyl-D-valyl-(4R)—N-((1R,2S)-1-((cyclopropylsulfonyl)carbamoyl)-2-vinyl-cyclopropyl)-4-((6-methoxy-1-isoquinolinyl)oxy)-L-prolinamide;

N-(6-methoxy-3-pyridinyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(6-methoxy-3-pyridinyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(6-(difluoromethoxy)-3-pyridinyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinyl-cyclopropyl)-L-prolinamide; and N-(6-(difluoromethoxy)-3-pyridinyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinyl-cyclopropyl)-L-prolinamide;

or a pharmaceutically acceptable salt thereof.

9. A composition comprising the compound of claim 1, or a pharmaceutically acceptable salt thereof, and a pharmaceutically acceptable carrier.

10. The composition of claim 9 further comprising at least one additional compound having anti-HCV activity.

11. The composition of claim 10 wherein at least one of the additional compounds is an interferon or a ribavirin.

12. The composition of claim 11 wherein the interferon is selected from interferon alpha 2B, pegylated interferon alpha, consensus interferon, interferon alpha 2A, and lymphoblastiod interferon tau.

13. The composition of claim 10 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

14. The composition of claim 10 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

15. A method of treating an HCV infection in a patient, in need thereof comprising administering to the patient a therapeutically effective amount of a compound of claim 1, or a pharmaceutically acceptable salt thereof.

16. The method of claim 15 further comprising administering at least one additional compounds having anti-HCV activity prior to, after, or simultaneously with the compound of claim 1, or a pharmaceutically acceptable salt thereof.

17. The method of claim 16 wherein at least one of the additional compounds is an interferon or a ribavirin.

18. The method of claim 17 wherein the interferon is selected from interferon alpha 2B, pegylated interferon alpha, consensus interferon, interferon alpha 2A, and lymphoblastiod interferon tau.

19. The method of claim 16 wherein at least one of the additional compounds is selected from interleukin 2, interleukin 6, interleukin 12, a compound that enhances the development of a type 1 helper T cell response, Imiqimod, ribavirin, an inosine 5'-monophospate dehydrogenase inhibitor, amantadine, and rimantadine.

20. The method of claim 16 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *

UNITED STATES PATENT AND TRADEMARK OFFICE
CERTIFICATE OF CORRECTION

| | | |
|---|---|---|
| PATENT NO. | : 7,772,180 B2 | Page 1 of 4 |
| APPLICATION NO. | : 11/934840 | |
| DATED | : August 10, 2010 | |
| INVENTOR(S) | : Ny Sin et al. | |

It is certified that error appears in the above-identified patent and that said Letters Patent is hereby corrected as shown below:

In the Specification:

Column 5, line 59, change "lymphoblastiod" to -- lymphoblastoid --.

Column 6, line 1, change "Imiqimod" to -- Imiquimod --.

Column 6, line 2, change "5'-monophospate" to -- 5'-monophosphate --.

Column 6, line 28, change "lymphoblastiod" to -- lymphoblastoid --.

Column 6, line 40, change "Imiqimod" to -- Imiquimod --.

Column 6, line 41, change "5'-monophospate" to -- 5'-monophosphate --.

In the Claims:

Claim 1:

Column 315, line 41, change "carbonyalkyl" to -- carbonylalkyl --.

Column 315, lines 46 and 47, change "substitutents" to -- substituents --.

Claim 3:

Column 316, lines 40 and 41, change "substitutents" to -- substituents --.

Claim 5:

Column 317, lines 25 and 26, change "substitutents" to -- substituents --.

Claim 6:

Column 317, line 50, change "substitutents" to -- substituents --.

Claim 7:

Column 317, line 60, change "substitutents" to -- substituents --.

Signed and Sealed this
Twenty-second Day of November, 2011

David J. Kappos
*Director of the United States Patent and Trademark Office*

CERTIFICATE OF CORRECTION (continued)

In the Claims:

Claim 8:

Column 319, line 34, after

"3-methyl-N-phenyl-D-valyl-(4R)-N-((1R,2S)-1-((cyclopropylsulfonyl)carbamoyl)-2-vinylcyclopropyl)-4-((3-(dimethylamino)-6-methoxy-1-isoquinolinyl)oxy)-L-prolinamide;", insert -- 3-methyl-N-phenyl-L-valyl-(4R)-N-((1R,2S)-1-((cyclopropylsulfonyl)carbamoyl)-2-vinylcyclopropyl)-4-((3,6-dimethoxy-1-isoquinolinyl)oxy)-L-prolinamide;

3-methyl-N-phenyl-D-valyl-(4R)-N-((1R,2S)-1-((cyclopropylsulfonyl)carbamoyl)-2-vinylcyclopropyl)-4-((3,6-dimethoxy-1-isoquinolinyl)oxy)-L-prolinamide;

N-(4,6-dimethyl-2-pyridinyl)valyl-(4R)-N-((1R,2S)-1-((cyclopropylsulfonyl)carbamoyl)-2-vinylcyclopropyl)-4-((3,6-dimethoxy-1-isoquinolinyl)oxy)-L-prolinamide;

N-(4,6-dimethyl-2-pyridinyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(4,6-dimethyl-2-pyridinyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(4-methyl-5-nitro-2-pyridinyl)valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-5-pyrimidinyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-5-pyrimidinyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(5-methyl-3-pyridinyl)valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(6-methyl-3-pyridinyl)-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

CERTIFICATE OF CORRECTION (continued)
U.S. Pat. No. 7,772,180 B2

Page 3 of 4

In the Claims:
Claim 8 (continued):

3-methyl-N-(6-methyl-3-pyridinyl)-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide; --.

Column 322, lines 17 to 57,
after

"N-(4-(tert-butylsulfamoyl)phenyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;", delete "3-methyl-N-phenyl-L-valyl-(4R)-N-((1R,2S)-1-((cyclopropylsulfonyl)carbamoyl)-2-vinylcyclopropyl)-4-((3,6-dimethoxy-1-isoquinolinyl)oxy)-L-prolinamide;

3-methyl-N-phenyl-D-valyl-(4R)-N-((1R,2S)-1-((cyclopropylsulfonyl)carbamoyl)-2-vinylcyclopropyl)-4-((3,6-dimethoxy-1-isoquinolinyl)oxy)-L-prolinamide;

N-(4,6-dimethyl-2-pyridinyl)valyl-(4R)-N-((1R,2S)-1-((cyclopropylsulfonyl)carbamoyl)-2-vinylcyclopropyl)-4-((3,6-dimethoxy-1-isoquinolinyl)oxy)-L-prolinamide;

N-(4,6-dimethyl-2-pyridinyl)-3-methyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-(4,6-dimethyl-2-pyridinyl)-3-methyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(4-methyl-5-nitro-2-pyridinyl)valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-5-pyrimidinyl-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

N-5-pyrimidinyl-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

CERTIFICATE OF CORRECTION (continued)
U.S. Pat. No. 7,772,180 B2

In the Claims:
Claim 8 (continued):

3-methyl-N-(5-methyl-3-pyridinyl)valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(6-methyl-3-pyridinyl)-L-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;

3-methyl-N-(6-methyl-3-pyridinyl)-D-valyl-(4R)-4-((7-chloro-4-methoxy-1-isoquinolinyl)oxy)-N-((1R,2S)-1-((cyclopropylsulfonyl)carbamoyl)-2-vinylcyclopropyl)-L-prolinamide;".

Claim 12:
    Column 325, lines 32 and 33, change "lymphoblastiod" to -- lymphoblastoid --.

Claim 13:
    Column 326, line 1, change "Imiqimod" to -- Imiquimod --.

Column 326, lines 1 and 2, change "5'-monophospate" to -- 5'-monophosphate --.

Claim 18:
    Column 326, lines 22 and 23, change "lymphoblastiod" to -- lymphoblastoid --.

Claim 19:
    Column 326, line 27, change "Imiqimod" to -- Imiquimod --.

Column 326, line 28, change "5'-monophospate" to -- 5'-monophosphate --.